US011298388B2

(12) United States Patent
Lightburn et al.

(10) Patent No.: US 11,298,388 B2
(45) Date of Patent: *Apr. 12, 2022

(54) PSYCHOACTIVE ALKALOID EXTRACTION AND COMPOSITION WITH CONTROLLED DEPHOSPHORYLATION

(71) Applicant: PSILO SCIENTIFIC LTD, Vancouver (CA)

(72) Inventors: Benjamin Lightburn, Vancouver (CA); Ryan Moss, Vancouver (CA); Lisa Ranken, Vancouver (CA)

(73) Assignee: PSILO SCIENTIFIC LTD., Vancouver (CA)

( * ) Notice: Subject to any disclaimer, the term of this patent is extended or adjusted under 35 U.S.C. 154(b) by 0 days.

This patent is subject to a terminal disclaimer.

(21) Appl. No.: 17/483,601

(22) Filed: Sep. 23, 2021

(65) Prior Publication Data

US 2022/0040246 A1    Feb. 10, 2022

Related U.S. Application Data

(63) Continuation of application No. 17/348,697, filed on Jun. 15, 2021, which is a continuation of application No. PCT/CA2021/050813, filed on Jun. 14, 2021.

(60) Provisional application No. 63/040,317, filed on Jun. 17, 2020, provisional application No. 63/046,089, filed on Jun. 30, 2020.

(30) Foreign Application Priority Data

| Jul. 29, 2020 | (CA) | 3088384 |
| Aug. 7, 2020 | (CA) | 3089455 |
| Oct. 23, 2020 | (CA) | 3097246 |
| Dec. 4, 2020 | (CA) | 3101765 |
| Dec. 18, 2020 | (CA) | 3103707 |

(51) Int. Cl.
| A61K 36/00 | (2006.01) |
| A61K 36/07 | (2006.01) |
| A61K 31/48 | (2006.01) |
| A61K 31/675 | (2006.01) |
| A61K 31/404 | (2006.01) |
| A61K 31/4045 | (2006.01) |
| A61K 31/42 | (2006.01) |

(52) U.S. Cl.
CPC ............ *A61K 36/07* (2013.01); *A61K 31/404* (2013.01); *A61K 31/4045* (2013.01); *A61K 31/42* (2013.01); *A61K 31/48* (2013.01); *A61K 31/675* (2013.01); *A61K 2236/331* (2013.01); *A61K 2236/333* (2013.01); *A61K 2236/39* (2013.01); *A61K 2236/51* (2013.01)

(58) Field of Classification Search
CPC ............ A61K 2236/333; A61K 31/404; A61K 31/4045; A61K 31/42; A61K 31/48; A61K 31/675; A61K 36/07
See application file for complete search history.

(56) References Cited

U.S. PATENT DOCUMENTS

| 3,183,172 A | 5/1965 | Roger et al. |
| 2019/0142851 A1 | 5/2019 | Chadeayne |
| 2020/0375967 A1 | 12/2020 | Stamets |

FOREIGN PATENT DOCUMENTS

| CA | 3078765 A1 | 4/2019 |
| CN | 101292727 A | 10/2008 |
| WO | WO-2019073379 A1 | 4/2019 |

OTHER PUBLICATIONS

Anastos N. et al., "The Determination of Psilocin and Psilocybin in Hallucinogenic Mushrooms by HPLC Utilizing a Dual Reagent Acidic Potassium Permanganate and Tris(2,20-bipyridyl)ruthenium(II) Chemiluminescence Detection System", J Forensic Sci 51(1): 45-51 (2006).
De Boer P, "Simple method of psilocybin extraction", Blog: Fresh Truffles and Growkits Jun. 24, 2017 (Jun. 24, 2017).
Gartz, Extraction and analysis of indole derivatives from fungal biomass. Journal of Basic Microbiology 34(1): 17-22 (1994).
Kunle et al., Standardization of herbal medicines—a review, Int. J. Biodivers. Conserv. 4(3): 101-112(2012).
Kysilka and Wurst, "A novel extraction procedure for psilocybin and psilocin determination in mushroom samples", Planta Medica 56(3): 327-328 (1990).
Moldavan et al., The effect of Psilocybe cubensis extract on hippocampal neurons in vitro, Fiziol Zh. 47(6): 15-23 (2001).
Psilocybin Expert, "Formulating New "Magic Mushroom" compositions", Psilocybin Technology, Feb. 13, 2018 (Feb. 13, 2018).
Roderick, "Psilocybin and Cannabis Cocktails", Psillow website, Dec. 29, 2019 (Dec. 29, 2019).
Uneasy1, "Psilocin HCl extraction" Chemistry mdma hiveboard (2003). Https://chemistry.mdma.ch/hiveboard/tryptamine/000448065.html.
Mikey's Psilly Ethanol Extract (2017).
PCT/CA2021/050822 International Search Report dated Oct. 19, 2021.
Poliwoda et al., Determination of muscimol and ibotenic acid in mushrooms of Amanitaceae by capillary electrophoresis. Electrophoresis 35(18):2593-2599 (2014).
Truffle Magic—Simple Method of Psilocybin Extraction (2017).
Tuan et al., Optimization of Spray Drying Condition from Trametes Versicolor Mushroom Extract. Journal of Science and Technology 39A: 25-30 (2019).

(Continued)

*Primary Examiner* — Qiuwen Mi
(74) *Attorney, Agent, or Firm* — Wilson Sonsini Goodrich & Rosati

(57) ABSTRACT

This invention relates to the extraction of psychoactive compounds from organisms for use in medicine. Extraction is carried out with a strong acid or strong base to either promote or inhibit dephosphorylation. The extract in the slurry form is standardized with added excipient so that when it is dried the powdered composition has a specified total psychoactive alkaloid concentration, with a known ratio of phosphorylated to dephosphorylated psychoactive alkaloids.

7 Claims, 30 Drawing Sheets

(56) References Cited

OTHER PUBLICATIONS

U.S. Appl. No. 17/348,697 Non-Final Office Action dated Dec. 13, 2021.
U.S. Appl. No. 17/351,149 Non-Final Office Action dated Oct. 13, 2021.
PCT/CA2021/050813 International Search Report dated Sep. 9, 2021.
PCT/CA2021/050823 International Search Report dated Sep. 20, 2021.
Perkal, M., et al. "Determination of hallucinogenic components of Psilocybe mushrooms using high-performance liquid chromatography." J. Chromatography A 196 (1980), pp. 180-184.
U.S. Appl. No. 17/348,697 Notice of Allowance dated Feb. 7, 2022.
U.S. Appl. No. 17/351,149 Final Office Action dated Jan. 24, 2022.

PSYCHOACTIVE ALKALOID EXTRACTION AND COMPOSITION WITH CONTROLLED DEPHOSPHORYLATION

RELATED APPLICATIONS

This application is a continuation of U.S. patent application Ser. No. 17/348,697 filed Jun. 15, 2021, which is a continuation of International Application No. PCT/CA2021/050813 filed Jun. 14, 2021, which claims priority from Canadian Application No. 3089455 filed on Aug. 7, 2020, Canadian Application No. 3088384 filed on Jul. 29, 2020, which claim the benefit of U.S. Provisional Patent Application No. 63/040,317 filed on Jun. 17, 2020, and U.S. Provisional Patent Application No. 63/046,089 filed on Jun. 30, 2020, each of which are incorporated by reference in their entireties, International Application No. PCT/CA2021/050813 also claims priority to Canadian Application No. 3097246 filed on Oct. 23, 2020, Canadian Application No. 3101765 filed on Dec. 4, 2020, and Canadian Application No. 3103707 filed on Dec. 18, 2020, each of which are incorporated by reference in their entireties.

TECHNICAL FIELD

This application relates to a process of obtaining psychoactive alkaloid extracts. More specifically, the present invention relates to controlling dephosphorylation during extraction. Further, the present invention relates to psychoactive alkaloid compositions with controlled dephosphorylation.

BACKGROUND

Varieties of mushrooms have played important roles in most societies. The active ingredients in mushrooms have been found to have medicinal properties including relief of symptoms of various diseases and conditions. The concentration of active ingredients for these applications may vary not only from species to species, but also from mushroom to mushroom inside a given species, subspecies, or variety. The same holds true even for different parts of the same mushroom or mycelium.

Various methods of extraction, which have been used to separate natural extracts from a variety of mushrooms, have resulted in difficulties with large crop-to-crop variability. A large variability within a single plant or fungus sometimes causes inconsistent concentration of the active psychoactive compound and its stability. Different solvent choices extract the psychoactive compounds equally, some of them electively extract one or the other, and some convert the compounds between each other or degrade them into non-psychoactive compounds. Many extraction processes for extracting standardized concentrations of the compounds for direct medical use are usually complex. This results in expensive extraction processes and a high cost of isolated, natural extracts.

U.S. Patent 3183172 to Heim et al. relates to an industrial process for the isolation of active compounds from mushrooms grown under predetermined conditions. With the predetermined growing conditions, mushrooms grew with ten times more active mycelium and sclerotium and increased concentrations of psychoactive compounds. However, a large portion of the target compounds were lost during the extraction process or not extracted at all. In addition, the solvent and solvent systems used during the extraction process were materials such as methanol, acetone, dichloromethane, diethyl ether, or others known to be toxic to humans, even in small quantities.

Extraction methods currently described in the art are inefficient such that a large portion of the target compounds were lost during the extraction process or not extracted at all. They lack analytical data as evidence. We have replicated and measured these methods to prove they are ineffective. In addition, they describe the use of solvents which are known to be toxic to humans, even in small quantities.

To date, the focus has largely been on synthetic preparations of these compounds because of the many difficulties associated with naturally extracted preparations. It is currently infeasible and expensive to extract psilocybin from mushrooms, and even the best chemical synthesis methods require expensive and difficult-to-source starting substrates.

Accordingly, there is a need of methods to produce high efficiency, standardized preparations of the target compounds for medical use while using acceptable solvent systems to create a more consistent supply chain.

SUMMARY OF INVENTION

A psychoactive alkaloid composition comprising of, by weight: 0.1-99.9% of a psychoactive alkaloid extract; and one or more preservatives up to 10%, a flow agent up to 2%, 0-94% of one or more carriers, or any combination thereof. In some embodiments, the composition comprises 2-99.7% of the psychoactive alkaloid extract. In some embodiments, the composition comprises an antioxidant up to 0.5% by weight. In some embodiments, the composition comprises a bioavailability agent up to 0.5% by weight. In some embodiments, the psychoactive alkaloid extract has a psychoactive alkaloid concentration ranging from 0.1% to 99% by weight of the extract. In some embodiments, the one or more preservatives are selected from ascorbic acid, citric acid, lactose, vitamin A, vitamin E, retinyl palmitate, selenium, sodium citrate, sodium ascorbate, calcium ascorbate, sodium benzoate, and potassium benzoate. In some embodiments, the psychoactive alkaloid extract has a psychoactive alkaloid concentration ranging from 0.1% to 20% by weight of the extract. In some embodiments, the psychoactive alkaloid extract is a purified psychoactive alkaloid extract, and the purified psychoactive alkaloid extract has a psychoactive alkaloid concentration ranging from 10% to 99% by weight. In some embodiments, the composition is in a powder form. In some embodiments, the composition comprises 10% or more of the carrier. In some embodiments, the psychoactive alkaloid is psilocybin, psilocin, baeocystin, norbaeocystin, norpsilocin, aeruginascin, bufotenin, bufotenidine, 5-MeO-DMT (5-methoxy-N.Ndimethyltryptamine), N,N-dimethyltryptamine (DMT), 4-hydroxytryptamine, N,N,N-trimethyl-4-hydroxytryptamine ergine (LSA), ergonovine, ergometrine, muscimol, ibotenic acid, lysergic acid hydroxyethylamide (LSH), elymoclavine, ergometrinine, and/or chanoclavine, or any combination selected therefrom. In some embodiments, the psychoactive alkaloid extract comprises naturally occurring substances selected from the group consisting of fats, sugars, carbohydrates, chitin, chitosan, minerals, waxes and proteins. In some embodiments, the naturally occurring substances are present in the psychoactive alkaloid extract in a concentration ranging from 1%-99.9% by weight. In some embodiments, the psychoactive alkaloid extract is from fungi. In some embodiments, the psychoactive alkaloid extract is from *Psilocybe cyanescens, Psilocybe cubensis, Amanita muscaria*, or any selection therefrom. In some embodiments, the psychoactive alkaloid extract is from psychoactive plants. In some embodiments, the psychoactive alkaloid extract is from *Anadenanthera colubrina*. In some embodiments, the psychoactive alkaloid extract is from *Anadenanthera peregrina*. In some embodiments, the psychoactive alkaloid extract is from psychoactive animals. In some embodiments, the psychoactive alkaloid extract is from *Incilius alvarius*. In some embodiments, the psychoactive alkaloid extract is from psychoactive yeasts. In some embodiments, the flow agent is selected from silicon dioxide, stearic acid, magnesium stearate, or talc. In some embodiments, the one or more carriers are selected from starch, maltodextrin, alpha and beta cyclodextrin, microcrystalline cellulose (MCC), gum arabic, xanthum gum, guar gum, mannitol, or cellulose gum. In some embodiments, the maltodextrin is tapioca maltodextrin or rice maltodextrin. In some embodiments, the starch is potato starch. In some embodiments, the flow agent is present in the composition at 0.1 to 1.2%. In some embodiments, a first preservative of the one or more preservatives is present in the composition at 0.1 to 3%. In some embodiments, a second preservative of the one or more preservatives is present in the composition at 0.1 to 3%. In some embodiments, a first carrier of the one or more carriers is present in the composition at 10 to 20%. In some embodiments, a second carrier of the one or more carriers is present in the composition at 10 to 20%. In some embodiments, the composition comprises: the flow agent present in the composition at 0.1 to 1.2%; the one or more preservatives present in the composition at 0.1 to 2%; and the one or more carriers present in the composition at 10 to 20%. In some embodiments, the flow agent is silicon dioxide; the carrier comprises maltodextrin and mannitol; and the one or more preservatives comprise ascorbic acid and citric acid. In some embodiments, the silicon dioxide is present in the composition at 0.1 to 1.2%. In some embodiments, the ascorbic acid is present in the composition at 0.1 to 2%. In some embodiments, the citric acid is present in the composition at 0.1 to 2%. In some embodiments, the maltodextrin is present in the composition at 10 to 20%. In some embodiments, the mannitol is present in the composition at 10 to 20%. In some embodiments, the flow agent is silicon dioxide; the carrier comprises starch and mannitol; and the one or more preservatives comprise ascorbic acid and citric acid. In some embodiments, the silicon dioxide is present in the composition at 0.1 to 1.2%. In some embodiments, the ascorbic acid is present in the composition at 0.1 to 2%. In some embodiments, the citric acid is present in the composition at 0.1 to 2%. In some embodiments, the starch is present in the composition at 10 to 20%. In some embodiments, the mannitol is present in the composition at 10 to 20%.

A method for generating a psychoactive alkaloid extract from a psychoactive organism, the method comprising: providing a biomass of the psychoactive organism; contacting the biomass with 10 to 100 milliliters (mL) of solvent per gram (g) of the biomass; and evaporating the solvent from the biomass to yield the psychoactive alkaloid extract. In some embodiments, the solvent is selected from 100% methanol, an alcohol:water mixture wherein the alcohol comprises 60% to 99% of the alcohol:water mixture, an alcohol:acid mixture wherein the alcohol comprises 60% to 99% of the alcohol:acid mixture, and acidified water.

A method for generating a psychoactive alkaloid extract from a psychoactive organism, the method comprising: providing a biomass of the psychoactive organism; contacting the biomass with a solvent, wherein the solvent is selected from 100% methanol, an alcohol:water mixture wherein the alcohol comprises 60% to 99% of the alcohol:water mixture, an alcohol:acid mixture wherein the alcohol comprises 60% to 99% of the alcohol:acid mixture, and acidified water; and evaporating the solvent from the biomass to yield the psychoactive alkaloid extract. In some embodiments, the solvent is present at 10 to 100 milliliters (mL) of solvent per gram (g) of the biomass. In some embodiments, the solvent is present at 10 to 60 mL of solvent per gram of the biomass. In some embodiments, the solvent is present at 40 to 60 mL of solvent per gram of the biomass. In some embodiments, the biomass of the psychoactive organism is dried prior to contacting with the solvent. In some embodiments, the biomass of the psychoactive organism is reduced to a particle size of 6 millimeters (mm) to 0.03 mm prior to contacting with the solvent. In some embodiments, the biomass of the psychoactive organism is reduced to a particle size of 1 mm to 0.03 mm prior to contacting with the solvent. In some embodiments, the biomass of the psychoactive organism is reduced to a particle size of at least 0.074 mm prior to contacting with the solvent. In some embodiments, the biomass of the psychoactive organism is contacted with the solvent at 5° C. to 95° C. In some embodiments, the biomass of the psychoactive organism is contacted with the solvent at 20° C. to 70° C. In some embodiments, the biomass of the psychoactive organism is contacted with the solvent at 25° C. In some embodiments, the biomass of the psychoactive organism is contacted with the solvent for 1 to 720 minutes. In some embodiments, the biomass of the psychoactive organism is contacted with the solvent for 20 to 60 minutes. In some embodiments, the biomass of the psychoactive organism is contacted with the solvent for 30 minutes. In some embodiments, following (b), the biomass is filtered through a filter. In some embodiments, the filter comprises a 1 micron (μm) to 10 μm mesh. In some embodiments, following (b), the biomass is contracted with a second solvent. In some embodiments, the second solvent is selected from 100% methanol, an alcohol:water mixture wherein the alcohol comprises 60% to 99% of the alcohol:water mixture, an alcohol:acid mixture wherein the alcohol comprises 60% to 99% of the alcohol:acid mixture, and acidified water. In some embodiments, the second solvent is present at 10 to 100 milliliters (mL) of solvent per gram (g) of the biomass. In some embodiments, the solvent is present at 10 to 60 mL of solvent per gram of the biomass. In some embodiments, the solvent is present at 40 to 60 mL of solvent per gram of the biomass. In some embodiments, the alcohol of the alcohol:water mixture, the alcohol:acid mixture, or both, is a C1-C4 primary aliphatic alcohol. In some embodiments, the C1-C4 primary aliphatic alcohol is ethanol or methanol. In some embodiments, the acid in the alcohol:acid mixture, the acidified water, or both, is acetic acid, adipic acid, ascorbic acid, phosphoric acid, ammonium aluminum sulphate, ammonium citrate dibasic, ammonium citrate monobasic, calcium citrate, calcium fumarate, calcium gluconate, calcium phosphate dibasic, calcium phosphate, hydrochloric acid, sulphuric acid monobasic, calcium phosphate tribasic, citric acid, fumaric acid, gluconic acid, magnesium fumarate, malic acid, phosphoric acid, potassium acid tartrate, potassium citrate, potassium fumarate, sodium citrate, sodium fumarate, sodium gluconate, sodium lactate, sodium potassium hexametaphosphate, sodium potassium tartrate, sodium potassium tripolyphosphate, sodium pyrophosphate tetrabasic, sodium tripolyphosphate, tartaric acid, and any combination therefrom. In some embodiments, the solvent, second solvent, or both is buffered to a pH of either 4 or less, or 10 or greater. In some embodiments, the solvent, second solvent, or both is buffered with ammonium bicarbonate, ammonium carbonate, ammonium hydroxide, calcium acetate, calcium carbonate, calcium chloride, calcium hydroxide, calcium lactate, calcium oxide, calcium phosphate, dibasic, calcium phosphate monobasic, magnesium carbonate, potassium aluminum sulphate, potassium bicarbonate, potassium carbonate, potassium hydroxide, potassium lactate, potassium phosphate, dibasic, potassium pyrophosphate, tetrabasic, potassium phosphate tribasic, potassium tripolyphosphate, sodium acetate, sodium acid pyrophosphate, sodium aluminum phosphate, sodium aluminum sulphate, sodium bicarbonate, sodium bisulphate, sodium carbonate, sodium hexametaphosphate, sodium hydroxide, sodium lactate, sodium phosphate dibasic, sodium phosphate monobasic, sodium phosphate tribasic, and any combination therefrom. In some embodiments, the solvent, second solvent, or both is buffered with acetic acid, adipic acid, ascorbic acid, phosphoric acid, ammonium aluminum sulphate, ammonium citrate dibasic, ammonium citrate monobasic, calcium citrate, calcium fumarate, calcium gluconate, calcium phosphate dibasic, calcium phosphate, hydrochloric acid, sulphuric acid monobasic, calcium phosphate tribasic, citric acid, fumaric acid, gluconic acid, magnesium fumarate, malic acid, phosphoric acid, potassium acid tartrate, potassium citrate, potassium fumarate, sodium citrate, sodium fumarate, sodium gluconate, sodium lactate, sodium potassium hexametaphosphate, sodium potassium tartrate, sodium potassium tripolyphosphate, sodium pyrophosphate tetrabasic, sodium tripolyphosphate, tartaric acid, and any combination therefrom. In some embodiments, the psychoactive alkaloid is psilocybin, psilocin, baeocystin, norbaeocystin, norpsilocin, aeruginascin, bufotenin, bufotenidine, 5-MeO-DMT (5-methoxy-N.Ndimethyltryptamine), N,N-dimethyltryptamine (DMT), 4-hydroxytryptamine, N,N,N-trimethyl-4-hydroxytryptamine ergine (LSA), ergonovine, ergometrine, muscimol, ibotenic acid, lysergic acid hydroxyethylamide (LSH), elymoclavine, ergometrinine, and/or chanoclavine, or any combination selected therefrom. In some embodiments, the solvent has a pH of 10 or greater and the psychoactive alkaloid extract comprises greater than 50% of the phosphorylated psychoactive alkaloid. In some embodiments, the psychoactive alkaloid extract comprises greater than 90% of a phosphorylated psychoactive alkaloid. In some embodiments, the phosphorylated alkaloid is psilocybin, baeocystin, norbaeocystin, aeruginascin, or any combination therefrom. In some embodiments, the solvent has a pH of 4 or less and the psychoactive alkaloid extract comprises greater than 50% of a dephosphorylated psychoactive alkaloid. In some embodiments, the psychoactive alkaloid extract comprises greater than 90% of the dephosphorylated psychoactive alkaloid. In some embodiments, the dephosphorylated alkaloid is psilocin, norpsilocin, 4-hydroxytryptamine, N,N,N-trimethyl-4-hydroxytryptamine, or any combination therefrom. In some embodiments, the psychoactive organism is a plant, animal, fungus, protist, or bacterium. In some embodiments, the psychoactive organism is *Psilocybe cyanescens, Psilocybe cubensis, Amanita muscaria*, or any selection therefrom. In some embodiments, the psychoactive organism is *Anadenanthera colubrina* or *Anadenanthera peregrina*. In some embodiments, the psychoactive organism is *Incilius alvarius*. In some embodiments, the psychoactive organism is yeast.

A process for forming an extract of psychoactive alkaloids from psychoactive organisms comprising the steps of: soaking a biomass of dried, raw psychedelic fungus in a solvent selected from the group consisting of ethanol, a water-ethanol mixture, methanol, and a water-methanol mixture in order to dissolve the psychoactive alkaloids in the solvent; filtering an undissolved portion of the biomass from the solvent; evaporating the solvent sufficiently to remove the solvent completely, leaving a concentrated slurry or a residue that is converted to the concentrated slurry by adding water thereto: and standardizing the concentrated slurry by adding thereto a quantity of carrier measured to achieve a specified purity of extract. In some embodiments, the standardizing comprises: measuring a psychoactive alkaloid content in the concentrated slurry; and using the psychoactive alkaloid content, the specified purity and a volume of the concentrated slurry to determine the quantity of carrier. In some embodiments, the process comprises drying the concentrated slurry to result in the extract, wherein the extract is a powdered extract. In some embodiments, the solvent is a water-ethanol or water-methanol alkaline buffered solution. In some embodiments, the solvent has a pH of 11-12. In some embodiments, the solvent is buffered with sodium hydroxide, the process comprising, between the filtering and evaporating steps, adjusting the solvent to a pH of 4-9 using phosphoric acid. In some embodiments, the solvent is a water-ethanol or water-methanol acid buffered solution. In some embodiments, the solvent has a pH of 1.8-3. In some embodiments, the solvent is buffered with citric acid, the process comprising, between the filtering and evaporating steps, adjusting the solvent to a pH of 4-9 using sodium hydroxide. In some embodiments, the solvent comprises 100% reverse osmosis water. In some embodiments, the soaking is at a temperature of 5-95° C. In some embodiments, the process comprises applying a pressure of 50 kPa-100 MPa to the solvent during the soaking step. In some embodiments, the process comprises agitating the solvent during the soaking step, wherein the soaking step has a duration of 10 minutes to 12 hours. In some embodiments, the psychedelic organism is a plant, animal, fungus, protist, or bacterium. In some embodiments, the fungus comprises *Amanita muscaria, Psilocybe cubensis, Psilocybe cyanescens*, or any combination thereof. In some embodiments, the psychoactive alkaloids comprise psilocybin, psilocin, baeocystin, norbaeocystin, ibotenic acid or any mixture thereof. In some embodiments, the solvent to biomass ratio is in a range from 1 L:1 kg to 50 L:1 kg. In some embodiments, the specified purity is 0.1-10%. In some embodiments, the specified purity is specified as a percentage with a precision of two decimal places. In some embodiments, the carrier comprises ascorbic acid, silicon dioxide, maltodextrin, gum arabic, microcrystalline cellulose, sodium citrate, sodium benzoate, sodium phosphate, rice, rice hulls, or any combination of the foregoing. In some embodiments, the process comprises repeating, using further solvent, the soaking and filtering steps for the filtered biomass; and combining the filtered solvent with the filtered further solvent.

A process for obtaining a purified psychoactive alkaloid solution, the process comprising: extracting a psychoactive alkaloid from a psychoactive alkaloid source to obtain a psychoactive alkaloid extract; contacting the psychoactive alkaloid extract with an adsorbent material to obtain an adsorbed psychoactive alkaloid; and eluting the adsorbed psychoactive alkaloid using a solvent to obtain a purified psychoactive alkaloid solution, wherein the solvent is water, an organic solvent or a combination thereof, under basic, acidic or neutral pH. In some embodiments, the process comprises prior to the treating step, adding an acid or a base to the psychoactive alkaloid extract. In some embodiments, after adding the acid or base, the psychoactive alkaloid extract has a pH ranging from 2.5-4.5 or from 9-10 respectively. In some embodiments, the acid is selected from the group consisting of acetic acid, adipic acid, ascorbic acid, phosphoric acid, ammonium aluminum sulphate, ammonium citrate dibasic, ammonium citrate monobasic, calcium citrate, calcium fumarate, calcium gluconate, calcium phosphate dibasic, calcium phosphate, hydrochloric acid, sulphuric acid monobasic, calcium phosphate tribasic, citric acid, fumaric acid, gluconic acid, magnesium fumarate, malic acid, phosphoric acid, potassium acid tartrate, potassium citrate, potassium fumarate, sodium citrate, sodium fumarate, sodium gluconate, sodium lactate, sodium potassium hexametaphosphate, sodium potassium tartrate, sodium potassium tripolyphosphate, sodium pyrophosphate tetrabasic, sodium tripolyphosphate, tartaric acid, and any combination therefrom. In some embodiments, the base is selected from the group consisting of ammonium bicarbonate, ammonium carbonate, ammonium hydroxide, calcium acetate, calcium carbonate, calcium chloride, calcium hydroxide, calcium lactate, calcium oxide, calcium phosphate, dibasic, calcium phosphate monobasic, magnesium carbonate, potassium aluminum sulphate, potassium bicarbonate, potassium carbonate, potassium hydroxide, potassium lactate, potassium phosphate, dibasic, potassium pyrophosphate, tetrabasic, potassium phosphate tribasic, potassium tripolyphosphate, sodium acetate, sodium acid pyrophosphate, sodium aluminum phosphate, sodium aluminum sulphate, sodium bicarbonate, sodium bisulphate, sodium carbonate, sodium hexametaphosphate, sodium hydroxide, sodium lactate, sodium phosphate dibasic, sodium phosphate monobasic, sodium phosphate tribasic, and any combination therefrom. In some embodiments, the adsorbent material is a gel resin, a macroporous resin, or a combination thereof. In some embodiments, the macroporous resin is a non-ionic macroporous resin, an ion-exchange macroporous resin, or a combination thereof. In some embodiments, the psychoactive alkaloid source comprises psilocybin, psilocin, baeocystin, norbaeocystin, norpsilocin, aeruginascin, bufotenin, bufotenidine, 5-MeO-DMT (5-methoxy-N.N-dimethyltryptamine), N,N-dimethyltryptamine (DMT), ergine (LSA), ergonovine, ergometrine, muscimol, ibotenic acid, lysergic acid hydroxyethylamide (LSH), elymoclavine, ergometrinine, chanoclavine, or any combination therefrom. In some embodiments, the organic solvent is selected from a group consisting of C1-4 primary aliphatic alcohols, C3-4 ketones, and any combination therefrom. In some embodiments, the process comprises further purifying the obtained purified psychoactive alkaloid solution by repeating, with the obtained purified psychoactive alkaloid solution, the treating step with a different adsorbent material and the eluting step with another solvent. In some embodiments, the process comprises evaporating a portion of solvent from the purified psychoactive alkaloid solution to obtain a purified psychoactive alkaloid slurry. In some embodiments, the purified psychoactive alkaloid slurry comprises 5% by weight or more of a psychoactive alkaloid. In some embodiments, the process comprises standardizing the purified psychoactive alkaloid slurry by adding thereto a quantity of excipient measured to provide a specific concentration of psychoactive alkaloid when the purified psychoactive alkaloid slurry is dried; and drying the purified psychoactive alkaloid slurry by evaporating the remaining portion of the solvent to obtain a standardized, purified, powdered psychoactive alkaloid extract having the specific concentration of psychoactive alkaloid. In some embodiments, the psychoactive alkaloid comprises psilocybin, psilocin, baeocystin, norbaeocystin, norpsilocin, aeruginascin, bufotenin, bufotenidine, 5-MeO-DMT (5-methoxy-N.N-dimethyltryptamine), N,N-dimethyltryptamine (DMT), ergine (LSA), ergonovine, ergometrine, muscimol, ibotenic acid, lysergic acid hydroxyethylamide (LSH), elymoclavine, ergometrinine, chanoclavine, or any combination therefrom; and the standardized, purified, powdered psychoactive alkaloid extract has a psychoactive alkaloid concentration ranging from 0.1-99% by weight. In some embodiments, the excipient is selected from the group consisting of silicon dioxide, ascorbic acid, maltodextrin, gum arabic, microcrystalline cellulose, sodium benzoate, sodium phosphate, sodium citrate, rice hulls, rice and any combination therefrom. In some embodiments, the process comprises prior to the treating step: adding an acid to the psychoactive alkaloid extract to bring its pH to 4±0.5; and removing solids from the psychoactive alkaloid extract; and after the treating step and before the eluting step: washing the adsorbent material with purified water; wherein: the adsorbent material is a non-ionic macroporous resin; and the solvent used for the eluting step is a hydro-ethanol solvent. In some embodiments, the hydro-ethanol solvent is 5% ethanol. In some embodiments, the process comprises prior to the treating step: adding an acid to the psychoactive alkaloid extract to bring its pH to 3±0.5; after the treating step and before the eluting step: washing the adsorbent material with 100% ethanol, wherein the adsorbent material is a macroporous strong cation exchange resin in an $H^+$ or an $Na^+$ form; and washing the adsorbent material with purified water; wherein the solvent used for the eluting step is 2% hydrochloric acid and 80% ethanol; and after the eluting step: adding alkali to the purified psychoactive alkaloid solution to bring its pH to 4±0.5; removing solids from the purified psychoactive alkaloid solution; evaporating a portion of the solvent from the purified psychoactive alkaloid solution; removing further solids from the purified psychoactive alkaloid solution; treating the purified psychoactive alkaloid extract with a non-ionic macroporous resin to obtain a second adsorbed psychoactive alkaloid; washing the non-ionic macroporous resin with purified water; and eluting the second adsorbed psychoactive alkaloid from the non-ionic macroporous resin using a hydro-ethanol solvent to obtain a twice purified psychoactive alkaloid solution. In some embodiments, the process comprises prior to the treating step: adding a base to the psychoactive alkaloid extract to bring its pH to 9.5±0.5; after the treating step and before the eluting step: washing the adsorbent material with 100% ethanol, wherein the adsorbent material is a macroporous strong anion exchange resin in an $OH^-$ or a $Cl^-$ form; and washing the adsorbent material with purified water; wherein the solvent used for the eluting step is 2% sodium chloride and 80% ethanol; and after the eluting step: adding acid to the purified psychoactive alkaloid solution to bring its pH to 4±0.5; removing solids from the purified psychoactive alkaloid solution; evaporating a portion of the solvent from the purified psychoactive alkaloid solution; removing further solids from the purified psychoactive alkaloid solution; treating the purified psychoactive alkaloid extract with a non-ionic macroporous resin to obtain a second adsorbed psychoactive alkaloid; washing the non-ionic macroporous resin with purified water; and eluting the second adsorbed psychoactive alkaloid from the non-ionic macroporous resin using a hydro-ethanol solvent to obtain a twice purified psychoactive alkaloid solution. In some embodiments, the psychoactive alkaloid source comprises psychoactive fungus and the extracting step comprises: drying and pulverizing the psychoactive alkaloid source to obtain a dried biomass; heating the dried biomass in a first solvent to obtain a first slurry, and filtering the first slurry to obtain a first filtrate and a first residue; heating the first residue in a second solvent to obtain a second slurry, and filtering the second slurry to obtain a second filtrate and a second residue; and mixing the first filtrate and the second filtrate to obtain the psychoactive alkaloid extract. In some embodiments, the first solvent and the second solvent are selected from a group consisting of a primary aliphatic alcohol, a ketone, purified water, and any combination therefrom; and the heating is carried out at a temperature ranging from 5-95° C. and for a time duration ranging from 10 minutes to 12 hours. In some embodiments, the psychoactive alkaloid source is *Anadenanthera peregrina*, the process comprising: prior to the treating step: adding an acid to the psychoactive alkaloid extract to bring its pH to 4±0.5; and removing solids from the psychoactive alkaloid extract; and after the treating step and before the eluting step: washing the adsorbent material with purified water then with 10% ethanol; wherein: the adsorbent material is a macroporous resin; and the solvent used for the eluting step is 50% ethanol. In some embodiments, the psychoactive alkaloid source comprises a plant, animal, fungus, protist, or bacterium. In some embodiments, the psychoactive alkaloid source comprises *Psilocybe cyanescens, Psilocybe cubensis, Amanita muscaria*, or any selection therefrom. In some embodiments, the psychoactive alkaloid source comprises *Anadenanthera colubrina* or *Anadenanthera peregrina*. In some embodiments, the psychoactive alkaloid source comprises *Incilius alvarius*. In some embodiments, the psychoactive alkaloid source comprises yeast. In some embodiments, the psychoactive alkaloid extract is contacted with the adsorbent material at a flow rate of 1 bed volume per hour (BV/h) to 10 BV/h. In some embodiments, the psychoactive alkaloid extract is contacted with the adsorbent material at a flow rate of 2 bed volumes per hour (BV/h) to 6 BV/h.

A process for obtaining a psychoactive alkaloid extract with a desired amount of a phosphorylated psychoactive alkaloid and a desired amount of a dephosphorylated psychoactive alkaloid, the process comprising: drying and pulverizing a psychoactive alkaloid source to obtain a dried powdered biomass; extracting a psychoactive alkaloid from the dried powdered biomass with an acidified solvent or a basified solvent to obtain a psychoactive alkaloid liquid with a specific pH, wherein the specific pH is lower than 3.5 or greater than 10.5; adjusting the pH of the psychoactive alkaloid liquid to a pH ranging from 3.5-4.5; and evaporating the solvent from the psychoactive alkaloid liquid to obtain the psychoactive alkaloid extract with the desired amount of the phosphorylated psychoactive alkaloid and the desired amount of the dephosphorylated psychoactive alkaloid; wherein: the desired amount of the phosphorylated psychoactive alkaloid is 0-100% by weight of a total phosphorylatable psychoactive alkaloid content in the psychoactive alkaloid extract; and the desired amount of the dephosphorylated psychoactive alkaloid is the remainder of the total phosphorylatable psychoactive alkaloid content in the psychoactive alkaloid extract. In some embodiments, the phosphorylated alkaloid is psilocybin, baeocystin, norbaeocystin, aeruginascin, or any combination therefrom; and the dephosphorylated alkaloid is psilocin, norpsilocin, 4-hydroxytryptamine, N,N,N-trimethyl-4-hydroxytryptamine, or any combination therefrom. In some embodiments, the psychoactive alkaloid source comprises psilocybin, baeocystin, norbaeocystin, aeruginascin, psilocin, norpsilocin, 4-hydroxytryptamine, N,N,N-trimethyl-4-hydroxytryptamine, or any combination therefrom. In some embodiments, the extracting step comprises: mixing the dried powdered biomass with the acidified solvent or the basified solvent to obtain a slurry; and filtrating the slurry to obtain a filtrate residue and the psychoactive alkaloid liquid. In some embodiments, the extracting step comprises further extracting the psychoactive alkaloid by repeating, with the obtained filtrate residue, the extracting step with the same or a different acidified solvent, or the same or a different basified solvent. In some embodiments, after the mixing step the acidified solvent or the basified solvent, the slurry has a pH ranging from 0.5-3.5 or from 10.5-13.5 respectively. In some embodiments, the acidified solvent is a mixture of an acid; and a C1-C4 primary aliphatic alcohol, a C3-C4 ketone, water, or any combination selected therefrom. In some embodiments, the basified solvent is a mixture of a base; and a C1-C4 primary aliphatic alcohol, a C3-C4 ketone, water, or any combination selected therefrom. In some embodiments, the extraction is performed: at a temperature ranging from 5-95° C.; and for a time period ranging from 10-720 minutes. In some embodiments, the extraction is performed at a pressure ranging from 50 kPa-138 MPa (7 to 20,000 psi). In some embodiments, the extraction is performed with a solvent to solid proportion of 1 L:1 kg to 50 L:1 kg, wherein the solid is the dried powdered biomass. In some embodiments, the specific pH is lower than 3.5, and the desired amount of the phosphorylated psychoactive alkaloid is 0% by weight of the total phosphorylatable psychoactive alkaloid content in the psychoactive alkaloid extract, and the desired amount of the dephosphorylated psychoactive alkaloid is 100% by weight of the total phosphorylatable psychoactive alkaloid content in the psychoactive alkaloid extract. In some embodiments, the specific pH is greater than 10.5, and the desired amount of the phosphorylated psychoactive alkaloid is 100% by weight of the total phosphorylatable psychoactive alkaloid content in the psychoactive alkaloid extract, and the desired amount of the dephosphorylated psychoactive alkaloid is 0% by weight of the total phosphorylatable psychoactive alkaloid content in the psychoactive alkaloid extract. In some embodiments, the specific pH is greater than 10.5, and a maximum desired amount of the phosphorylated alkaloid is limited by an amount of the dephosphorylated alkaloid in the psychoactive alkaloid source. In some embodiments, the specific pH is greater than 10.5, and the desired amount of the phosphorylated psychoactive alkaloid is 1-99% by weight of the total phosphorylatable psychoactive alkaloid content in the psychoactive alkaloid extract. In some embodiments, the process comprises pausing the evaporating step when a portion of the solvent has been evaporated from the psychoactive alkaloid liquid to obtain a psychoactive alkaloid slurry; standardizing the psychoactive alkaloid slurry by adding thereto a measured quantity of one or more excipients to obtain a standardized slurry with a specific amount of psychoactive alkaloid content; and continuing the evaporating step by drying the standardized slurry to obtain a psychoactive alkaloid composition comprising the psychoactive alkaloid extract, and one or more excipients; wherein a total psychoactive alkaloid content in the psychoactive alkaloid composition is specified as a result of the standardizing step. In some embodiments, the desired amount of the phosphorylated psychoactive alkaloid is 100% by weight of the total phosphorylatable psychoactive alkaloid content in the psychoactive alkaloid composition, the process comprising: preparing another psychoactive alkaloid composition comprising another psychoactive alkaloid extract of some embodiments disclosed herein wherein the desired amount of the dephosphorylated psychoactive alkaloid is 100% by weight of the total phosphorylatable psychoactive alkaloid content in the other psychoactive alkaloid extract; mixing the psychoactive alkaloid composition and the other psychoactive composition in a measured ratio to obtain a psychoactive alkaloid composition comprising the phosphorylated psychoactive alkaloid of the psychoactive alkaloid composition and the dephosphorylated psychoactive alkaloid of the other psychoactive alkaloid composition in a specific ratio; wherein the specific ratio of phosphorylated psychoactive alkaloid to dephosphorylated psychoactive alkaloid ranges from 1:1000 to 1000:1.

A process for obtaining a psychoactive alkaloid composition with a specific ratio of a phosphorylated psychoactive alkaloid to a dephosphorylated psychoactive alkaloid, the process comprising: extracting a psychoactive alkaloid from a dried powdered biomass with a basified solvent to obtain a psychoactive alkaloid liquid with a pH greater than 10.5, wherein a majority of a total phosphorylatable psychoactive alkaloid content is the phosphorylated alkaloid and a remainder thereof is the dephosphorylated alkaloid; adjusting the pH of the psychoactive alkaloid liquid to a pH ranging from 3.5-4.5; extracting another psychoactive alkaloid from another dried powdered biomass with an acidified solvent to obtain another psychoactive alkaloid liquid with a pH lower than 3.5, wherein all of a total phosphorylatable psychoactive alkaloid is the dephosphorylated alkaloid; adjusting the pH of the other psychoactive alkaloid liquid to a pH ranging from 3.5-4.5; evaporating a portion of the basified solvent from the psychoactive alkaloid liquid and a portion of the acidified solvent from the other psychoactive alkaloid liquid to obtain a psychoactive alkaloid extract slurry and another psychoactive alkaloid extract slurry respectively; mixing measured portions of the psychoactive alkaloid extract slurry and the other psychoactive alkaloid extract slurry to obtain a bulk psychoactive alkaloid extract slurry comprising the phosphorylated psychoactive alkaloid and the dephosphorylated psychoactive alkaloid in the specific ratio; standardizing the bulk psychoactive alkaloid extract slurry by adding thereto a measured quantity of one or more excipients to obtain a standardized bulk slurry; and drying the standardized bulk psychoactive alkaloid slurry to obtain the psychoactive alkaloid composition, wherein the phosphorylated psychoactive alkaloid and the dephosphorylated psychoactive alkaloid are in the specific ratio; wherein the specific ratio of phosphorylated psychoactive alkaloid to dephosphorylated psychoactive alkaloid ranges from 1:1000 to 1000:1. A psychoactive alkaloid composition comprising: a psychoactive alkaloid extract comprising a desired amount of a phosphorylated psychoactive alkaloid and a desired amount of a dephosphorylated psychoactive alkaloid, wherein: the desired amount of the phosphorylated psychoactive alkaloid is 0-100% by weight of a total phosphorylatable psychoactive alkaloid content in the psychoactive alkaloid extract, and the desired amount of the dephosphorylated psychoactive alkaloid is the remainder of the total phosphorylatable psychoactive alkaloid content in the psychoactive alkaloid extract; and one or more excipients. In some embodiments, the composition is in powder form. In some embodiments, the desired amount of the phosphorylated psychoactive alkaloid is 0% by weight of the total phosphorylatable psychoactive alkaloid content in the psychoactive alkaloid extract, and the desired amount of the dephosphorylated psychoactive alkaloid is 100% by weight of the total phosphorylatable psychoactive alkaloid content in the psychoactive alkaloid extract. In some embodiments, the desired amount of the phosphorylated psychoactive alkaloid is 100% by weight of the total phosphorylatable psychoactive alkaloid content in the psychoactive alkaloid extract, and the desired amount of the dephosphorylated psychoactive alkaloid is 0% by weight of the total phosphorylatable psychoactive alkaloid content in the psychoactive alkaloid extract. In some embodiments, the phosphorylated alkaloid is psilocybin, baeocystin, norbaeocystin, aeruginascin, or any combination selected therefrom; and the dephosphorylated alkaloid is psilocin, norpsilocin, 4-hydroxytryptamine, N,N,N-trimethyl-4-hydroxytryptamine, or any combination selected therefrom.

A psychoactive alkaloid composition with a specific ratio of a phosphorylated psychoactive alkaloid and a dephosphorylated psychoactive alkaloid, the composition comprising: a psychoactive alkaloid extract having a total phosphorylatable psychoactive alkaloid content of 100% of a phosphorylated psychoactive alkaloid; another psychoactive alkaloid extract having a total phosphorylatable psychoactive alkaloid content of 100% of a dephosphorylated psychoactive alkaloid; and one or more excipients; wherein the psychoactive alkaloid extract and the other psychoactive alkaloid extract are present in a proportion such that the specific ratio of phosphorylated psychoactive alkaloid to phosphorylated psychoactive alkaloid ranges from 1:1000 to 1000:1.

The present invention is directed to an extraction process of psychoactive compounds from psychedelic fungus, for example, the *Psilocybe cubensis* species of psychedelic mushroom. The principal psychoactive compounds in *Psilocybe cubensis* include psilocybin and psilocin. In particular, the extraction process of psychoactive compounds involves drying fresh *Psilocybe cubensis*, followed by grinding, extraction with a solvent in one or more steps, one or more steps of filtration, optional adjustment of the pH if the solvent is acidic (acid/water/alcohol) or alkaline (base/water/alcohol), evaporation of the solvent, and standardization. Optionally, the process includes drying to result in a final powdered psilocybin mushroom extract.

The invention described here consists of a never-before-described method to produce high-efficiency, standardized preparations of the target compounds all while using acceptable solvent systems.

The drying of fresh fungal biomass done in a fashion that does not greatly reduce the natural psilocybin, psilocin, or baeocystin concentrations.

The temperature of extraction is between 5 and 95° C. and uses a 1 to 50:1 solvent:solid ratio of extraction. Time of extraction from 10 to 720 minutes. Pressure may be applied, ranging from 50 kPa to 137 MPa (0.5 atm to 20,000 psi). Multiple species of psilocybe mushrooms may be used.

Disclosed herein is a process for forming an extract of psychoactive alkaloids from psychoactive organisms such as psychedelic fungus comprising the steps of: soaking a biomass of dried, raw psychedelic fungus in a solvent selected from the group consisting of water-ethanol and water-methanol mixture in order to dissolve the psychoactive alkaloids in the solvent; filtering an undissolved portion of the biomass from the solvent; evaporating the solvent to remove the methanol or ethanol completely, leaving a concentrated slurry or a residue that is converted to the concentrated slurry by adding water thereto: and standardizing the concentrated slurry by adding thereto a quantity of carrier measured to achieve a specified purity of extract. In some embodiments the solvent is water-methanol. In some embodiments the solvent is water-methanol, the concentration being a trace to about 100%. In some embodiments the solvent is water-methanol, about 10% to about 90%. In some embodiments the solvent is water-methanol, about 20% to about 80%. In some embodiments the solvent is water-methanol, about 30% to about 70%. In some embodiments the solvent is water-methanol, about 40% to about 60%. In some embodiments the solvent is water-methanol, about 50% to about 50%. In some embodiments the solvent is water-methanol, about 60% to about 40%. In some embodiments the solvent is water-methanol, about 70% to about 30%. In some embodiments the solvent is water-methanol, about 80% to about 20%. In some embodiments the solvent is water-methanol, about 90% to about 10%. In some embodiments the solvent is water-methanol, about 100% to a trace. In some embodiments the solvent is water-ethanol. In some embodiments the solvent is water-ethanol, the concentration being a trace to about 100%. In some embodiments the solvent is water-ethanol, about 10% to about 90%. In some embodiments the solvent is water-ethanol, about 20% to about 80%. In some embodiments the solvent is water-ethanol, about 30% to about 70%. In some embodiments the solvent is water-ethanol, about 40% to about 60%. In some embodiments the solvent is water-ethanol, about 50% to about 50%. In some embodiments the solvent is water-ethanol, about 60% to about 40%. In some embodiments the solvent is water-ethanol, about 70% to about 30%. In some embodiments the solvent is water-ethanol, about 80% to about 20%. In some embodiments the solvent is water-ethanol, about 90% to about 10%. In some embodiments the solvent is water-ethanol, about 100% to a trace. In some embodiments, the standardizing comprises measuring a psychoactive alkaloid content in the concentrated slurry, and using the psychoactive alkaloid content, the specified purity and a volume of the concentrated slurry to determine the quantity of carrier.

The present invention relates to a process for obtaining a purified psychoactive alkaloid solution from a psychoactive alkaloid source. The purification process of the present invention allows for producing standardized preparations of psychoactive alkaloids, all while using acceptable solvent and processing systems.

Standardization is a method that can be used to solve the problem of inconsistency in the finished product. However, when dealing with a low-potency feedstock material, it may be difficult to standardize the active ingredients to a high percentage content and achieve the desired therapeutic effects. We therefore need to concentrate the active ingredients beforehand, using a purification process. It may also be desirable to concentrate the active ingredients to a high enough degree that the resulting volume of the final product is limited for a specific application, such as to fit into a standard size two-piece capsule.

A psychoactive alkaloid source is used to provide a psychoactive alkaloid extract. The source may be a species containing psychedelic alkaloids or a prior extract therefrom. Psychoactive alkaloids in the extract are adsorbed onto a resin or other adsorbent material, from which they are then eluted to provide a purified psychoactive alkaloid solution. The process may be repeated with different resins, different pH values, and different elution solvents. Solids present in the extract may be removed at various stages by filtering or centrifuging.

The purification process of the present invention allows for purifying relatively low-potency feedstocks to result in a purified psychoactive alkaloid solution that may have a relatively high concentration of psychoactive alkaloid. Depending on the embodiment, the process may be a purification process that enriches the psychoactive alkaloid content of the final formulation compared to the alkaloid content in the raw materials. Purification may also be the removal of some of the impurities, irrespective of the final alkaloid content. The process of purification in the present invention allows use of the lowest-grade raw materials to obtain a product capable of standardization to a desired specification.

The purification process of the present invention may be, depending on the embodiment, a relatively simple and robust psychoactive alkaloid purification process, which is suitable for the production of food-grade, nutraceutical-grade, or pharmaceutical-grade standardized extracts, especially of psilocybin, psilocin, baeocystin, norbaeocystin, norpsilocin, aeruginascin, bufotenin, bufotenidine, 5-MeO-DMT (5-methoxy-N.N-dimethyltryptamine), N,N-dimethyltryptamine (DMT), ergine (LSA), ergonovine, ergometrine, muscimol, ibotenic acid, lysergic acid hydroxyethylamide (LSH), elymoclavine, ergometrinine, and/or chanoclavine.

The present invention also relates to a standardization process for preparation of standardized extracts of psychoactive alkaloids. The standardization process of the present invention allows for standardizing the purified psychoactive alkaloid solution to result in a purified psychoactive alkaloid extract with a specific concentration of psychoactive alkaloids. The standardization process of the present invention may also be a simple and cost-efficient process.

The standardized psychoactive alkaloid extracts of the present invention can be used in, for example, medical research on the use of psychedelic substances as treatments for addiction, post-traumatic stress disorder, depression, cluster headaches, and other illnesses. They may also be used in traditional entheogenic practices or consumed recreationally where such activity is permitted by law.

Disclosed herein is a process for obtaining a purified psychoactive alkaloid solution, the process comprising: extracting a psychoactive alkaloid from a psychoactive alkaloid source to obtain a psychoactive alkaloid extract; treating the psychoactive alkaloid extract with an adsorbent material to obtain an adsorbed psychoactive alkaloid; and eluting the adsorbed psychoactive alkaloid using a solvent to obtain a purified psychoactive alkaloid solution, wherein the solvent is water, an organic solvent or a combination thereof, under basic, acidic or neutral pH.

In some embodiments, the process includes: evaporating a portion of solvent from the purified psychoactive alkaloid solution to obtain a concentrated slurry; standardizing the concentrated slurry by adding thereto a quantity of excipient measured to provide a specific concentration of psychoactive alkaloid when the concentrated slurry is dried; and drying the slurry by evaporating the remaining portion of the solvent to obtain a standardized, purified, powdered psychoactive alkaloid extract having the specific concentration of psychoactive alkaloid.

An aim of the invention is to standardize the amount of psychoactive alkaloid present in the composition. Depending on the embodiment and the specific types of excipient added, a secondary, optional aspect of the invention is the provision of a psychoactive alkaloid extract in the form of a dry, flowable and shelf-stable powder. The powder may be used as a dietary supplement or medicine and can be added to various edible products, tablets, or capsules, or it may be used for medical research, including the study of the treatment of mental illnesses.

By increasing the active alkaloid concentration through extraction and then titrating back to a lower, standardized alkaloid concentration, the product achieves consistency in bioactive content from lot to lot. By the addition of specific types of excipient, flowability and stability may also be improved in the composition, as compared to the extract.

A useful formulation needs to contain a minimum amount of the active ingredient and also be of an acceptable total size. For example, a psilocybin dose might be 25 mg. If this is required in a single capsule and the powder has a concentration of the active ingredient of only 1%, then 2500 mg of powder would be needed. This would be too much for a single capsule. However, if the extract can be concentrated to approx. 15%, then there is room to add an excipient to get it down to say, a repeatable 10%, which now means that only 250 mg of powder is needed in the capsule, which is an acceptable size.

While the concentration of psychoactive alkaloid in the composition may, in some embodiments, be lower than that found in some of the source raw material (mushrooms or seeds for example), it is a known concentration, which can be stable from batch to batch, eliminating the variability found in the natural sources. This allows for control and standardization of the dose, even if it is lower than some of the raw materials themselves.

Disclosed herein is a psychoactive alkaloid composition consisting essentially of, by weight: 0.1-99.9% of a psychoactive alkaloid extract; one or more preservatives up to 10%, a flow agent up to 2%, or both the one or more preservatives up to 10% and the flow agent up to 2%; and 0-94% of a carrier.

The inventors have realized that there are occasions where it would be beneficial to control, either by halting or promoting, the conversion of phosphorylated alkaloids such as psilocybin during extraction and any subsequent purification process. For example, there may be occasions where extracts with phosphorylated psychoactive alkaloids as the only or majority of the total psychoactive alkaloid in the extract are required. Likewise, there may be occasions where extracts with dephosphorylated psychoactive alkaloids as the only or majority of the total psychoactive alkaloid in the extract are required.

For example, the alkaloid in the psychoactive extract may be entirely psilocin, resulting from promotion of the conversion, or all or mostly psilocybin, from the halting or inhibition of the conversion. There will likely, but not necessarily, be some psilocin present in the process where the conversion is halted, as the harvesting of the mushrooms can often cause unavoidable conversion into psilocin.

Controlling the promotion or inhibition of dephosphorylation of the aforementioned alkaloids to result in a psychoactive alkaloid extract with a specific desired content of both phosphorylated and dephosphorylated psychoactive alkaloid has not been seen in the industry or academia to date. Likewise, compositions resulting from such control have not yet been seen.

Thus, there is a need in the art of a process for controlling the dephosphorylation of the aforementioned alkaloids to result in a psychoactive alkaloid extract with specific desired amounts of phosphorylated and dephosphorylated psychoactive alkaloid. Also required in the art is a psychoactive alkaloid composition having an accurate psychoactive alkaloid content, with specific desired amounts of phosphorylated and dephosphorylated psychoactive alkaloid.

Disclosed herein is a process for obtaining a psychoactive alkaloid extract with a desired amount of a phosphorylated psychoactive alkaloid and a desired amount of a dephosphorylated psychoactive alkaloid, the process comprising: drying and pulverizing a psychoactive alkaloid source to obtain a dried powdered biomass; extracting a psychoactive alkaloid from the dried powdered biomass with an acidified solvent or a basified solvent to obtain a psychoactive alkaloid liquid with a specific pH, wherein the specific pH is lower than 3.5 or greater than 10.5; adjusting the pH of the psychoactive alkaloid liquid to a pH ranging from 3.5-4.5; and evaporating the solvent from the psychoactive alkaloid liquid to obtain the psychoactive alkaloid extract with the desired amount of the phosphorylated psychoactive alkaloid and the desired amount of the dephosphorylated psychoactive alkaloid; wherein: the desired amount of the phosphorylated psychoactive alkaloid is 0-100% by weight of a total phosphorylatable psychoactive alkaloid content in the psychoactive alkaloid extract; and the desired amount of the dephosphorylated psychoactive alkaloid is the remainder of the total phosphorylatable psychoactive alkaloid content in the psychoactive alkaloid extract.

Also disclosed is a process for obtaining a psychoactive alkaloid composition with a specific ratio of a phosphorylated psychoactive alkaloid to a dephosphorylated psychoactive alkaloid, the process comprising: extracting a psychoactive alkaloid from a dried powdered biomass with a basified solvent to obtain a psychoactive alkaloid liquid with a pH greater than 10.5, wherein a majority of a total phosphorylatable psychoactive alkaloid content is the phosphorylated alkaloid and a remainder thereof is the dephosphorylated alkaloid; adjusting the pH of the psychoactive alkaloid liquid to a pH ranging from 3.5-4.5; extracting another psychoactive alkaloid from another dried powdered biomass with an acidified solvent to obtain another psychoactive alkaloid liquid with a pH lower than 3.5, wherein all of a total phosphorylatable psychoactive alkaloid is the dephosphorylated alkaloid; adjusting the pH of the other psychoactive alkaloid liquid to a pH ranging from 3.5-4.5; evaporating a portion of the basified solvent from the psychoactive alkaloid liquid and a portion of the acidified solvent from the other psychoactive alkaloid liquid to obtain a psychoactive alkaloid extract slurry and another psychoactive alkaloid extract slurry respectively; mixing measured portions of the psychoactive alkaloid extract slurry and the other psychoactive alkaloid extract slurry to obtain a bulk psychoactive alkaloid extract slurry comprising the phosphorylated psychoactive alkaloid and the dephosphorylated psychoactive alkaloid in the specific ratio; standardizing the bulk psychoactive alkaloid extract slurry by adding thereto a measured quantity of one or more excipients to obtain a standardized bulk slurry; and drying the standardized bulk psychoactive alkaloid slurry to obtain the psychoactive alkaloid composition, wherein the phosphorylated psychoactive alkaloid and the dephosphorylated psychoactive alkaloid are in the specific ratio; wherein the specific ratio of phosphorylated psychoactive alkaloid to dephosphorylated psychoactive alkaloid ranges from 1:1000 to 1000:1.

Further disclosed is a psychoactive alkaloid composition comprising: a psychoactive alkaloid extract comprising a desired amount of a phosphorylated psychoactive alkaloid and a desired amount of a dephosphorylated psychoactive alkaloid, wherein: the desired amount of the phosphorylated psychoactive alkaloid is 0-100% by weight of a total phosphorylatable psychoactive alkaloid content in the psychoactive alkaloid extract, and the desired amount of the dephosphorylated psychoactive alkaloid is the remainder of the total phosphorylatable psychoactive alkaloid content in the psychoactive alkaloid extract; and one or more excipients.

Still further disclosed is a psychoactive alkaloid composition with a specific ratio of a phosphorylated psychoactive alkaloid and a dephosphorylated psychoactive alkaloid, the composition comprising: a psychoactive alkaloid extract having a total phosphorylatable psychoactive alkaloid content of 100% of a phosphorylated psychoactive alkaloid; another psychoactive alkaloid extract having a total phosphorylatable psychoactive alkaloid content of 100% of a dephosphorylated psychoactive alkaloid; and one or more excipients; wherein the psychoactive alkaloid extract and the other psychoactive alkaloid extract are present in a proportion such that the specific ratio of phosphorylated psychoactive alkaloid to phosphorylated psychoactive alkaloid ranges from 1:1000 to 1000:1.

A method for generating a psychoactive alkaloid extract comprising 0.1% to 99% by weight of a psychoactive alkaloid from a psychoactive organism, the method comprising: providing a biomass of the psychoactive organism; contacting the biomass with 10 to 100 milliliters (mL) of solvent per gram (g) of the biomass; and evaporating the solvent from the biomass to yield the psychoactive alkaloid extract comprising 0.1% to 99% by weight of the psychoactive alkaloid. In some embodiments, following (b), the biomass is contacted with a second solvent. In some embodiments, the solvent is selected from 100% methanol, an alcohol:water mixture wherein the alcohol comprises 60% to 99% of the alcohol:water mixture, an alcohol:acid mixture wherein the alcohol comprises 60% to 99% of the alcohol:acid mixture, an alcohol:base mixture wherein the alcohol comprises 60% to 99% of the alcohol:base mixture, an alcohol:water mixture wherein the alcohol comprises 70% to 80% of the alcohol:water mixture, an alcohol:acid mixture wherein the alcohol comprises 70% to 80% of the alcohol:acid mixture, an alcohol:base mixture wherein the alcohol comprises 70% to 80% of the alcohol:base mixture, acidified water, and basified water. In some embodiments, the alcohol of the alcohol:water mixture, the alcohol:acid mixture, or alcohol:base mixture, is a C1-C4 primary aliphatic alcohol. In some embodiments, the C1-C4 primary aliphatic alcohol is ethanol or methanol. In some embodiments, the solvent is buffered to a pH of either 4 or less, or 9 or greater. In some embodiments, the solvent has a pH of 10 or greater and the psychoactive alkaloid extract comprises greater than 50% of a phosphorylated psychoactive alkaloid. In some embodiments, the solvent has a pH of 4 or less and the psychoactive alkaloid extract comprises greater than 50% of a dephosphorylated psychoactive alkaloid. In some embodiments, the solvent is buffered with ammonium bicarbonate, ammonium carbonate, ammonium hydroxide, calcium acetate, calcium carbonate, calcium chloride, calcium hydroxide, calcium lactate, calcium oxide, calcium phosphate, dibasic, calcium phosphate monobasic, magnesium carbonate, potassium aluminum sulphate, potassium bicarbonate, potassium carbonate, potassium hydroxide, potassium lactate, potassium phosphate, dibasic, potassium pyrophosphate, tetrabasic, potassium phosphate tribasic, potassium tripolyphosphate, sodium acetate, sodium acid pyrophosphate, sodium aluminum phosphate, sodium aluminum sulphate, sodium bicarbonate, sodium bisulphate, sodium carbonate, sodium hexametaphosphate, sodium hydroxide, sodium lactate, sodium phosphate dibasic, sodium phosphate monobasic, sodium phosphate tribasic, and any combination thereof. In some embodiments, the solvent is buffered with acetic acid, adipic acid, ascorbic acid, phosphoric acid, ammonium aluminum sulphate, ammonium citrate dibasic, ammonium citrate monobasic, calcium citrate, calcium fumarate, calcium gluconate, calcium phosphate dibasic, calcium phosphate, hydrochloric acid, sulphuric acid monobasic, calcium phosphate tribasic, citric acid, fumaric acid, gluconic acid, magnesium fumarate, malic acid, phosphoric acid, potassium acid tartrate, potassium citrate, potassium fumarate, sodium citrate, sodium fumarate, sodium gluconate, sodium lactate, sodium potassium hexametaphosphate, sodium potassium tartrate, sodium potassium tripolyphosphate, sodium pyrophosphate tetrabasic, sodium tripolyphosphate, tartaric acid, and any combination thereof. In some embodiments, the psychoactive organism is Psilocybe cyanescens, Psilocybe cubensis, Amanita muscaria, or any selection thereof. In some embodiments, the psychoactive alkaloid is psilocybin, psilocin, baeocystin, norbaeocystin, norpsilocin, aeruginascin, bufotenin, bufotenidine, 5-MeO-DMT (5-methoxy-N, N-dimethyltryptamine), N,N-dimethyltryptamine (DMT), 4-hydroxytryptamine, N,N,N-trimethyl-4-hydroxytryptamine ergine (LSA), ergonovine, ergometrine, muscimol, ibotenic acid, lysergic acid hydroxyethylamide (LSH), elymoclavine, ergometrinine, and/or chanoclavine, or any combination thereof.

A method for generating a phosphorylated psychoactive alkaloid extract comprising 0.1% to 99% by weight of a psychoactive alkaloid from a psychoactive organism, the method comprising: providing a biomass of the psychoactive organism; contacting the biomass with 10 to 100 milliliters (mL) of solvent per gram (g) of the biomass wherein the solvent has a pH of 9 or greater and the psychoactive alkaloid comprises greater than 50% of a phosphorylated psychoactive alkaloid; and evaporating the solvent from the biomass to yield the phosphorylated psychoactive alkaloid extract comprising 0.1% to 99% by weight of the psychoactive alkaloid. In some embodiments, following (b), the biomass is contacted with a second solvent. In some embodiments, the solvent is selected from 100% methanol, an alcohol:water mixture wherein the alcohol comprises 60% to 99% of the alcohol:water mixture, an alcohol:acid mixture wherein the alcohol comprises 60% to 99% of the alcohol:acid mixture, an alcohol:base mixture wherein the alcohol comprises 60% to 99% of the alcohol:base mixture, an alcohol:water mixture wherein the alcohol comprises 70% to 80% of the alcohol:water mixture, an alcohol:acid mixture wherein the alcohol comprises 70% to 80% of the alcohol:acid mixture, an alcohol:base mixture wherein the alcohol comprises 70% to 80% of the alcohol:base mixture, acidified water, and basified water. In some embodiments, the alcohol of the alcohol:water mixture, the alcohol:acid mixture, or the alcohol:base mixture, is a C1-C4 primary aliphatic alcohol. In some embodiments, the C1-C4 primary aliphatic alcohol is ethanol or methanol. In some embodiments, the solvent is buffered with ammonium bicarbonate, ammonium carbonate, ammonium hydroxide, calcium acetate, calcium carbonate, calcium chloride, calcium hydroxide, calcium lactate, calcium oxide, calcium phosphate, dibasic, calcium phosphate monobasic, magnesium carbonate, potassium aluminum sulphate, potassium bicarbonate, potassium carbonate, potassium hydroxide, potassium lactate, potassium phosphate, dibasic, potassium pyrophosphate, tetrabasic, potassium phosphate tribasic, potassium tripolyphosphate, sodium acetate, sodium acid pyrophosphate, sodium aluminum phosphate, sodium aluminum sulphate, sodium bicarbonate, sodium bisulphate, sodium carbonate, sodium hexametaphosphate, sodium hydroxide, sodium lactate, sodium phosphate dibasic, sodium phosphate monobasic, sodium phosphate tribasic, and any combination thereof. In some embodiments, the solvent is buffered with acetic acid, adipic acid, ascorbic acid, phosphoric acid, ammonium aluminum sulphate, ammonium citrate dibasic, ammonium citrate monobasic, calcium citrate, calcium fumarate, calcium gluconate, calcium phosphate dibasic, calcium phosphate, hydrochloric acid, sulphuric acid monobasic, calcium phosphate tribasic, citric acid, fumaric acid, gluconic acid, magnesium fumarate, malic acid, phosphoric acid, potassium acid tartrate, potassium citrate, potassium fumarate, sodium citrate, sodium fumarate, sodium gluconate, sodium lactate, sodium potassium hexametaphosphate, sodium potassium tartrate, sodium potassium tripolyphosphate, sodium pyrophosphate tetrabasic, sodium tripolyphosphate, tartaric acid, and any combination thereof. In some embodiments, the psychoactive organism is *Psilocybe cyanescens*, *Psilocybe cubensis*, *Amanita muscaria*, or any selection thereof. In some embodiments, the phosphorylated psychoactive alkaloid is psilocybin, baeocystin, norbaeocystin, aeruginascin, or any combination thereof.

A method for generating a dephosphorylated psychoactive alkaloid extract comprising 0.1% to 99% by weight of a psychoactive alkaloid from a psychoactive organism, the method comprising: providing a biomass of the psychoactive organism; contacting the biomass with 10 to 100 milliliters (mL) of solvent per gram (g) of the biomass wherein the solvent has a pH of 4 or less and the psychoactive alkaloid comprises greater than 50% of a dephosphorylated psychoactive alkaloid; and evaporating the solvent from the biomass to yield the dephosphorylated psychoactive alkaloid extract comprising 0.1% to 99% by weight of the psychoactive alkaloid. In some embodiments, following (b), the biomass is contacted with a second solvent. In some embodiments, the solvent is selected from 100% methanol, an alcohol:water mixture wherein the alcohol comprises 60% to 99% of the alcohol:water mixture, an alcohol:acid mixture wherein the alcohol comprises 60% to 99% of the alcohol:acid mixture, an alcohol:base mixture wherein the alcohol comprises 60% to 99% of the alcohol:base mixture, an alcohol:water mixture wherein the alcohol comprises 70% to 80% of the alcohol:water mixture, an alcohol:acid mixture wherein the alcohol comprises 70% to 80% of the alcohol:acid mixture, an alcohol:base mixture wherein the alcohol comprises 70% to 80% of the alcohol:base mixture, acidified water, and basified water. In some embodiments, the alcohol of the alcohol:water mixture, the alcohol:acid mixture, or the alcohol:base mixture, is a C1-C4 primary aliphatic alcohol. In some embodiments, the C1-C4 primary aliphatic alcohol is ethanol or methanol. In some embodiments, the solvent is buffered with ammonium bicarbonate, ammonium carbonate, ammonium hydroxide, calcium acetate, calcium carbonate, calcium chloride, calcium hydroxide, calcium lactate, calcium oxide, calcium phosphate, dibasic, calcium phosphate monobasic, magnesium carbonate, potassium aluminum sulphate, potassium bicarbonate, potassium carbonate, potassium hydroxide, potassium lactate, potassium phosphate, dibasic, potassium pyrophosphate, tetrabasic, potassium phosphate tribasic, potassium tripolyphosphate, sodium acetate, sodium acid pyrophosphate, sodium aluminum phosphate, sodium aluminum sulphate, sodium bicarbonate, sodium bisulphate, sodium carbonate, sodium hexametaphosphate, sodium hydroxide, sodium lactate, sodium phosphate dibasic, sodium phosphate monobasic, sodium phosphate tribasic, and any combination thereof. In some embodiments, the solvent is buffered with acetic acid, adipic acid, ascorbic acid, phosphoric acid, ammonium aluminum sulphate, ammonium citrate dibasic, ammonium citrate monobasic, calcium citrate, calcium fumarate, calcium gluconate, calcium phosphate dibasic, calcium phosphate, hydrochloric acid, sulphuric acid monobasic, calcium phosphate tribasic, citric acid, fumaric acid, gluconic acid, magnesium fumarate, malic acid, phosphoric acid, potassium acid tartrate, potassium citrate, potassium fumarate, sodium citrate, sodium fumarate, sodium gluconate, sodium lactate, sodium potassium hexametaphosphate, sodium potassium tartrate, sodium potassium tripolyphosphate, sodium pyrophosphate tetrabasic, sodium tripolyphosphate, tartaric acid, and any combination thereof. In some embodiments, the psychoactive organism is *Psilocybe cyanescens*, *Psilocybe cubensis*, *Amanita muscaria*, or any selection thereof. In some embodiments, the dephosphorylated psychoactive alkaloid is psilocin, norpsilocin, 4-hydroxytryptamine, N,N,N-trimethyl-4-hydroxytryptamine, or any combination thereof.

This summary does not necessarily describe all features of the invention, and different embodiments thereof may provide at least one but not necessarily all of the benefits described herein.

BRIEF DESCRIPTION OF DRAWINGS

The following drawings illustrate embodiments of the invention, which should not be construed as restricting the scope of the invention in any way.

DETAILED DESCRIPTION

Figure 1:
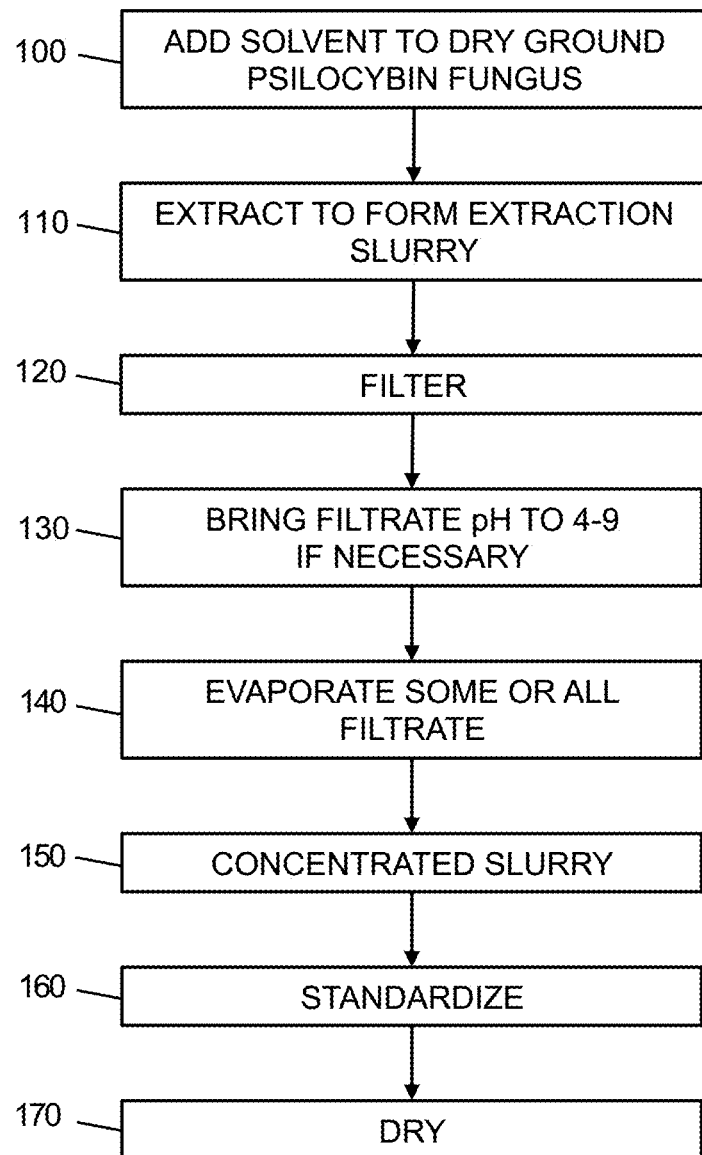
FIG. 1 is a high-level flowchart showing the key steps of a process for extracting psychoactive alkaloids from psychedelic fungus, according to an embodiment of the present invention.

Naturally-occurring psychoactive alkaloid comprising species have inconsistent and often low contents of active psychoactive alkaloid (e.g., 0.1-1% dry wt). Considering fresh weight, this would mean a further 20× reduction in content due to the large moisture content of, for example, fresh mushrooms. The content of psychoactive alkaloid in natural sources depends on various factors such as the type of source, harvesting season, and type of extraction process, to name a few. Thus, the lack of compositions having a specific desired psychoactive alkaloid content with no or minimal variability between different batches is a major issue.

Maintaining physical and chemical stability is another challenge with psychoactive alkaloid compositions. Usually a psychoactive alkaloid extract is in the form of a sticky tar, which would be difficult to handle and formulate into standardized compositions with specified amounts of ingredients. Extracts are not usually amenable to processing due to poor flowability. Extracts themselves are often not amenable to drying because many of the components that are pulled out of a plant or fungus with a lower alcohol solvent are not "dry" at room temperature (reduced sugars, oils, and waxes, for example). These same compounds even in low concentration can cause the product to be hygroscopic and become clumpy, which makes encapsulation impossible, and makes tabulation difficult because the powder will not "flow" in the equipment.

Thus, exposure to moisture causes psychoactive alkaloid extracts to absorb moisture to form clumps and become susceptible to microbial growth. Further, the alkaloids in these extracts can degrade, usually because of oxidation.

Psychoactive alkaloids present in natural sources can be broadly divided into two categories, which are phosphorylated psychoactive alkaloids and dephosphorylated psychoactive alkaloids, although other non-phosphorylatable psychoactive alkaloids may also be present.

Phosphorylated psychoactive alkaloids are phosphoric acid esters of dephosphorylated psychoactive alkaloids. For example, psilocybin is a phosphoric acid ester of psilocin, at the 4th position. Phosphorylated psychoactive alkaloids are biosynthesized in natural sources. Dephosphorylated psychoactive alkaloids are the bioactive forms that are converted from phosphorylated alkaloids, through phosphatase action or chemical hydrolysis, and released when the natural source is damaged, harvested, or eaten. Because of this phenomenon, phosphorylated psychoactive alkaloids are often either partially or entirely converted to dephosphorylated psychoactive alkaloids during the alkaloid extraction process, which involves harvesting as a necessary prior step.

Although the dephosphorylated psychoactive alkaloids are the bioactive form of their counterpart phosphorylated psychoactive alkaloids, dephosphorylated psychoactive alkaloids are easily degraded into non-bioactive compounds in the presence of light, heat, and oxygen. For example, oxidation of psilocin, the dephosphorylated counterpart to psilocybin, a phosphorylated alkaloid produced by biological synthesis in mushrooms, begins rapidly when exposed to air, especially in solution, and heat increases the oxidation rate. From our own data, the oxidation of psilocin in a moist and/or high light environment begins immediately, leading to about 10% decay within 30 minutes, 25% after 5 hours, and 40-60% at 20 hours when shielded from light. Due to this instability of the dephosphorylated psychoactive alkaloids, the bioactivity of the psychoactive alkaloid extracts may also be unstable over time.

Extracts or compositions with an active ingredient made from natural sources generally have increased consumer acceptance and lower cost of production compared to synthetic compositions. There may be potential benefits of multiple natural compounds working synergistically, colloquially known as the "entourage" or "halo" effect. However, the availability of psychoactive alkaloid compositions with a desired specific psychoactive alkaloid content is a major challenge faced by researchers. The variability in the content of the psychoactive alkaloids extracted from their natural sources is a hurdle in trying to avoid variability in the psychoactive alkaloid concentration in extracted compositions. It is even more challenging to produce consistent formulations when the concentration of active ingredients being extracted is typically very low in the natural source. Maintaining physical and chemical stability is also an issue with these compositions. Extracts or compositions containing psychoactive alkaloids are often not amenable to drying, processing (due to poor flowability), or packaging methods such as tabulation or encapsulation.

This application relates to the extraction of active ingredients from fungus and processes of purifying them. More specifically, it relates to extracting psychoactive compounds from fungus and forming an extract of specific purities appropriate for uses of the psychoactive compounds in therapeutic formulations. More specifically, the present invention relates to a purification process for obtaining a purified psychoactive alkaloid solution from an extract. Further, the present invention also relates to a process of forming a standardized extract from the purified psychoactive alkaloid solution, wherein the extract has a desired, specific concentration of psychoactive alkaloids.

This application relates to a process of obtaining psychoactive alkaloid extracts. More specifically, the present invention relates to controlling dephosphorylation during extraction. Further, the present invention relates to psychoactive alkaloid compositions with controlled dephosphorylation.

This application relates to a composition. Particularly, this application relates to psychoactive alkaloid compositions comprising a natural extract.

A. Glossary

To facilitate the understanding of this invention, a number of terms are defined below. Terms used herein have meanings as commonly understood by a person of ordinary skill in the areas relevant to the present invention, unless otherwise defined. Terms such as "a", "an" and "the" are not intended to refer to only a singular entity but include the general class of which a specific example may be used for illustration. The terminology herein is used to describe specific embodiments of the invention, but its usage does not delimit the invention, except as outlined in the claims.

Psilocybin fungi or psilocybin mushrooms—these are a group of fungi that contain at least one psychoactive alkaloid, and generally contain psilocybin and psilocin. They may also contain other psychoactive alkaloids such as baeocystin, norbaeocystin, ibotenic acid and norpsilocin. The genera of these mushrooms include *Copelandia, Gymnopilus, Inocybe, Panaeolus, Pholiotina, Pluteus, Amanita*, and *Psilocybe*.

*Psilocybe* mushrooms—these form a genus of gilled mushrooms in the family Hymenogastraceae. Most species contain the psychedelic alkaloids psilocybin, psilocin, and baeocystin.

Psilocybin—this is a psychedelic prodrug produced by numerous species of mushrooms, collectively known as psilocybin mushrooms. Psilocybin is converted by the body to psilocin, which has mind-altering effects such as euphoria and hallucinations, but can also lead to nausea and panic attacks.

The term "psychoactive alkaloid extract" or "extract" refers to a psychoactive alkaloid extract that is obtained after a psychoactive alkaloid source has been extracted according to a process described herein. The extract may be a fluid, as either a liquid or a slurry, or is made into a fluid by the addition of a solvent. The term "extract" may also be used for the dried form of the fluid extract.

The term "psychoactive alkaloid extract" used herein refers to a psychoactive alkaloid extract obtained by an extraction process of the present invention. The extract can be in a solid, solid-powdered, semi-solid or a slurry form.

The term "psychoactive alkaloid" as used herein refers to alkaloids that upon ingestion are capable of changing brain function, resulting in alterations in perception, mood, consciousness, cognition, or behavior, for example. Psychoactive alkaloids are abundant in nature and can be obtained from sources such as a fungus, an animal, a mycelium, a spore, a plant, a bacterium, or a yeast. Examples of psychoactive alkaloids include, but are not limited to, psilocybin, psilocin, baeocystin, norbaeocystin, norpsilocin, aeruginascin, bufotenin, bufotenidine, 5-MeO-DMT (5-methoxy-N,N-dimethyltryptamine), N,N-dimethyltryptamine (DMT), ergine (LSA), ergonovine, ergometrine, ibotenic acid, muscimol, lysergic acid hydroxyethylamide (LSH), elymoclavine, ergometrinine, and/or chanoclavine. The source of the psychoactive alkaloid can also be an extract or a solution comprising a psychoactive alkaloid.

The term "psychoactive alkaloid" used herein refers to alkaloids that upon introduction to the human body are capable of changing brain function, for example resulting in alterations in perception, mood, consciousness, cognition, or behavior. The psychoactive alkaloid to which the present invention applies is either a phosphorylated psychoactive alkaloid or a dephosphorylated psychoactive alkaloid, and there may be multiple different compounds in each.

The term "psychoactive alkaloid source" used herein refers to a fungus, a mycelium, a spore, a plant, a bacterium, a Protista, an animal or a yeast, which has in it a phosphorylated psychoactive alkaloid, a dephosphorylated psychoactive alkaloid, or a combination or both. The source of the psychoactive alkaloid can also be another extract or a solution with a phosphorylated psychoactive alkaloid, a dephosphorylated psychoactive alkaloid, or a combination of both.

The term "phosphorylatable psychoactive alkaloid" refers to psychoactive alkaloids that have phosphorylated derivatives and includes psychoactive alkaloids in both their phosphorylated and dephosphorylated forms.

The term "psychoactive alkaloid composition" used herein can also be referred to as "composition" and describes a mixture of psychoactive alkaloid and one or more excipients. The composition can be of pharmaceutical, nutraceutical, or veterinarian grade.

The term "psychoactive alkaloid liquid" used herein refers to psychoactive alkaloid obtained in liquid form after a dried powdered biomass of a psychoactive alkaloid source has been extracted using an acidified solvent or a basified solvent. The liquid form can be a solution or a slurry.

The term "purified psychoactive alkaloid extract" refers to a purified extract that is obtained after a psychoactive alkaloid extract is treated with one or more resins for purification as described herein, or by other means of purifying the concentration of the psychoactive alkaloid concentration. This purified psychoactive alkaloid extract is substantially free of impurities, or contains fewer impurities compared to a similar psychoactive alkaloid extract that has not undergone any purification. The purified psychoactive alkaloid extract is a fluid, either a liquid or a slurry, or is made into a fluid by the addition of a solvent.

The term "purified psychoactive alkaloid solution" refers to a solution of one or more desired psychoactive alkaloids, where the solution is free of impurities or contains fewer impurities compared to a similar psychoactive alkaloid solution that has not undergone any purification. The purified solution is obtained after a psychoactive alkaloid extracted from its source has been purified by the purification process of the present invention. The impurities that are commonly encountered while extracting psychoactive alkaloids from a natural source include sugars, carbohydrates, chitin, chitosan, fats, minerals, waxes, and/or proteins. The impurities being removed from the psychoactive alkaloid extract will vary depending on the source of the psychoactive alkaloid.

The "impurities" herein are commonly undesired, but not necessarily harmful, substances encountered while extracting psychoactive alkaloids from psychoactive organisms. Impurities may include sugars, carbohydrates, chitin, chitosan, fats, minerals, waxes, and/or proteins. The impurities being removed from a psychoactive alkaloid extract will vary depending on the source of the psychoactive alkaloid. Their removal increases the concentration of the desired psychoactive alkaloids remaining in the extract.

The term "standardized psychoactive alkaloid extract" is used herein to describe a formulation derived from the purified psychoactive alkaloid solution, which has been standardized using a process described herein. The standardized psychoactive alkaloid extract includes psychoactive alkaloids in a specific concentration.

The term "resin" as used herein is intended to refer to a solid or highly-viscous substance of plant, mineral, or synthetic origin that has been typically converted into a polymer. Resins are usually mixtures of organic compounds. They are typically used in chromatographic techniques as a stationary phase to purify and separate compounds depending on their polarity. Resins can be physically or chemically modified to provide specificity to bind or repel particular molecules within sometimes very complex mixtures. A resin is an example of an adsorbent material.

As used herein, the term "ion exchange resin" refers to an insoluble organic polymer containing charged groups that tract and hold oppositely charged ions present in a surrounding solution in exchange for counterions previously held. Suitable ion exchange resins to be used herein contain cationic groups that tract and hold anions present in a surrounding solution and are sometimes referred to as "anion ion-exchange resins". Similarly, other ion exchange resins to be used herein contain anionic groups that tract and hold cations present in a surrounding solution and are sometimes referred to as "cation ion-exchange resins".

The term "macroporous resin" as used herein refers to a nonionic, cation, or anion resin with very small, highly cross-linked polymer particles with tiny channels. Macroporous resins are generally used for the adsorption of organic constituents due to their hydrophobic properties and are thus used to separate and purify compounds. The adsorption capacity of macroporous resins not only correlates with the physical and chemical properties of the adsorbent, but also with the size and chemical features of the adsorbed substance.

The term "adsorbed psychoactive alkaloid" refers to one or more alkaloids that are adsorbed onto an adsorbent material such as a resin.

The term "other adsorbent material" as used herein refers to materials which can be used in place of the resin(s) to adsorb the psychoactive alkaloids. Examples of such materials include, but are not limited to, zeolites, clays, bentonite, minerals, alumina, diatomaceous earth, activated carbon, charred biomass, and others.

The term "purification process" may be used herein to refer to the process described herein, i.e. a process for obtaining a purified psychoactive alkaloid solution. The purification process is a separate process to the standardization process.

The term "standardization" when used herein refers to a process for obtaining a standardized psychoactive alkaloid composition, i.e., a composition with a defined concentration by weight of psychoactive alkaloid.

The term "standardization process" as used herein refers to the process of obtaining a psychoactive alkaloid extract that has a defined percentage content of psychoactive alkaloids. The standardization process may be applied to an extract that has gone through a purification process or to an extract that has not gone through a purification process.

As used herein, the expression "standardizing" the psychoactive alkaloid slurry or bulk psychoactive alkaloid extract slurry refers to adding an excipient to an extract to obtain a slurry with a specific, total concentration of alkaloid, by weight. The slurry may then be dried to form a powdered composition with a pre-calculated percentage concentration by weight of psychoactive alkaloid. The total amount of alkaloid content can be specified to an accuracy of up to three significant figures.

The term "psychoactive alkaloid composition" or "composition" or "standardized composition" or "standardized purified composition" is used herein to describe a composition including a psychoactive alkaloid extract or a purified psychoactive alkaloid extract, which has been standardized by the addition of excipients according to a presently described process. The standardized psychoactive alkaloid composition includes the psychoactive alkaloid in a specific amount.

As used herein, the term "specific amount" when referring to a psychoactive alkaloid content means a desired percentage, accurate to one or two decimal places or one or two significant figures, of the psychoactive alkaloid content in a psychoactive alkaloid composition. The specific amount is defined as a percentage by weight and can be selected by a person of skill in the art according to preference.

The term "excipient" means any component added to an active ingredient to make a composition. An excipient is inert in relation to the active ingredient, in that it essentially does not act in the same way as the active ingredient. An excipient may be completely inert, or it may have some other property that protects the integrity of the active ingredient or assists its uptake into the human body. There are multiple types of excipient, each having a different purpose, and a given excipient may fulfill more than one purpose. Examples of types of excipient include flowability agents, flavorants, colorants, palatants, antioxidants, bioavailability-increasing agents, viscosity modifying agents, tonicity agents, drug carriers, sustained-release agents, comfort-enhancing agents, emulsifiers, solubilizing aids, lubricants, binding agents and stabilizing agents. Specific excipients include pectin, rice husks, rice, xanthum gum, gum arabic, beta cyclodextrin, alpha cyclodextrin, microcrystalline cellulose, sorbitol, dextrose, guar gum, acacia gum, cellulose gum, talc, magnesium stearate.

The phrase "one or more excipients" is used herein to refer that one excipient or more than one excipient can be used in any combination. The number of excipients to be used will be at the discretion of a person skilled in the art, and they may be of different types.

The term "carrier" means an excipient that aids in delivery of the active ingredient or provides bulk to the composition. The amount of carrier included in a composition can vary widely in order to control the concentration of the active ingredient in the composition. An example of a carrier is mannitol, starch, maltodextrin, tapioca maltodextrin or rice maltodextrin, alpha and beta cyclodextrin, microcrystalline cellulose (MCC), gum arabic, xanthum gum, guar gum, or cellulose gum. In some embodiments, the starch is potato starch, corn starch, tapioca starch, arrowroot starch, wheat starch, rice starch, sweet potato starch, sago starch, rung bean starch, and any combination of thereof. In some embodiments, mannitol is a cryoprotectant (allowing for efficient freeze-drying) and bulking agent.

The term "flow agent", "flowability agent" or "anti-caking agent" or "anti-adherent" means an excipient that prevents or reduces the formation of lumps in a powdered composition. An example of a flow agent is silicon dioxide, stearic acid, magnesium stearate, or talc.

The term "preservative" means an excipient that is added to the composition to prevent microbial growth or microbial degradation of the composition. Examples of preservative are ascorbic acid, citric acid, lactose, vitamin A, vitamin E, retinyl palmitate, selenium, sodium citrate, sodium ascorbate, calcium ascorbate, sodium benzoate, and potassium benzoate.

The term "purified water" includes deionized water, distilled water, reverse osmosis water, or otherwise purified water which is substantially without free ions.

The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more.

The term "specific pH" herein refers to a desired pH value of a solvent or a psychoactive alkaloid liquid obtained by adding an acidified solvent or a basified solvent.

The term "specific pH psychoactive alkaloid solution" used herein refers to a solution that is obtained after addition of a suitable acid or a base to a psychoactive alkaloid extract to achieve a solution with a desired pH level.

The term "% wt" is used to describe the weight percentage of one component in a mixture of components.

The term "a trace" herein refers more than, but close to about 0%.

The term "about" herein refers to ±10%, ±20%, ±30%, ±40%, or ±50%, or to the nearest significant figure.

The term "specific ratio" herein refers to a weight ratio between a phosphorylated psychoactive alkaloid and a dephosphorylated psychoactive alkaloid present in a psychoactive alkaloid composition. The ratio can be altered by a person of skill in the art according to preference.

The term "desired amount" herein refers to an amount of a phosphorylated psychoactive alkaloid or a dephosphorylated psychoactive alkaloid in a total phosphorylatable psychoactive alkaloid content, in the psychoactive alkaloid liquid, extract or composition. The amount of each of these alkaloids is controlled by the process for making the psychoactive alkaloid extract or psychoactive alkaloid composition. The amount can be altered by a person of skill in the art according to preference. The amount is usually a percentage ratio by weight that may be accurate up to two significant figures.

The term "therapeutic effects" is intended to qualify the amount of active ingredients required in the treatment of a disease or disorder or on the effecting of a clinical endpoint. Reference to "treatment" of a patient is intended to include prophylaxis. Treatment may also be preemptive in nature, i.e., it may include prevention of disease. Prevention of a disease may involve complete protection from disease, for example as in the case of prevention of infection with a pathogen or may involve prevention of disease progression. For example, prevention of a disease may not mean complete foreclosure of any effect related to the diseases at any level, but instead may mean prevention of the symptoms of a disease to a clinically significant or detectable level. Prevention of diseases may also mean prevention of progression of a disease to a later stage of the disease.

In some embodiments, as the ranges become narrower and more central compared to the greatest range, the properties of the embodiments generally become more balanced, such properties being solubility, viscosity, flowability, stability, taste, potency, immediate potency, delayed potency, cost of production, efficiency of production, production time, compatibility of the psychoactive alkaloid composition, psychoactive efficacy of the psychoactive alkaloid extract, psychoactive efficacy of the psychoactive alkaloid composition, and so on. As the ranges become narrower towards one extreme or other of the widest range, a particular property of the composition or process becomes more pronounced relative to the other properties. The specific range is to be chosen depending on how the properties are to be traded-off against each other.

Throughout the description, specific details have been set forth in order to provide a more thorough understanding of the invention. However, the invention may be practiced without these particulars. In other instances, well-known elements have not been shown or described in detail and repetitions of steps and features have been omitted to avoid unnecessarily obscuring the invention. Accordingly, the specification and drawings are to be regarded in an illustrative, rather than a restrictive, sense.

It will be clear to one having skill in the art that further variations to the specific details disclosed herein can be made, resulting in other embodiments that are within the scope of the invention disclosed. Steps in the flowchart may be performed in a different order, other steps may be added, or one or more may be removed without altering the main outcome of the process.

B. Compositions

Source of Psychoactive Alkaloid Extract

In one embodiment, the psychoactive alkaloid source is a psychoactive organism. In one embodiment, the psychoactive organism is a fungus. In one embodiment, the fungus is a mushroom from the genus *Conocybe, Copelandia, Galerina, Gymnopilus, Inocybe, Panaeolus, Pholiotina, Pluteus* or *Psilocybe*, or any combination of mushrooms selected therefrom. In one embodiment, gills, caps, stems, or the whole of the fungi is used as the alkaloid source.

The psychoactive organism may be a fungus, a mycelium, an animal, a spore, a plant, a bacterium, a protista, or a yeast. The psychoactive alkaloid source in some embodiments may be a prior extract of one or more psychoactive alkaloids, where the prior extract is to undergo a further extraction process. The psychoactive alkaloid may include, but is not limited to, psilocybin, psilocin, baeocystin, norbaeocystin, norpsilocin, aeruginascin, bufotenin, bufotenidine, 5-methoxy-N,N-dimethyltryptamine (5-MeO-DMT), N,N-dimethyltryptamine (DMT), ergine (LSA), ergonovine, ergometrine, muscimol, ibotenic acid, lysergic acid hydroxyethylamide (LSH), elymoclavine, ergometrinine, and/or chanoclavine, or any combination selected therefrom. It is possible that other psychoactive alkaloids, not yet discovered, may also be extracted using the methods disclosed herein.

In some embodiments, the psychoactive alkaloid is a combination of psilocybin and psilocin. In another embodiment, the psychoactive alkaloid is psilocybin. In yet another embodiment, the psychoactive alkaloid is psilocin.

Although the examples of the present invention have been formulated specifically using *Psilocybe cubensis* and *Anadenanthera peregrina* as sources to obtain a psychoactive alkaloid extract, the extract including psilocybin and psilocin in the first case and bufotenin, bufotenidine, and 5-MeO-DMT in the second, other sources are also possible. A person skilled in the art would appreciate that *Psilocybe cubensis* and *Anadenanthera peregrina* can be readily substituted by other sources of psychoactive alkaloids to obtain a variety of purified psychoactive alkaloids having similar properties, such alkaloids being, besides those mentioned above, baeocystin, norbaeocystin, norpsilocin, aeruginascin, N,N-dimethyltryptamine (DMT), ergine (LSA), ibotenic acid, ergonovine, ergometrine, muscimol, lysergic acid hydroxyethylamide (LSH), elymoclavine, ergometrinine, and/or chanoclavine, to name a few, and to result in compositions with similar efficacy and efficiency as well. For example, the venom of the toad *Incilius alvarius*, the *Anandenanthera colubrina* tree or the *Amanita muscaria* mushroom may be used as other sources of psychoactive alkaloids. Note that the lists of sources and psychoactive alkaloids are included to provide examples and are non-exhaustive lists.

Psychoactive Ingredient

In some embodiments, the present disclosure comprises a composition having, by weight, 2-99.7% of a psychoactive alkaloid extract, and 0.3-98%, i.e., the remainder, being one or more excipients. In some embodiments, the psychoactive ingredient is present in the composition at, by weight, about 50% to about 99.7%. In some embodiments, the psychoactive ingredient is present in the composition at, by weight, about 50% to about 60%, about 50% to about 70%, about 50% to about 80%, about 50% to about 90%, about 50% to about 92%, about 50% to about 94%, about 50% to about 96%, about 50% to about 98%, about 50% to about 99%, about 50% to about 99.7%, about 60% to about 70%, about 60% to about 80%, about 60% to about 90%, about 60% to about 92%, about 60% to about 94%, about 60% to about 96%, about 60% to about 98%, about 60% to about 99%, about 60% to about 99.7%, about 70% to about 80%, about 70% to about 90%, about 70% to about 92%, about 70% to about 94%, about 70% to about 96%, about 70% to about 98%, about 70% to about 99%, about 70% to about 99.7%, about 80% to about 90%, about 80% to about 92%, about 80% to about 94%, about 80% to about 96%, about 80% to about 98%, about 80% to about 99%, about 80% to about 99.7%, about 90% to about 92%, about 90% to about 94%, about 90% to about 96%, about 90% to about 98%, about 90% to about 99%, about 90% to about 99.7%, about 92% to about 94%, about 92% to about 96%, about 92% to about 98%, about 92% to about 99%, about 92% to about 99.7%, about 94% to about 96%, about 94% to about 98%, about 94% to about 99%, about 94% to about 99.7%, about 96% to about 98%, about 96% to about 99%, about 96% to about 99.7%, about 98% to about 99%, about 98% to about 99.7%, or about 99% to about 99.7%. In some embodiments, the psychoactive ingredient is present in the composition at, by weight, about 50%, about 60%, about 70%, about 80%, about 90%, about 92%, about 94%, about 96%, about 98%, about 99%, or about 99.7%. In some embodiments, the psychoactive ingredient is present in the composition at, by weight, at least about 50%, about 60%, about 70%, about 80%, about 90%, about 92%, about 94%, about 96%, about 98, or about 99%. In some embodiments, the psychoactive ingredient is present in the composition at, by weight, at most about 60%, about 70%, about 80%, about 90%, about 92%, about 94%, about 96%, about 98%, about 99%, or about 99.7%.

While a broad range of psychoactive extract is possible, if it is above 90% (e.g., as much as 99.9%), it is likely not to be dryable and/or flowable. Nevertheless, such a composition, when standardized, may still have its uses, due to the reliability and repeatability of the psychoactive alkaloid content. Below about 2%, the composition may be considered to provide too low a dose of psychoactive alkaloid. However, compositions with less than 2% (e.g., down to 0.1%) may be possible if micro-dosing is desired. In some embodiments, the psychoactive ingredient is present in the composition at, by weight, about 0.05% to about 5%. In some embodiments, the psychoactive ingredient is present in the composition at, by weight, about 5% to about 4%, about 5% to about 3%, about 5% to about 2%, about 5% to about 1%, about 5% to about 0.8%, about 5% to about 0.6%, about 5% to about 0.4%, about 5% to about 0.2%, about 5% to about 0.1%, about 5% to about 0.05%, about 4% to about 3%, about 4% to about 2%, about 4% to about 1%, about 4% to about 0.8%, about 4% to about 0.6%, about 4% to about 0.4%, about 4% to about 0.2%, about 4% to about 0.1%, about 4% to about 0.05%, about 3% to about 2%, about 3% to about 1%, about 3% to about 0.8%, about 3% to about 0.6%, about 3% to about 0.4%, about 3% to about 0.2%, about 3% to about 0.1%, about 3% to about 0.05%, about 2% to about 1%, about 2% to about 0.8%, about 2% to about 0.6%, about 2% to about 0.4%, about 2% to about 0.2%, about 2% to about 0.1%, about 2% to about 0.05%, about 1% to about 0.8%, about 1% to about 0.6%, about 1% to about 0.4%, about 1% to about 0.2%, about 1% to about 0.1%, about 1% to about 0.05%, about 0.8% to about 0.6%, about 0.8% to about 0.4%, about 0.8% to about 0.2%, about 0.8% to about 0.1%, about 0.8% to about 0.05%, about 0.6% to about 0.4%, about 0.6% to about 0.2%, about 0.6% to about 0.1%, about 0.6% to about 0.05%, about 0.4% to about 0.2%, about 0.4% to about 0.1%, about 0.4% to about 0.05%, about 0.2% to about 0.1%, about 0.2% to about 0.05%, or about 0.1% to about 0.05%. In some embodiments, the psychoactive ingredient is present in the composition at, by weight, about 5%, about 4%, about 3%, about 2%, about 1%, about 0.8%, about 0.6%, about 0.4%, about 0.2%, about 0.1%, or about 0.05%. In some embodiments, the psychoactive ingredient is present in the composition at, by weight, at least about 5%, about 4%, about 3%, about 2%, about 1%, about 0.8%, about 0.6%, about 0.4%, about 0.2%, or about 0.1%. In some embodiments, the psychoactive ingredient is present in the composition at, by weight, at most about 4%, about 3%, about 2%, about 1%, about 0.8%, about 0.6%, about 0.4%, about 0.2%, about 0.1%, or about 0.05%.

In some embodiments, the psychoactive alkaloid extract has a psychoactive alkaloid concentration ranging from 0.1% to 99% by weight of the extract. It may be in the range of 1-10% dry wt/wt % for the non-purified extract concentration. However, as the composition may be made with purified extract, the psychoactive concentration could be as high as 99%. In some embodiments, the psychoactive alkaloid extract has a psychoactive alkaloid concentration ranging from 1.03% to 75.22% by weight of the dry extract. In some embodiments, the psychoactive alkaloid extract has a psychoactive alkaloid concentration ranging from 1.03% to 3.02% by weight of the extract. In other embodiments, the psychoactive alkaloid extract is a purified psychoactive alkaloid extract. In some embodiments, the purified psychoactive alkaloid extract has a psychoactive alkaloid concentration ranging from 10% to 99% by weight of the extract. In other embodiments, the purified psychoactive alkaloid extract has a psychoactive alkaloid concentration ranging from 16.12% to 75.22% by weight of the extract. In some embodiments, the psychoactive ingredient is present in the composition at, by weight, about 5% to about 76%. In some embodiments, the psychoactive ingredient is present in the composition at, by weight, about 5% to about 10%, about 5% to about 20%, about 5% to about 30%, about 5% to about 40%, about 5% to about 50%, about 5% to about 60%, about 5% to about 70%, about 5% to about 75%, about 5% to about 76%, about 10% to about 20%, about 10% to about 30%, about 10% to about 40%, about 10% to about 50%, about 10% to about 60%, about 10% to about 70%, about 10% to about 75%, about 10% to about 76%, about 20% to about 30%, about 20% to about 40%, about 20% to about 50%, about 20% to about 60%, about 20% to about 70%, about 20% to about 75%, about 20% to about 76%, about 30% to about 40%, about 30% to about 50%, about 30% to about 60%, about 30% to about 70%, about 30% to about 75%, about 30% to about 76%, about 40% to about 50%, about 40% to about 60%, about 40% to about 70%, about 40% to about 75%, about 40% to about 76%, about 50% to about 60%, about 50% to about 70%, about 50% to about 75%, about 50% to about 76%, about 60% to about 70%, about 60% to about 75%, about 60% to about 76%, about 70% to about 75%, about 70% to about 76%, or about 75% to about 76%. In some embodiments, the psychoactive ingredient is present in the composition at, by weight, about 5%, about 10%, about 20%, about 30%, about 40%, about 50%, about 60%, about 70%, about 75%, or about 76%. In some embodiments, the psychoactive ingredient is present in the composition at, by weight, at least about 5%, about 10%, about 20%, about 30%, about 40%, about 50%, about 60%, about 70%, or about 75%. In some embodiments, the psychoactive ingredient is present in the composition at, by weight, at most about 10%, about 20%, about 30%, about 40%, about 50%, about 60%, about 70%, about 75%, or about 76%.

The composition of the present invention has the psychoactive alkaloid present in a specific amount. In some embodiments, the specific amount of psychoactive alkaloid is accurate to one significant figure. In another embodiment, the specific amount psychoactive alkaloid is accurate to two, three or four significant figures. The presence of the psychoactive alkaloid in a specific amount in the composition allows for the same desired specific amount of the psychoactive alkaloid to be present in various batches of the psychoactive alkaloid composition.

The composition of the present invention is in a powder form. The components of the composition are also in powder form. The composition of the present invention may be in the form of a free-flowing powder depending on the embodiment. Such compositions are thus easy to handle during manufacturing and packaging processes. Further, the dry, free-flowing powder form allows the composition to be free from clumps and not be as susceptible to microbial growth as a composition with clumping due to moisture absorption.

Phosphorylatable Psychoactive Alkaloid

In one embodiment, the present invention also relates to a psychoactive alkaloid composition. The psychoactive alkaloid composition includes a specific amount of a total phosphorylatable psychoactive alkaloid content, made up of a desired amount of a phosphorylated psychoactive alkaloid and a desired amount of a dephosphorylated psychoactive alkaloid, and one or more excipients.

In some embodiments, the phosphorylated alkaloid is psilocybin, baeocystin, norbaeocystin, aeruginascin, or any combination therefrom; and the dephosphorylated alkaloid is psilocin, norpsilocin, 4-hydroxytryptamine, N,N,N-trimethyl-4-hydroxytryptamine, or any combination therefrom. In other embodiments, the phosphorylated alkaloid is psilocybin and the dephosphorylated alkaloid is psilocin.

In some embodiments, any source that contains phosphorylated psychoactive alkaloids may be used as the psychoactive alkaloid source.

In one embodiment, the specific amount of the total phosphorylatable psychoactive alkaloid content in the psychoactive alkaloid composition ranges from 0.1-99% by weight of the composition. In another embodiment, the specific amount of the total phosphorylatable psychoactive alkaloid content in the psychoactive alkaloid composition ranges from 0.1-10% by weight of the composition. In an exemplary embodiment, the specific amount of the total phosphorylatable psychoactive alkaloid content in the psychoactive alkaloid composition is 0.533% by weight of the composition. In yet another exemplary embodiment, the specific amount of the total phosphorylatable psychoactive alkaloid content in the psychoactive alkaloid composition is 0.501% by weight of the composition.

In one embodiment, the desired amount of the phosphorylated psychoactive alkaloid is 0-100% by weight of a total phosphorylatable psychoactive alkaloid content in the psychoactive alkaloid extract, and the desired amount of the dephosphorylated psychoactive alkaloid is the remainder of the total phosphorylatable psychoactive alkaloid content in the psychoactive alkaloid extract. In one embodiment, the desired amount of the phosphorylated psychoactive alkaloid is 10-90% by weight of the total phosphorylatable psychoactive alkaloid content in the psychoactive alkaloid extract, and the desired amount of the dephosphorylated psychoactive alkaloid is the remainder of the total phosphorylatable psychoactive alkaloid content in the psychoactive alkaloid extract. In another embodiment, the desired amount of the phosphorylated psychoactive alkaloid is 0% by weight of the total phosphorylatable psychoactive alkaloid content in the psychoactive alkaloid extract, and the desired amount of the dephosphorylated psychoactive alkaloid is 100% by weight of the total phosphorylatable psychoactive alkaloid content in the psychoactive alkaloid extract. In yet another embodiment, the desired amount of the phosphorylated psychoactive alkaloid is 100% by weight of the total phosphorylatable psychoactive alkaloid content in the psychoactive alkaloid extract, and the desired amount of the dephosphorylated psychoactive alkaloid is 0% by weight of the total phosphorylatable psychoactive alkaloid content in the psychoactive alkaloid extract.

In some embodiments, a maximum desired amount of the phosphorylated alkaloid is limited by an amount of the dephosphorylated alkaloid in the psychoactive alkaloid source.

In an exemplary embodiment, the desired amount of the phosphorylated psychoactive alkaloid is 0.503% by weight of the psychoactive alkaloid composition; and the desired amount of the dephosphorylated psychoactive alkaloid is by 0.03% weight of the psychoactive alkaloid composition. In yet another exemplary embodiment, the desired amount of the phosphorylated psychoactive alkaloid is 0.00% by weight of the psychoactive alkaloid composition, and the desired amount of the dephosphorylated psychoactive alkaloid is by 0.501% weight of the psychoactive alkaloid composition.

In one embodiment, the desired amount of the phosphorylated psychoactive alkaloid is 100% by weight of the total psychoactive alkaloid content in the psychoactive alkaloid extract.

In one embodiment, the desired amount of the dephosphorylated psychoactive alkaloid is 100% by weight of the total psychoactive alkaloid content in the psychoactive alkaloid extract.

The dephosphorylated psychoactive alkaloids are quicker in becoming bioavailable than their phosphorylated psychoactive alkaloids counterparts. Thus, the psychoactive compositions comprising dephosphorylated psychoactive alkaloids 100% by weight in the total phosphorylatable psychoactive alkaloid content may exhibit therapeutic effects faster than psychoactive alkaloid compositions comprising phosphorylated psychoactive alkaloids as the majority alkaloids in the total phosphorylatable psychoactive alkaloid content.

In one embodiment, the psychoactive alkaloid composition is obtained by the process for obtaining a psychoactive alkaloid extract with a desired amount of a phosphorylated psychoactive alkaloid and a desired amount of a dephosphorylated psychoactive alkaloid of the present invention.

In one embodiment, the present invention also relates to a psychoactive alkaloid composition with a specific ratio of a phosphorylated psychoactive alkaloid and a dephosphorylated psychoactive alkaloid. The composition includes a psychoactive alkaloid extract having a total phosphorylatable psychoactive alkaloid content of 100% by weight of a phosphorylated psychoactive alkaloid, another psychoactive alkaloid extract having a total phosphorylatable psychoactive alkaloid content of 100% by weight of a dephosphorylated psychoactive alkaloid, and one or more excipients.

In some embodiments, the composition includes a psychoactive alkaloid extract having a total phosphorylated psychoactive alkaloid content of a trace by weight to about 100% by weight. In some embodiments, the composition includes a psychoactive alkaloid extract having a total phosphorylated psychoactive alkaloid content of a trace by weight to about 10% by weight, a trace by weight to about 20% by weight, a trace by weight to about 30% by weight, a trace by weight to about 40% by weight, a trace by weight to about 50% by weight, a trace by weight to about 60% by weight, a trace by weight to about 70% by weight, a trace by weight to about 80% by weight, a trace by weight to about 90% by weight, a trace by weight to about 95% by weight, a trace by weight to about 100% by weight, about 10% by weight to about 20% by weight, about 10% by weight to about 30% by weight, about 10% by weight to about 40% by weight, about 10% by weight to about 50% by weight, about 10% by weight to about 60% by weight, about 10% by weight to about 70% by weight, about 10% by weight to about 80% by weight, about 10% by weight to about 90% by weight, about 10% by weight to about 95% by weight, about 10% by weight to about 100% by weight, about 20% by weight to about 30% by weight, about 20% by weight to about 40% by weight, about 20% by weight to about 50% by weight, about 20% by weight to about 60% by weight, about 20% by weight to about 70% by weight, about 20% by weight to about 80% by weight, about 20% by weight to about 90% by weight, about 20% by weight to about 95% by weight, about 20% by weight to about 100% by weight, about 30% by weight to about 40% by weight, about 30% by weight to about 50% by weight, about 30% by weight to about 60% by weight, about 30% by weight to about 70% by weight, about 30% by weight to about 80% by weight, about 30% by weight to about 90% by weight, about 30% by weight to about 95% by weight, about 30% by weight to about 100% by weight, about 40% by weight to about 50% by weight, about 40% by weight to about 60% by weight, about 40% by weight to about 70% by weight, about 40% by weight to about 80% by weight, about 40% by weight to about 90% by weight, about 40% by weight to about 95% by weight, about 40% by weight to about 100% by weight, about 50% by weight to about 60% by weight, about 50% by weight to about 70% by weight, about 50% by weight to about 80% by weight, about 50% by weight to about 90% by weight, about 50% by weight to about 95% by weight, about 50% by weight to about 100% by weight, about 60% by weight to about 70% by weight, about 60% by weight to about 80% by weight, about 60% by weight to about 90% by weight, about 60% by weight to about 95% by weight, about 60% by weight to about 100% by weight, about 70% by weight to about 80% by weight, about 70% by weight to about 90% by weight, about 70% by weight to about 95% by weight, about 70% by weight to about 100% by weight, about 80% by weight to about 90% by weight, about 80% by weight to about 95% by weight, about 80% by weight to about 100% by weight, about 90% by weight to about 95% by weight, about 90% by weight to about 100% by weight, or about 95% by weight to about 100% by weight. In some embodiments, the composition includes a psychoactive alkaloid extract having a total phosphorylated psychoactive alkaloid content of a trace by weight, about 10% by weight, about 20% by weight, about 30% by weight, about 40% by weight, about 50% by weight, about 60% by weight, about 70% by weight, about 80% by weight, about 90% by weight, about 95% by weight, or about 100% by weight. In some embodiments, the composition includes a psychoactive alkaloid extract having a total phosphorylated psychoactive alkaloid content of at least a trace by weight, about 10% by weight, about 20% by weight, about 30% by weight, about 40% by weight, about 50% by weight, about 60% by weight, about 70% by weight, about 80% by weight, about 90% by weight, or about 95% by weight. In some embodiments, the composition includes a psychoactive alkaloid extract having a total phosphorylated psychoactive alkaloid content of at most about 10% by weight, about 20% by weight, about 30% by weight, about 40% by weight, about 50% by weight, about 60% by weight, about 70% by weight, about 80% by weight, about 90% by weight, about 95% by weight, or about 100% by weight.

In some embodiments, the composition includes a psychoactive alkaloid extract having a total dephosphorylated psychoactive alkaloid content of a trace by weight to about 100% by weight. In some embodiments, the composition includes a psychoactive alkaloid extract having a total dephosphorylated psychoactive alkaloid content of a trace by weight to about 10% by weight, a trace by weight to about 20% by weight, a trace by weight to about 30% by weight, a trace by weight to about 40% by weight, a trace by weight to about 50% by weight, a trace by weight to about 60% by weight, a trace by weight to about 70% by weight, a trace by weight to about 80% by weight, a trace by weight to about 90% by weight, a trace by weight to about 95% by weight, a trace by weight to about 100% by weight, about 10% by weight to about 20% by weight, about 10% by weight to about 30% by weight, about 10% by weight to about 40% by weight, about 10% by weight to about 50% by weight, about 10% by weight to about 60% by weight, about 10% by weight to about 70% by weight, about 10% by weight to about 80% by weight, about 10% by weight to about 90% by weight, about 10% by weight to about 95% by weight, about 10% by weight to about 100% by weight, about 20% by weight to about 30% by weight, about 20% by weight to about 40% by weight, about 20% by weight to about 50% by weight, about 20% by weight to about 60% by weight, about 20% by weight to about 70% by weight, about 20% by weight to about 80% by weight, about 20% by weight to about 90% by weight, about 20% by weight to about 95% by weight, about 20% by weight to about 100% by weight, about 30% by weight to about 40% by weight, about 30% by weight to about 50% by weight, about 30% by weight to about 60% by weight, about 30% by weight to about 70% by weight, about 30% by weight to about 80% by weight, about 30% by weight to about 90% by weight, about 30% by weight to about 95% by weight, about 30% by weight to about 100% by weight, about 40% by weight to about 50% by weight, about 40% by weight to about 60% by weight, about 40% by weight to about 70% by weight, about 40% by weight to about 80% by weight, about 40% by weight to about 90% by weight, about 40% by weight to about 95% by weight, about 40% by weight to about 100% by weight, about 50% by weight to about 60% by weight, about 50% by weight to about 70% by weight, about 50% by weight to about 80% by weight, about 50% by weight to about 90% by weight, about 50% by weight to about 95% by weight, about 50% by weight to about 100% by weight, about 60% by weight to about 70% by weight, about 60% by weight to about 80% by weight, about 60% by weight to about 90% by weight, about 60% by weight to about 95% by weight, about 60% by weight to about 100% by weight, about 70% by weight to about 80% by weight, about 70% by weight to about 90% by weight, about 70% by weight to about 95% by weight, about 70% by weight to about 100% by weight, about 80% by weight to about 90% by weight, about 80% by weight to about 95% by weight, about 80% by weight to about 100% by weight, about 90% by weight to about 95% by weight, about 90% by weight to about 100% by weight, or about 95% by weight to about 100% by weight. In some embodiments, the composition includes a psychoactive alkaloid extract having a total dephosphorylated psychoactive alkaloid content of a trace by weight, about 10% by weight, about 20% by weight, about 30% by weight, about 40% by weight, about 50% by weight, about 60% by weight, about 70% by weight, about 80% by weight, about 90% by weight, about 95% by weight, or about 100% by weight. In some embodiments, the composition includes a psychoactive alkaloid extract having a total dephosphorylated psychoactive alkaloid content of at least a trace by weight, about 10% by weight, about 20% by weight, about 30% by weight, about 40% by weight, about 50% by weight, about 60% by weight, about 70% by weight, about 80% by weight, about 90% by weight, or about 95% by weight. In some embodiments, the composition includes a psychoactive alkaloid extract having a total dephosphorylated psychoactive alkaloid content of at most about 10% by weight, about 20% by weight, about 30% by weight, about 40% by weight, about 50% by weight, about 60% by weight, about 70% by weight, about 80% by weight, about 90% by weight, about 95% by weight, or about 100% by weight.

In one embodiment, one psychoactive alkaloid extract and another psychoactive alkaloid extract are present in a proportion such that the specific ratio of phosphorylated to dephosphorylated psychoactive alkaloid ranges from 1:1000 to 1000:1. In exemplary embodiments, a phosphorylated psychoactive alkaloid extract and a dephosphorylated psychoactive alkaloid extract are present in a proportion such that the specific ratio of phosphorylated to dephosphorylated psychoactive alkaloid is 1:1, 1:3, and 3:1.

In other embodiments, the psychoactive alkaloid composition is defined by a specific total amount of psychoactive alkaloid content, which has a known ratio of phosphorylated and dephosphorylated alkaloids.

In some embodiments, the psychoactive alkaloid composition with a specific ratio of a phosphorylated psychoactive alkaloid and a dephosphorylated psychoactive alkaloid is made by the process for obtaining a psychoactive alkaloid composition with a specific ratio of a phosphorylated psychoactive alkaloid to a dephosphorylated psychoactive alkaloid of the present invention.

The psychoactive alkaloid extract of the composition low in (e.g., <20%) or almost free of undesired impurities allows a smaller amount of the composition to achieve a desired therapeutic effect than if the extract were less concentrated, with more impurities.

The psychoactive alkaloid composition of the present invention is in powder form. This free-flowing powder form allows the composition to be easily handled. The components of the composition are also in powder form.

The psychoactive alkaloid composition of the present invention can be used, for example, in medical research on the use of psychedelic substances in treatments for mental illnesses.

Figure 22:
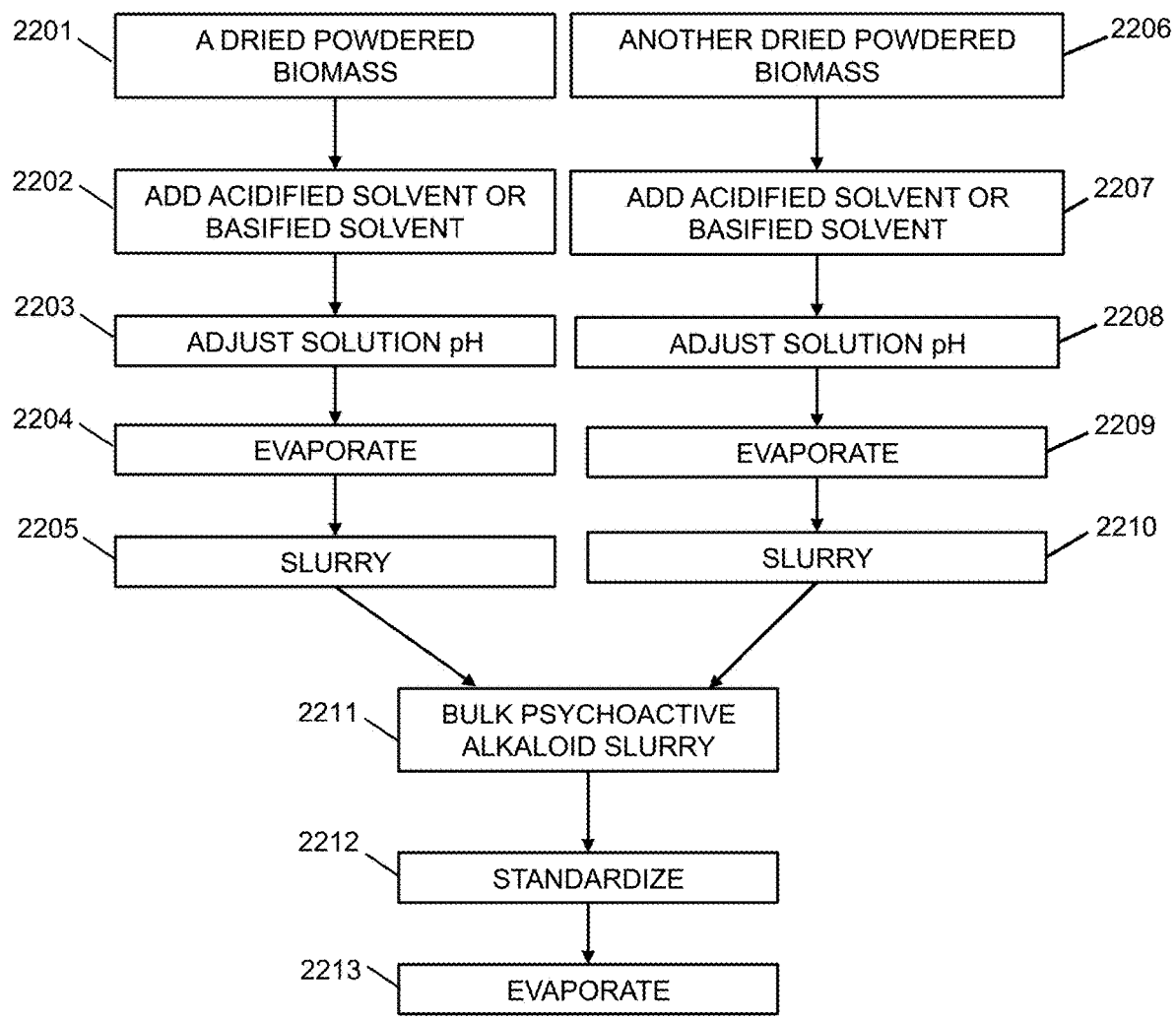
FIG. 22 illustrates detailed steps of a process for obtaining a psychoactive alkaloid composition with a specific ratio of a phosphorylated psychoactive alkaloid to a dephosphorylated psychoactive alkaloid, according to another embodiment of the present invention.
Figure 23:
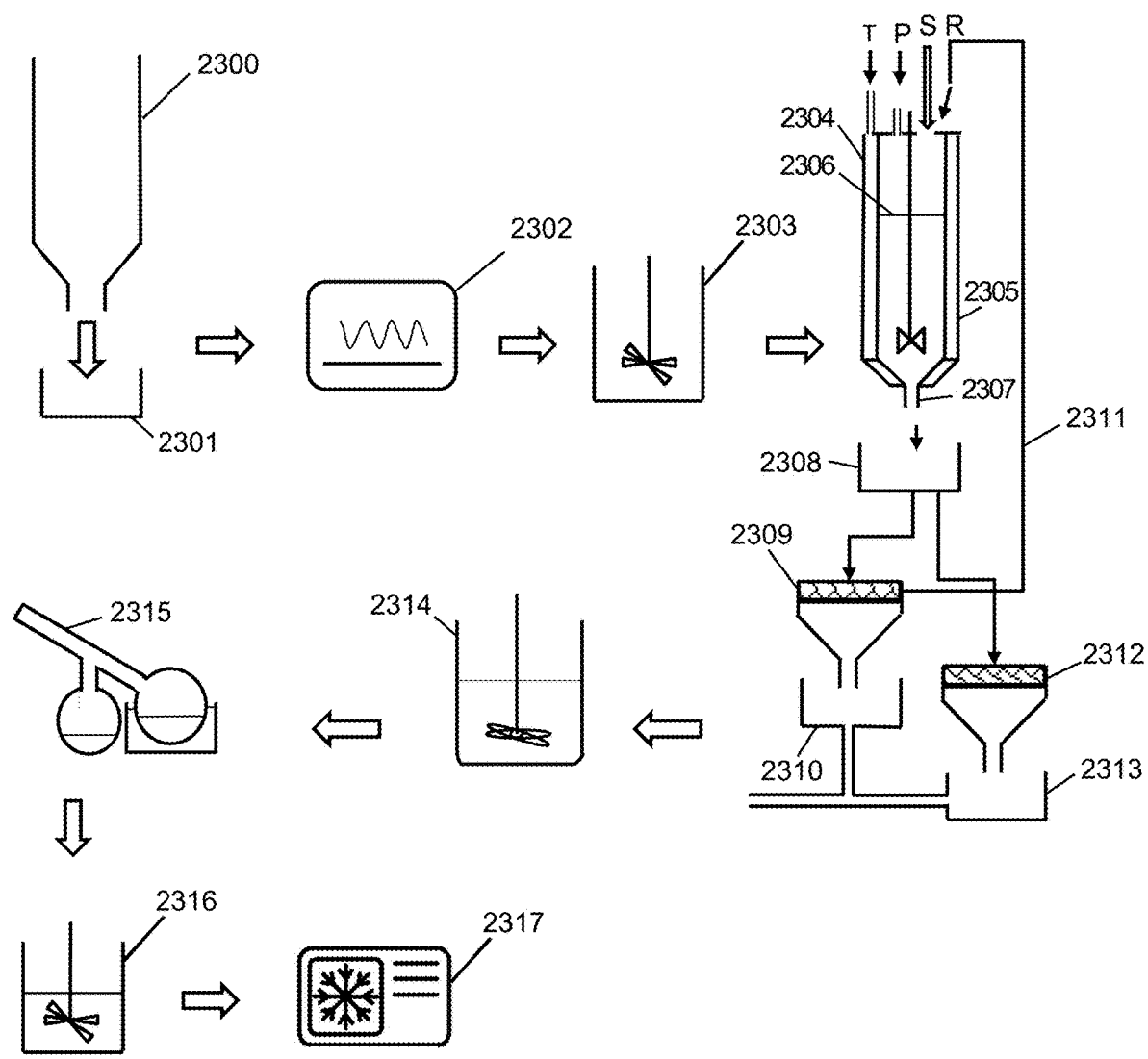
FIG. 23 illustrates a schematic diagram of the apparatus used for obtaining a psychoactive alkaloid extract and standardizing the same to result in a standardized psychoactive alkaloid extract, according to an embodiment of the present invention.

FIG. 22, in another embodiment, describes a process for preparing a psychoactive alkaloid composition having a phosphorylated psychoactive alkaloid from one psychoactive alkaloid extraction and a dephosphorylated psychoactive alkaloid from another psychoactive alkaloid extraction in a specific ratio.

A dried powdered biomass is obtained in step 2201. Step 2202 includes extracting a psychoactive alkaloid with a basified solvent to obtain a psychoactive alkaloid liquid with a pH greater than 10.5. A majority, or all, of a total phosphorylatable psychoactive alkaloid content is phosphorylated alkaloid and a remainder thereof is dephosphorylated alkaloid.

In step 2203 the pH of the resulting psychoactive alkaloid liquid is adjusted to a pH ranging from 3.5 to 4.5. The pH is adjusted by adding an acid.

Another dried powdered biomass is obtained in step 2206. Step 2207 includes extracting a psychoactive alkaloid with an acidified solvent to obtain another psychoactive alkaloid liquid with a pH lower than 3.5. All of the psychoactive alkaloid present is dephosphorylated.

Step 2208 involves adjusting the pH of the second psychoactive alkaloid liquid to a pH ranging from 3.5 to 4.5. The pH is adjusted by adding a base.

In steps 2204 and 2209, a portion of the basified solvent from the first psychoactive alkaloid liquid and a portion of the acidified solvent from the second psychoactive alkaloid liquid are evaporated to obtain first and second psychoactive alkaloid slurries 2205 and 2210 respectively.

In step 2211, measured portions of the psychoactive alkaloid slurries are mixed to obtain a bulk psychoactive alkaloid slurry. The bulk psychoactive alkaloid slurry includes the phosphorylated psychoactive alkaloid and the dephosphorylated psychoactive alkaloid in the specific ratio. The measured portions, by weight, of each of the psychoactive alkaloid slurries are chosen in such a manner as to achieve the specific ratio of the phosphorylated psychoactive alkaloid and the dephosphorylated psychoactive alkaloid, taking into account the percentage by weight of these psychoactive alkaloids in each of the initial slurries. In one exemplary embodiment, mixing 100 g of a 1.0% phosphorylated psychoactive alkaloid slurry, with 50 g of a 0.5% dephosphorylated psychoactive alkaloid slurry results in the specific ratio of 4:1 of phosphorylated to dephosphorylated alkaloid.

In step 2212, the obtained bulk psychoactive alkaloid slurry is standardized by adding thereto a measured quantity of one or more excipients to obtain a standardized bulk slurry with a specific total amount of psychoactive alkaloid.

Step 2213 includes drying the standardized bulk psychoactive alkaloid slurry by evaporation to obtain the psychoactive alkaloid composition. The obtained psychoactive alkaloid composition has a specific total amount of psychoactive alkaloid content, and the phosphorylated psychoactive alkaloid and dephosphorylated psychoactive alkaloid are in the specific ratio. In some embodiments of the psychoactive alkaloid composition, the specific ratio of phosphorylated psychoactive alkaloid to dephosphorylated psychoactive alkaloid ranges from 1:1000 to 1000:1.

Mixture

Figure 20:
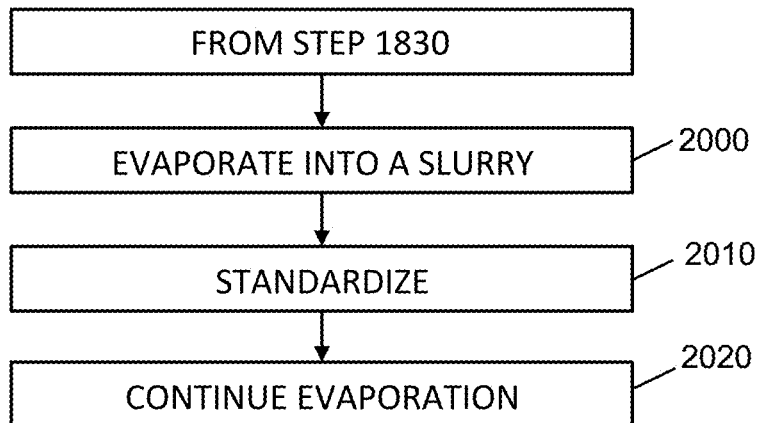
FIG. 20 illustrates a process for standardizing a psychoactive alkaloid extract to obtain a standardized psychoactive alkaloid extract.
Figure 21:
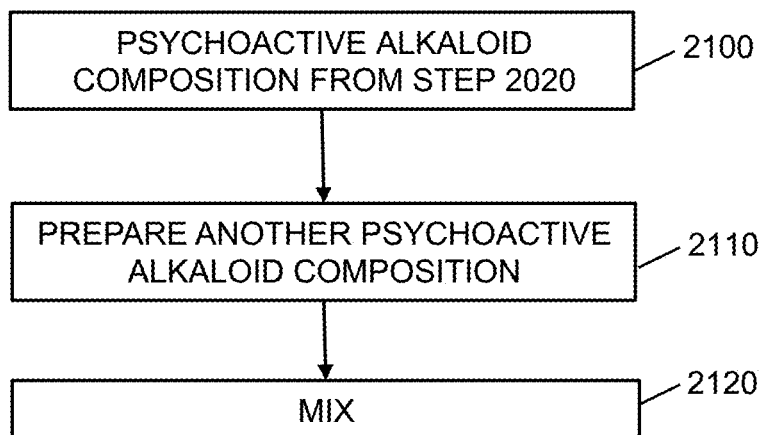
FIG. 21 illustrates a process for obtaining a psychoactive alkaloid composition with a specific ratio of a phosphorylated psychoactive alkaloid to a dephosphorylated psychoactive alkaloid, according to an embodiment of the present invention.

Referring to FIG. 21, in one embodiment, the present invention also relates to a process for preparing a psychoactive alkaloid composition by mixing a phosphorylated psychoactive alkaloid composition and a dephosphorylated psychoactive alkaloid composition in a specific ratio. In step 2100, the psychoactive alkaloid composition obtained after step 2020 (FIG. 20) is taken. The psychoactive alkaloid composition in step 2020 has the desired amount of the dephosphorylated psychoactive alkaloid of 100% by weight of the total phosphorylatable psychoactive alkaloid content in the psychoactive alkaloid extract. The aforesaid is achieved by extracting the psychoactive alkaloid from the dried powdered biomass with an acidified solvent having a specific pH lower than 3.5.

In step 2110, another psychoactive alkaloid composition is obtained according to the process described above. This other psychoactive alkaloid composition has a desired amount of phosphorylated psychoactive alkaloid of 100% by weight of the total phosphorylatable psychoactive alkaloid content. The aforesaid is achieved by extracting the psychoactive alkaloid from the dried powdered biomass with a basified solvent having a pH greater than 10.5, where the biomass is not dephosphorylated or not significantly dephosphorylated.

In some embodiments, the acidified solvent is a mixture of an acid and a C1-C4 primary aliphatic alcohol, a C3-C4 ketone, water, or any combination selected therefrom. The acid may be citric acid, ascorbic acid, formic acid, acetic acid, hydrochloric acid, phosphoric acid, sulfuric acid, or any combination selected therefrom. In other embodiments, the basified solvent is a mixture of a base and a C1-C4 primary aliphatic alcohol, a C3-C4 ketone, water, or any combination selected therefrom. The base may be sodium hydroxide, potassium hydroxide, ammonium hydroxide, sodium bicarbonate, calcium carbonate, or any combination selected therefrom.

In step 2120, both psychoactive alkaloid compositions are mixed in a measured ratio to obtain a psychoactive alkaloid composition. This composition includes the dephosphorylated psychoactive alkaloid of the first psychoactive alkaloid composition and the phosphorylated psychoactive alkaloid of the second psychoactive alkaloid composition in a specific ratio. In some embodiments, the specific ratio of phosphorylated psychoactive alkaloid to dephosphorylated psychoactive alkaloid is in the range from 1000:1 to 1:1000. If the total phosphorylatable psychoactive alkaloid concentrations are the same in both starting compositions, then the final ratio of phosphorylated to dephosphorylated alkaloids is the same as the ratio in which the starting compositions are mixed. However, in other embodiments, the mixing ratio may need to be modified to take into account the different starting concentrations of the phosphorylated and dephosphorylated alkaloids in their respective compositions. In yet other embodiments, one of the starting compositions may include both phosphorylated and dephosphorylated alkaloids, and the mixing ratio of the two compositions may be adjusted to take this into account.

Naturally Occurring Substances

In other embodiments, the psychoactive alkaloid extract includes naturally occurring substances selected from fats, sugars, carbohydrates, and proteins, or any combination selected therefrom. The aforesaid naturally occurring substances do not lead to any side effects or adverse effects when ingested as a part of the composition.

The naturally-occurring substances are present in the psychoactive alkaloid extract in a concentration ranging from 1-99.9% by dry weight. The concentration range of the naturally-occurring substances in the psychoactive alkaloid extract will vary due to various factors for example, but not limited to, the source of the psychoactive alkaloid extract, the extraction technique used, the efficiency of the extraction process, and the amount of the psychoactive alkaloid in the extract.

In some embodiments, the psychoactive alkaloid extract includes the psychoactive alkaloid and the naturally occurring substances.

Excipient

The excipients described herein refer to excipients which aid in the manufacturing and/or administration of the compositions described herein. Non-limiting examples of such excipients are well known in the art and include flavorants, colorants, palatants, antioxidants, viscosity modifying agents, tonicity agents, drug carriers, sustained-release agents, comfort-enhancing agents, emulsifiers, solubilizing aids, lubricants, binding agents, stabilizing agents and other agents to aid in the manufacturing and/or administration of the compositions. The excipients used in the present invention are acceptable for use in pharmaceutical or nutraceutical applications or as food ingredients. The amount of excipients will vary depending on the concentration of psychoactive alkaloids in the psychoactive alkaloid extract to result in a flowable psychoactive alkaloid composition, which will be obvious to a person of skill in the art.

In some embodiments, a bioavailability enhancing agent such as citric acid, beta cyclodextrin, or alpha cyclodextrin can be added (up to 0.5% by weight) as an excipient. In other embodiments, an antioxidant agent such as ascorbic acid may be added (up to 0.5% by weight) as an excipient.

In some embodiments, the excipients are selected from silicon dioxide, ascorbic acid, maltodextrin from corn, potato, or tapioca for example, gum arabic, microcrystalline cellulose, sodium benzoate, sodium phosphate, sodium citrate, rice hulls, and rice. A combination of any of these excipients may be used.

In some embodiments, the carrier comprises maltodextrin in the composition at 10% to 20%. In some embodiments, the carrier comprises maltodextrin in the composition at about 10% to about 12%, about 10% to about 14%, about 10% to about 16%, about 10% to about 18%, about 10% to about 20%, about 12% to about 14%, about 12% to about 16%, about 12% to about 18%, about 12% to about 20%, about 14% to about 16%, about 14% to about 18%, about 14% to about 20%, about 16% to about 18%, about 16% to about 20%, or about 18% to about 20%. In some embodiments, the carrier comprises maltodextrin in the composition at about 10%, about 12%, about 14%, about 16%, about 18%, or about 20%. In some embodiments, the carrier comprises maltodextrin in the composition at least about 10%, about 12%, about 14%, about 16%, or about 18%. In some embodiments, the carrier comprises maltodextrin in the composition at most about 12%, about 14%, about 16%, about 18%, or about 20%.

In some embodiments, the carrier comprises mannitol in the composition at 10% to 20%. In some embodiments, the carrier comprises mannitol in the composition at about 10% to about 12%, about 10% to about 14%, about 10% to about 16%, about 10% to about 18%, about 10% to about 20%, about 12% to about 14%, about 12% to about 16%, about 12% to about 18%, about 12% to about 20%, about 14% to about 16%, about 14% to about 18%, about 14% to about 20%, about 16% to about 18%, about 16% to about 20%, or about 18% to about 20%. In some embodiments, the carrier comprises mannitol in the composition at about 10%, about 12%, about 14%, about 16%, about 18%, or about 20%. In some embodiments, the carrier comprises mannitol in the composition at least about 10%, about 12%, about 14%, about 16%, or about 18%. In some embodiments, the carrier comprises mannitol in the composition at most about 12%, about 14%, about 16%, about 18%, or about 20%.

Other embodiments are also possible. While only specific neutralizing agents, food grade acids and food grade bases have been mentioned herein, other neutralizing agents, food grade acids and food grade bases may be used.

In some embodiments, the excipient is a carrier, a flowability agent, a preservative or any combination selected therefrom. The amount of excipient in the composition will vary depending on the desired amount of the psychoactive alkaloid extract in the composition, and on the concentration of psychoactive alkaloids in the extract. It will also depend on the degree of flowability required and the stability required.

In some embodiments, the excipients include a flowability agent, in an amount up to 2% by weight of the composition. Above 2%, little extra benefit is gained. In other embodiments, the excipients include a flowability agent in a concentration equal to or less than 2% by weight of the composition. In some embodiments, the flowability agent is present in the composition at, by weight, about 0.1% to about 2%. In some embodiments, the flowability agent is present in the composition at, by weight, about 2% to about 1.75%, about 2% to about 1.5%, about 2% to about 1.25%, about 2% to about 1%, about 2% to about 0.75%, about 2% to about 0.5%, about 2% to about 0.25%, about 2% to about 0.1%, about 1.75% to about 1.5%, about 1.75% to about 1.25%, about 1.75% to about 1%, about 1.75% to about 0.75%, about 1.75% to about 0.5%, about 1.75% to about 0.25%, about 1.75% to about 0.1%, about 1.5% to about 1.25%, about 1.5% to about 1%, about 1.5% to about 0.75%, about 1.5% to about 0.5%, about 1.5% to about 0.25%, about 1.5% to about 0.1%, about 1.25% to about 1%, about 1.25% to about 0.75%, about 1.25% to about 0.5%, about 1.25% to about 0.25%, about 1.25% to about 0.1%, about 1% to about 0.75%, about 1% to about 0.5%, about 1% to about 0.25%, about 1% to about 0.1%, about 0.75% to about 0.5%, about 0.75% to about 0.25%, about 0.75% to about 0.1%, about 0.5% to about 0.25%, about 0.5% to about 0.1%, or about 0.25% to about 0.1%. In some embodiments, the flowability agent is present in the composition at, by weight, about 2%, about 1.75%, about 1.5%, about 1.25%, about 1%, about 0.75%, about 0.5%, about 0.25%, or about 0.1%. In some embodiments, the flowability agent is present in the composition at, by weight, at least about 2%, about 1.75%, about 1.5%, about 1.25%, about 1%, about 0.75%, about 0.5%, or about 0.25%. In some embodiments, the flowability agent is present in the composition at, by weight, at most about 1.75%, about 1.5%, about 1.25%, about 1%, about 0.75%, about 0.5%, about 0.25%, or about 0.1%.

In some embodiments, the flowability agent is silicon dioxide. In other embodiments, the flowability agent is magnesium stearate, stearic acid or talc, or is selected from any other known, suitable flowability agent. A combination of any of these flowability agents may be used. It is also envisaged that other flowability agents can be used. The impurities present in the extract tend to have a negative effect on the flowability, and flow agents are added to counter these effects. While there are known methods of measuring flowability, this is not always necessary as the product's lack of adequate flowability is often very evident when one handles the product.

In some embodiments, the excipients include a carrier, in an amount up to 94% by weight of the composition. In some embodiments, the excipients include a carrier ranging from 10-94% by weight of the composition. In some embodiments, the carrier is present in the composition at, by weight, about 10% to about 94%. In some embodiments, the carrier is present in the composition at, by weight, about 10% to about 20%, about 10% to about 30%, about 10% to about 40%, about 10% to about 50%, about 10% to about 60%, about 10% to about 70%, about 10% to about 80%, about 10% to about 90%, about 10% to about 94%, about 20% to about 30%, about 20% to about 40%, about 20% to about 50%, about 20% to about 60%, about 20% to about 70%, about 20% to about 80%, about 20% to about 90%, about 20% to about 94%, about 30% to about 40%, about 30% to about 50%, about 30% to about 60%, about 30% to about 70%, about 30% to about 80%, about 30% to about 90%, about 30% to about 94%, about 40% to about 50%, about 40% to about 60%, about 40% to about 70%, about 40% to about 80%, about 40% to about 90%, about 40% to about 94%, about 50% to about 60%, about 50% to about 70%, about 50% to about 80%, about 50% to about 90%, about 50% to about 94%, about 60% to about 70%, about 60% to about 80%, about 60% to about 90%, about 60% to about 94%, about 70% to about 80%, about 70% to about 90%, about 70% to about 94%, about 80% to about 90%, about 80% to about 94%, or about 90% to about 94%. In some embodiments, the carrier is present in the composition at, by weight, about 10%, about 20%, about 30%, about 40%, about 50%, about 60%, about 70%, about 80%, about 90%, or about 94%. In some embodiments, the carrier is present in the composition at, by weight, at least about 10%, about 20%, about 30%, about 40%, about 50%, about 60%, about 70%, about 80%, or about 90%. In some embodiments, the carrier is present in the composition at, by weight, at most about 20%, about 30%, about 40%, about 50%, about 60%, about 70%, about 80%, about 90%, or about 94%.

In some embodiments, the carrier is mannitol, maltodextrin, or in other embodiments it is microcrystalline cellulose, coconut flour or corn starch, or any other known, suitable carrier. A combination of any of these carriers may be used. It is also envisaged that other carriers can be used.

The preservative is selected from ascorbic acid, citric acid, lactose, vitamin A, vitamin E, retinyl palmitate, selenium, sodium citrate, sodium ascorbate, calcium ascorbate, sodium benzoate, and potassium benzoate. A combination of any of these preservatives may be used. It is also envisaged that other preservatives can be used.

In some embodiments, the excipients include a preservative, up to 10% by weight of the composition. In some embodiments, preservatives are not added to the composition. There may be cases where a preservative is not required, or not wanted in the final product, and the concentration of preservative will be 0%. At a certain point (>10% in this example), the preservative will not give any further benefit, and so the upper limit of preservative is 10%. In some embodiments, the preservatives are present in the composition at, by weight, about 0.1% to about 10%. In some embodiments, the preservatives are present in the composition at, by weight, about 10% to about 9%, about 10% to about 8%, about 10% to about 7%, about 10% to about 6%, about 10% to about 5%, about 10% to about 4%, about 10% to about 3%, about 10% to about 2%, about 10% to about 1%, about 10% to about 0.5%, about 10% to about 0.1%, about 9% to about 8%, about 9% to about 7%, about 9% to about 6%, about 9% to about 5%, about 9% to about 4%, about 9% to about 3%, about 9% to about 2%, about 9% to about 1%, about 9% to about 0.5%, about 9% to about 0.1%, about 8% to about 7%, about 8% to about 6%, about 8% to about 5%, about 8% to about 4%, about 8% to about 3%, about 8% to about 2%, about 8% to about 1%, about 8% to about 0.5%, about 8% to about 0.1%, about 7% to about 6%, about 7% to about 5%, about 7% to about 4%, about 7% to about 3%, about 7% to about 2%, about 7% to about 1%, about 7% to about 0.5%, about 7% to about 0.1%, about 6% to about 5%, about 6% to about 4%, about 6% to about 3%, about 6% to about 2%, about 6% to about 1%, about 6% to about 0.5%, about 6% to about 0.1%, about 5% to about 4%, about 5% to about 3%, about 5% to about 2%, about 5% to about 1%, about 5% to about 0.5%, about 5% to about 0.1%, about 4% to about 3%, about 4% to about 2%, about 4% to about 1%, about 4% to about 0.5%, about 4% to about 0.1%, about 3% to about 2%, about 3% to about 1%, about 3% to about 0.5%, about 3% to about 0.1%, about 2% to about 1%, about 2% to about 0.5%, about 2% to about 0.1%, about 1% to about 0.5%, about 1% to about 0.1%, or about 0.5% to about 0.1%. In some embodiments, the preservatives are present in the composition at, by weight, about 10%, about 9%, about 8%, about 7%, about 6%, about 5%, about 4%, about 3%, about 2%, about 1%, about 0.5%, or about 0.1%. In some embodiments, the preservatives are present in the composition at, by weight, at least about 10%, about 9%, about 8%, about 7%, about 6%, about 5%, about 4%, about 3%, about 2%, about 1%, or about 0.5%. In some embodiments, the preservatives are present in the composition at, by weight, at most about 9%, about 8%, about 7%, about 6%, about 5%, about 4%, about 3%, about 2%, about 1%, about 0.5%, or about 0.1%.

In some embodiments, a psychoactive alkaloid composition comprises one or more preservatives up to 10%.

In some embodiments, a first preservative of the one or more preservatives is present in the composition from about 0.1% to about 3%. In some embodiments, a first preservative of the one or more preservatives is present in the composition from about 0.1% to about 0.5%, about 0.1% to about 0.9%, about 0.1% to about 1.3%, about 0.1% to about 1.7%, about 0.1% to about 2.1%, about 0.1% to about 2.4%, about 0.1% to about 2.7%, about 0.1% to about 3%, about 0.5% to about 0.9%, about 0.5% to about 1.3%, about 0.5% to about 1.7%, about 0.5% to about 2.1%, about 0.5% to about 2.4%, about 0.5% to about 2.7%, about 0.5% to about 3%, about 0.9% to about 1.3%, about 0.9% to about 1.7%, about 0.9% to about 2.1%, about 0.9% to about 2.4%, about 0.9% to about 2.7%, about 0.9% to about 3%, about 1.3% to about 1.7%, about 1.3% to about 2.1%, about 1.3% to about 2.4%, about 1.3% to about 2.7%, about 1.3% to about 3%, about 1.7% to about 2.1%, about 1.7% to about 2.4%, about 1.7% to about 2.7%, about 1.7% to about 3%, about 2.1% to about 2.4%, about 2.1% to about 2.7%, about 2.1% to about 3%, about 2.4% to about 2.7%, about 2.4% to about 3%, or about 2.7% to about 3%. In some embodiments, a first preservative of the one or more preservatives is present in the composition from about 0.1%, about 0.5%, about 0.9%, about 1.3%, about 1.7%, about 2.1%, about 2.4%, about 2.7%, or about 3%. In some embodiments, a first preservative of the one or more preservatives is present in the composition from at least about 0.1%, about 0.5%, about 0.9%, about 1.3%, about 1.7%, about 2.1%, about 2.4%, or about 2.7%. In some embodiments, a first preservative of the one or more preservatives is present in the composition from at most about 0.5%, about 0.9%, about 1.3%, about 1.7%, about 2.1%, about 2.4%, about 2.7%, or about 3%.

In some embodiments, a first preservative of the one or more preservatives is present in the composition from about 0.1% to about 2%. In some embodiments, a first preservative of the one or more preservatives is present in the composition from about 0.1% to about 0.3%, about 0.1% to about 0.5%, about 0.1% to about 0.7%, about 0.1% to about 0.9%, about 0.1% to about 1.1%, about 0.1% to about 1.3%, about 0.1% to about 1.5%, about 0.1% to about 1.7%, about 0.1% to about 2%, about 0.3% to about 0.5%, about 0.3% to about 0.7%, about 0.3% to about 0.9%, about 0.3% to about 1.1%, about 0.3% to about 1.3%, about 0.3% to about 1.5%, about 0.3% to about 1.7%, about 0.3% to about 2%, about 0.5% to about 0.7%, about 0.5% to about 0.9%, about 0.5% to about 1.1%, about 0.5% to about 1.3%, about 0.5% to about 1.5%, about 0.5% to about 1.7%, about 0.5% to about 2%, about 0.7% to about 0.9%, about 0.7% to about 1.1%, about 0.7% to about 1.3%, about 0.7% to about 1.5%, about 0.7% to about 1.7%, about 0.7% to about 2%, about 0.9% to about 1.1%, about 0.9% to about 1.3%, about 0.9% to about 1.5%, about 0.9% to about 1.7%, about 0.9% to about 2%, about 1.1% to about 1.3%, about 1.1% to about 1.5%, about 1.1% to about 1.7%, about 1.1% to about 2%, about 1.3% to about 1.5%, about 1.3% to about 1.7%, about 1.3% to about 2%, about 1.5% to about 1.7%, about 1.5% to about 2%, or about 1.7% to about 2%. In some embodiments, a first preservative of the one or more preservatives is present in the composition from about 0.1%, about 0.3%, about 0.5%, about 0.7%, about 0.9%, about 1.1%, about 1.3%, about 1.5%, about 1.7%, or about 2%. In some embodiments, a first preservative of the one or more preservatives is present in the composition from at least about 0.1%, about 0.3%, about 0.5%, about 0.7%, about 0.9%, about 1.1%, about 1.3%, about 1.5%, or about 1.7%. In some embodiments, a first preservative of the one or more preservatives is present in the composition from at most about 0.3%, about 0.5%, about 0.7%, about 0.9%, about 1.1%, about 1.3%, about 1.5%, about 1.7%, or about 2%.

In some embodiments, a second preservative of the one or more preservatives is present in the composition from about 0.1% to about 2%. In some embodiments, a second preservative of the one or more preservatives is present in the composition from about 0.1% to about 0.3%, about 0.1% to about 0.5%, about 0.1% to about 0.7%, about 0.1% to about 0.9%, about 0.1% to about 1.1%, about 0.1% to about 1.3%, about 0.1% to about 1.5%, about 0.1% to about 1.7%, about 0.1% to about 2%, about 0.3% to about 0.5%, about 0.3% to about 0.7%, about 0.3% to about 0.9%, about 0.3% to about 1.1%, about 0.3% to about 1.3%, about 0.3% to about 1.5%, about 0.3% to about 1.7%, about 0.3% to about 2%, about 0.5% to about 0.7%, about 0.5% to about 0.9%, about 0.5% to about 1.1%, about 0.5% to about 1.3%, about 0.5% to about 1.5%, about 0.5% to about 1.7%, about 0.5% to about 2%, about 0.7% to about 0.9%, about 0.7% to about 1.1%, about 0.7% to about 1.3%, about 0.7% to about 1.5%, about 0.7% to about 1.7%, about 0.7% to about 2%, about 0.9% to about 1.1%, about 0.9% to about 1.3%, about 0.9% to about 1.5%, about 0.9% to about 1.7%, about 0.9% to about 2%, about 1.1% to about 1.3%, about 1.1% to about 1.5%, about 1.1% to about 1.7%, about 1.1% to about 2%, about 1.3% to about 1.5%, about 1.3% to about 1.7%, about 1.3% to about 2%, about 1.5% to about 1.7%, about 1.5% to about 2%, or about 1.7% to about 2%. In some embodiments, a second preservative of the one or more preservatives is present in the composition from about 0.1%, about 0.3%, about 0.5%, about 0.7%, about 0.9%, about 1.1%, about 1.3%, about 1.5%, about 1.7%, or about 2%. In some embodiments, a second preservative of the one or more preservatives is present in the composition from at least about 0.1%, about 0.3%, about 0.5%, about 0.7%, about 0.9%, about 1.1%, about 1.3%, about 1.5%, or about 1.7%. In some embodiments, a second preservative of the one or more preservatives is present in the composition from at most about 0.3%, about 0.5%, about 0.7%, about 0.9%, about 1.1%, about 1.3%, about 1.5%, about 1.7%, or about 2%.

The main consideration is that, depending on the source material's concentration and the efficiency of the extraction, the concentration of the extract needs to be blended down to the required value of standardization. This dictates the amount of excipient for each batch, which may be different. Therefore, the amount of excipient that can be added can be anywhere between say 0.100% to 99.9%, depending on the source concentration before blending. The other excipient components may be held relatively constant between batches, or within a much narrower range (i.e., 0-2% flowability agent, 0-10% preservative, 0-0.5% antioxidant, or 0-0.5% bioavailability agent).

C. Apparatus

Figure 8:
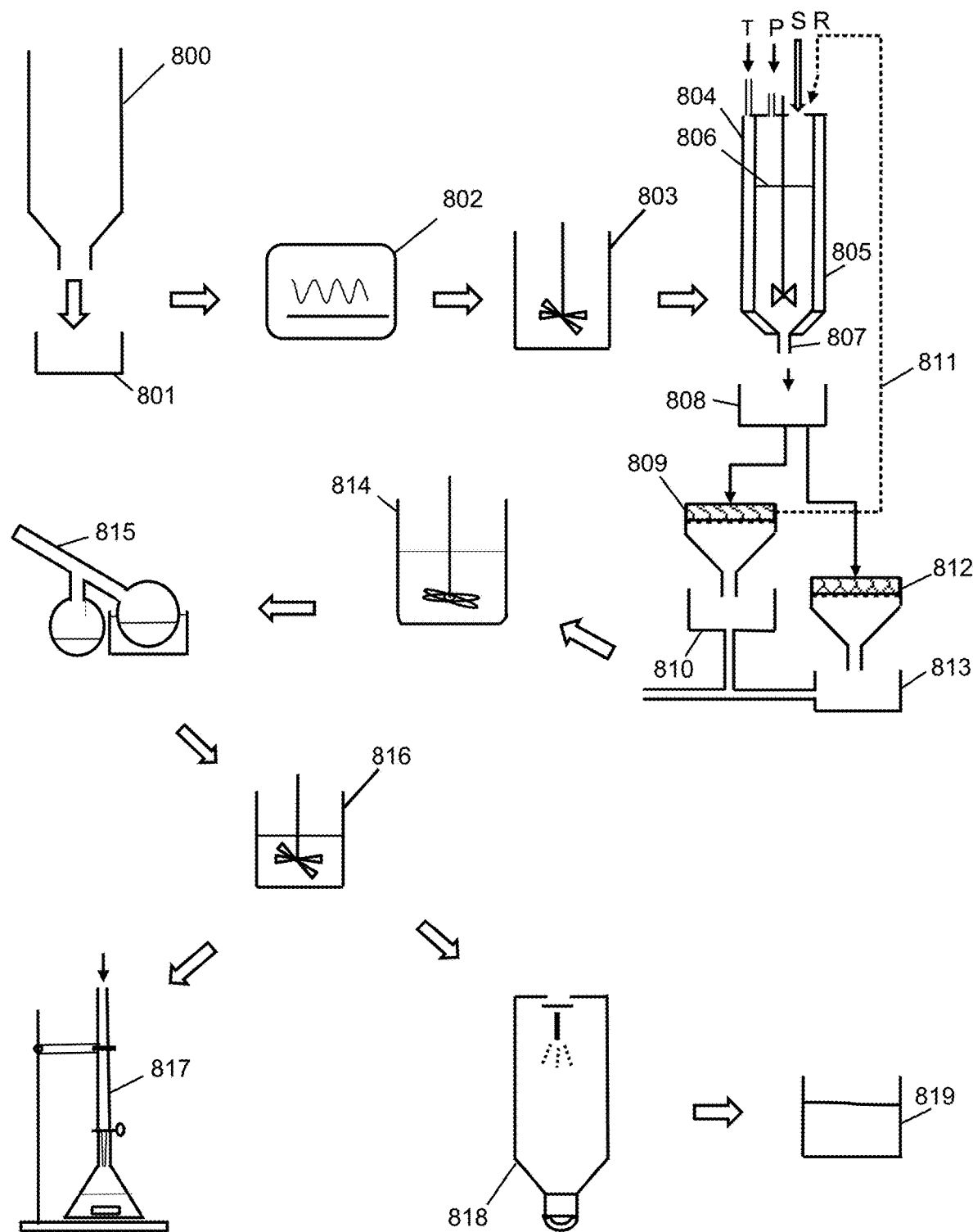
FIG. 8 is a schematic diagram of the apparatus used for the extraction of psychoactive compounds according to an embodiment of the present invention.

Referring to FIG. 8, an example of the apparatus is shown schematically. Raw psilocybin mushrooms are provided in a hopper 800, for example, and are released in batches into container 801. The raw fungal material is then dried in a forced air oven 802. The dried biomass is placed into a grinder 803 for grinding.

After the drying and grinding steps, the ground biomass is placed in an agitated, heat-controlled extraction vessel 805. The vessel holds the biomass and solvent 806, such as lower aliphatic alcohols, water, buffered acid or buffered alkaline, or a mixture thereof. The vessel may be surrounded by an insulating wall 804. Alternately, there may be an insulating jacket wrapped around the vessel. The insulating wall 804 or jacket helps to maintain the contents 806 under a constant temperature (T) between 5-95° C. The pressure (P) inside the extraction vessel 805 may be regulated up to 100 MPa (15000 psig).

After the extraction, the bottom of the extraction vessel 805 is opened at outlet 807, and the extraction slurry is collected in container 808. The extraction slurry is then fed into filter 809. After filtration, the first filtrate leaves the filter 809 and is collected in container 810. The first filtrate residue 811 is then fed back at R into agitated, heat-controlled vessel 805 and more solvent (S) is added. After the second extraction, the extraction slurry is collected in container 808 and is then fed into filter 812 (or filter 809). After filtration, the second filtrate and solvent mixture leaves the filter 812 and is collected in container 813.

After the two filtration stages, if there are two, the filtrates are mixed in container 814. Otherwise, if there is only a single filtration step, mixing is unnecessary. Neutralizer is added as necessary to the filtrate in container 814. The extraction slurry, pH-adjusted where necessary, is then passed to rotary evaporator 815 in which all or part of the solvent is evaporated, depending on the embodiment. If all the solvent is evaporated, then reverse osmosis water is added to the solids remaining after the evaporation.

The concentrated slurry is then passed to container 816 and tested to determine its alkaloid content, using a titration setup 817. Carriers are added to container 816 with the concentrated slurry, and mixed. The standardized slurry is then placed in a bench-top spray drier 818 to produce psilocybin mushroom extract that is collected in container 819.

Figure 13:
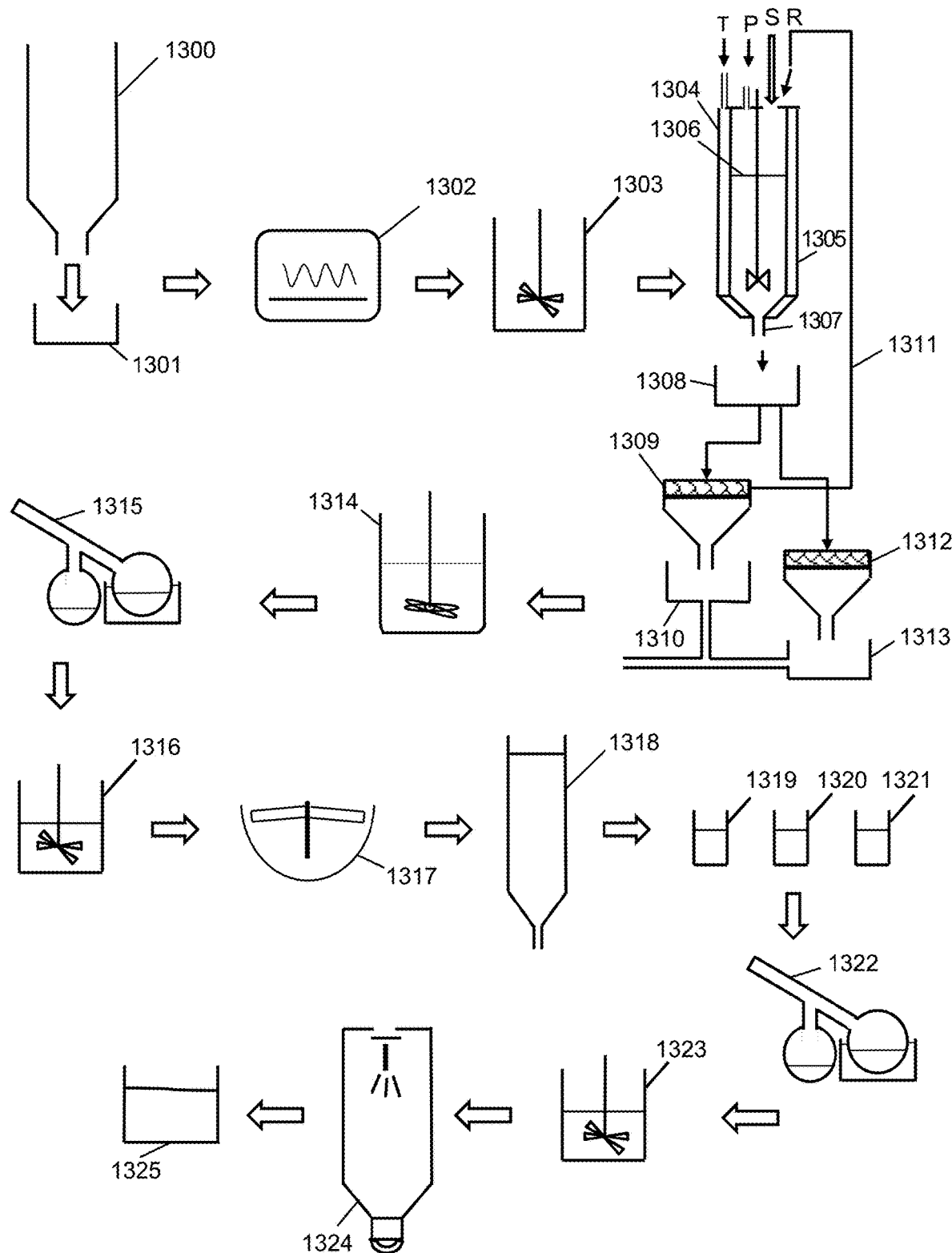
FIG. 13 is a schematic diagram of an apparatus used for obtaining a purified psychoactive alkaloid solution and standardizing the same to result in a standardized psychoactive alkaloid extract, according to an embodiment of the present invention.

Referring to FIG. 13, an example of the apparatus is shown schematically. Raw *Psilocybe cubensis* mushrooms are added to a hopper 1300 and then released in batches into container 1301. The raw fungal material is then dried in a forced air oven 1302 to result in dried biomass. The dried biomass is placed into a grinder 1303 for grinding.

The dried powdered biomass is placed into a heat-controlled vessel 1305, and solvent (S) is added to the heat-controlled vessel. The vessel 1305 is surrounded by an insulating wall 1304. Alternately, an insulating jacket may be wrapped around the vessel. The insulating wall 1304 or jacket helps to maintain the contents 1306 under a constant temperature (T) between 5-95° C. The pressure (P) inside the extraction vessel 1305 may be regulated up to 100 MPa (15,000 psig).

After the extraction, the bottom of the extraction vessel 1305 was opened at outlet 1307 and the extraction slurry was collected in a container 1308. The extraction slurry was then fed into a filter 1309 and a first filtrate was collected in container 1310. The first filtrate residue 1311 was then fed back (R) into the agitated, heat-controlled vessel 1305 and more solvent (S) was added for a second extraction. After the second extraction, the extraction slurry was collected in the container 1308 and was then fed into a filter 1312. After filtration, the obtained second filtrate was collected in container 1313.

After the two filtration stages, the filtrates were mixed in container 1314 to obtain a bulk filtrate. In other embodiments, if there is only a single filtration step, this mixing step is not required.

The bulk filtrate is placed in a rotary evaporator 1315, and part of the solvent is evaporated from the bulk filtrate. The resultant extract is transferred to a container 1316, where the pH of the extract is adjusted, followed by centrifugation 1317 to remove the solid precipitates. The resultant supernatant is loaded onto a column 1318 of resin. An initial wash is given to the column with a solvent to remove impurities from the resin, and fraction 1319 is collected. A second wash is given to the column with another solvent to elute the psychoactive alkaloids from the column and results in fraction 1320. A final wash is given to the column with another solvent to wash any impurities from the column and to prepare the column for use again, and the fraction 1321 is obtained. The elution fraction 1320 with the psychoactive alkaloids is then concentrated in a rotary evaporator 1322 to result in the purified psychoactive alkaloid solution.

In a container 1323 the purified psychoactive alkaloid solution and desired excipients are added together and thoroughly mixed to result in a final standardized slurry having a specified concentration of alkaloids. The final standardized slurry is then subjected to spray-drying 1324 to obtain a final powdered alkaloid extract 1325 with a total psilocybin/psilocin concentration defined as a percentage to two decimal places or two significant figures by dry weight.

In other embodiments, parts of the apparatus may be reused or duplicated. For example, if desired, the elution fraction 1320 may be reloaded into the container 1316 for pH adjustment, and the steps from thereon can be repeated to allow for further purification of the obtained purified psychoactive alkaloid solution.

Referring to FIG. 17, an example of the apparatus is shown schematically. Raw *Psilocybe cubensis* mushrooms are added to a hopper 1700 and released in batches into container 1701. The raw fungal material is then dried in a forced air oven 1702 to result in dried biomass. The dried biomass is placed into a grinder 1703 for grinding.

The dried powdered biomass is placed into a heat-controlled vessel 1705, and solvent (S) is added to the heat-controlled vessel. The vessel 1705 is surrounded by an insulating wall 1704. Alternately, an insulating jacket can be wrapped around the vessel. The insulating wall 1704 or jacket helps to maintain the contents 1706 under a constant temperature (T) between 5-95° C. The pressure (P) inside the extraction vessel 1705 may be regulated up to 100 MPa (15,000 psig).

After the extraction, the bottom of the extraction vessel 1705 is opened at outlet 1707 and the extraction slurry is collected in a container 1708. The extraction slurry is then fed into a filter 1709, and a first filtrate is collected in container 1710. The first filtrate residue 1711 is then fed back (R) into the agitated, heat-controlled vessel 1705, and more solvent (S) is added for a second extraction. After the second extraction, the extraction slurry is collected in the container 1708 and is then fed into a filter 1712. After filtration, the obtained second filtrate is collected in container 1713.

After the two filtration stages, the filtrates are mixed in container 1714 to obtain a bulk filtrate. In other embodiments, if there is only a single filtration step, this mixing step is not required.

The bulk filtrate was placed in a rotary evaporator 1715, and part of the solvent is evaporated from the bulk filtrate. The resultant extract is transferred to a container 1716, where the pH of the extract is adjusted, followed by centrifugation 1717 to remove the solid precipitates. The resultant supernatant is loaded onto a column 1718 of resin. An initial wash is given to the column with a solvent to remove impurities from the resin, and fraction 1719 is collected. A second wash is given to the column with another solvent to elute the psychoactive alkaloids from the column and result in fraction 1720. A final wash is given to the column with another solvent to wash any impurities from the column and to prepare the column for use again, and the fraction 1721 was obtained. The elution fraction 1720 with the psychoactive alkaloids is then concentrated in a rotary evaporator 1722 to result in the purified psychoactive alkaloid extract.

In a container 1723 the purified psychoactive alkaloid extract and desired excipients are added together and thoroughly mixed to result in a final standardized slurry having a specific amount of alkaloids. The final standardized slurry is then subjected to spray-drying 1724 to obtain a final powdered composition 1725 with a total psilocybin/psilocin concentration defined as a percentage to two decimal places or two significant figures by dry weight.

In other embodiments, parts of the apparatus may be reused or duplicated. For example, if desired, the elution fraction 1720 may be reloaded into the container 1716 for pH adjustment, and the steps from thereon can be repeated to allow for further purification of the obtained purified psychoactive alkaloid extract.

In one embodiment, the psychoactive alkaloid extract is obtained after evaporating the solvent from the bulk filtrate. The psychoactive alkaloid extract is transferred to a container 1723, and desired excipients are added together, and thoroughly mixed to result in a final standardized slurry having a specific amount of alkaloids. The final standardized slurry is then subjected to spray-drying 1724 to obtain a final powdered composition 1725 with a total psilocybin/psilocin concentration defined as a percentage to two decimal places or two significant figures by dry weight.

Referring to FIG. 23, an example of the apparatus is shown schematically. Raw *Psilocybe cubensis* mushrooms are added to a hopper 2300 and then released in batches into container 2301. The raw fungal material is then dried in a forced air oven 2302 to result in the dried biomass. The dried biomass is placed into a grinder 2303 for grinding to result in dried powdered biomass.

The dried powdered biomass is placed into a heat-controlled vessel 2305, and acidified/basified solvent (S) is added to the vessel to obtain a specific pH (lower than 3.5 or greater than 10.5). The vessel 2305 is surrounded by an insulating wall 2304. Alternately, an insulating jacket may be wrapped around the vessel. The insulating wall 108 or jacket helps to maintain the contents 2306 under a constant temperature (T) between 5-95° C. The pressure (P) inside the extraction vessel 2305 may be regulated from 7 to 20,000 psi. The extraction is performed with a solvent to solid (dried powdered biomass) proportion in the range of 1 L:1 kg to 50 L:1 kg.

After the extraction, the bottom of the extraction vessel 2305 is opened at outlet 2307, and the extraction slurry is collected in a container 2308. The extraction slurry is then fed into a filter 2309, and a first filtrate is collected in container 2310. The first filtrate residue 2311 is then fed back (R) into the agitated, heat-controlled vessel 2305, and more solvent (S) is added for a second extraction. After the second extraction, the extraction slurry is collected in the container 2308 and then fed into a filter 2312. After filtration, the obtained second filtrate is collected in container 2313.

After the two filtration stages, the filtrates are mixed in container 2314 to obtain a mixed filtrate, i.e., the psychoactive alkaloid liquid. In other embodiments, if there is only a single filtration step, this mixing step is not required. By adding an acid or a base, the pH of the psychoactive alkaloid liquid is brought to a pH ranging from 3.5-4.5.

The pH-adjusted, mixed filtrate is then placed in a rotary evaporator 2315, and part of the solvent is evaporated from the mixed filtrate to form the psychoactive alkaloid extract, which is here a slurry.

For obtaining the psychoactive alkaloid composition, the evaporation in the rotary evaporator 2315 is stopped after a desired portion of solvent is evaporated. The resultant slurry is transferred to a container 2316 where a measured quantity of one or more excipients is added to obtain a standardized slurry. The obtained standardized slurry is dried in a freeze dryer 2317 to obtain the psychoactive alkaloid composition.

In other embodiments, parts of the apparatus may be reused or duplicated. For example, if desired, for further extraction, the filtrate residue may be reloaded into the extraction vessel 2305, and the obtained filtrate can be added to mixed filtrate container of 2314, and the steps from thereon can be repeated to obtain the psychoactive alkaloid extract.

D. Extraction

Extraction Process 1

Referring to FIG. 1, a flowchart is shown of the basic steps of the extraction process for extracting psychoactive compounds from psychedelic fungus. In step 100, a solvent is added to a biomass of dried and ground, raw psychedelic fungus. The raw psychedelic fungus includes psilocybin fungi, including *Psilocybe cubensis* mushrooms, *Psilocybe cyanescens* mushrooms, *Amanita muscaria* mushrooms or a mixture of these. Other species of psychedelic mushrooms may also be used.

The parts of the mushrooms used include, for example, caps, gills, stems, and hyphae, and more particularly, any part of the psilocybin mushroom or mycelium can be included. In other cases, the raw psychedelic fungus parts used include only caps, or only stems, or only gills, or only hyphae or only mycelium or any mixture thereof. In still other cases, parts of the raw psychedelic fungus used are those that would normally be considered waste, in which valuable psychoactive compounds are found only in lower concentrations. The mushroom parts may be ground using a milling machine or pulverization device, for example.

Ideally, the moisture content of the raw plant material after drying is low compared to the total dried biomass weight. For example, the moisture content may be under 5% for smaller scale extractions and under 10% for larger scale extractions. Wet mushrooms, e.g. with a moisture above 80%, may degrade rapidly. Dried biomass lends itself well to extraction since the drying process usually breaks down cell walls, allowing solvent to capture the molecules inside. The temperature of the oven and the drying time depend on how much moisture is in the raw psychedelic fungus, and on the quantity of raw psychedelic fungus.

The solvent may be selected from a range of different solvents, including lower aliphatic alcohols (C=1, 2, 3 or 4), water, alcohol-water mixtures, strong alkaline buffers, and strong acidic buffers. A wide range of solvent to solid ratios can be used. Typically, a 1 to 50:1 solvent-solid ratio (L:kg) may be used for the extraction. The amount of solvent used generally varies according to the weight of the raw psychedelic fungus.

In step 110, as a result of adding the solvent and soaking the biomass of dried, raw psychedelic fungus in the solvent, essential elements or psychoactive alkaloids found in the biomass, dissolve into the solvent. The solvent may be at a low or high temperature, and pressure may be applied to the solvent. In some embodiments the solvent is at room temperature. The optimal temperature of extraction varies depending on the solvent type used for the process. However, the optimal temperature for extraction is in range of 5-95° C. The useful temperature range spans most of the liquid state of the solvent used, and upper and lower limits are determined by physical practicalities and limits of the available apparatus. Still, the temperature of the solvent may be outside of this range in other embodiments. The duration of the extraction is from 10 minutes to 12 hours, with or without agitation. Optimum duration is determined by experimentation and depends on the chosen solvent and the strength of agitation in the extraction vessel.

If pressure is applied, it may be in the range of 50 kPa-100 MPa above atmospheric (7-15000 psig). The lower limit of pressure is indicative of when a benefit is seen in the rate at which the psychoactive alkaloids dissolve in the solvent, since the increased pressure may increase the reaction kinetics of the dissolution of the psychoactive alkaloids into the solvent. The upper limit is determined by what is physically practical given the constraints of equipment to safely operate under high pressure. Nevertheless, other pressures may be used. Solvent composition, particle size, and extraction temperature may determine how much pressure needs to be applied.

In some embodiments, the biomass of the psychoactive organism is reduced to a particle size of 6 millimeters (mm) to 0.03 mm prior to contacting with the solvent. In some embodiments, prior to contacting with the solvent, the biomass of the psychoactive organism is reduced to a particle size of about 0.03 mm to about 6 mm. In some embodiments, prior to contacting with the solvent, the biomass of the psychoactive organism is reduced to a particle size of about 6 mm to about 5 mm, about 6 mm to about 4 mm, about 6 mm to about 3 mm, about 6 mm to about 2 mm, about 6 mm to about 1 mm, about 6 mm to about 0.5 mm, about 6 mm to about 0.1 mm, about 6 mm to about 0.05 mm, about 6 mm to about 0.03 mm, about 5 mm to about 4 mm, about 5 mm to about 3 mm, about 5 mm to about 2 mm, about 5 mm to about 1 mm, about 5 mm to about 0.5 mm, about 5 mm to about 0.1 mm, about 5 mm to about 0.05 mm, about 5 mm to about 0.03 mm, about 4 mm to about 3 mm, about 4 mm to about 2 mm, about 4 mm to about 1 mm, about 4 mm to about 0.5 mm, about 4 mm to about 0.1 mm, about 4 mm to about 0.05 mm, about 4 mm to about 0.03 mm, about 3 mm to about 2 mm, about 3 mm to about 1 mm, about 3 mm to about 0.5 mm, about 3 mm to about 0.1 mm, about 3 mm to about 0.05 mm, about 3 mm to about 0.03 mm, about 2 mm to about 1 mm, about 2 mm to about 0.5 mm, about 2 mm to about 0.1 mm, about 2 mm to about 0.05 mm, about 2 mm to about 0.03 mm, about 1 mm to about 0.5 mm, about 1 mm to about 0.1 mm, about 1 mm to about 0.05 mm, about 1 mm to about 0.03 mm, about 0.5 mm to about 0.1 mm, about 0.5 mm to about 0.05 mm, about 0.5 mm to about 0.03 mm, about 0.1 mm to about 0.05 mm, about 0.1 mm to about 0.03 mm, or about 0.05 mm to about 0.03 mm. In some embodiments, prior to contacting with the solvent, the biomass of the psychoactive organism is reduced to a particle size of about 6 mm, about 5 mm, about 4 mm, about 3 mm, about 2 mm, about 1 mm, about 0.5 mm, about 0.1 mm, about 0.05 mm, or about 0.03 mm. In some embodiments, prior to contacting with the solvent, the biomass of the psychoactive organism is reduced to a particle size of at least about 6 mm, about 5 mm, about 4 mm, about 3 mm, about 2 mm, about 1 mm, about 0.5 mm, about 0.1 mm, or about 0.05 mm. In some embodiments, prior to contacting with the solvent, the biomass of the psychoactive organism is reduced to a particle size of at most about 5 mm, about 4 mm, about 3 mm, about 2 mm, about 1 mm, about 0.5 mm, about 0.1 mm, about 0.05 mm, or about 0.03 mm.

In some embodiments, the biomass of the psychoactive organism is reduced to a particle size of 1 millimeters (mm) to 0.03 mm prior to contacting with the solvent. In some embodiments, prior to contacting with the solvent, the biomass of the psychoactive organism is reduced to a particle size of about 0.03 mm to about 1 mm. In some embodiments, prior to contacting with the solvent, the biomass of the psychoactive organism is reduced to a particle size of about 1 mm to about 0.9 mm, about 1 mm to about 0.8 mm, about 1 mm to about 0.7 mm, about 1 mm to about 0.6 mm, about 1 mm to about 0.5 mm, about 1 mm to about 0.4 mm, about 1 mm to about 0.3 mm, about 1 mm to about 0.2 mm, about 1 mm to about 0.1 mm, about 1 mm to about 0.05 mm, about 1 mm to about 0.03 mm, about 0.9 mm to about 0.8 mm, about 0.9 mm to about 0.7 mm, about 0.9 mm to about 0.6 mm, about 0.9 mm to about 0.5 mm, about 0.9 mm to about 0.4 mm, about 0.9 mm to about 0.3 mm, about 0.9 mm to about 0.2 mm, about 0.9 mm to about 0.1 mm, about 0.9 mm to about 0.05 mm, about 0.9 mm to about 0.03 mm, about 0.8 mm to about 0.7 mm, about 0.8 mm to about 0.6 mm, about 0.8 mm to about 0.5 mm, about 0.8 mm to about 0.4 mm, about 0.8 mm to about 0.3 mm, about 0.8 mm to about 0.2 mm, about 0.8 mm to about 0.1 mm, about 0.8 mm to about 0.05 mm, about 0.8 mm to about 0.03 mm, about 0.7 mm to about 0.6 mm, about 0.7 mm to about 0.5 mm, about 0.7 mm to about 0.4 mm, about 0.7 mm to about 0.3 mm, about 0.7 mm to about 0.2 mm, about 0.7 mm to about 0.1 mm, about 0.7 mm to about 0.05 mm, about 0.7 mm to about 0.03 mm, about 0.6 mm to about 0.5 mm, about 0.6 mm to about 0.4 mm, about 0.6 mm to about 0.3 mm, about 0.6 mm to about 0.2 mm, about 0.6 mm to about 0.1 mm, about 0.6 mm to about 0.05 mm, about 0.6 mm to about 0.03 mm, about 0.5 mm to about 0.4 mm, about 0.5 mm to about 0.3 mm, about 0.5 mm to about 0.2 mm, about 0.5 mm to about 0.1 mm, about 0.5 mm to about 0.05 mm, about 0.5 mm to about 0.03 mm, about 0.4 mm to about 0.3 mm, about 0.4 mm to about 0.2 mm, about 0.4 mm to about 0.1 mm, about 0.4 mm to about 0.05 mm, about 0.4 mm to about 0.03 mm, about 0.3 mm to about 0.2 mm, about 0.3 mm to about 0.1 mm, about 0.3 mm to about 0.05 mm, about 0.3 mm to about 0.03 mm, about 0.2 mm to about 0.1 mm, about 0.2 mm to about 0.05 mm, about 0.2 mm to about 0.03 mm, about 0.1 mm to about 0.05 mm, about 0.1 mm to about 0.03 mm, or about 0.05 mm to about 0.03 mm. In some embodiments, prior to contacting with the solvent, the biomass of the psychoactive organism is reduced to a particle size of about 1 mm, about 0.9 mm, about 0.8 mm, about 0.7 mm, about 0.6 mm, about 0.5 mm, about 0.4 mm, about 0.3 mm, about 0.2 mm, about 0.1 mm, about 0.05 mm, or about 0.03 mm. In some embodiments, prior to contacting with the solvent, the biomass of the psychoactive organism is reduced to a particle size of at least about 1 mm, about 0.9 mm, about 0.8 mm, about 0.7 mm, about 0.6 mm, about 0.5 mm, about 0.4 mm, about 0.3 mm, about 0.2 mm, about 0.1 mm, or about 0.05 mm. In some embodiments, prior to contacting with the solvent, the biomass of the psychoactive organism is reduced to a particle size of at most about 0.9 mm, about 0.8 mm, about 0.7 mm, about 0.6 mm, about 0.5 mm, about 0.4 mm, about 0.3 mm, about 0.2 mm, about 0.1 mm, about 0.05 mm, or about 0.03 mm.

In some embodiments, the biomass of the psychoactive organism is reduced to a particle size of at least 0.074 mm prior to contacting with the solvent.

The extraction results in an extraction slurry, which is formed of undissolved and insoluble solids from the mixture of biomass and solvent, which now carries dissolved extract. Some of the undissolved solids may be undesirable components.

In step 120, the extraction slurry is filtered, resulting in a residue (i.e., the undissolved portion of the biomass) and filtrate. The filtering step may be carried out with the extraction slurry still hot, or it may first be allowed to cool. The extraction and filtration steps may be repeated multiple times on the same residue, with a fresh batch of solvent, which may have the same composition as the first solvent, or it may be a different solvent.

In step 130, if the filtrate results from using a strongly acidic or alkaline solvent, then the filtrate is brought closer to neutral, e.g., to a pH between 4 and 9 or thereabouts. Desirable effects, such as more complete extraction, preservation of the alkaloids from decomposition, or the ability to selectively extract certain specific alkaloids, are seen during the extraction stage when stronger acids or alkalis are used compared to weaker ones.

In step 140, evaporation of some or all of the solvent from the filtrate results in a concentrated slurry 150 (liquid and solids) or just solids. If the solvent is methanol, then all of it is evaporated to reduce the likelihood of toxicity. For other solvents, only some of the solvent needs to be evaporated. In the case where solids are obtained from the evaporation, water is added to the solids to form the concentrated slurry 150. The solids tend not to dissolve back into solution because they are less soluble in methanol and ethanol, for example, than water. Also, the solids may be less soluble in the colder water that is added back than the warmer or hotter water that is used for the extraction. Another reason is saturation of the solution or that some of the solids are irreversibly precipitated.

In step 160, standardization of the concentrated slurry takes place. The aim is to stabilize the extract by adding stabilizer (e.g., ascorbic acid and silica), and then titrating with a carrier (e.g., maltodextrin) to result in a known concentration of psychoactive alkaloids. The slurry is analyzed for dry mass concentration and alkaloid content. The liquid component of the concentrated slurry is first analyzed using a loss-on-drying analysis and high-performance liquid chromatography coupled with diode array detection or mass spectrometry to determine the alkaloid content. Depending on the determined alkaloid content, non-toxic carriers are added to the concentrated slurry to provide a desired ratio between the weight of alkaloid and weight of carrier in the concentrated slurry. The added carriers, blending agents, excipients, flow aids, etc., that may be used include maltodextrin from corn, potato, or tapioca, for example, gum arabic, silicon dioxide, microcrystalline cellulose, ascorbic acid, sodium benzoate, sodium phosphate, sodium citrate, rice hulls, and rice. A combination of any of these carriers may be used.

In step 170, the concentrated slurry is dried to remove the remaining solvent or water, resulting in a powdered psilocybin mushroom extract with a known concentration by weight of psychoactive compound(s). The extract is a powdered psilocybin mushroom extract that may have, for example, a total psychoactive alkaloid concentration of 0.1-10% by dry weight. Other compounds may be included in the extract. These may be sugars, proteins, carbohydrates, and fats, and may make up about half of the extract. Step 170 is optional, as it may be the intention to produce a liquid extract instead of a powdered extract.

In some embodiments, the extraction is performed at a temperature ranging from 5-95° C. In some embodiments, the extraction is performed at a temperature ranging from about 5° C. to about 95° C. In some embodiments, the extraction is performed at a temperature ranging from about 5° C. to about 10° C., about 5° C. to about 20° C., about 5° C. to about 30° C., about 5° C. to about 40° C., about 5° C. to about 50° C., about 5° C. to about 60° C., about 5° C. to about 70° C., about 5° C. to about 80° C., about 5° C. to about 90° C., about 5° C. to about 95° C., about 10° C. to about 20° C., about 10° C. to about 30° C., about 10° C. to about 40° C., about 10° C. to about 50° C., about 10° C. to about 60° C., about 10° C. to about 70° C., about 10° C. to about 80° C., about 10° C. to about 90° C., about 10° C. to about 95° C., about 20° C. to about 30° C., about 20° C. to about 40° C., about 20° C. to about 50° C., about 20° C. to about 60° C., about 20° C. to about 70° C., about 20° C. to about 80° C., about 20° C. to about 90° C., about 20° C. to about 95° C., about 30° C. to about 40° C., about 30° C. to about 50° C., about 30° C. to about 60° C., about 30° C. to about 70° C., about 30° C. to about 80° C., about 30° C. to about 90° C., about 30° C. to about 95° C., about 40° C. to about 50° C., about 40° C. to about 60° C., about 40° C. to about 70° C., about 40° C. to about 80° C., about 40° C. to about 90° C., about 40° C. to about 95° C., about 50° C. to about 60° C., about 50° C. to about 70° C., about 50° C. to about 80° C., about 50° C. to about 90° C., about 50° C. to about 95° C., about 60° C. to about 70° C., about 60° C. to about 80° C., about 60° C. to about 90° C., about 60° C. to about 95° C., about 70° C. to about 80° C., about 70° C. to about 90° C., about 70° C. to about 95° C., about 80° C. to about 90° C., about 80° C. to about 95° C., or about 90° C. to about 95° C. In some embodiments, the extraction is performed at a temperature ranging from about 5° C., about 10° C., about 20° C., about 30° C., about 40° C., about 50° C., about 60° C., about 70° C., about 80° C., about 90° C., or about 95° C. In some embodiments, the extraction is performed at a temperature ranging from at least about 5° C., about 10° C., about 20° C., about 30° C., about 40° C., about 50° C., about 60° C., about 70° C., about 80° C., or about 90° C. In some embodiments, the extraction is performed at a temperature ranging from at most about 10° C., about 20° C., about 30° C., about 40° C., about 50° C., about 60° C., about 70° C., about 80° C., about 90° C., or about 95° C.

In other embodiments, the extraction is performed at a temperature ranging from 50-75° C. In some embodiments, the extraction is performed at a temperature ranging from about 50° C. to about 75° C. In some embodiments, the extraction is performed at a temperature ranging from about 50° C. to about 55° C., about 50° C. to about 60° C., about 50° C. to about 65° C., about 50° C. to about 70° C., about 50° C. to about 75° C., about 55° C. to about 60° C., about 55° C. to about 65° C., about 55° C. to about 70° C., about 55° C. to about 75° C., about 60° C. to about 65° C., about 60° C. to about 70° C., about 60° C. to about 75° C., about 65° C. to about 70° C., about 65° C. to about 75° C., or about 70° C. to about 75° C. In some embodiments, the extraction is performed at a temperature ranging from about 50° C., about 55° C., about 60° C., about 65° C., about 70° C., or about 75° C. In some embodiments, the extraction is performed at a temperature ranging from at least about 50° C., about 55° C., about 60° C., about 65° C., or about 70° C. In some embodiments, the extraction is performed at a temperature ranging from at most about 55° C., about 60° C., about 65° C., about 70° C., or about 75° C.

In some embodiments, the extraction is performed for a time period ranging from 10-720 minutes. For most cases, a time below 10 min would result in a mostly incomplete yield, and above 720 min the extraction may be incomplete but would be continuing at a negligible rate. In some embodiments, the extraction is performed for a time period ranging from about 10 min to about 720 min. In some embodiments, the extraction is performed for a time period ranging from about 10 min to about 100 min, about 10 min to about 200 min, about 10 min to about 300 min, about 10 min to about 400 min, about 10 min to about 500 min, about 10 min to about 600 min, about 10 min to about 720 min, about 100 min to about 200 min, about 100 min to about 300 min, about 100 min to about 400 min, about 100 min to about 500 min, about 100 min to about 600 min, about 100 min to about 720 min, about 200 min to about 300 min, about 200 min to about 400 min, about 200 min to about 500 min, about 200 min to about 600 min, about 200 min to about 720 min, about 300 min to about 400 min, about 300 min to about 500 min, about 300 min to about 600 min, about 300 min to about 720 min, about 400 min to about 500 min, about 400 min to about 600 min, about 400 min to about 720 min, about 500 min to about 600 min, about 500 min to about 720 min, or about 600 min to about 720 min. In some embodiments, the extraction is performed for a time period ranging from about 10 min, about 100 min, about 200 min, about 300 min, about 400 min, about 500 min, about 600 min, or about 720 min. In some embodiments, the extraction is performed for a time period ranging from at least about 10 min, about 100 min, about 200 min, about 300 min, about 400 min, about 500 min, or about 600 min. In some embodiments, the extraction is performed for a time period ranging from at most about 100 min, about 200 min, about 300 min, about 400 min, about 500 min, about 600 min, or about 720 min.

In another embodiment, and more usually, the extraction is performed for a time period ranging from 30-240 minutes. In some embodiments, the extraction is performed for a time period ranging from about 30 min to about 240 min. In some embodiments, the extraction is performed for a time period ranging from about 30 min to about 60 min, about 30 min to about 90 min, about 30 min to about 120 min, about 30 min to about 150 min, about 30 min to about 180 min, about 30 min to about 210 min, about 30 min to about 240 min, about 60 min to about 90 min, about 60 min to about 120 min, about 60 min to about 150 min, about 60 min to about 180 min, about 60 min to about 210 min, about 60 min to about 240 min, about 90 min to about 120 min, about 90 min to about 150 min, about 90 min to about 180 min, about 90 min to about 210 min, about 90 min to about 240 min, about 120 min to about 150 min, about 120 min to about 180 min, about 120 min to about 210 min, about 120 min to about 240 min, about 150 min to about 180 min, about 150 min to about 210 min, about 150 min to about 240 min, about 180 min to about 210 min, about 180 min to about 240 min, or about 210 min to about 240 min. In some embodiments, the extraction is performed for a time period ranging from about 30 min, about 60 min, about 90 min, about 120 min, about 150 min, about 180 min, about 210 min, or about 240 min. In some embodiments, the extraction is performed for a time period ranging from at least about 30 min, about 60 min, about 90 min, about 120 min, about 150 min, about 180 min, or about 210 min. In some embodiments, the extraction is performed for a time period ranging from at most about 60 min, about 90 min, about 120 min, about 150 min, about 180 min, about 210 min, or about 240 min.

In some embodiments, the extraction is performed at a pressure ranging from 7 to 20,000 psi (50 kPa-138 MPa). In some embodiments, the extraction is performed at a pressure ranging from about 7 psi (50 kPa) to about 2,000 psi (14 MPa). In some embodiments, the extraction is performed at a pressure ranging from about 7 psi (50 kPa) to about 300 psi (2 MPa), about 7 psi (50 kPa) to about 600 psi (4 MPa), about 7 psi (50 kPa) to about 900 psi (6 MPa), about 7 psi (50 kPa) to about 1,200 psi (8 MPa), about 7 psi (50 kPa) to about 1,500 psi (10 MPa), about 7 psi (50 kPa) to about 1,800 psi (12 MPa), about 7 psi (50 kPa) to about 2,000 psi (14 MPa), about 300 psi (2 MPa) to about 600 psi (4 MPa), about 300 psi (2 MPa) to about 900 psi (6 MPa), about 300 psi (2 MPa) to about 1,200 psi (8 MPa), about 300 psi (2

MPa) to about 1,500 psi (10 MPa), about 300 psi (2 MPa) to about 1,800 psi (12 MPa), about 300 psi (2 MPa) to about 2,000 psi (14 MPa), about 600 psi (4 MPa) to about 900 psi (6 MPa), about 600 psi (4 MPa) to about 1,200 psi (8 MPa), about 600 psi (4 MPa) to about 1,500 psi (10 MPa), about 600 psi (4 MPa) to about 1,800 psi (12 MPa), about 600 psi (4 MPa) to about 2,000 psi (14 MPa), about 900 psi (6 MPa) to about 1,200 psi (8 MPa), about 900 psi (6 MPa) to about 1,500 psi (10 MPa), about 900 psi (6 MPa) to about 1,800 psi (12 MPa), about 900 psi (6 MPa) to about 2,000 psi (14 MPa), about 1,200 psi (8 MPa) to about 1,500 psi (10 MPa), about 1,200 psi (8 MPa) to about 1,800 psi (12 MPa), about 1,200 psi (8 MPa) to about 2,000 psi (14 MPa), about 1,500 psi (10 MPa) to about 1,800 psi (12 MPa), about 1,500 psi (10 MPa) to about 2,000 psi (14 MPa), or about 1,800 psi (12 MPa) to about 2,000 psi (14 MPa). In some embodiments, the extraction is performed at a pressure ranging from about 7 psi (50 kPa), about 300 psi (2 MPa), about 600 psi (4 MPa), about 900 psi (6 MPa), about 1,200 psi (8 MPa), about 1,500 psi (10 MPa), about 1,800 psi (12 MPa), or about 2,000 psi (14 MPa). In some embodiments, the extraction is performed at a pressure ranging from at least about 7 psi (50 kPa), about 300 psi (2 MPa), about 600 psi (4 MPa), about 900 psi (6 MPa), about 1,200 psi (8 MPa), about 1,500 psi (10 MPa), or about 1,800 psi (12 MPa). In some embodiments, the extraction is performed at a pressure ranging from at most about 300 psi (2 MPa), about 600 psi (4 MPa), about 900 psi (6 MPa), about 1,200 psi (8 MPa), about 1,500 psi (10 MPa), about 1,800 psi (12 MPa), or about 2,000 psi (14 MPa).

In yet another embodiment, the extraction is performed at a pressure ranging from 10 to 20 psi (70-140 kPa). In some embodiments, the extraction is performed at a pressure ranging from about 10 psi (70 kPa) to about 20 psi (140 kPa). In some embodiments, the extraction is performed at a pressure ranging from about 10 psi (70 kPa) to about 12 psi (80 kPa), about 10 psi (70 kPa) to about 14 psi (100 kPa), about 10 psi (70 kPa) to about 16 psi (110 kPa), about 10 psi (70 kPa) to about 18 psi (120 kPa), about 10 psi (70 kPa) to about 20 psi (140 kPa), about 12 psi (80 kPa) to about 14 psi (100 kPa), about 12 psi (80 kPa) to about 16 psi(110 kPa), about 12 psi (80 kPa) to about 18 psi (120 kPa), about 12 psi (80 kPa) to about 20 psi (140 kPa), about 14 psi (100 kPa) to about 16 psi (110 kPa), about 14 psi (100 kPa) to about 18 psi (120 kPa), about 14 psi (100 kPa) to about 20 psi (140 kPa), about 16 psi (110 kPa) to about 18 psi (120 kPa), about 16 psi (110 kPa) to about 20 psi (140 kPa), or about 18 psi (120 kPa) to about 20 psi (140 kPa). In some embodiments, the extraction is performed at a pressure ranging from about 10 psi (70 kPa), about 12 psi (80 kPa), about 14 psi (100 kPa), about 16 psi (110 kPa), about 18 psi (120 kPa), or about 20 psi (140 kPa). In some embodiments, the extraction is performed at a pressure ranging from at least about 10 psi (70 kPa), about 12 psi (80 kPa), about 14 psi (100 kPa), about 16 psi (110 kPa), or about 18 psi (120 kPa). In some embodiments, the extraction is performed at a pressure ranging from at most about 12 psi (80 kPa), about 14 psi (100 kPa), about 16 psi (110 Pa), about 18 psi (120 kPa), or about 20 psi (140 kPa).

In some embodiments, the extraction is performed with a solvent to solid ratio in the range 10 to 100 mL/g, wherein the solid is the dried powdered biomass. In one embodiment, the extraction is performed with a solvent to solid ratio of 20 mL/g. In some embodiments, the extraction is performed with a solvent to solid ratio in the range of about 10 mL/g to about 100 mL/g. In some embodiments, the extraction is performed with a solvent to solid ratio in the range of about 10 mL/g to about 20 mL/g, about 10 mL/g to about 30 mL/g, about 10 mL/g to about 40 mL/g, about 10 mL/g to about 50 mL/g, about 10 mL/g to about 60 mL/g, about 10 mL/g to about 70 mL/g, about 10 mL/g to about 80 mL/g, about 10 mL/g to about 90 mL/g, about 10 mL/g to about 100 mL/g, about 20 mL/g to about 30 mL/g, about 20 mL/g to about 40 mL/g, about 20 mL/g to about 50 mL/g, about 20 mL/g to about 60 mL/g, about 20 mL/g to about 70 mL/g, about 20 mL/g to about 80 mL/g, about 20 mL/g to about 90 mL/g, about 20 mL/g to about 100 mL/g, about 30 mL/g to about 40 mL/g, about 30 mL/g to about 50 mL/g, about 30 mL/g to about 60 mL/g, about 30 mL/g to about 70 mL/g, about 30 mL/g to about 80 mL/g, about 30 mL/g to about 90 mL/g, about 30 mL/g to about 100 mL/g, about 40 mL/g to about 50 mL/g, about 40 mL/g to about 60 mL/g, about 40 mL/g to about 70 mL/g, about 40 mL/g to about 80 mL/g, about 40 mL/g to about 90 mL/g, about 40 mL/g to about 100 mL/g, about 50 mL/g to about 60 mL/g, about 50 mL/g to about 70 mL/g, about 50 mL/g to about 80 mL/g, about 50 mL/g to about 90 mL/g, about 50 mL/g to about 100 mL/g, about 60 mL/g to about 70 mL/g, about 60 mL/g to about 80 mL/g, about 60 mL/g to about 90 mL/g, about 60 mL/g to about 100 mL/g, about 70 mL/g to about 80 mL/g, about 70 mL/g to about 90 mL/g, about 70 mL/g to about 100 mL/g, about 80 mL/g to about 90 mL/g, about 80 mL/g to about 100 mL/g, or about 90 mL/g to about 100 mL/g. In some embodiments, the extraction is performed with a solvent to solid ratio in the range of about 10 mL/g, about 20 mL/g, about 30 mL/g, about 40 mL/g, about 50 mL/g, about 60 mL/g, about 70 mL/g, about 80 mL/g, about 90 mL/g, or about 100 mL/g. In some embodiments, the extraction is performed with a solvent to solid ratio in the range of at least about 10 mL/g, about 20 mL/g, about 30 mL/g, about 40 mL/g, about 50 mL/g, about 60 mL/g, about 70 mL/g, about 80 mL/g, or about 90 mL/g. In some embodiments, the extraction is performed with a solvent to solid ratio in the range of at most about 20 mL/g, about 30 mL/g, about 40 mL/g, about 50 mL/g, about 60 mL/g, about 70 mL/g, about 80 mL/g, about 90 mL/g, or about 100 m L/g.

Extraction Process 2

Figure 15:
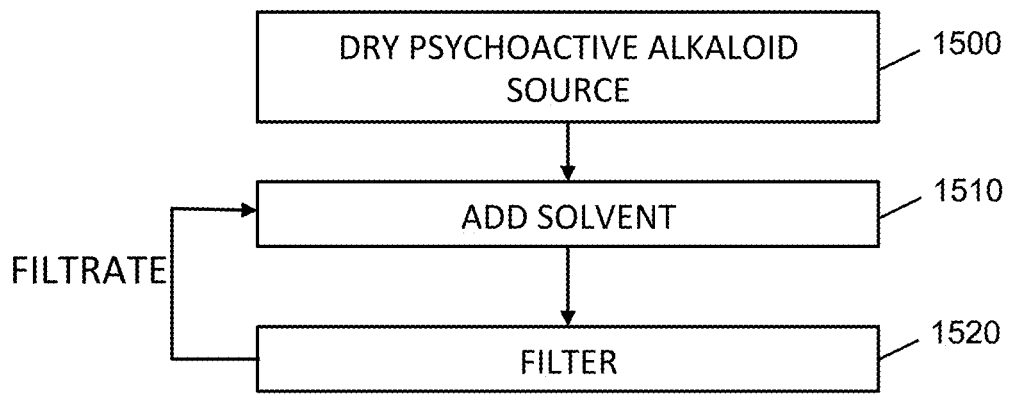
FIG. 15 illustrates a process for extracting psychoactive alkaloid from *Psilocybe cubensis*, according to an embodiment of the present invention.

In some embodiments, referring to FIG. 15, a process for extracting the psychoactive alkaloid is shown. The psychoactive alkaloid source is dried in step 1500 by techniques known in the art, such as using a forced air oven.

In step 1510, the dried psychoactive alkaloid source or dried biomass is mixed with a solvent and/or left to soak. The solvent in which the extract is carried or dissolved may be a primary aliphatic alcohol, a ketone, water, and any combination selected therefrom. In some embodiments, the primary aliphatic alcohol is a C1-4 alcohol. In some embodiments, the primary aliphatic alcohol is 5% ethanol. In some embodiments, the primary aliphatic alcohol is ethanol. In some embodiments, the ketone is a C3-4 ketone. In yet other embodiments, the water is selected from deionized, distilled, reverse osmosis, or otherwise purified water, which is substantially without free ions. In other embodiments, the water is not purified. In an exemplary embodiment, the solvent is a hydro-ethanol mixture with 3 parts of ethanol to 1 part of water, by weight.

In step 1520, the mixture of the solvent and the dried psychoactive alkaloid source is filtered to obtain a filtrate and a filtrate residue. Some or all of the solvent is evaporated from the filtrate residue to obtain the psychoactive alkaloid extract. Standardization of the obtained psychoactive alkaloid extract is carried out according to the standardization step 160 described above.

Optionally, the filtrate residue obtained in step 1520 is extracted with the solvent again. The filtrate residue is extracted by repeating the steps 1510 and 1520. This results in another filtrate. The first filtrate and the second filtrate are mixed together after their respective filtration steps to result in a bulk filtrate. The solvent from this bulk filtrate is partially evaporated to obtain the psychoactive alkaloid extract in a slurry form for the standardization step 160.

In one embodiment, the extraction is carried out at a temperature ranging from 5-95° C. The useful temperature range spans most of the liquid state of the solvent used, and upper and lower limits are determined by physical practicalities and limits of the available apparatus. Still, the temperature of the solvent may be outside of this range in other embodiments.

In other embodiments, the extraction is carried out at a temperature of 70° C. Temperature, and pressure if applied, are generally selected so that the solvent does not boil if elevated temperatures are used. In one embodiment, the extraction is carried out for a time duration ranging from 10 minutes to 12 hours. In yet another embodiment, the extraction is carried out for a time duration of 4 hours.

Extraction Process 3

Figure 10:
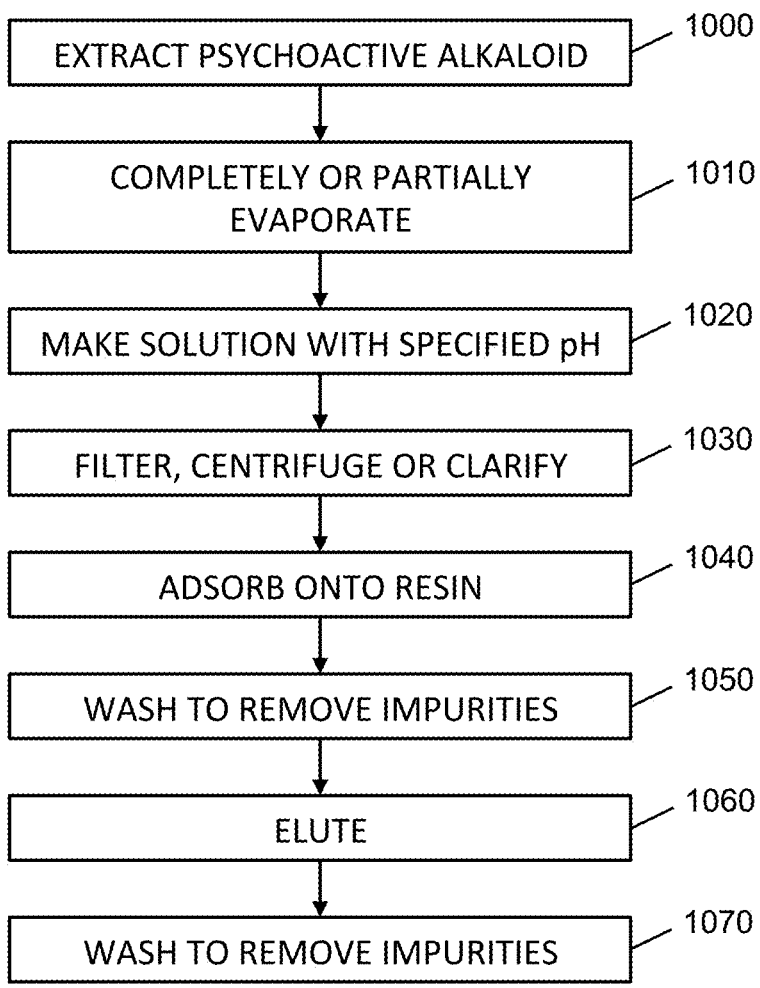
FIG. 10 illustrates in detail the basic and optional steps of a process for purification of a psychoactive alkaloid extract, according to an embodiment of the present invention.

In FIG. 10, the extracting step 1000 may include, as an example, extracting psychoactive alkaloids from raw, psychedelic mushrooms. The mushrooms are dried and ground to result in a dried biomass. The next step involves heating the dried biomass in a solvent in order for the extraction to occur. The obtained slurry is filtered to obtain a first filtrate and a first residue. The first residue undergoes a second extraction, using a second solvent to obtain a second slurry, which is then filtered to obtain a second filtrate and a second residue. The first filtrate and the second filtrate are mixed to obtain the psychoactive alkaloid extract. More extract can be obtained this way, i.e., by splitting the solvent into two or more batches and using each one sequentially to soak the biomass, compared to using a single volume of solvent.

The extraction may further include completely or partially concentrating the obtained psychoactive alkaloid extract, by evaporation of the solvent from the combined filtrates.

In one embodiment, the first solvent and the second solvent are selected from a primary aliphatic alcohol, a ketone, water, and any combination therefrom. In one embodiment, the primary aliphatic alcohol is a C1-4 alcohol. In one embodiment, the ketone is a C3-4 ketone. In another embodiment, the first solvent is an ethanol-water mixture with 3 parts ethanol to 1 part water by weight. In another embodiment, the second solvent is an ethanol-water mixture with 3 parts ethanol to 1 part water by weight. In yet another embodiment, the water is selected from deionized, distilled, reverse osmosis, or otherwise purified water, which has substantially no free ions. The selection of the solvent will depend on the nature of the starting material for extraction and the reaction conditions, according to which a person of skill in the art can make the appropriate solvent selection.

In one embodiment, the extraction is carried out at a temperature ranging from 5-95° C. The useful temperature range spans most of the liquid state of the solvent used, and upper and lower limits are determined by physical practicalities and limits of the available apparatus. Still, the temperature of the solvent may be outside of this range in other embodiments.

In another embodiment, the extraction is carried out at a temperature of 70° C. Temperature and pressure, if applied, are generally selected so that the solvent does not boil if elevated temperatures are used. In one embodiment, the extraction is carried out for a time duration ranging from 10 minutes to 12 hours. In yet another embodiment, the extraction is carried out for a time duration of 4 hours.

Extraction Process 4

Figure 18:
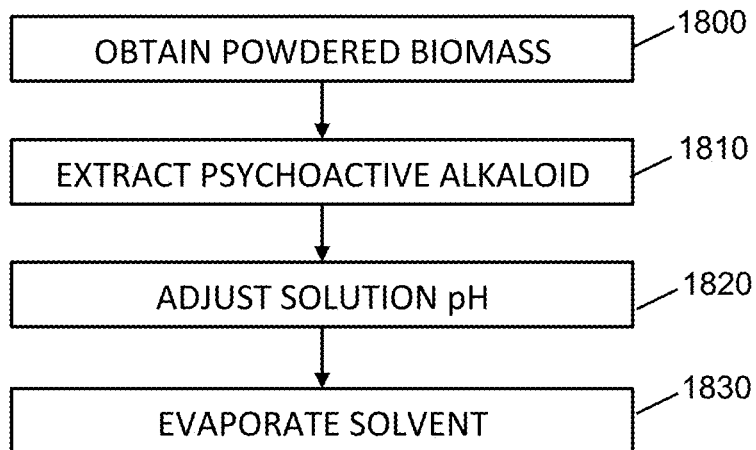
FIG. 18 illustrates the key steps of a process for obtaining a psychoactive alkaloid extract with dephosphorylation control, according to an embodiment of the present invention.

In one embodiment, referring to FIG. 18, a basic process for obtaining a psychoactive alkaloid extract with a desired amount of a phosphorylated psychoactive alkaloid and a desired amount of a dephosphorylated psychoactive alkaloid is shown. The phosphorylated alkaloid may be psilocybin, baeocystin, norbaeocystin, aeruginascin, or any combination selected therefrom. The dephosphorylated alkaloid may be psilocin, norpsilocin, 4-hydroxytryptamine, N,N,N-trimethyl-4-hydroxytryptamine, or any combination selected therefrom. The control aspect of the present invention relates to psychoactive alkaloids that have phosphorylated forms and not to other psychoactive alkaloids that may be present in a psychoactive alkaloid source. Depending on the strain or harvest, there may be no or substantially no phosphorylatable psychoactive alkaloids in the psychoactive alkaloid source, or they may represent as much 80-90% of the total alkaloid content.

The process includes step 1800 of obtaining powdered biomass from a psychoactive alkaloid source. The powdered biomass is obtained by drying and pulverizing a psychoactive alkaloid source. The drying is carried out via vacuum desiccation, freeze drying, timed forced air drying, or other existing drying method, to obtain a dried biomass. The pulverization is carried out by milling, grinding, or other method to reduce the particle size of the dried biomass. In one embodiment, the drying is carried out in a forced air oven completely shielded from all light at 20-30° C. for a time period of 5-10 hours. However, there is room for optimization of the drying step, using different temperatures (e.g., 10-50° C.) and different durations.

In one embodiment, the drying is carried out in a manner to not promote the conversion of phosphorylated psychoactive alkaloid. Taking care not to bruise while harvesting the psychoactive alkaloid source, harvesting at the right time of the fruiting body life cycle, potentially freeze-drying the fruiting body, low heat desiccation, and gentle air drying are all ways that reduce the conversion of phosphorylated psychoactive alkaloid to dephosphorylated psychoactive alkaloid. It may be feasible to harvest the fungi in a basic or methanol environment or soak the whole mycelium in methanol and cut the fruits while soaked. Once dried, there is negligible conversion, so that subsequent pulverization has little effect on it, unless moisture is added back. The prevention of conversion of phosphorylated psychoactive alkaloid to dephosphorylated psychoactive alkaloid during harvesting allows for the preparation of psychoactive alkaloid extracts, by the present process, having a total phosphorylatable psychoactive alkaloid content that is up to 100% by weight of phosphorylated psychoactive alkaloid.

Step 1810 involves extracting a psychoactive alkaloid from the dried powdered biomass with an acidified solvent or a basified solvent to obtain a psychoactive alkaloid liquid with a specific pH, wherein the specific pH is lower than 3.5 or greater than 10.5. Between pH 3.5 and pH 10.5, the conditions are such that psilocybin is readily converted to psilocin, and psilocin is converted to the quinoid dimer, which is completely inactive.

When used, the acid may be acetic acid, adipic acid, ascorbic acid, phosphoric acid, ammonium aluminum sulphate, ammonium citrate dibasic, ammonium citrate monobasic, calcium citrate, calcium fumarate, calcium gluconate, calcium phosphate dibasic, calcium phosphate monobasic, hydrochloric acid, sulfuric acid monobasic, calcium phosphate tribasic, citric acid, fumaric acid, gluconic acid, magnesium fumarate, malic acid, phosphoric acid, potassium acid tartrate, potassium citrate, potassium fumarate, sodium citrate, sodium fumarate, sodium gluconate, sodium lactate, sodium potassium hexametaphosphate, sodium potassium tartrate, sodium potassium tripolyphosphate, sodium pyrophosphate tetrabasic, sodium tripolyphosphate, tartaric acid, and any combination of one or more of these. In some embodiments, the acid is either only hydrochloric acid or only phosphoric acid, for example. It is also envisaged that other acids may be used, for example, non-food-grade acids that may be used by pharmaceuticals.

When used, the base may be ammonium bicarbonate, ammonium carbonate, ammonium hydroxide, calcium acetate, calcium carbonate, calcium chloride, calcium hydroxide, calcium lactate, calcium oxide, calcium phosphate dibasic, calcium phosphate monobasic, magnesium carbonate, potassium aluminum sulphate, potassium bicarbonate, potassium carbonate, potassium hydroxide, potassium lactate, potassium phosphate dibasic, potassium pyrophosphate tetrabasic, potassium phosphate tribasic, potassium tripolyphosphate, sodium acetate, sodium acid pyrophosphate, sodium aluminum phosphate, sodium aluminum sulphate, sodium bicarbonate, sodium bisulphate, sodium carbonate, sodium hexametaphosphate, sodium hydroxide, sodium lactate, sodium phosphate dibasic, sodium phosphate monobasic, sodium phosphate tribasic, or any combination therefrom. In one embodiment, the base is solely sodium hydroxide, for example. Other bases may be used in other embodiments, for example, non-food-grade bases that may be used by pharmaceuticals.

After adding the acidified solvent or the basified solvent, the psychoactive alkaloid liquid has a pH ranging from 0.5 to 3.5 or from 10.5 to 13.5, respectively. In an exemplary embodiment, the pH of the psychoactive alkaloid liquid obtained after addition of the basified solvent is 13. In another exemplary embodiment, the pH of the psychoactive alkaloid liquid obtained after addition of the acidified solvent is 2.

The pH is adjusted in the extraction step 1810 to halt or promote conversion of phosphorylated psychoactive alkaloid to dephosphorylated psychoactive alkaloid, thus allowing the preparation of the psychoactive alkaloid liquid with the desired amount of a phosphorylated psychoactive alkaloid and a desired amount of a dephosphorylated psychoactive alkaloid. A specific pH lower than 3.5 promotes the conversion of the phosphorylated psychoactive alkaloid to the dephosphorylated psychoactive alkaloid. A specific pH greater than 10.5 halts the conversion of the phosphorylated psychoactive alkaloid to the dephosphorylated psychoactive alkaloid.

In step 1820 of the process, the pH of the obtained psychoactive alkaloid liquid is adjusted to a pH ranging from 3.5 to 4.5. The pH is adjusted by adding a base or an acid. The pH is adjusted to a value in this range as the psychoactive alkaloid liquid exhibits a good anti-microbial stability in this pH range. Also, there is no dephosphorylation at this pH after the alkaloids are removed from the biomass, which points to enzymatic hydrolysis being responsible for conversion in the source of the psychoactive alkaloids. In exemplary embodiments, the base is sodium hydroxide, and the acid is citric acid. Any other appropriate acid or base can be used to adjust the pH, which a person of skill in the art may determine. The selection of the acid or the base will depend upon the nature of the pH of the psychoactive alkaloid liquid prior to adjusting it to the range of 3.5-4.5, according to which a person of skill in the art can make the appropriate acid or base selection.

Step 1830 of the process involves evaporating the solvent from the psychoactive alkaloid solution to obtain the psychoactive alkaloid extract with the desired amount of the phosphorylated psychoactive alkaloid and the desired amount of the dephosphorylated psychoactive alkaloid. The solvent is completely or partially evaporated to result in the psychoactive alkaloid extract (slurry or powder) with the desired amount of the phosphorylated psychoactive alkaloid and the desired amount of the dephosphorylated psychoactive alkaloid. The evaporation is carried out by methods such as air drying, rotary evaporation, or other existing methods to evaporate solvent from psychoactive alkaloid liquid. At this point in time, away from the biomass, psilocybin and/or psilocin are fairly heat resistant, more so under vacuum, thus, rotary evaporation, for example, is a suitable process. The desired amount of the phosphorylated psychoactive alkaloid is 0-100% of a phosphorylatable psychoactive alkaloid content in the psychoactive alkaloid extract. The desired amount of the dephosphorylated psychoactive alkaloid is the remainder of the total phosphorylatable psychoactive alkaloid content in the psychoactive alkaloid extract.

In some embodiments, when the psychoactive alkaloid liquid has a pH greater than 10.5 during the extraction step, the desired amount of the phosphorylated psychoactive alkaloid is 50-90% by weight (crude extraction) of the total phosphorylatable psychoactive alkaloid content in the psychoactive alkaloid extract, without going to onerous lengths in selecting the raw material. The desired amount of the dephosphorylated psychoactive alkaloid is the remainder of the total phosphorylatable psychoactive alkaloid content in the psychoactive alkaloid extract.

In another embodiment, when using a psychoactive alkaloid source that has not undergone conversion (i.e. no significant conversion) of any phosphorylated alkaloid to dephosphorylated psychoactive alkaloid, and when the psychoactive alkaloid liquid has a pH greater than 10.5 during the extraction step, the desired amount of the phosphorylated psychoactive alkaloid is 100% by weight of the total phosphorylatable psychoactive alkaloid content in the psychoactive alkaloid extract. The desired amount of the dephosphorylated psychoactive alkaloid is 0% by weight of the total phosphorylatable psychoactive alkaloid content in the psychoactive alkaloid extract.

In yet another embodiment, when the psychoactive alkaloid liquid has a pH lower than 3.5 during the extraction step, the desired amount of the phosphorylated psychoactive alkaloid is 0% by weight of the total phosphorylatable psychoactive alkaloid content in the psychoactive alkaloid extract. The desired amount of the dephosphorylated psychoactive alkaloid is 100% by weight of the total phosphorylatable psychoactive alkaloid content in the psychoactive alkaloid extract. Even with neutral hydro-ethanol extraction, a large portion of psilocybin may be converted to psilocin. However, the low pH environment (<3.5) protects the psilocin from oxidation.

Extraction Process 5

Figure 19:
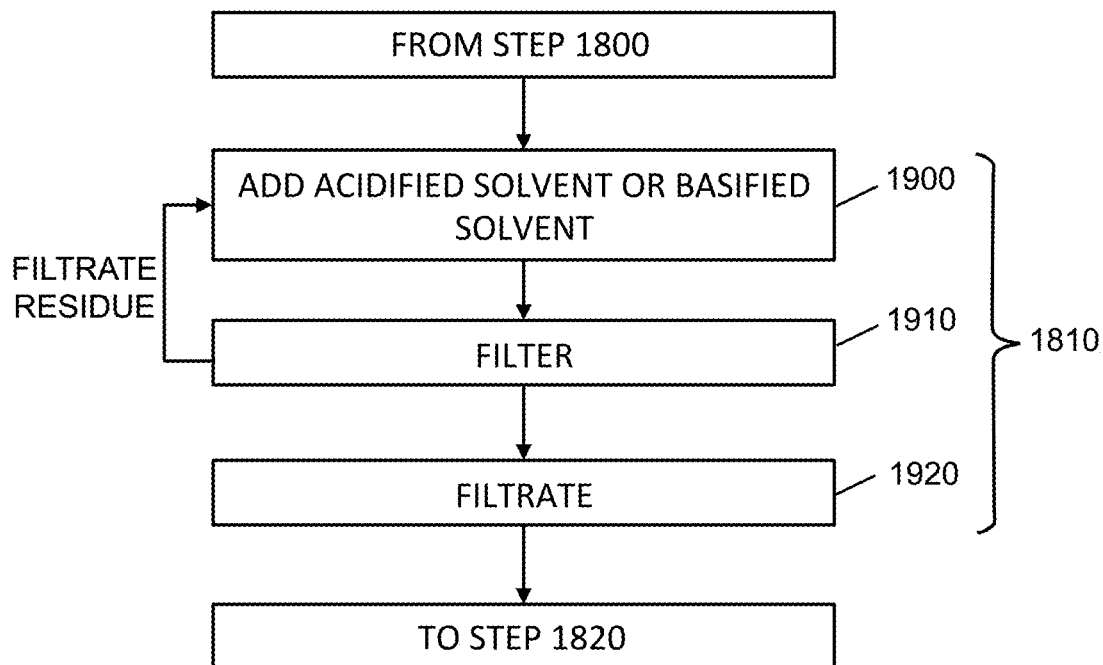
FIG. 19 illustrates in detailed steps of a process for obtaining a psychoactive alkaloid extract with dephosphorylation control, according to an embodiment of the present invention.

In some embodiments, referring to FIG. 19, additional, optional steps in the extraction step 1810 are shown. Step 1900 is performed by adding the acidified solvent or the basified solvent to the powered biomass. The obtained psychoactive liquid has a specific pH, the specific pH being lower than 3.5 or greater than 10.5. After the addition of the acidified solvent or the basified solvent, the powered biomass and the solvent are mixed, followed by step 1910 of filtration to result in the extracted filtrate of step 1920 (i.e.

psychoactive alkaloid liquid). To this obtained filtrate, the acid or the base of step 1820 is added to adjust the pH to within the range of 3.5-4.5.

In some embodiments, the extraction step comprises further extracting the psychoactive alkaloid by repeating the extraction step. Filtrate residue from step 1910 is collected, and to this filtrate residue, the same or a different acidified solvent or the same or a different basified solvent is added. The resulting mixture is mixed followed by filtration to obtain another filtrate. This filtrate and the previous filtrate are mixed together to result in a bulk filtrate. To this bulk filtrate the acid or the base is added to adjust the pH to 3.5-4.5 according to step 1820.

In some embodiments, further extraction of the filtrate obtained after extraction with the acidified or the basified solvent is repeated until a required amount of the phosphorylated psychoactive alkaloid and/or the dephosphorylated psychoactive alkaloid is extracted. The number of extraction cycles to be repeated may depend on various variable factors such as the source of the psychoactive alkaloid and the solubility of the psychoactive alkaloid in the acidified or the basified solvent.

The solvent in the evaporation step can be completely or partially evaporated, to result in a powdered solid or a slurry. Evaporation may be paused, for standardization, and continued after.

Extraction Process 6

Referring to FIG. 20, the present invention also relates to a process for obtaining a psychoactive alkaloid composition with a psychoactive alkaloid extract and one or more excipients.

At step 2000 the evaporation step 1830 (FIG. 18) is paused when a portion of the solvent has been evaporated from the psychoactive alkaloid liquid to obtain a psychoactive alkaloid slurry. The evaporation of a portion of the solvent, before collection of the psychoactive alkaloid slurry for standardization, is done to obtain a quantity of a psychoactive alkaloid slurry that is easy to handle in the subsequent steps of the standardization process. The quantity of the portion of the solvent to be evaporated before pausing the evaporation is not so much as to make it too viscous to handle well. The quantity of the portion of the solvent to be evaporated will depend on various factors, for example, but not limited to, the contents of the psychoactive alkaloid liquid and the quantity of the psychoactive alkaloid liquid present at the beginning of the evaporation step.

Step 2010 includes standardizing the obtained psychoactive alkaloid slurry by adding thereto a measured quantity of one or more excipients to obtain a standardized slurry with a specific amount of psychoactive alkaloid content. The specified amount of the total psychoactive alkaloid content in the psychoactive alkaloid composition is achieved by first determining the proportion, by weight, of solids in the psychoactive alkaloid slurry. The weight proportion of the psychoactive alkaloids in the slurry is also determined. Then, a measured amount of one or more excipients is added to a measured amount of the psychoactive alkaloid slurry. Thus, after evaporation of the remaining solvent, the resultant composition is a standardized composition with a specified total psychoactive alkaloid content.

Step 2020 includes continuing the evaporating step 1830 (FIG. 18) by drying the standardized slurry to obtain a psychoactive alkaloid composition with the psychoactive alkaloid extract and the one or more excipients.

The evaporation in the standardization process is carried out by methods such as air drying, rotary evaporation, or other methods known in the art to suitably evaporate solvent from psychoactive alkaloid slurry.

The psychoactive alkaloid composition obtained has a specific total psychoactive alkaloid content in the composition due to the standardizing step. The specified amount of the total psychoactive alkaloid content may be accurate to one or two decimal places, or one or two significant figures depending on how accurately the measurements are made during the standardization process.

Thus, the psychoactive alkaloid composition obtained has a specific amount of a total psychoactive alkaloid content, which is made up of a desired amount of phosphorylated psychoactive alkaloid and a desired amount of dephosphorylated psychoactive alkaloid, and possibly other psychoactive alkaloids that are not phosphorylatable.

In one embodiment, the specific amount of the total psychoactive alkaloid content in the psychoactive alkaloid composition ranges from 0.1-99% by weight of the composition, the higher concentrations being obtained when purifying steps are included. Purifying may involve treating the extract with a resinous material prior to the standardization step, to remove impurities such as sugars and proteins. In another embodiment, the specific amount of the total psychoactive alkaloid content in the psychoactive alkaloid composition ranges from 0.1-10% by weight of the composition, which may be achieved without purifying steps. In an exemplary embodiment, the specific amount of the total psychoactive alkaloid content in the psychoactive alkaloid composition is 0.53% by weight of the composition. In yet another exemplary embodiment, the specific amount of the total psychoactive alkaloid content in the psychoactive alkaloid composition is 0.501% by weight of the composition.

In some embodiments, the desired amount of the phosphorylated psychoactive alkaloid is 0-100% by weight of a total phosphorylatable psychoactive alkaloid content in the psychoactive alkaloid extract, and the desired amount of the dephosphorylated psychoactive alkaloid is the remainder of the total phosphorylatable psychoactive alkaloid content in the psychoactive alkaloid extract. In one embodiment, the desired amount of the phosphorylated psychoactive alkaloid is 10-90% by weight of the total phosphorylatable psychoactive alkaloid content in the psychoactive alkaloid extract, and the desired amount of the dephosphorylated psychoactive alkaloid is the remainder of the total phosphorylatable psychoactive alkaloid content in the psychoactive alkaloid extract. In another embodiment, the desired amount of the phosphorylated psychoactive alkaloid is 0% by weight of the total phosphorylatable psychoactive alkaloid content in the psychoactive alkaloid extract, and the desired amount of the dephosphorylated psychoactive alkaloid is 100% by weight of the total phosphorylatable psychoactive alkaloid content in the psychoactive alkaloid extract. In yet another embodiment, the desired amount of the phosphorylated psychoactive alkaloid is 100% by weight of the total phosphorylatable psychoactive alkaloid content in the psychoactive alkaloid extract, and the desired amount of the dephosphorylated psychoactive alkaloid is 0% by weight of the total phosphorylatable psychoactive alkaloid content in the psychoactive alkaloid extract.

Further Processes

Referring to FIG. 10 additional, optional steps are shown well as the basic steps in the process. In one embodiment, the extraction step 1000 is followed by completely or partially concentrating the obtained psychoactive alkaloid extract (or solution) by evaporation of the solvent from the extract in step 1010. In other embodiments, step 1010 of partially or completely evaporating the solvent may be considered to be a part of the extraction step 1000. If the solvent from the extract has been completely evaporated in step 1010, then reverse osmosis water, more solvent, or another solvent is added back.

In some embodiments, the process includes adding, in step 1020, an acid or a base to the psychoactive alkaloid extract obtained in step 1000 to obtain a psychoactive alkaloid solution with a specific pH.

When used, the acid may be acetic acid, adipic acid, ascorbic acid, phosphoric acid, ammonium aluminum sulphate, ammonium citrate dibasic, ammonium citrate monobasic, calcium citrate, calcium fumarate, calcium gluconate, calcium phosphate dibasic, calcium phosphate monobasic, hydrochloric acid, sulfuric acid monobasic, calcium phosphate tribasic, citric acid, fumaric acid, gluconic acid, magnesium fumarate, malic acid, phosphoric acid, potassium acid tartrate, potassium citrate, potassium fumarate, sodium citrate, sodium fumarate, sodium gluconate, sodium lactate, sodium potassium hexametaphosphate, sodium potassium tartrate, sodium potassium tripolyphosphate, sodium pyrophosphate tetrabasic, sodium tripolyphosphate, tartaric acid, and any combination of one or more of these. In some embodiments, the acid is either only hydrochloric acid or only phosphoric acid, for example. It is also envisaged that other acids may be used.

When used, the base may be ammonium bicarbonate, ammonium carbonate, ammonium hydroxide, calcium acetate, calcium carbonate, calcium chloride, calcium hydroxide, calcium lactate, calcium oxide, calcium phosphate dibasic, calcium phosphate monobasic, magnesium carbonate, potassium aluminum sulphate, potassium bicarbonate, potassium carbonate, potassium hydroxide, potassium lactate, potassium phosphate dibasic, potassium pyrophosphate tetrabasic, potassium phosphate tribasic, potassium tripolyphosphate, sodium acetate, sodium acid pyrophosphate, sodium aluminum phosphate, sodium aluminum sulphate, sodium bicarbonate, sodium bisulphate, sodium carbonate, sodium hexametaphosphate, sodium hydroxide, sodium lactate, sodium phosphate dibasic, sodium phosphate monobasic, sodium phosphate tribasic, or any combination therefrom. In one embodiment, the base is solely sodium hydroxide, for example. Other bases may be used in other embodiments.

In one embodiment, the specific pH psychoactive alkaloid solution has a pH ranging from 2.5 to 4.5, or from 9 to 10. In other embodiments, the specific pH psychoactive alkaloid solution has a pH of 3, 4, or 9.5. The selection of the pH is chosen in a manner to allow for the efficient adsorption of the psychoactive alkaloids onto the resin(s).

In one embodiment, the process includes adding phosphoric acid to the psychoactive alkaloid extract to achieve a pH of 4. In another embodiment, the process includes adding hydrochloric acid to the psychoactive alkaloid extract to achieve a pH of 3. In yet another embodiment, the process includes adding sodium hydroxide to the psychoactive alkaloid extract to achieve a pH of 9.5.

The process includes, in step 1030, optionally filtering, centrifuging, or clarifying the psychoactive alkaloid solution or specific pH psychoactive alkaloid solution, as the case may be, and utilizing the obtained filtrate for the next step 1040 of adsorption. Clarifying may be performed, for example, by adding an agglomeration agent.

In step 1040, the process involves adsorbing the psychoactive alkaloid(s) in the solution onto the resin to obtain an adsorbed psychoactive alkaloid.

In step 1050, the process involves washing the resin to remove adsorbed impurities from the resin. While not all the impurities are adsorbed onto the resin, some of them may be. The washing step, substantially, does not remove the adsorbed psychoactive alkaloids. The washing solvent may be 100% ethanol, 100% reverse osmosis water, or any other washing solvent used in ion-exchange resin chromatography, provided that the washing removes impurities or by-products that are adsorbed on the resin. Impurities or by-products may include, for example, sugars, carbohydrates, chitin, chitosan, fats, minerals, waxes, or proteins. There may be one, two, or more washing steps depending on the embodiment, and the same or different washing solvents may be used for each wash. In other embodiments, the solvent(s) for washing may include a primary aliphatic alcohol, a ketone, water, and any combination therefrom. In one embodiment, the primary aliphatic alcohol is a C1-4 alcohol. In one embodiment, the primary aliphatic alcohol is 5% ethanol. In one embodiment, the primary aliphatic alcohol is ethanol. In one embodiment, the ketone is a C3-4 ketone. In yet another embodiment, the water is selected from deionized, distilled, reverse osmosis, or otherwise purified water that is substantially without free ions.

After the washing, the process involves eluting, in step 1060, the adsorbed psychoactive alkaloid from the resin using a solvent to obtain a purified psychoactive alkaloid solution. The solvent may be an organic solvent, an acid, a base, or water, a combination of an organic solvent and a base, or a combination of an organic solvent and an acid, a combination of an organic solvent and water, a combination of water and a base, or combination of water and an acid. The result of the elution step is a purified psychoactive alkaloid solution.

Following the elution, a further washing step 1070 may be employed using 100% ethanol, for example, to wash the resin. This may be considered to be a cleaning step, to refresh the resin and make it ready to be used again in a subsequent step or in another process. In other embodiments, the solvent for further washing may be a primary aliphatic alcohol, a ketone, water, and any combination therefrom. In one embodiment, the primary aliphatic alcohol is a C1-4 alcohol. In one embodiment, the primary aliphatic alcohol is 5% ethanol. In one embodiment, the ketone is a C3-4 ketone. In yet another embodiment, the water is selected from deionized, distilled, reverse osmosis, or otherwise purified water that is substantially without free ions.

The result of the elution is a purified psychoactive alkaloid solution. In one embodiment, the purified psychoactive alkaloid solution has a concentration of 0.07% by weight of a psychoactive alkaloid, which is the concentration before removal of some or all of the solvent. This concentration may be different in other embodiments, depending on the amount solvent used for the elution and the potency of the raw materials. In one embodiment, the purified psychoactive alkaloid solution is concentrated by evaporating the solvent to form a purified psychoactive slurry that has at least of 5% by weight or more of a psychoactive alkaloid. In another embodiment, the purified psychoactive alkaloid slurry has 5-68% by weight of a psychoactive alkaloid. In yet other embodiments, the purified psychoactive alkaloid slurry has a concentration of psychoactive alkaloid outside these ranges, and, when dried, can be as low as 0.1% or as high as 99% dry wt/wt %.

Optionally, the obtained purified psychoactive alkaloid solution is further purified by filtering the obtained purified psychoactive alkaloid solution to obtain a filtrate, and then repeating at least steps 1040 and 1060 with the obtained filtrate.

Different processes may employ the steps in a different order, and some of the steps may be repeated with the same or different parameters. For example, in one embodiment, starting from a solution of dissolved extract, the order of the steps may be 1020, 1040, 1030, 1050, 1060, 1020, 1030, 1010, 1030, 1040, 1050 and 1060.

Variations

Other water may be used in place of reverse osmosis water, which may be selected for its purity.

Water purified by other purification technologies may be used instead of reverse osmosis water. In alternative embodiments, the solvent is 0.02% to 1.5% acetic acid in water. In alternate embodiment, the solvent comprises 75% ethanol, 25% water, and 0.1M sodium hydroxide. In alternative embodiments the solvent is a hydro-methanol mixture, with a methanol content in the range of below 1% to 100%. The hydro-methanol based extraction follows the same steps as the extraction with a mixture of ethanol and water (FIG. 3) and may use lower soaking temperatures due to the lower boiling point of methanol. Also, the methanol/water mixture can be evaporated to dryness instead of the partial evaporation in step 360, for safety. If evaporated to dryness, the extract is then formed by adding to the residual solid. If not evaporated to dryness, the residual slurry is diluted, if necessary for ease of handling, by adding reverse osmosis water to form the slurry. If not diluted, the residual slurry is used as the concentrated slurry. The result of evaporating the methanol is a residue that is either solid or a slurry. Furthermore, the hydro-methanol solvent may be buffered with a strong acid or a strong alkali, following the processes in FIGS. 6 and 7. Again, however, the solvent may be completely evaporated instead of partially (612, 712) in order to fully remove the methanol, with reverse osmosis water being added to the solid to form the concentrated slurry. If the solvent is not completely evaporated, it should be evaporated enough to remove all the methanol and leave a residual slurry. The residual slurry may optionally then be diluted, for ease of handling, with reverse osmosis water to form the concentrated slurry. If not diluted, the residual slurry is used as the concentrated slurry.

The solvent may also be propan-1-ol, propan-2-ol, a butanol isomer, or a mixture of any or all of these with water, in any percentage ratio.

Any of the solvents described herein may be used with any of the mushroom varieties that include psychoactive alkaloids.

The temperature of extraction may be lowered to reduce conversion, and the duration may be in the range of 30 to 240 minutes.

In other embodiments, other drying techniques, temperatures and durations may be used. It is possible in other embodiments to grind the dried biomass to lower or higher particle size than 200 mesh. For example, grinding to a mesh size of 40 would work in some embodiments. The choice of solvent may have an impact on which mesh size to grind the dried mushrooms to. Note that, in other embodiments, the grinding step 614 may take place before or after the drying step 613.

In general, unless otherwise indicated, singular elements may be in the plural and vice versa with no loss of generality.

Temperatures that have been given to the nearest degree include all temperatures within a range of ±0.5° C. of the given value. Likewise, numbers and percentages are specified to the nearest significant digit. Values of pH are specified to ±0.5.

While exemplary pH ranges are given in some examples, other pH ranges are possible.

The process may be scaled up using larger quantities and modified apparatus.

The extraction process in other embodiments may use varying applied pressures and temperatures, which vary during the soaking steps.

Chemical and physical stability may be determined using rigorous stability testing protocols. This would be a necessary study for the product to be considered made using a good manufacturing process. The initial specifications and ongoing specifications of the extract should be determined during a testing regime over time, temperature, relative humidity, etc. to determine the physical and chemical stability. Studies are on-going, but a 5-year shelf life with a minimum of 2 years is targeted in terms of physical and chemical stability.

E. Purification

Purification Process 1

Figure 9:
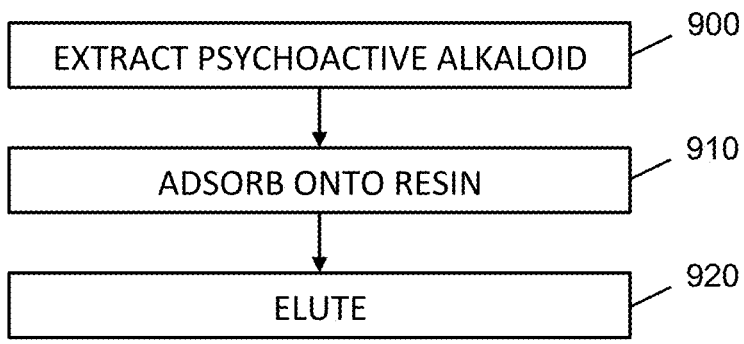
FIG. 9 illustrates the steps of a basic process for obtaining a purified psychoactive alkaloid solution, according to an embodiment of the present invention.

In one embodiment, referring to FIG. 9, a basic process for obtaining a purified psychoactive alkaloid solution from extracted psychoactive compounds is shown. The process includes the step 900 of extracting a psychoactive alkaloid from a psychoactive alkaloid source to obtain a psychoactive alkaloid extract. The psychoactive alkaloid source may be a fungus, a mycelium, an animal, a spore, a plant, a bacterium, or a yeast. The psychoactive alkaloid source in some embodiments may be a prior extract of one or more psychoactive alkaloids, where the prior extract is to undergo a further extraction/purification process. The psychoactive alkaloid may include, but is not limited to, psilocybin, psilocin, baeocystin, norbaeocystin, norpsilocin, aeruginascin, bufotenin, bufotenidine, 5-MeO-DMT (5-methoxy-N,N-dimethyltryptamine), N,N-dimethyltryptamine (DMT), ergine (LSA), ergonovine, ergometrine, muscimol, ibotenic acid, lysergic acid hydroxyethylamide (LSH), elymoclavine, ergometrinine, and/or chanoclavine. or any combination therefrom. The extract from the psychoactive alkaloid source may be a fluid, as either a liquid or a slurry, or is made into a fluid by the addition of a solvent.

The solvent in which the extract is carried or dissolved may be a primary aliphatic alcohol, a ketone, water, and any combination therefrom. In one embodiment, the primary aliphatic alcohol is a C1-4 alcohol. In one embodiment, the primary aliphatic alcohol is 5% ethanol. In one embodiment, the primary aliphatic alcohol is ethanol. In one embodiment, the ketone is a C3-4 ketone. In yet another embodiment, the water is selected from deionized, distilled, reverse osmosis, or otherwise purified water, which is substantially without free ions. In other embodiments, the water is not purified.

The process then involves adsorbing, in step 910, the psychoactive alkaloid(s) in the extract obtained in step 900 onto a resin to obtain an adsorbed psychoactive alkaloid, which may include one or more adsorbed psychoactive alkaloids.

In one embodiment, the resin is an adsorbent resin of the macroporous type, such as, a cation or anion ion-exchange resin, a non-ionic resin, or any combination therefrom. Representative pharmaceutical, nutraceutical or food-grade grade resins for use in accordance with the present invention are known to those skilled in the art. For example, pharmaceutical grade non-ionic macroporous resins are commercially available, e.g. Amberlite® XAD4. In one embodiment, the resin is a cationic ion-exchange resin or an anionic-exchange resin. The cationic ion-exchange resin may be selected from commercially available cationic ion-exchange resins known in the art, including, but not limited to, Amberlite® MAC-3 H. The cationic ion-exchange resin may be in an $H^+$ form or an $Na^+$ form. The anionic ion-exchange resin may be selected from commercially available anion exchange resins known in the art, including, but not limited to, Amberchrom® 50WX8. The anionic ion-exchange resin may be in an OH⁻ form or a Cl⁻ form. The resins used may be of any particle size. In some embodiments, the resins may be gel type resins, with any size of gel bead.

Next, the process involves eluting, in step 920, the adsorbed psychoactive alkaloid using a solvent to obtain a purified psychoactive alkaloid solution. The solvent may be, for example, an organic solvent, an acid, a base, a combination of an organic solvent and a base, a combination an organic solvent and an acid, water, a combination of water and acid, a combination of water and base, or a combination of water and an organic solvent. Usually, the solvent is different from the solvent in which the extract is initially provided and is either a different type of solvent or a different composition of solvent. It may be at a different temperature than the initial solvent.

In some embodiments, the solvent used in the elution step 920 may be a primary aliphatic alcohol, a ketone, water, and any combination therefrom. In one embodiment, the primary aliphatic alcohol is a C1-4 alcohol. In one embodiment, the primary aliphatic alcohol is 5% ethanol. In one embodiment, the primary aliphatic alcohol is ethanol. In one embodiment, the ketone is a C3-4 ketone. In yet another embodiment, the water is deionized, distilled, reverse osmosis, or otherwise purified water, which is substantially without free ions. In other embodiments, the water is not purified.

In one embodiment, the solvent used in the elution step 920 is a combination of an organic solvent and an acid. In one embodiment, the combination of an acid and an organic solvent is 2% hydrochloric acid and 80% ethanol, for example. In general, any acidic environment will displace some of the ions from the resin, but the rate and optimization of the desorption will be affected by the acid concentration. In one embodiment, the solvent used in the elution step 920 is a combination of an organic solvent and a base. In one embodiment, the combination of an organic solvent and a base is of 2% sodium chloride and 80% ethanol, for example. In general, any basic environment will displace some of the ions from the resin, but the rate and optimization of the desorption will be affected by the concentration of the base.

All the above solvents and combinations thereof are suitable for the elution step because all of the psychoactive alkaloids of interest are soluble therein and, depending on the choice of resin, they are all capable of pulling the alkaloids of interest off a resin. There are many different resins available, and it is a straightforward matter to select a suitable resin and elution solvent pair.

In one embodiment, the elution step is carried out at a temperature in the range of 4-75° C. These temperatures are limited by the boiling point of the solvent used, as well as the specifications of allowable food-grade resins, as determined by the manufacturers of the resins and governmental food and drug administrations. In another embodiment, the elution step is carried out at room temperature for convenience, i.e., at 21-25° C.

In other embodiments, the process for obtaining the purified psychoactive alkaloid solution further includes repeating the steps 910 and 920 with the obtained purified psychoactive alkaloid solution to obtain a further or twice purified psychoactive alkaloid solution. For the repeated steps in these embodiments, the resin may be the same or a different resin, and the solvent may be the same or a different solvent. While the purified psychoactive alkaloid solution may have a low psychoactive alkaloid content, this may be increased by evaporation of some or all of the solvent.

Purification Process 2

Figure 16:
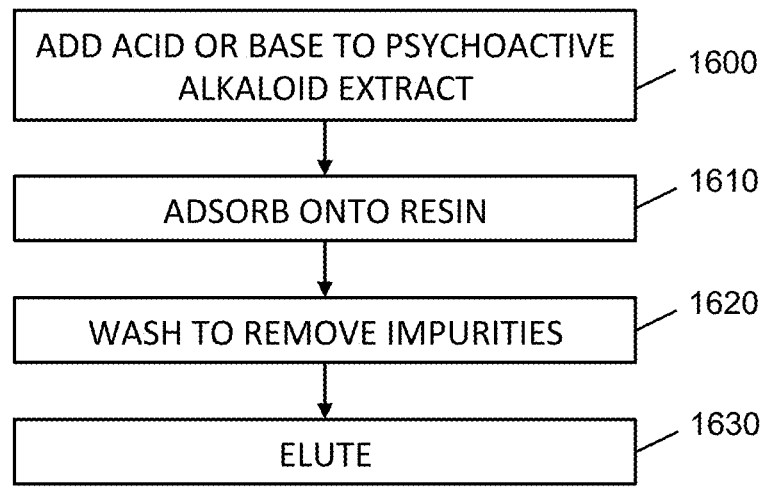
FIG. 16 illustrates detailed steps of a process for purifying psychoactive alkaloid from *Psilocybe cubensis*, according to an embodiment of the present invention.
Figure 17:
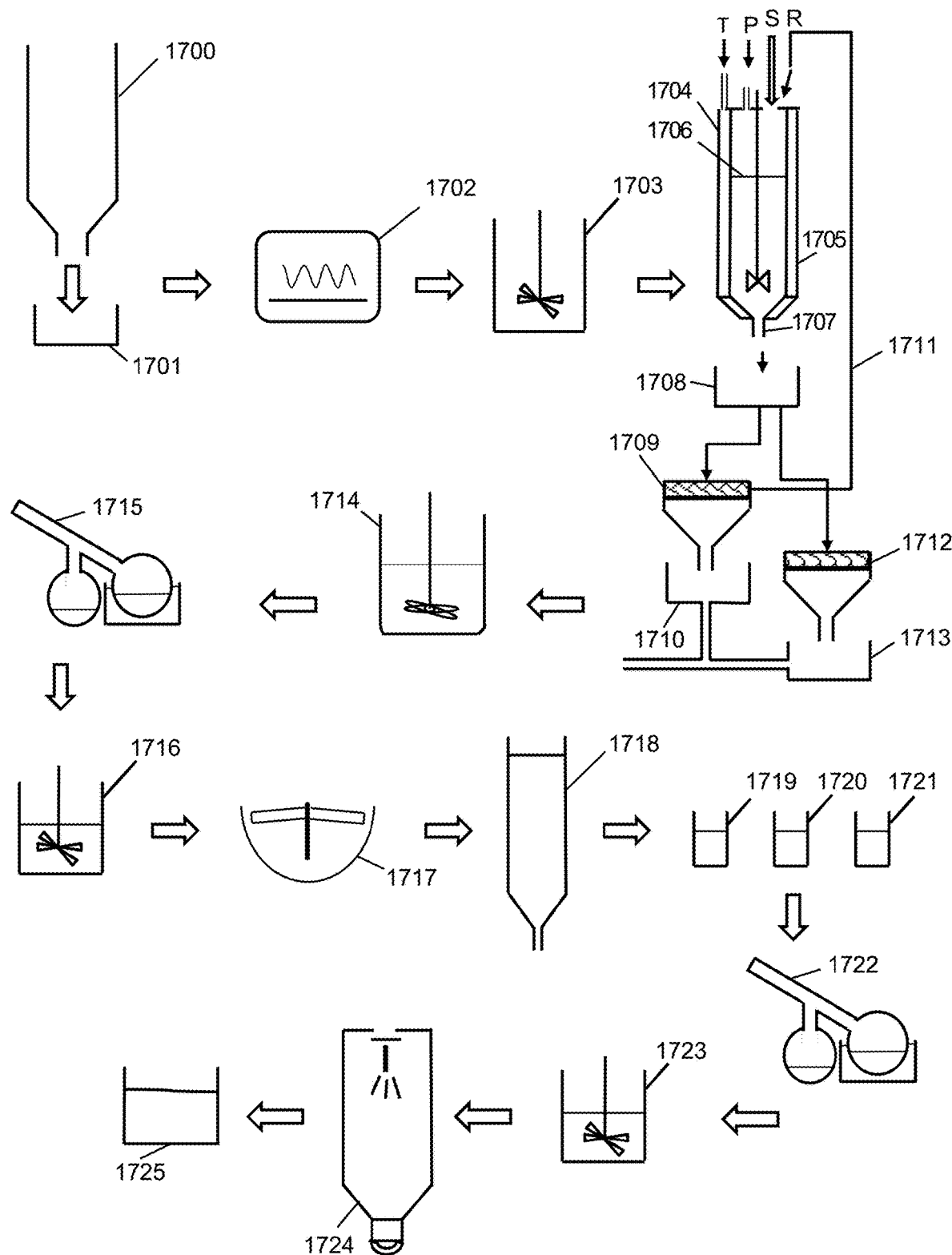
FIG. 17 is a schematic diagram of the apparatus used for obtaining a psychoactive alkaloid composition, according to an embodiment of the present invention.

In some embodiments, referring to FIG. 16, a process for purifying the psychoactive alkaloid extract obtained in step 1410 (FIG. 14) or step 1520 (FIG. 15) is shown.

The process includes adding, in step 1600, an acid or a base to the psychoactive alkaloid extract previously obtained, to result in a specific pH psychoactive alkaloid solution.

When used, the acid may be acetic acid, adipic acid, ascorbic acid, phosphoric acid, ammonium aluminum sulphate, ammonium citrate dibasic, ammonium citrate monobasic, calcium citrate, calcium fumarate, calcium gluconate, calcium phosphate dibasic, calcium phosphate monobasic, hydrochloric acid, sulfuric acid monobasic, calcium phosphate tribasic, citric acid, fumaric acid, gluconic acid, magnesium fumarate, malic acid, phosphoric acid, potassium acid tartrate, potassium citrate, potassium fumarate, sodium citrate, sodium fumarate, sodium gluconate, sodium lactate, sodium potassium hexametaphosphate, sodium potassium tartrate, sodium potassium tripolyphosphate, sodium pyrophosphate tetrabasic, sodium tripolyphosphate, tartaric acid, or any combination of one or more of these. In some embodiments, the acid is either only hydrochloric acid or only phosphoric acid, for example. It is also envisaged that other acids may be used.

When used, the base may be ammonium bicarbonate, ammonium carbonate, ammonium hydroxide, calcium acetate, calcium carbonate, calcium chloride, calcium hydroxide, calcium lactate, calcium oxide, calcium phosphate dibasic, calcium phosphate monobasic, magnesium carbonate, potassium aluminum sulphate, potassium bicarbonate, potassium carbonate, potassium hydroxide, potassium lactate, potassium phosphate dibasic, potassium pyrophosphate tetrabasic, potassium phosphate tribasic, potassium tripolyphosphate, sodium acetate, sodium acid pyrophosphate, sodium aluminum phosphate, sodium aluminum sulphate, sodium bicarbonate, sodium bisulphate, sodium carbonate, sodium hexametaphosphate, sodium hydroxide, sodium lactate, sodium phosphate dibasic, sodium phosphate monobasic, sodium phosphate tribasic, or any combination selected therefrom. In one embodiment, the base is solely sodium hydroxide, for example. Other bases may be used in other embodiments.

In some embodiments, the specific pH psychoactive alkaloid solution has a pH ranging from 2.5 to 4.5 or from 9 to 10. In other embodiments, the specific pH psychoactive alkaloid solution has a pH of 3, 4, or 9.5. The selection of the pH is chosen in a manner to allow for the efficient adsorption of the psychoactive alkaloids onto the resin(s).

The process optionally includes partially evaporating the solvent from the specific pH psychoactive alkaloid solution.

The process optionally includes filtering, centrifuging, or clarifying the psychoactive alkaloid solution or specific pH psychoactive alkaloid solution, as the case may be, and utilizing the obtained filtrate for the next step 1610 of adsorption. Clarifying may be performed, for example, by adding an agglomeration agent.

In step 1610, the process involves adsorbing the psychoactive alkaloid(s) in the specific pH psychoactive alkaloid solution onto a resin to obtain an adsorbed psychoactive alkaloid.

In step 1620, the process involves washing the resin to remove adsorbed impurities from the resin. While not all the impurities are adsorbed onto the resin, some of them may be. The washing step, substantially, does not remove the adsorbed psychoactive alkaloids. The washing solvent may be 100% ethanol, 100% reverse osmosis water, or any other washing solvent used in ion-exchange resin chromatography, provided that the washing removes impurities or by-products that are adsorbed on the resin. Impurities or by-products may include, for example, sugars, carbohydrates, chitin, chitosan, fats, minerals, waxes, or proteins. There may be one, two or more washing steps depending on the embodiment, and the same or different washing solvents may be used for each wash.

In other embodiments, the solvent(s) for washing may include a primary aliphatic alcohol, a ketone, water, and any combination selected therefrom. In some embodiments, the primary aliphatic alcohol is a C1-4 alcohol. In some embodiments, the primary aliphatic alcohol is 5% ethanol. In some embodiments, the primary aliphatic alcohol is ethanol. In some embodiments, the ketone is a C3-4 ketone. In yet other embodiments, the water is selected from deionized, distilled, reverse osmosis, or otherwise purified water that is substantially without free ions.

After the washing, the process involves eluting, in step 1630, the adsorbed psychoactive alkaloid from the resin using a solvent to obtain a purified psychoactive alkaloid extract. The solvent may be an organic solvent, an acid, a base, or water, a combination of an organic solvent and a base, or a combination of an organic solvent and an acid, a combination of an organic solvent and water, a combination of water and a base, or combination of water and an acid. The solvent from the purified psychoactive alkaloid extract is partially evaporated to obtain the purified psychoactive alkaloid extract in a slurry form for the standardization step 1420.

In some embodiments, the solvent used in the elution step 1630 may be a C1-4 alcohol, a C3-4 ketone, water, and any combination selected therefrom. In one embodiment, the primary aliphatic alcohol is 5% ethanol. In yet another embodiment, the water is deionized, distilled, reverse osmosis, or otherwise purified water, which is substantially without free ions. In one embodiment, the solvent used in the elution step 14 is a combination of an organic solvent and an acid. In general, any acidic environment will displace some of the ions from the resin, but the rate and optimization of the desorption will be affected by the acid concentration. In one embodiment, the solvent used is a combination of an organic solvent and a base. In general, any basic environment will displace some of the ions from the resin, but the rate and optimization of the desorption will be affected by the concentration of the base.

All the above solvents and combinations thereof are suitable for the elution step because all of the psychoactive alkaloids of interest are soluble therein and, depending on the choice of resin, they are all capable of pulling the alkaloids of interest off a resin. There are many different resins available, and it is a straightforward matter to select a suitable resin and elution solvent pair.

In one embodiment, the elution step is carried out at a temperature in the range of 4-75° C. These temperatures are limited by the boiling point of the solvent used, as well as the specifications of allowable food-grade resins, as determined by the manufacturers of the resins and governmental food and drug administrations. In another embodiment, the elution step is carried out at room temperature for convenience, i.e., at 21-25° C.

In other embodiments, the process for obtaining the purified psychoactive alkaloid The extraction step further includes repeating the steps 1600 to 1630 with the purified psychoactive alkaloid extract obtained in step 1630 to obtain a further or twice purified psychoactive alkaloid extract. For the repeated steps in these embodiments, the resin may be the same or a different resin, and the solvent may be the same or a different solvent. While the purified psychoactive alkaloid extract may have a low psychoactive alkaloid content, this may be increased by evaporation of some or all of the solvent.

F. Standardization

Standardization of Psychoactive Alkaloid 1

Figure 14:
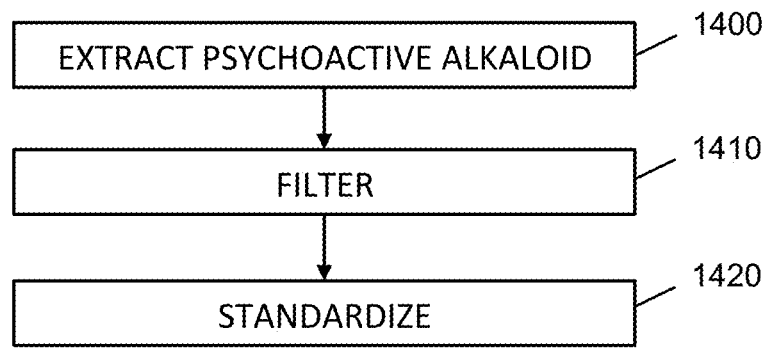
FIG. 14 illustrates steps of a process for obtaining a standardized psychoactive alkaloid composition, according to an embodiment of the present invention.

In one embodiment, referring to FIG. 14, a process for obtaining the composition is shown. The process includes the step 1400 of extracting a psychoactive alkaloid from a psychoactive alkaloid source to obtain a psychoactive alkaloid extract. The extract from the psychoactive alkaloid source may be a fluid, as either a liquid or a slurry, or is made into a fluid by the addition of a solvent. In one embodiment, the extraction step 1400 is followed by completely or partially concentrating the obtained psychoactive alkaloid extract (or solution) by evaporation of the solvent from the extract. In other embodiments, partially or completely evaporating the solvent may be considered to be part of the extraction step 1400. If the solvent from the extract has been completely evaporated, then water, more solvent, or another solvent is added back.

In step 1410, the extract obtained is filtered, followed by concentration to obtain a concentrated psychoactive alkaloid extract. Filtration is performed by any suitable known technique.

In step 1420, the concentrated psychoactive alkaloid extract is then standardized by adding one or more excipients to the extract, followed by drying to obtain the standardized psychoactive alkaloid composition. The concentration of alkaloids in the extract is measured, and the proportion of dry weight in the extract is calculated. Based on this concentration and dry weight content, the amount of excipient to be added is chosen to result in a powered composition with a specific amount of psychoactive alkaloid when the concentrated extract is dried.

The drying can be achieved by any technique known in the art for drying moist compositions including, for example, spray drying or freeze drying.

Standardization of Psychoactive Alkaloid 2

Figure 11:
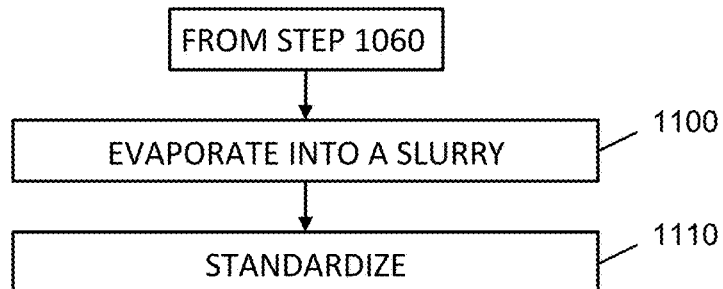
FIG. 11 illustrates a process for standardizing a purified psychoactive alkaloid solution to obtain a standardized psychoactive alkaloid extract, according to an embodiment of the present invention.

Referring to FIG. 11, the present invention also relates to a process of obtaining a standardized, purified, psychoactive alkaloid extract. In one embodiment, the process includes, in step 1100, concentrating the purified psychoactive alkaloid solution to obtain a purified psychoactive alkaloid slurry. The slurry is then standardized, in step 1110, to obtain a standardized psychoactive alkaloid extract.

In one embodiment, the standardizing step 1110 includes adding excipients to the purified psychoactive alkaloid slurry to obtain the standardized psychoactive alkaloid extract. The concentration of alkaloids in the slurry is measured, and the proportion of dry weight in the slurry is calculated. Knowing this concentration and the dry weight content, the amounts of excipients are chosen to result in a powder of known alkaloid concentration after the solvent in the slurry has been evaporated.

In one embodiment, the excipients are selected from silicon dioxide, ascorbic acid, maltodextrin from corn, potato or tapioca for example, gum arabic, microcrystalline cellulose, sodium benzoate, sodium phosphate, sodium citrate, rice hulls, and rice. A combination of any of these excipients may be used.

Depending on the concentration of the purified psychoactive alkaloid slurry and the quantity of excipients added, the standardized psychoactive alkaloid extract may have a psychoactive alkaloid concentration ranging from 0.1-99% by weight, and the concentration may be specified to two decimal places or two significant figures. For the highest percentage, only 1% of the standardized psychoactive extract will be excipient.

In exemplary embodiments, the standardized psychoactive alkaloid extracts have psychoactive alkaloid concentrations of 5.00% by weight, 54% by weight, and 68% by weight.

Numbered Embodiments

1. A psychoactive alkaloid composition comprising of, by weight: 0.1-99.9% of a psychoactive alkaloid extract; and one or more preservatives up to 10%, a flow agent up to 2%, 0-94% of one or more carriers, or any combination thereof.

2. The composition of embodiment 1, comprising 2-99.7% of the psychoactive alkaloid extract.

3. The composition of embodiment 1, comprising an antioxidant up to 0.5% by weight.

4. The composition of embodiment 1, comprising a bioavailability agent up to 0.5% by weight.

5. The composition of embodiment 1, wherein the psychoactive alkaloid extract has a psychoactive alkaloid concentration ranging from 0.1% to 99% by weight of the extract.

6. The composition of embodiment 5 wherein the one or more preservatives are selected from ascorbic acid, citric acid, lactose, vitamin A, vitamin E, retinyl palmitate, selenium, sodium citrate, sodium ascorbate, calcium ascorbate, sodium benzoate, and potassium benzoate.

7. The composition of embodiment 1, wherein the psychoactive alkaloid extract has a psychoactive alkaloid concentration ranging from 0.1% to 20% by weight of the extract.

8. The composition of embodiment 1, wherein the psychoactive alkaloid extract is a purified psychoactive alkaloid extract, and the purified psychoactive alkaloid extract has a psychoactive alkaloid concentration ranging from 10% to 99% by weight.

9. The composition as in embodiment 1, in a powder form.

10. The composition of embodiment 1, comprising 10% or more of the carrier.

11. The composition of embodiment 1, wherein the psychoactive alkaloid is psilocybin, psilocin, baeocystin, norbaeocystin, norpsilocin, aeruginascin, bufotenin, bufotenidine, 5-MeO-DMT (5-methoxy-N.Ndimethyltryptamine), N,N-dimethyltryptamine (DMT), 4-hydroxytryptamine, N,N,N-trimethyl-4-hydroxytryptamine ergine (LSA), ergonovine, ergometrine, muscimol, ibotenic acid, lysergic acid hydroxyethylamide (LSH), elymoclavine, ergometrinine, and/or chanoclavine, or any combination selected therefrom.

12. The composition of embodiment 1, wherein the psychoactive alkaloid extract comprises naturally occurring substances selected from the group consisting of fats, sugars, carbohydrates, chitin, chitosan, minerals, waxes and proteins.

13. The composition of embodiment 10, wherein the naturally occurring substances are present in the psychoactive alkaloid extract in a concentration ranging from 1%-99.9% by weight.

14. The composition of embodiment 1, wherein the psychoactive alkaloid extract is from fungi.

15. The composition of embodiment 14, wherein the psychoactive alkaloid extract is from *Psilocybe cyanescens*, *Psilocybe cubensis, Amanita muscaria*, or any selection therefrom.

16. The composition of embodiment 1, wherein the psychoactive alkaloid extract is from psychoactive plants.

17. The composition of embodiment 16, wherein the psychoactive alkaloid extract is from *Anadenanthera colubrina*.

18. The composition of embodiment 16, wherein the psychoactive alkaloid extract is from *Anadenanthera peregrina*.

19. The composition of embodiment 1, wherein the psychoactive alkaloid extract is from psychoactive animals.

20. The composition of embodiment 19, wherein the psychoactive alkaloid extract is from *Incilius alvarius*.

21. The composition of embodiment 1, wherein the psychoactive alkaloid extract is from psychoactive yeasts.

22. The composition of embodiment 1, wherein the flow agent is selected from silicon dioxide, stearic acid, magnesium stearate, or talc.

23. The composition of embodiment 1, wherein the one or more carriers are selected from starch, maltodextrin, alpha and beta cyclodextrin, microcrystalline cellulose (MCC), gum arabic, xanthum gum, guar gum, mannitol, or cellulose gum.

24. The composition of embodiment 23, wherein the maltodextrin is tapioca maltodextrin or rice maltodextrin.

25. The composition of embodiment 23, wherein the starch is potato starch.

26. The composition of embodiment 1, wherein the flow agent is present in the composition at 0.1 to 1.2%.

27. The composition of embodiment 1, wherein a first preservative of the one or more preservatives is present in the composition at 0.1 to 3%.

28. The composition of embodiment 27, wherein a second preservative of the one or more preservatives is present in the composition at 0.1 to 3%.

29. The composition of embodiment 1, wherein a first carrier of the one or more carriers is present in the composition at 10 to 20%.

30. The composition of embodiment 29, wherein a second carrier of the one or more carriers is present in the composition at 10 to 20%.

31. The composition of embodiment 1, comprising: the flow agent present in the composition at 0.1 to 1.2%; the one or more preservatives present in the composition at 0.1 to 2%; and the one or more carriers present in the composition at 10 to 20%.

32. The composition of embodiment 1, wherein: the flow agent is silicon dioxide; the carrier comprises maltodextrin and mannitol; and the one or more preservatives comprise ascorbic acid and citric acid.

33. The composition of embodiment 32, wherein the silicon dioxide is present in the composition at 0.1 to 1.2%.

34. The composition of embodiment 32, wherein the ascorbic acid is present in the composition at 0.1 to 2%.

35. The composition of embodiment 32, wherein the citric acid is present in the composition at 0.1 to 2%.

36. The composition of embodiment 32, wherein the maltodextrin is present in the composition at 10 to 20%.

37. The composition of embodiment 32, wherein the mannitol is present in the composition at 10 to 20%.

38. The composition of embodiment 1, wherein: the flow agent is silicon dioxide; the carrier comprises starch and mannitol; and the one or more preservatives comprise ascorbic acid and citric acid.

39. The composition of embodiment 38, wherein the silicon dioxide is present in the composition at 0.1 to 1.2%.

40. The composition of embodiment 38, wherein the ascorbic acid is present in the composition at 0.1 to 2%.

41. The composition of embodiment 38, wherein the citric acid is present in the composition at 0.1 to 2%.

42. The composition of embodiment 38, wherein the starch is present in the composition at 10 to 20%.

43. The composition of embodiment 38, wherein the mannitol is present in the composition at 10 to 20%.

44. A method for generating a psychoactive alkaloid extract from a psychoactive organism, the method comprising: a. providing a biomass of the psychoactive organism; b. contacting the biomass with 10 to 100 milliliters (mL) of solvent per gram (g) of the biomass; and c. evaporating the solvent from the biomass to yield the psychoactive alkaloid extract.

45. The method of embodiment 44, wherein the solvent is selected from 100% methanol, an alcohol:water mixture wherein the alcohol comprises 60% to 99% of the alcohol:water mixture, an alcohol:acid mixture wherein the alcohol comprises 60% to 99% of the alcohol:acid mixture, and acidified water.

46. A method for generating a psychoactive alkaloid extract from a psychoactive organism, the method comprising: a. providing a biomass of the psychoactive organism; b. contacting the biomass with a solvent, wherein the solvent is selected from 100% methanol, an alcohol:water mixture wherein the alcohol comprises 60% to 99% of the alcohol:water mixture, an alcohol:acid mixture wherein the alcohol comprises 60% to 99% of the alcohol:acid mixture, and acidified water; and c. evaporating the solvent from the biomass to yield the psychoactive alkaloid extract.

47. The method of embodiment 46, wherein the solvent is present at 10 to 100 milliliters (mL) of solvent per gram (g) of the biomass.

48. The method of any one of embodiments 44 to 47, wherein the solvent is present at 10 to 60 mL of solvent per gram of the biomass.

49. The method of any one of embodiments 44 to 48, wherein the solvent is present at 40 to 60 mL of solvent per gram of the biomass.

50. The method of any one of embodiments 44 to 49, wherein the biomass of the psychoactive organism is dried prior to contacting with the solvent.

51. The method of any one of embodiments 44 to 50, wherein the biomass of the psychoactive organism is reduced to a particle size of 6 millimeters (mm) to 0.03 mm prior to contacting with the solvent.

52. The method of any one of embodiments 44 to 51, wherein the biomass of the psychoactive organism is reduced to a particle size of 1 mm to 0.03 mm prior to contacting with the solvent.

53. The method of any one of embodiments 44 to 52, wherein the biomass of the psychoactive organism is reduced to a particle size of at least 0.074 mm prior to contacting with the solvent.

54. The method of any one of embodiments 44 to 53, wherein the biomass of the psychoactive organism is contacted with the solvent at 5° C. to 95° C.

55. The method of any one of embodiments 44 to 54, wherein the biomass of the psychoactive organism is contacted with the solvent at 20° C. to 70° C.

56. The method of any one of embodiments 44 to 55, wherein the biomass of the psychoactive organism is contacted with the solvent at 25° C.

57. The method of any one of embodiments 44 to 56, wherein the biomass of the psychoactive organism is contacted with the solvent for 1 to 720 minutes.

58. The method of any one of embodiments 44 to 57, wherein the biomass of the psychoactive organism is contacted with the solvent for 20 to 60 minutes.

59. The method of any one of embodiments 44 to 58, wherein the biomass of the psychoactive organism is contacted with the solvent for 30 minutes.

60. The method of any one of embodiments 44 to 59, wherein, following (b), the biomass is filtered through a filter.

61. The method of embodiment 60, wherein the filter comprises 1 micron ($\mu$m) to 10 $\mu$m mesh.

62. The method of any one of embodiments 44 to 61, wherein, following (b), the biomass is contracted with a second solvent.

63. The method of embodiment 62, wherein the second solvent is selected from 100% methanol, an alcohol:water mixture wherein the alcohol comprises 60% to 99% of the alcohol:water mixture, an alcohol:acid mixture wherein the alcohol comprises 60% to 99% of the alcohol:acid mixture, and acidified water.

64. The method of embodiment 62 or 63, wherein the second solvent is present at 10 to 100 milliliters (mL) of solvent per gram (g) of the biomass.

65. The method of any one of embodiments 62 to 64, wherein the solvent is present at 10 to 60 mL of solvent per gram of the biomass.

66. The method of any one of embodiments 62 to 65, wherein the solvent is present at 40 to 60 mL of solvent per gram of the biomass.

67. The method of any one of embodiments 44 to 66, wherein the alcohol of the alcohol:water mixture, the alcohol:acid mixture, or both, is a C1-C4 primary aliphatic alcohol.

68. The method of embodiment 67, wherein the C1-C4 primary aliphatic alcohol is ethanol or methanol.

69. The method of any one of embodiments 44 to 68, wherein the acid in the alcohol:acid mixture, the acidified water, or both, is acetic acid, adipic acid, ascorbic acid, phosphoric acid, ammonium aluminum sulphate, ammonium citrate dibasic, ammonium citrate monobasic, calcium citrate, calcium fumarate, calcium gluconate, calcium phosphate dibasic, calcium phosphate, hydrochloric acid, sulphuric acid monobasic, calcium phosphate tribasic, citric acid, fumaric acid, gluconic acid, magnesium fumarate, malic acid, phosphoric acid, potassium acid tartrate, potassium citrate, potassium fumarate, sodium citrate, sodium fumarate, sodium gluconate, sodium lactate, sodium potassium hexametaphosphate, sodium potassium tartrate, sodium potassium tripolyphosphate, sodium pyrophosphate tetrabasic, sodium tripolyphosphate, tartaric acid, and any combination therefrom.

70. The method of any one of embodiments 44 to 68, wherein the solvent, second solvent, or both is buffered to a pH of either 4 or less, or 10 or greater.

71. The method of embodiment 70, wherein the solvent, second solvent, or both is buffered with ammonium bicarbonate, ammonium carbonate, ammonium hydroxide, calcium acetate, calcium carbonate, calcium chloride, calcium hydroxide, calcium lactate, calcium oxide, calcium phosphate, dibasic, calcium phosphate monobasic, magnesium carbonate, potassium aluminum sulphate, potassium bicarbonate, potassium carbonate, potassium hydroxide, potassium lactate, potassium phosphate, dibasic, potassium pyrophosphate, tetrabasic, potassium phosphate tribasic, potassium tripolyphosphate, sodium acetate, sodium acid pyrophosphate, sodium aluminum phosphate, sodium aluminum sulphate, sodium bicarbonate, sodium bisulphate, sodium carbonate, sodium hexametaphosphate, sodium hydroxide, sodium lactate, sodium phosphate dibasic, sodium phosphate monobasic, sodium phosphate tribasic, and any combination therefrom.

72. The method of embodiment 70 or 71, wherein the solvent, second solvent, or both is buffered with acetic acid, adipic acid, ascorbic acid, phosphoric acid, ammonium aluminum sulphate, ammonium citrate dibasic, ammonium citrate monobasic, calcium citrate, calcium fumarate, calcium gluconate, calcium phosphate dibasic, calcium phosphate, hydrochloric acid, sulphuric acid monobasic, calcium phosphate tribasic, citric acid, fumaric acid, gluconic acid, magnesium fumarate, malic acid, phosphoric acid, potassium acid tartrate, potassium citrate, potassium fumarate, sodium citrate, sodium fumarate, sodium gluconate, sodium lactate, sodium potassium hexametaphosphate, sodium potassium tartrate, sodium potassium tripolyphosphate, sodium pyrophosphate tetrabasic, sodium tripolyphosphate, tartaric acid, and any combination therefrom.

73. The method of any one or embodiments 44 to 72, wherein the psychoactive alkaloid is psilocybin, psilocin, baeocystin, norbaeocystin, norpsilocin, aeruginascin, bufotenin, bufotenidine, 5-MeO-DMT (5-methoxy-N. Ndimethyltryptamine), N,N-dimethyltryptamine (DMT), 4-hydroxytryptamine, N,N,N-trimethyl-4-hydroxytryptamine ergine (LSA), ergonovine, ergometrine, muscimol, ibotenic acid, lysergic acid hydroxyethylamide (LSH), elymoclavine, ergometrinine, and/or chanoclavine, or any combination selected therefrom.

74. The method of any one or embodiments 44 to 72, wherein the solvent has a pH of 10 or greater and the psychoactive alkaloid extract comprises greater than 50% of the phosphorylated psychoactive alkaloid.

75. The method of embodiment 74, wherein the psychoactive alkaloid extract comprises greater than 90% of a phosphorylated psychoactive alkaloid.

76. The method of embodiment 74 or 75, wherein the phosphorylated alkaloid is psilocybin, baeocystin, norbaeocystin, aeruginascin, or any combination therefrom.

77. The method of any one or embodiments 44 to 72, wherein the solvent has a pH of 4 or less and the psychoactive alkaloid extract comprises greater than 50% of a dephosphorylated psychoactive alkaloid.

78. The method of embodiment 77, wherein the psychoactive alkaloid extract comprises greater than 90% of the dephosphorylated psychoactive alkaloid.

79. The method of embodiment 77 or 78, wherein the dephosphorylated alkaloid is psilocin, norpsilocin, 4-hydroxytryptamine, N,N,N-trimethyl-4-hydroxytryptamine, or any combination therefrom.

80. The method of any one or embodiments 44 to 79, wherein the psychoactive organism is a plant, animal, fungus, Protist, or bacterium.

81. The method of any one or embodiments 44 to 80, wherein the psychoactive organism is *Psilocybe cyanescens*, *Psilocybe cubensis*, *Amanita muscaria*, or any selection therefrom.

82. The method of any one or embodiments 44 to 80, wherein the psychoactive organism is *Anadenanthera colubrina* or *Anadenanthera peregrina*.

83. The method of any one or embodiments 44 to 80, wherein the psychoactive organism is *Incilius alvarius*.

84. The method of any one or embodiments 44 to 80, wherein the psychoactive organism is yeast.

85. A process for forming an extract of psychoactive alkaloids from psychoactive organisms comprising the steps of: soaking a biomass of dried, raw psychedelic fungus in a solvent selected from the group consisting of ethanol, a water-ethanol mixture, methanol, and a water-methanol mixture in order to dissolve the psychoactive alkaloids in the solvent; filtering an undissolved portion of the biomass from the solvent; evaporating the solvent sufficiently to remove the solvent completely, leaving a concentrated slurry or a residue that is converted to the concentrated slurry by adding water thereto: and standardizing the concentrated slurry by adding thereto a quantity of carrier measured to achieve a specified purity of extract.

86. The process of embodiment 85, wherein the standardizing comprises: measuring a psychoactive alkaloid content in the concentrated slurry; and using the psychoactive alkaloid content, the specified purity and a volume of the concentrated slurry to determine the quantity of carrier.

87. The process of embodiment 85, comprising drying the concentrated slurry to result in the extract, wherein the extract is a powdered extract.

88. The process of embodiment 85, wherein the solvent is a water-ethanol or water-methanol alkaline buffered solution.

89. The process of embodiment 88, wherein the solvent has a pH of 11-12.

90. The process of embodiment 88, wherein the solvent is buffered with sodium hydroxide, the process comprising, between the filtering and evaporating steps, adjusting the solvent to a pH of 4-9 using phosphoric acid.

91. The process of embodiment 85, wherein the solvent is a water-ethanol or water-methanol acid buffered solution.

92. The process of embodiment 91, wherein the solvent has a pH of 1.8-3.

93. The process of embodiment 91, wherein the solvent is buffered with citric acid, the process comprising, between the filtering and evaporating steps, adjusting the solvent to a pH of 4-9 using sodium hydroxide.

94. The process of embodiment 85, wherein the solvent comprises 100% reverse osmosis water.

95. The process of embodiment 85, wherein the soaking is at a temperature of 5-95° C.

96. The process of embodiment 85, comprising applying a pressure of 50 kPa-100 MPa to the solvent during the soaking step.

97. The process of embodiment 85, comprising agitating the solvent during the soaking step, wherein the soaking step has a duration of 10 minutes to 12 hours.

98. The process of embodiment 85, wherein the psychedelic organism is a plant, animal, fungus, Protist, or bacterium.

99. The process of embodiment 93, wherein the fungus comprises *amanita muscaria, psilocybe cubensis, psilocybe cyanescens*, or any combination thereof.

100. The process of embodiment 85, wherein the psychoactive alkaloids comprise psilocybin, psilocin, baeocystin, norbaeocystin, ibotenic acid or any mixture thereof.

101. The process of embodiment 85, wherein the solvent to biomass ratio is in a range from 1 L:1 kg to 50 L:1 kg.

102. The process of embodiment 85, wherein the specified purity is 0.1-10%.

103. The process of embodiment 85, wherein the specified purity is specified as a percentage with a precision of two decimal places.

104. The process of embodiment 85, wherein the carrier comprises ascorbic acid, silicon dioxide, maltodextrin, gum arabic, microcrystalline cellulose, sodium citrate, sodium benzoate, sodium phosphate, rice, rice hulls, or any combination of the foregoing.

105. The process of embodiment 85, comprising: repeating, using further solvent, the soaking and filtering steps for the filtered biomass; and combining the filtered solvent with the filtered further solvent.

106. A process for obtaining a purified psychoactive alkaloid solution, the process comprising: extracting a psychoactive alkaloid from a psychoactive alkaloid source to obtain a psychoactive alkaloid extract; contacting the psychoactive alkaloid extract with an adsorbent material to obtain an adsorbed psychoactive alkaloid; and eluting the adsorbed psychoactive alkaloid using a solvent to obtain a purified psychoactive alkaloid solution, wherein the solvent is water, an organic solvent or a combination thereof, under basic, acidic or neutral pH.

107. The process of embodiment 106, comprising, prior to the treating step, adding an acid or a base to the psychoactive alkaloid extract.

108. The process of embodiment 107, wherein, after adding the acid or base, the psychoactive alkaloid extract has a pH ranging from 2.5-4.5 or from 9-10 respectively.

109. The process of embodiment 107, wherein the acid is selected from the group consisting of acetic acid, adipic acid, ascorbic acid, phosphoric acid, ammonium aluminum sulphate, ammonium citrate dibasic, ammonium citrate monobasic, calcium citrate, calcium fumarate, calcium gluconate, calcium phosphate dibasic, calcium phosphate, hydrochloric acid, sulphuric acid monobasic, calcium phosphate tribasic, citric acid, fumaric acid, gluconic acid, magnesium fumarate, malic acid, phosphoric acid, potassium acid tartrate, potassium citrate, potassium fumarate, sodium citrate, sodium fumarate, sodium gluconate, sodium lactate, sodium potassium hexametaphosphate, sodium potassium tartrate, sodium potassium tripolyphosphate, sodium pyrophosphate tetrabasic, sodium tripolyphosphate, tartaric acid, and any combination therefrom.

110. The process of embodiment 107, wherein the base is selected from the group consisting of ammonium bicarbonate, ammonium carbonate, ammonium hydroxide, calcium acetate, calcium carbonate, calcium chloride, calcium hydroxide, calcium lactate, calcium oxide, calcium phosphate, dibasic, calcium phosphate monobasic, magnesium carbonate, potassium aluminum sulphate, potassium bicarbonate, potassium carbonate, potassium hydroxide, potassium lactate, potassium phosphate, dibasic, potassium pyrophosphate, tetrabasic, potassium phosphate tribasic, potassium tripolyphosphate, sodium acetate, sodium acid pyrophosphate, sodium aluminum phosphate, sodium aluminum sulphate, sodium bicarbonate, sodium bisulphate, sodium carbonate, sodium hexametaphosphate, sodium hydroxide, sodium lactate, sodium phosphate dibasic, sodium phosphate monobasic, sodium phosphate tribasic, and any combination therefrom.

111. The process of embodiment 106, wherein the adsorbent material is a gel resin, a macroporous resin, or a combination thereof.

112. The process of embodiment 111, wherein the macroporous resin is a non-ionic macroporous resin, an ion-exchange macroporous resin, or a combination thereof.

113. The process of embodiment 106, wherein the psychoactive alkaloid source comprises psilocybin, psilocin, baeocystin, norbaeocystin, norpsilocin, aeruginascin, bufotenin, bufotenidine, 5-MeO-DMT (5-methoxy-N.N-dimethyltryptamine), N,N-dimethyltryptamine (DMT), ergine (LSA), ergonovine, ergometrine, muscimol, ibotenic acid, lysergic acid hydroxyethylamide (LSH), elymoclavine, ergometrinine, chanoclavine, or any combination therefrom.

114. The process of embodiment 106, wherein the organic solvent is selected from a group consisting of C1-4 primary aliphatic alcohols, C3-4 ketones, and any combination therefrom.

115. The process of embodiment 106, wherein the process comprises further purifying the obtained purified psychoactive alkaloid solution by repeating, with the obtained purified psychoactive alkaloid solution, the treating step with a different adsorbent material and the eluting step with another solvent.

116. The process of embodiment 106, comprising: evaporating a portion of solvent from the purified psychoactive alkaloid solution to obtain a purified psychoactive alkaloid slurry.

117. The process of embodiment 116, wherein the purified psychoactive alkaloid slurry comprises 5% by weight or more of a psychoactive alkaloid.

118. The process of embodiment 116, comprising:
standardizing the purified psychoactive alkaloid slurry by adding thereto a quantity of excipient measured to provide a specific concentration of psychoactive alkaloid when the purified psychoactive alkaloid slurry is dried; and drying the purified psychoactive alkaloid slurry by evaporating the remaining portion of the solvent to obtain a standardized, purified, powdered psychoactive alkaloid extract having the specific concentration of psychoactive alkaloid.

119. The process of embodiment 116, wherein: the psychoactive alkaloid comprises psilocybin, psilocin, baeocystin, norbaeocystin, norpsilocin, aeruginascin, bufotenin, bufotenidine, 5-MeO-DMT (5-methoxy-N.N-dimethyltryptamine), N,N-dimethyltryptamine (DMT), ergine (LSA), ergonovine, ergometrine, muscimol, ibotenic acid, lysergic acid hydroxyethylamide (LSH), elymoclavine, ergometrinine, chanoclavine, or any combination therefrom; and the standardized, purified, powdered psychoactive alkaloid extract has a psychoactive alkaloid concentration ranging from 0.1-99% by weight.

120. The process of embodiment 118, wherein the excipient is selected from the group consisting of silicon dioxide, ascorbic acid, maltodextrin, gum arabic, microcrystalline cellulose, sodium benzoate, sodium phosphate, sodium citrate, rice hulls, rice and any combination therefrom.

121. The process of embodiment 106, comprising: prior to the treating step: adding an acid to the psychoactive alkaloid extract to bring its pH to 4±0.5; and removing solids from the psychoactive alkaloid extract; and after the treating step and before the eluting step: washing the adsorbent material with purified water; wherein: the adsorbent material is a non-ionic macroporous resin; and the solvent used for the eluting step is a hydro-ethanol solvent.

122. The process of embodiment 121, wherein the hydro-ethanol solvent is 5% ethanol.

123. The process of embodiment 106, comprising: prior to the treating step: adding an acid to the psychoactive alkaloid extract to bring its pH to 3±0.5; after the treating step and before the eluting step: washing the adsorbent material with 100% ethanol, wherein the adsorbent material is a macroporous strong cation exchange resin in an H+ or an Na+ form; and washing the adsorbent material with purified water; wherein the solvent used for the eluting step is 2% hydrochloric acid and 80% ethanol; and after the eluting step: adding alkali to the purified psychoactive alkaloid solution to bring its pH to 4±0.5; removing solids from the purified psychoactive alkaloid solution; evaporating a portion of the solvent from the purified psychoactive alkaloid solution; removing further solids from the purified psychoactive alkaloid solution; treating the purified psychoactive alkaloid extract with a non-ionic macroporous resin to obtain a second adsorbed psychoactive alkaloid; washing the non-ionic macroporous resin with purified water; and eluting the second adsorbed psychoactive alkaloid from the non-ionic macroporous resin using a hydro-ethanol solvent to obtain a twice purified psychoactive alkaloid solution.

124. The process of embodiment 106, comprising: prior to the treating step: adding a base to the psychoactive alkaloid extract to bring its pH to 9.5±0.5; after the treating step and before the eluting step: washing the adsorbent material with 100% ethanol, wherein the adsorbent material is a macroporous strong anion exchange resin in an OH— or a Cl— form; and washing the adsorbent material with purified water; wherein the solvent used for the eluting step is 2% sodium chloride and 80% ethanol; and after the eluting step: adding acid to the purified psychoactive alkaloid solution to bring its pH to 4±0.5; removing solids from the purified psychoactive alkaloid solution; evaporating a portion of the solvent from the purified psychoactive alkaloid solution; removing further solids from the purified psychoactive alkaloid solution; treating the purified psychoactive alkaloid extract with a non-ionic macroporous resin to obtain a second adsorbed psychoactive alkaloid; washing the non-ionic macroporous resin with purified water; and eluting the second adsorbed psychoactive alkaloid from the non-ionic macroporous resin using a hydro-ethanol solvent to obtain a twice purified psychoactive alkaloid solution.

125. The process of embodiment 106, wherein the psychoactive alkaloid source comprises psychoactive fungus and the extracting step comprises: drying and pulverizing the psychoactive alkaloid source to obtain a dried biomass; heating the dried biomass in a first solvent to obtain a first slurry, and filtering the first slurry to obtain a first filtrate and a first residue; heating the first residue in a second solvent to obtain a second slurry, and filtering the second slurry to obtain a second filtrate and a second residue; and mixing the first filtrate and the second filtrate to obtain the psychoactive alkaloid extract.

126. The process of embodiment 125, wherein: the first solvent and the second solvent are selected from a group consisting of a primary aliphatic alcohol, a ketone, purified water, and any combination therefrom; and the heating is carried out at a temperature ranging from 5-95° C. and for a time duration ranging from 10 minutes to 12 hours.

127. The process of embodiment 106, wherein the psychoactive alkaloid source is *Anadenanthera peregrina*, the process comprising: prior to the treating step: adding an acid to the psychoactive alkaloid extract to bring its pH to 4±0.5; and removing solids from the psychoactive alkaloid extract; and after the treating step and before the eluting step: washing the adsorbent material with purified water then with 10% ethanol; wherein: the adsorbent material is a macroporous resin; and the solvent used for the eluting step is 50% ethanol.

128. The process of embodiment 106, wherein the psychoactive alkaloid source comprises a plant, animal, fungus, protist, or bacterium.

129. T The process of embodiment 106, wherein the psychoactive alkaloid source comprises *Psilocybe cyanescens, Psilocybe cubensis, Amanita muscaria*, or any selection therefrom.

130. The process of embodiment 106, wherein the psychoactive alkaloid source comprises *Anadenanthera colubrina* or *Anadenanthera peregrina*.

131. The process of embodiment 106, wherein the psychoactive alkaloid source comprises *Incilius alvarius*.

132. The process of embodiment 106, wherein the psychoactive alkaloid source comprises yeast.

133. The process of embodiment 106, wherein the psychoactive alkaloid extract is contacted with the adsorbent material at a flow rate of 1 bed volume per hour (BV/h) to 10 BV/h.

134. The process of embodiment 133, wherein the psychoactive alkaloid extract is contacted with the adsorbent material at a flow rate of 2 bed volume per hour (BV/h) to 6 BV/h.

135. A process for obtaining a psychoactive alkaloid extract with a desired amount of a phosphorylated psychoactive alkaloid and a desired amount of a dephosphorylated psychoactive alkaloid, the process comprising: drying and pulverizing a psychoactive alkaloid source to obtain a dried powdered biomass; extracting a psychoactive alkaloid from the dried powdered biomass with an acidified solvent or a basified solvent to obtain a psychoactive alkaloid liquid with a specific pH, wherein the specific pH is lower than 3.5 or greater than 10.5; adjusting the pH of the psychoactive alkaloid liquid to a pH ranging from 3.5-4.5; and evaporating the solvent from the psychoactive alkaloid liquid to obtain the psychoactive alkaloid extract with the desired amount of the phosphorylated psychoactive alkaloid and the desired amount of the dephosphorylated psychoactive alkaloid; wherein: the desired amount of the phosphorylated psychoactive alkaloid is 0-100% by weight of a total phosphorylatable psychoactive alkaloid content in the psychoactive alkaloid extract; and the desired amount of the dephosphorylated psychoactive alkaloid is the remainder of the total phosphorylatable psychoactive alkaloid content in the psychoactive alkaloid extract.

136. The process of embodiment 135, wherein the phosphorylated alkaloid is psilocybin, baeocystin, norbaeocystin, aeruginascin, or any combination therefrom; and the dephosphorylated alkaloid is psilocin, norpsilocin, 4-hydroxytryptamine, N,N,N-trimethyl-4-hydroxytryptamine, or any combination therefrom.

137. The process of embodiment 135, wherein the psychoactive alkaloid source comprises psilocybin, baeocystin, norbaeocystin, aeruginascin, psilocin, norpsilocin, 4-hydroxytryptamine, N,N,N-trimethyl-4-hydroxytryptamine, or any combination therefrom.

138. The process of embodiment 135, wherein the extracting step comprises: mixing the dried powdered biomass with the acidified solvent or the basified solvent to obtain a slurry; and filtrating the slurry to obtain a filtrate residue and the psychoactive alkaloid liquid.

139. The process of embodiment 138, wherein the extracting step comprises further extracting the psychoactive alkaloid by repeating, with the obtained filtrate residue, the extracting step with the same or a different acidified solvent, or the same or a different basified solvent.

140. The process of embodiment 138, wherein after the mixing step the acidified solvent or the basified solvent, the slurry has a pH ranging from 0.5-3.5 or from 10.5-13.5 respectively.

141. The process of embodiment 135, wherein the acidified solvent is a mixture of an acid; and a C1-C4 primary aliphatic alcohol, a C3-C4 ketone, water, or any combination selected therefrom.

142. The process of embodiment 135, wherein the basified solvent is a mixture of a base; and a C1-C4 primary aliphatic alcohol, a C3-C4 ketone, water, or any combination selected therefrom.

143. The process of embodiment 135, wherein the extraction is performed: at a temperature ranging from 5-95° C.; and for a time period ranging from 10-720 minutes.

144. The process of embodiment 135, wherein the extraction is performed at a pressure ranging from 7 to 20,000 psi (50 kPa-138 MPa).

145. The process of embodiment 135, wherein the extraction is performed with a solvent to solid proportion of 1 L:1 kg to 50 L:1 kg, wherein the solid is the dried powdered biomass.

146. The process of embodiment 135, wherein the specific pH is lower than 3.5; and wherein: the desired amount of the phosphorylated psychoactive alkaloid is 0% by weight of the total phosphorylatable psychoactive alkaloid content in the psychoactive alkaloid extract, and the desired amount of the dephosphorylated psychoactive alkaloid is 100% by weight of the total phosphorylatable psychoactive alkaloid content in the psychoactive alkaloid extract.

147. The process of embodiment 135, wherein the specific pH is greater than 10.5; and wherein the desired amount of the phosphorylated psychoactive alkaloid is 100% by weight of the total phosphorylatable psychoactive alkaloid content in the psychoactive alkaloid extract, and the desired amount of the dephosphorylated psychoactive alkaloid is 0% by weight of the total phosphorylatable psychoactive alkaloid content in the psychoactive alkaloid extract.

148. The process of embodiment 135, wherein the specific pH is greater than 10.5, and a maximum desired amount of the phosphorylated alkaloid is limited by an amount of the dephosphorylated alkaloid in the psychoactive alkaloid source.

149. The process of embodiment 135, wherein the specific pH is greater than 10.5, and wherein: the desired amount of the phosphorylated psychoactive alkaloid is 1-99% by weight of the total phosphorylatable psychoactive alkaloid content in the psychoactive alkaloid extract.

150. The process of embodiment 135, comprising: pausing the evaporating step when a portion of the solvent has been evaporated from the psychoactive alkaloid liquid to obtain a psychoactive alkaloid slurry; standardizing the psychoactive alkaloid slurry by adding thereto a measured quantity of one or more excipients to obtain a standardized slurry with a specific amount of psychoactive alkaloid content; and continuing the evaporating step by drying the standardized slurry to obtain a psychoactive alkaloid composition comprising the psychoactive alkaloid extract, and one or more excipients; wherein a total psychoactive alkaloid content in the psychoactive alkaloid composition is specified as a result of the standardizing step.

151. The process of embodiment 150, wherein the desired amount of the phosphorylated psychoactive alkaloid is 100% by weight of the total phosphorylatable psychoactive alkaloid content in the psychoactive alkaloid composition, the process comprising: preparing another psychoactive alkaloid composition comprising another psychoactive alkaloid extract according to embodiment 150, wherein the desired amount of the dephosphorylated psychoactive alkaloid is 100% by weight of the total phosphorylatable psychoactive alkaloid content in the other psychoactive alkaloid extract; mixing the psychoactive alkaloid composition and the other psychoactive composition in a measured ratio to obtain a psychoactive alkaloid composition comprising the phosphorylated psychoactive alkaloid composition and the dephosphorylated psychoactive alkaloid of the other psychoactive alkaloid composition in a specific ratio; wherein the specific ratio of phosphorylated psychoactive alkaloid to dephosphorylated psychoactive alkaloid ranges from 1:1000 to 1000:1.

152. A process for obtaining a psychoactive alkaloid composition with a specific ratio of a phosphorylated psychoactive alkaloid to a dephosphorylated psychoactive alkaloid, the process comprising: extracting a psychoactive alkaloid from a dried powdered biomass with a basified solvent to obtain a psychoactive alkaloid liquid with a pH greater than 10.5, wherein a majority of a total phosphorylatable psychoactive alkaloid content is the phosphorylated alkaloid and a remainder thereof is the dephosphorylated alkaloid; adjusting the pH of the psychoactive alkaloid liquid to a pH ranging from 3.5-4.5; extracting another psychoactive alkaloid from another dried powdered biomass with an acidified solvent to obtain another psychoactive alkaloid liquid with a pH lower than 3.5, wherein all of a total phosphorylatable psychoactive alkaloid is the dephosphorylated alkaloid; adjusting the pH of the other psychoactive alkaloid liquid to a pH ranging from 3.5-4.5; evaporating a portion of the basified solvent from the psychoactive alkaloid liquid and a portion of the acidified solvent from the other psychoactive alkaloid liquid to obtain a psychoactive alkaloid extract slurry and another psychoactive alkaloid extract slurry respectively; mixing measured portions of the psychoactive alkaloid extract slurry and the other psychoactive alkaloid extract slurry to obtain a bulk psychoactive alkaloid extract slurry comprising the phosphorylated psychoactive alkaloid and the dephosphorylated psychoactive alkaloid in the specific ratio; standardizing the bulk psychoactive alkaloid extract slurry by adding thereto a measured quantity of one or more excipients to obtain a standardized bulk slurry; and drying the standardized bulk psychoactive alkaloid slurry to obtain the psychoactive alkaloid composition, wherein the phosphorylated psychoactive alkaloid and the dephosphorylated psychoactive alkaloid are in the specific ratio; wherein the specific ratio of phosphorylated psychoactive alkaloid to dephosphorylated psychoactive alkaloid ranges from 1:1000 to 1000:1.

153. A psychoactive alkaloid composition comprising: a psychoactive alkaloid extract comprising a desired amount of a phosphorylated psychoactive alkaloid and a desired amount of a dephosphorylated psychoactive alkaloid, wherein: the desired amount of the phosphorylated psychoactive alkaloid is 0-100% by weight of a total phosphorylatable psychoactive alkaloid content in the psychoactive alkaloid extract, and the desired amount of the dephosphorylated psychoactive alkaloid is the remainder of the total phosphorylatable psychoactive alkaloid content in the psychoactive alkaloid extract; and one or more excipients.

154. The composition of embodiment 153, wherein the composition is in powder form.

155. The composition of embodiment 153, wherein: the desired amount of the phosphorylated psychoactive alkaloid is 0% by weight of the total phosphorylatable psychoactive alkaloid content in the psychoactive alkaloid extract, and the desired amount of the dephosphorylated psychoactive alkaloid is 100% by weight of the total phosphorylatable psychoactive alkaloid content in the psychoactive alkaloid extract.

156. The composition of embodiment 153, wherein: the desired amount of the phosphorylated psychoactive alkaloid is 100% by weight of the total phosphorylatable psychoactive alkaloid content in the psychoactive alkaloid extract, and the desired amount of the dephosphorylated psychoactive alkaloid is 0% by weight of the total phosphorylatable psychoactive alkaloid content in the psychoactive alkaloid extract.

157. The composition of embodiment 153, wherein: the phosphorylated alkaloid is psilocybin, baeocystin, norbaeocystin, aeruginascin, or any combination selected therefrom; and the dephosphorylated alkaloid is psilocin, norpsilocin, 4-hydroxytryptamine, N,N,N-trimethyl-4-hydroxytryptamine, or any combination selected therefrom.

158. A psychoactive alkaloid composition with a specific ratio of a phosphorylated psychoactive alkaloid and a dephosphorylated psychoactive alkaloid, the composition comprising: a psychoactive alkaloid extract having a total phosphorylatable psychoactive alkaloid content of 100% of a phosphorylated psychoactive alkaloid; another psychoactive alkaloid extract having a total phosphorylatable psychoactive alkaloid content of 100% of a dephosphorylated psychoactive alkaloid; and one or more excipients; wherein the psychoactive alkaloid extract and the other psychoactive alkaloid extract are present in a proportion such that the specific ratio of phosphorylated psychoactive alkaloid to phosphorylated psychoactive alkaloid ranges from 1:1000 to 1000:1.

EXAMPLES

In order to further illustrate the present invention, the following specific examples are given with the understanding that these examples are intended only to be illustrations without serving as a limitation on the scope of the present invention. All parameters, dimensions, materials, quantities, and configurations described herein are examples only and may be changed depending on the specific embodiment. Accordingly, the scope of the invention is to be construed in accordance with the substance defined by the claims. The process may be scaled up using larger quantities and modified apparatus.

Although the examples of the present invention have been formulated specifically using *Psilocybe cubensis* as a source to obtain a psychoactive alkaloid extract, the extract including psilocybin and psilocin, other sources are possible. A person skilled in the art would appreciate that the *Psilocybe cubensis* can be readily substituted by other sources of psychoactive alkaloids to obtain a variety of other psychoactive alkaloids having similar properties, such as psilocybin, psilocin, baeocystin, norbaeocystin, norpsilocin, aeruginascin, bufotenin, bufotenidine, 4-hydroxytryptamine, 5-MeO-DMT (5-methoxy-N,N-dimethyltryptamine), N,N-dimethyltryptamine (DMT), N,N,N-trimethyl-4-hydroxytryptamine, ergine (LSA), ergonovine, ergometrine, muscimol, ibotenic acid, lysergic acid hydroxyethylamide (LSH), elymoclavine, ergometrinine, chanoclavine, or any combination therefrom, to result in compositions with similar efficacy and efficiency as well. For example, mushrooms from the genus *Conocybe, Copelandia, Galerina, Gymnopilus, Inocybe, Panaeolus, Pholiotina, Pluteus, Psilocybe*, or any combination therefrom may be used. For example, *psilocybe cyanescens* and *amanita muscaria* fungi may be used. For example, the venom of the toad *Incilius alvarius*, the *Anadenanthera colubrina* tree or the *Anadenanthera peregrina* tree may be used as other sources of psychoactive alkaloids. Note that the lists of sources and psychoactive alkaloids are included to provide examples and are non-exhaustive lists.

Example 1: Preparation of Psychoactive Alkaloid Extract

Figure 12:
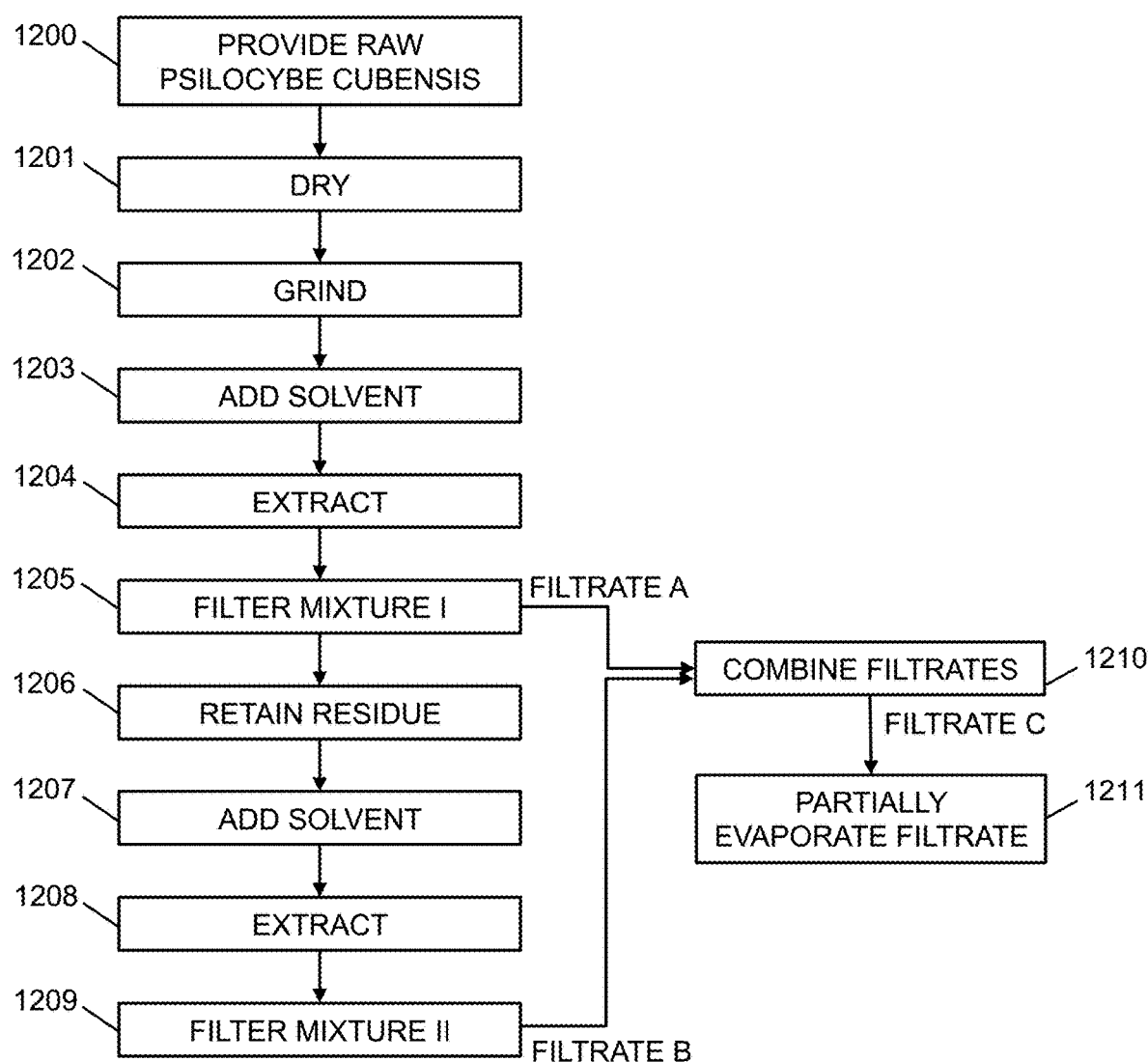
FIG. 12 illustrates detailed steps of a process for extracting psychoactive alkaloids from *Psilocybe cubensis*, according to an embodiment of the present invention.

Referring to FIG. 12, 2.5 kg of fresh *Psilocybe cubensis* (caps, stems and gills) was taken (step 1200) and dried (step 1201) in a forced air oven at 25° C. for 5-10 hours. A mass of 140 g of dried biomass was obtained. The dried biomass was pulverized (step 1202) to a size of 200 mesh with a hammer mill to result in a dried, powdered biomass. The dried, powdered biomass was placed in an agitated, heat-controlled extraction vessel with 5 kg of a hydro-ethanol mixture, with 3 parts ethanol to 1 part water by weight, as a solvent (step 1203). The extraction (step 1204) was carried out for 4 hours at a controlled temperature of 70° C. to obtain an extract in the form of a slurry. The extraction slurry was filtered (step 1205) while it was hot, and filtrate A was collected. The filter residue was retained (step 1206) and placed back into the extraction vessel, followed by addition (step 1207) of another 5 kg of 3:1 ethanol:water mixture by weight as a solvent. The extraction was repeated (step 1208). The temperature of extraction was again carried out at 70° C. for a duration of 4 hours. The obtained extraction slurry was filtered (step 1209) while hot and filtrate B was collected. Filtrate A and filtrate B from the first and second extractions were mixed (step 1210). Using a rotary evaporator, the mixture was then partially concentrated by evaporation (step 1211) of the solvent from the combined filtrates to provide a 2.5 liter volume of psychoactive alkaloid extract solution. Step 1211 is similar to step 1010 of FIG. 10.

Example 2: Preparation of Psychoactive Alkaloid Extract

In another example, the process of Example 1 was followed, except that the combined filtrates A and B were left to cool to room temperature, and any precipitate that formed was filtered out and discarded.

Example 3. Preparation of *Anadenanthera peregrina* Seed Extract 1.00 kg of dried *Anadenanthera peregrina* seeds were pulverized to a size of 200 mesh with a grinder. The dried powdered biomass was placed into an agitated, heat-controlled vessel with 20 kg of solvent. In this embodiment, the solvent was a hydro-ethanol mixture of 4 parts ethanol to 1 part water by weight. The extraction was controlled to a constant 70° C., and the time of extraction was 4 hours. The extraction slurry was filtered while hot, and the filter residue was placed back into the extraction vessel and extracted again with an additional 10 kg of 4:1 ethanol:water mixture by weight. The temperature of extraction was again 70° C. and the time was 4 hours. The extraction slurry was filtered while hot and the filtrates from the first and second extractions were mixed together. The resulting bulk filtrate was immediately placed into an evaporation still and the solvent was removed until the final volume of the filtrate was reduced to about 6 liters, which resulted in a solids concentration in the filtrate of 6.8%.

Example 4: Extraction Using a Solvent Mixture of Ethanol (0-100 wt %) and Water

Figure 3:
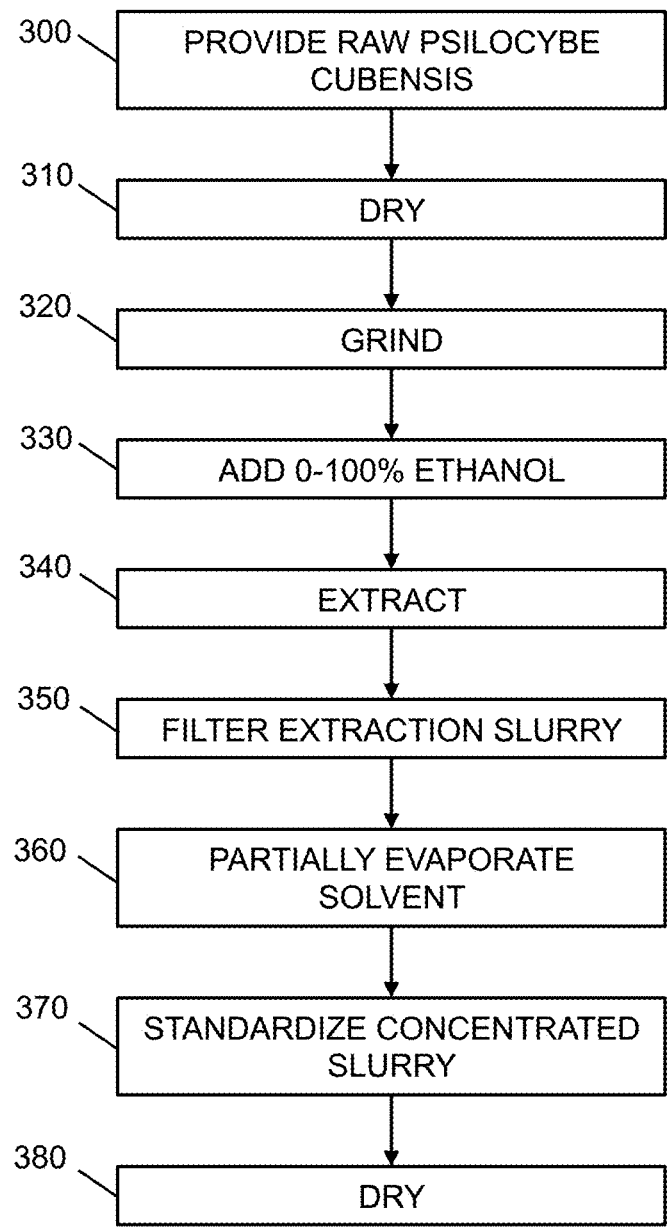
FIG. 3 is a flowchart showing more detailed steps of a process for extracting psychoactive alkaloids from *Psilocybe cubensis* using a hydro-ethanol solvent, according to an embodiment of the present invention.

Referring to FIG. 3, a process is shown for the extraction of psychoactive compounds from *Psilocybe cubensis* using a general hydro-ethanol solvent. The solvent may range from a percentage of <1% of ethanol in water to 100% ethanol.

In step 300, 2.5 kg of raw psilocybin mushrooms from the *psilocybe cubensis* species was provided. In step 310, the raw *psilocybe cubensis* was dried in a forced air oven at 25°

C. for 10 hours. In step 320, the resulting dried biomass was ground in a hammer mill or the equivalent, to particle size of 200 mesh.

In step 330, 5 kg of solvent, having a 0-100% ethanol concentration was added to an extraction vessel into which the ground biomass was placed. The extraction vessel was an agitated, heat-controlled vessel.

In step 340, the extraction proceeds as the biomass was soaked. The temperature of the extraction was elevated above room temperature to 70° C. Temperature and pressure, if applied, were generally selected so that the solvent does not boil if elevated temperatures were used. The duration of the extraction was 4 hours.

In the step 350, the extraction slurry was filtered to remove residue with undissolved *Psilocybe cubensis* from the filtrate. The residue may be treated with another extraction step if desired, and if so, the filtrate from the subsequent step was combined with the filtrate from the first filtration.

In step 360, the solvent from the filtrate was partially evaporated using a rotary evaporator. The resulting concentrated slurry was subjected to a standardization process in step 370. The standardized concentrated slurry was then dried using a bench-top spray dryer in step 380 to result in a powder with an accurately determined concentration by weight of psychoactive alkaloids.

Example 5: Extraction Using a Solvent Mixture of Ethanol and Water (3:1 wt %)

Figure 2:
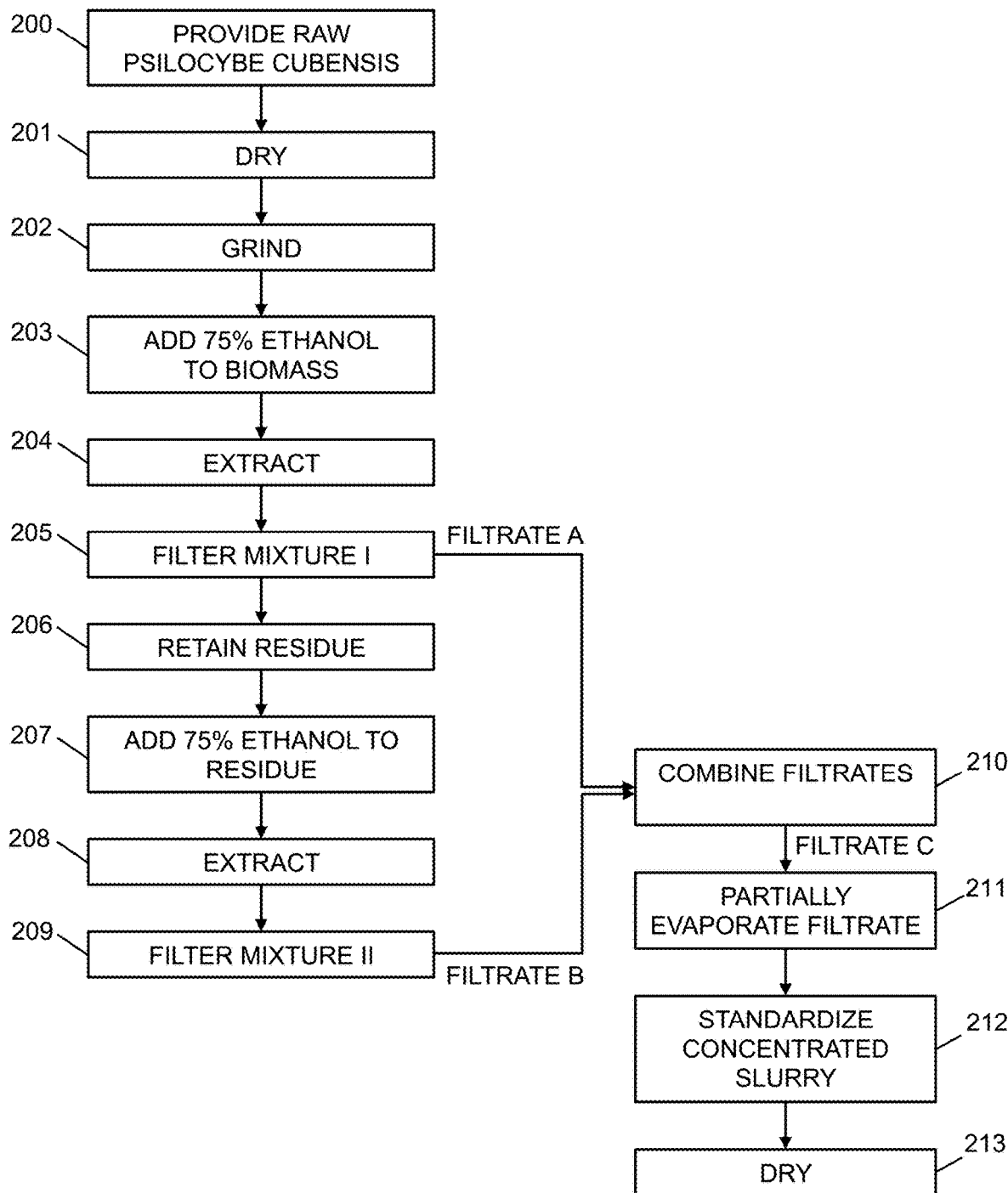
FIG. 2 is a flowchart showing more detailed steps of a process for extracting psychoactive alkaloids from *Psilocybe cubensis* using a 75% ethanol solvent, according to an embodiment of the present invention.

Referring to FIG. 2, an exemplary detailed process is shown for the extraction of psychoactive compounds from *Psilocybe cubensis* mushrooms using a 75% ethanol solvent.

In step 200, 2.5 kg of raw psilocybin mushrooms from the *psilocybe cubensis* species was provided. In step 201, the raw psilocybin mushrooms were dried in a forced air oven at 25° C., for 10 hours. The aim was to dry the mushrooms so as not to significantly reduce their psychoactive alkaloid concentration. For example, if too high a temperature or too long a time at a specific temperature were used, the alkaloids may start to decompose. The resulting, dried biomass was 140 g. In step 202, the dried biomass was ground using a hammer mill or the equivalent, to a particle size of 200 mesh.

In step 203, a 5 kg quantity of the 75% (by weight) ethanol solvent, formed by mixing 3 parts of ethanol to 1 part of water by weight, was placed in an extraction vessel. The dried, ground biomass was also placed in the extraction vessel, which was heat-controlled and agitated.

The extraction proceeds in step 204 as the biomass soaks in the solvent. The temperature of the extraction process was 70° C., and the duration of extraction was 4 hours. The temperature remained constant during the extraction process.

In step 205, the resulting mixture of biomass solids and solvent with dissolved extract, was filtered while still hot, i.e. still at 70° C., or slightly lower due to ambient cooling. This removed a residue with undissolved psilocybin mushroom components from the filtrate. The filter used was a 10 µm sieve. The filtrate from this step was filtrate A. In step 206, the residue was retained and placed back into the extraction vessel. In step 207, another 5 kg of 75% ethanol was added to the retained residue.

In step 208, the extraction process of the residue continued at the same temperature as for the initial extraction step, i.e. at 70° C., for a time of 4 hours. Again, the temperature remained constant during the extraction process.

In step 209, the second resulting mixture, of biomass solids and solvent with dissolved extract, was filtered to remove the residue of unwanted solid material. The filter used was a 10 µm sieve. Note that in other embodiments a differently sized filter may be used here or in the prior filtration step, or the liquid may be decanted from the residue without filtering. In some embodiments, a centrifuge may be used to help separate the liquid from the residue. Filtrate B from the second filtration process may have a lower concentration of psychoactive compounds than filtrate A from the first filtration step. Filtrates A and B were then mixed in step 210 to result in bulk filtrate C. More extract can be obtained by splitting the solvent into two or more batches and using each one sequentially to soak the biomass, compared to using a single volume of solvent.

The bulk filtrate C was then processed with a rotary evaporator in step 211 to remove solvent until the volume of filtrate C is 2.5 liters. At this point, the reduced amount of filtrate C was a concentrated slurry, due to the precipitation of water-insoluble components, for example.

The volume of 2.5 L was chosen because the mixture now has a low enough ethanol content that the carriers can be mixed in. By preferentially removing ethanol over water, which occurs naturally during the evaporation, it also gives the later spray-drying step a lower risk of explosion compared to if a 75% ethanol slurry were sprayed directly.

In step 212, after some of the solvent has been removed using the rotary evaporator, the concentrated slurry was then standardized. The standardization process uses a titration procedure to determine the concentration of the psychoactive alkaloids in the concentrated slurry. The standardization procedure entails adjusting the concentration of psychoactive alkaloids the concentrated slurry to a desired target, such as 1.00% by dry weight. In this example, 4.7 g of ascorbic acid, 1.9 g of $SiO_2$ and 47 g of maltodextrin were added to the concentrated slurry.

In step 213, after the standardization process, the standardized concentrated slurry was dried using a bench-top spray dryer. This resulted in 100 g of powdered psilocybin mushroom extract with a total alkaloid concentration of 1.00% by weight. As can be seen, the purity of the extract can be defined as a percentage to a precision of two decimal places.

Example 6: Extraction Using a Buffered Solvent Mixture of Ethanol and Water (3:1 wt %) (Alkaline Solvent)

Figure 7:
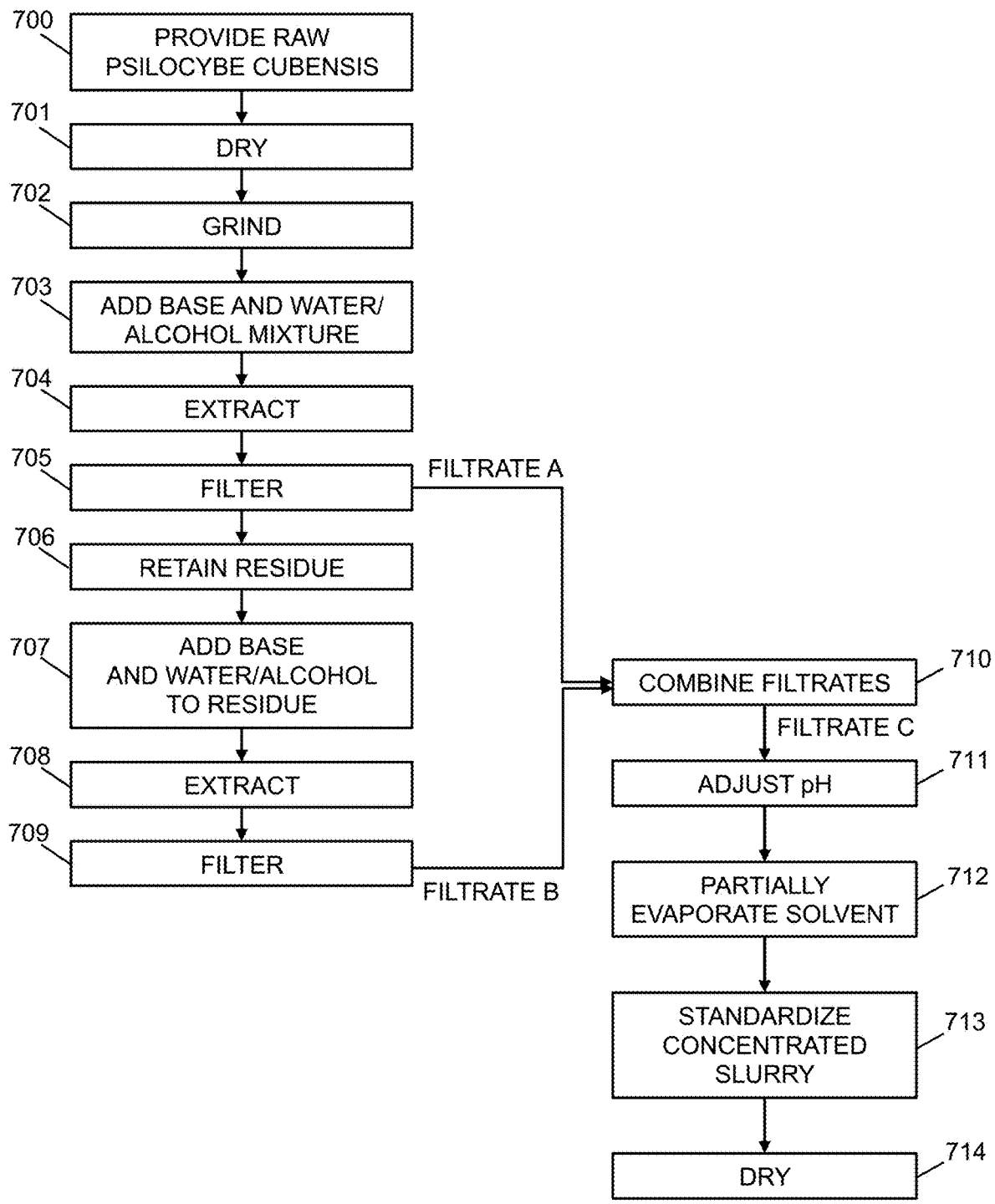
FIG. 7 is a flowchart showing more detailed steps of a process for extracting psychoactive alkaloids *Psilocybe cubensis* using a buffered alkaline solvent, according to an embodiment of the present invention.

Referring to FIG. 7, a process is shown for the extraction of psychoactive compounds from *Psilocybe cubensis* mushrooms using a buffered alkaline solvent. In step 700, 2.5 kg of raw psilocybin mushrooms from the *Psilocybe cubensis* species was provided. In step 701, the raw *Psilocybe cubensis* was dried in a forced air oven at 25° C. for 10 hours. The dried biomass was 140 g. In step 702, the dried biomass was ground in a hammer mill or the equivalent, to a particle size of 200 mesh.

In step 703, 5 liters of solvent was added with the biomass to an extraction vessel, which was heat-controlled and agitated. The solvent was a pH-adjusted, hydro-ethanol mixture. For its preparation, 200 g of sodium hydroxide pellets were placed into a 5 L vessel, with 1.25 L of reverse osmosis water followed by 3.75 L of ethanol. The contents were mixed until completely dissolved. The pH of this solution was between pH 11 and pH 12.

In step 704, the extraction proceeded. The temperature of the extraction process was 30° C., and the duration of the extraction was 4 hours. In step 705, the extraction slurry was filtered to remove residue with undissolved *psilocybe cubensis* from the filtrate. The filtrate from this step was named filtrate A. In step 706, the residue was retained and placed back in the extraction vessel. In step 707, another 5 L of the same solvent was added to the residue. In step 708, the extraction process of the residue continued at a temperature of 30° C., for 4 hours. The temperature remained constant during the extraction process. In step 709, the second extraction slurry was filtered to remove the residue of unwanted solid material. Filtrates A and B were then mixed in step 710 to result in bulk filtrate C.

Bulk filtrate C was brought to a pH of 5 with 5M phosphoric acid in step 711. The pH-adjusted concentrated slurry was processed with a rotary evaporator in step 712 to remove solvent until the volume of filtrate C was 2.5 liters. At this point, the reduced amount of filtrate C was a concentrated slurry, due to the precipitation of some of the psychoactive alkaloids.

In step 713, the concentrated slurry was standardized. In this example, 4.7 g of ascorbic acid, 1.9 g of $SiO_2$, and 47 g of maltodextrin were added to the concentrated slurry. In step 714, the standardized concentrated slurry was dried using a bench-top spray dryer. This resulted in 100 g of powdered psilocybin mushroom extract with a total alkaloid concentration of 1.00% by weight.

Example 7: Extraction Using a Buffered Solvent Mixture of Ethanol and Water (3:1 wt %) (Acid Solvent)

Figure 6:
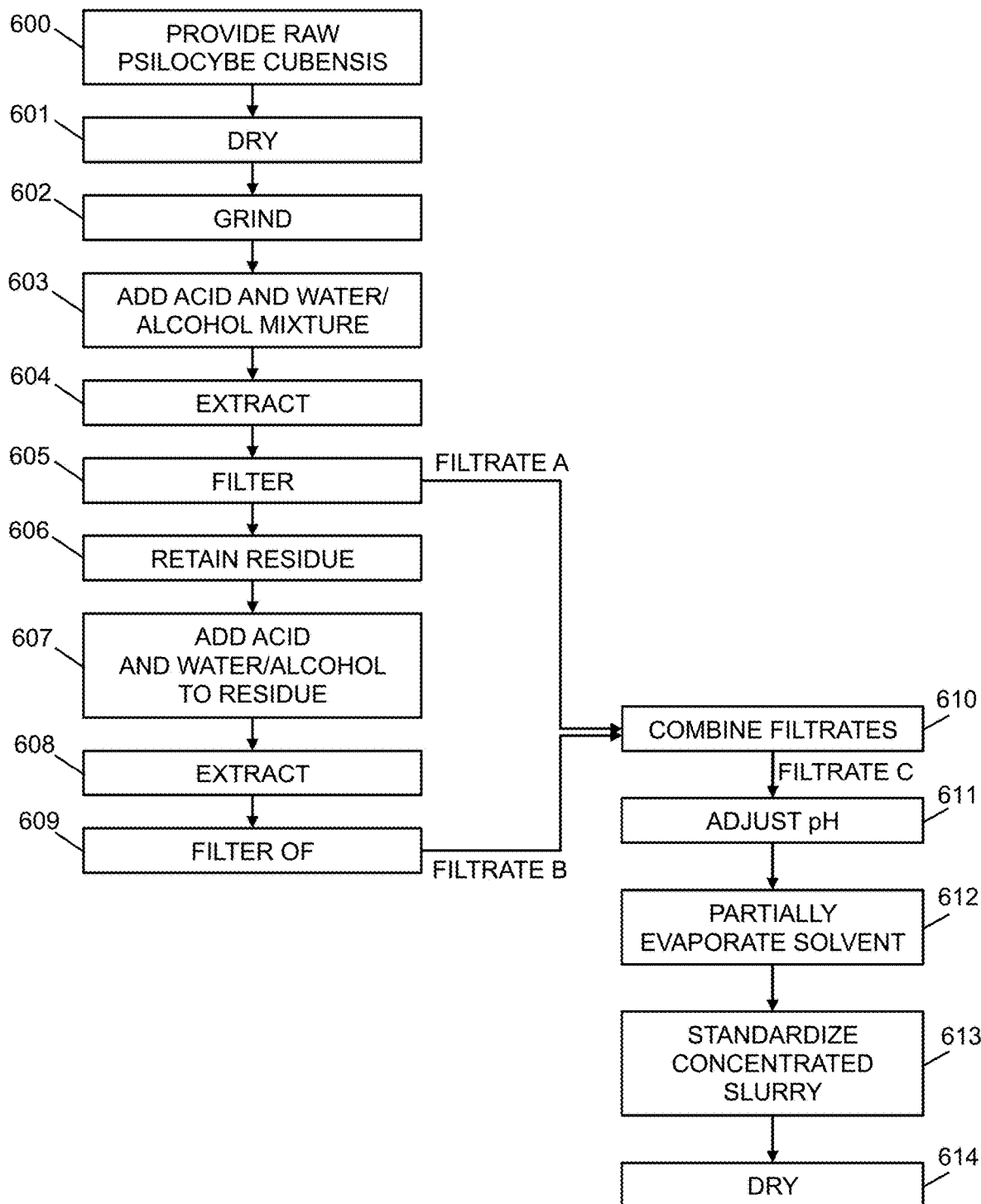
FIG. 6 is a flowchart showing more detailed steps of a process for extracting psychoactive alkaloids from *Psilocybe cubensis* using a buffered acidic solvent, according to an embodiment of the present invention.

Referring to FIG. 6, a process is shown for the extraction of psychoactive compounds from *Psilocybe cubensis* mushrooms using a buffered acidic solvent. In step 600, 2.5 kg of raw psilocybin mushrooms from the *Psilocybe cubensis* species was provided. In step 601, the raw *Psilocybe cubensis* was dried in a forced air oven at 25° C. for 5-10 hours. The dried biomass was 140 g. In step 602, the dried biomass was ground in a hammer mill or the equivalent, to particle size of 200 mesh.

In step 603, 5 L of solvent was added with the dried biomass to an extraction vessel, which was heat-controlled and agitated. The solvent was a pH-adjusted, hydro-ethanol mixture. For its preparation, 44 g of anhydrous citric acid was placed into a 5 L vessel with 1.25 L of reverse osmosis water followed by 3.75 L of ethanol. The contents were mixed until completely dissolved. The pH of this solution was between pH 1.8 and pH 3.

In step 604, the extraction proceeded. The temperature of the extraction process was 30° C., and the duration of the extraction was 4 hours. In step 605, the extraction slurry was filtered to remove residue with undissolved *psilocybe cubensis* from the filtrate. The filtrate from this step was named filtrate A. In step 606, the residue was retained and placed back in the extraction vessel. In step 607, another 5 L of the same solvent was added to the residue. In step 608, the extraction process of the residue continued at a temperature of 30° C., for 4 hours. The temperature remained constant during the extraction process. In step 609, the second extraction slurry was filtered to remove the residue of unwanted solid material. Filtrates A and B were then mixed in step 610 to result in bulk filtrate C.

Bulk filtrate C was brought to a pH of 5 with 5M sodium hydroxide in step 611. The amount of sodium hydroxide depends on the specific mushroom matrix extracted and was not possible to predict accurately. The pH-adjusted, concentrated slurry was then processed with a rotary evaporator in step 612 to remove solvent until the volume of filtrate C was 2.5 liters. At this point, the reduced amount of filtrate C was a concentrated slurry, due to the precipitation of some of the psychoactive alkaloids.

In step 613, the concentrated slurry was standardized. In this example, 4.7 g of ascorbic acid, 1.9 g of $SiO_2$, and 47 g of maltodextrin were added to the concentrated slurry. In step 614, the standardized concentrated slurry was dried using a bench-top spray dryer. This resulted in 100 g of powdered psilocybin mushroom extract with a total alkaloid concentration of 1.00% by weight.

Example 8: Extraction Using 100% Methanol as a Solvent

Figure 5:
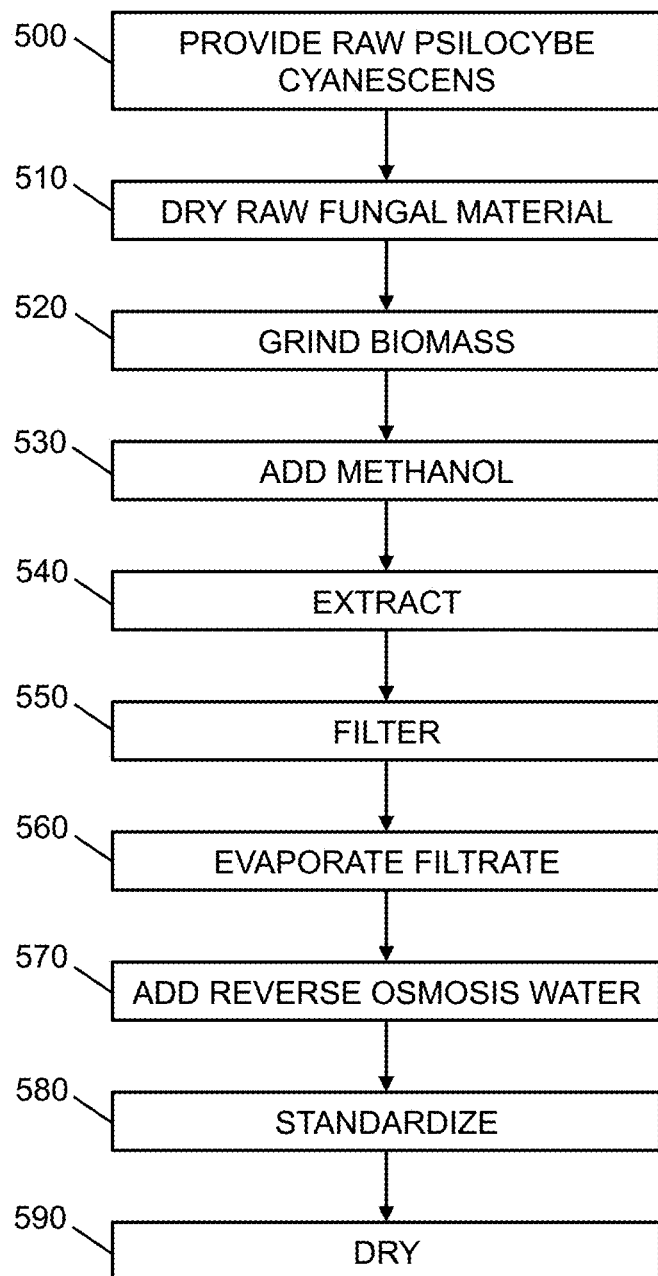
FIG. 5 is a flowchart showing more detailed steps of a process for extracting psychoactive alkaloids from *Psilocybe cyanescens* using a methanol solvent, according to an embodiment of the present invention.

Referring to FIG. 5, a process is shown for the extraction of psychoactive compounds from *Psilocybe cyanescens* mushrooms using 100% methanol as the solvent.

In step 500, 2.5 kg of raw psilocybin mushrooms from the *Psilocybe cyanescens* species was provided. In step 510, the raw *Psilocybe cyanescens* was dried in a forced air oven at 25° C. for 10 hours. The dried biomass was 140 g. In step 520, the dried biomass was ground in a cutting mill or the equivalent, to particle size of 200 mesh. In step 530, 5 kg of solvent, which was 100% methanol, was added to an extraction vessel, which was heat-controlled and agitated. The dries biomass was also added to the extraction vessel.

In step 540, the extraction proceeded. The temperature of the extraction process was a constant 25° C., and the duration of the extraction was 4 hours. A pressure of 100 kPa above atmospheric (15 psi) was applied to the mixture of solvent and biomass during the extraction. In step 550, the extraction slurry was filtered to remove residue with undissolved *Psilocybe cyanescens* from the filtrate.

The filtrate was then processed with a rotary evaporator in step 560 to evaporate all the methanol from the filtrate. In this embodiment, all the solvent was removed at this stage because methanol was not regarded as safe for human consumption, and there should be no trace amounts of it remaining in the final product. In step 570, 1.25 liters of reverse osmosis water at room temperature was added to the solid that is remaining after the evaporation step, to form a concentrated slurry.

In step 580, the concentrated slurry was standardized. In this example, 1.84 g of $SiO_2$ and 46 g of maltodextrin were added to the concentrated slurry. In step 590, the standardized concentrated slurry was dried using a bench-top spray dryer. This resulted in 95 g of powdered psilocybin mushroom extract with a total alkaloid concentration of 1.50% by weight.

Example 9: Extraction Using 100% Water as a Solvent

Figure 4:
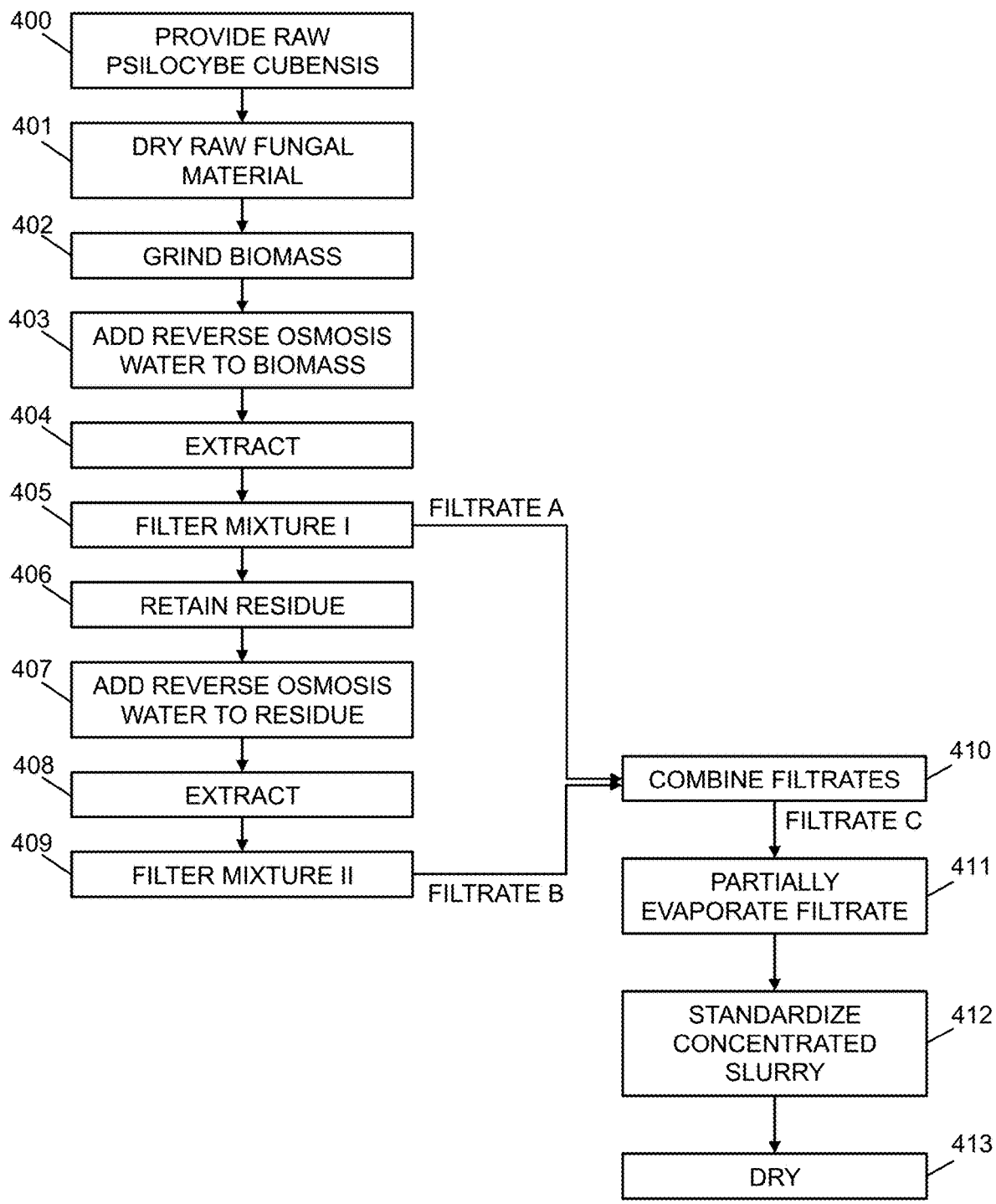
FIG. 4 is a flowchart showing more detailed steps of a process for extracting psychoactive alkaloids from *Psilocybe cubensis* using a water solvent, according to an embodiment of the present invention.

Referring to FIG. 4, a detailed process is shown for the extraction of psychoactive compounds *Psilocybe cubensis* using 100% reverse osmosis water as the solvent.

In step 400, 2.5 kg of raw psilocybin mushrooms from the *Psilocybe cubensis* species was provided. In step 401, the raw *Psilocybe cubensis* was dried in a forced air oven at 25° C. for 10 hours. The dried biomass was 140 g. Note that the dried biomass was the same weight in different examples because the mushrooms were from the same starting batch. In step 402, the dried biomass was ground in a hammer mill or the equivalent, to a particle size of 200 mesh.

In step 403, 5 liters of solvent, which was 100% reverse osmosis water, was placed in an extraction vessel with the dried biomass, which was heat-controlled and agitated.

In step 404, the extraction proceeded. The temperature of the extraction process was 90° C., and the duration of the extraction was 12 hours. In the step 405, the extraction slurry was filtered while still hot to remove residue with undissolved *Psilocybe cubensis* from the filtrate. The filtrate from this step was considered as filtrate A. In step 406, the residue was retained and placed back in the extraction vessel. In step 407, another 5 liters of 100% reverse osmosis water was added to the residue. In step 408, the extraction process of the residue continued at a temperature of 90° C., for 10 hours. The temperature remained constant during the extraction process. In step 409, the second resulting mixture, of biomass solids and water with dissolved extract, was filtered while still hot to remove the residue of unwanted solid material. Filtrates A and B are then mixed in step 410 to result in bulk filtrate C.

The bulk filtrate C was then processed with a rotary evaporator in step 411 to remove solvent until the volume of filtrate C is 2.5 liters. At this point, the reduced amount of filtrate C was a concentrated slurry, due to the precipitation of some of the psychoactive alkaloids.

In step 412, after some of the solvent has been removed using the rotary evaporator, the concentrated slurry was then standardized. The standardization process used a titration procedure to determine the concentration of the psychoactive alkaloids in the concentrated slurry. The standardization procedure entailed adjusting the concentration of the psychoactive alkaloids in the concentrated slurry to a desired dry target. In this example, 6.3 g of ascorbic acid, 2.5 g of $SiO_2$ and 63 g of maltodextrin were added to the concentrated slurry.

In step 413, after the standardization process, the standardized concentrated slurry was dried using a bench-top spray dryer. This resulted in 140 g of powdered psilocybin mushroom extract with a total alkaloid concentration of 0.50% by weight.

Example 10. Process with Prevention of Dephosphorylation 2.5 kg of *Psilocybe cubensis* were dried in a forced air oven at 25° C. for 10 hours to result in 140 g of dried biomass. The dried biomass was then pulverized to a size of 200 mesh with a mill.

A basified solvent, i.e. a pH-adjusted, hydro-ethanol mixture, was prepared. 50 g of sodium hydroxide pellets were placed into a 5 L vessel with 1.25 L of RO (reverse osmosis) water followed by addition of 3.75 L of ethanol. The contents were mixed until completely dissolved. A basified solvent with 75% EtOH v/v % and a pH of 13 was obtained.

The dried powdered biomass was placed into an agitated, heat-controlled vessel with 5 L of the basified solvent and mixed for extraction of psychoactive alkaloid. The extraction was controlled to a constant 75° C., and the time of extraction was 1 hour. The extraction slurry was then filtered. Filtration resulted in a filtrate, i.e. the psychoactive alkaloid liquid, and a filter residue. The filter residue was placed back into the extraction vessel and extracted with an additional 5 L of the basified solvent. The temperature of extraction was again 75° C. and the time was again 1 hour. The resulting extraction slurry was then filtered. The filtrates from the first and second extractions were mixed to form 10 L of mixed filtrate. The pH of the mixed filtrate was then reduced with 3 M citric acid until a pH of 4.5 was achieved. Immediately after adjusting the pH, the mixed filtrate was placed into a rotary evaporator at 50° C. and 250 torr, and the solvent was partially or completely evaporated to obtain a psychoactive alkaloid extract in a slurry or powdered form respectively. Final stages of evaporation were performed using a freeze dryer. When dried to a powder, the desired amount of the phosphorylated psychoactive alkaloid obtained was 0.80% by weight (measured by HPLC analysis) in the psychoactive alkaloid extract. The desired amount of the dephosphorylated psychoactive alkaloid obtained was 0.05% by weight in the psychoactive alkaloid extract.

Example 11. Process for Heavily Phosphorylated Psychoactive Alkaloid Composition The evaporation of the solvent from the mixed filtrate from Example 10 was paused when the final volume of the filtrate was reduced to 2.5 L. The resulting slurry contained 236.9 mg/L psilocybin and 15.12 mg/L psilocin. The obtained psychoactive alkaloid slurry was standardized by the addition of 38.64 g of maltodextrin, 1.12 g of ascorbic acid, and 2.24 g of silicon dioxide. The standardization was followed by drying by freeze drying to yield 112 g of the psychoactive alkaloid composition in free-flowing powder form. The composition had a psilocybin content of 0.503% dry wt/wt % and a psilocin content of 0.003% dry wt/wt %. Further, the composition had a total phosphorylatable psychoactive alkaloid content of 0.506% dry wt/wt %.

Example 12. Process with Promotion of Dephosphorylation 2.5 kg of *Psilocybe cubensis* were dried in a forced air oven at 25° C. for 10 hours to result in 140 g of dried biomass. The dried biomass was then pulverized to a size of 200 mesh with a hammer mill.

An acidified solvent, i.e. a pH-adjusted, hydro-ethanol mixture, was prepared. 144 g of anhydrous citric acid was placed into a 5 L vessel with 1.25 L of RO water followed by the addition of 3.75 L of ethanol. The contents were mixed until completely dissolved. An acidified solvent with a pH of 2 was obtained.

The dried powdered biomass was placed into an agitated, heat-controlled vessel with 5 L of the acidified solvent and mixed for the extraction of psychoactive alkaloid. The extraction was controlled to a constant 75° C., and the duration of extraction was 1 hour. The extraction slurry was then filtered. Filtration resulted in a filtrate, i.e. the psychoactive alkaloid liquid, and a filter residue. The filter residue was placed back into the extraction vessel and extracted with an additional 5 L of the acidified solvent. The temperature of extraction was again 75° C. and the time was 1 hour. The extraction slurry was filtered. The filtrates from the first and second extraction were mixed to form 10 L of mixed filtrate. The pH of the mixed filtrate was then increased with 5 M sodium hydroxide until a pH of 4.5 was achieved. Immediately after adjusting the pH, the mixed filtrate was placed into a roto-evaporator at 50° C. and 250 torr, and the solvent was partially or completely evaporated to obtain a psychoactive alkaloid extract. Final stages of evaporation were performed using a freeze dryer. When dried to a powder, the desired amount of the phosphorylated psychoactive alkaloid obtained was 0.00% by weight in the psychoactive alkaloid extract. The desired amount of the dephosphorylated psychoactive alkaloid obtained was 0.86% by weight in the psychoactive alkaloid extract.

Example 13. Process for Preparation of a Psychoactive Alkaloid Composition

The evaporation of the solvent from the mixed filtrate from Example 12 was paused until the final volume of the filtrate was reduced to 2.5 L. The obtained psychoactive alkaloid slurry had a 241.85 mg/L of psilocin and a 0 mg/L of psilocybin. The slurry was standardized by the addition of 47.07 g of maltodextrin, 1.21 g of ascorbic acid, and 2.41 g of silicon dioxide. The standardization was followed by freeze drying to yield 120.7 g of the psychoactive alkaloid composition in free-flowing powder form. The composition had a psilocybin content of 0.00% dry wt/wt % and a psilocin content of 0.501% dry wt/wt %. Further, the composition had a total phosphorylatable psychoactive alkaloid content of 0.501% dry wt/wt %.

Example 14. Process for Preparation of a Psychoactive Alkaloid Composition Containing a Mixture of Phosphorylated and Dephosphorylated Alkaloids In an alternate method, the slurry from Examples 12 and 13 can be combined to form 5 L of slurry containing 118.45 mg/L of psilocybin and 128.49 mg/L of psilocin. The slurry was standardized by the addition of 85.70 g of maltodextrin, 2.33 g of ascorbic acid, and 4.65 g of silicon dioxide. The standardization was followed by lyophilization to yield 232.70 g of the psychoactive alkaloid composition in the free-flowing powder form. The composition had a psilocybin content of 0.255% dry wt/wt % and a psilocin content of 0.276% dry wt/wt %. Further, the composition had a total phosphorylatable psychoactive alkaloid content of 0.502% dry wt/wt %.

Example 15: Purifying the Psychoactive Alkaloid Extract Using a Non-Ionic Macroporous Resin The pH of the partially concentrated extract of Example 1, which was an aqueous extract, was adjusted to pH 4.0 (+/−0.5) by adding 2 M phosphoric acid and centrifuged for 15 minutes at 3000 g to remove any solid precipitate. The pH of 4 corresponds to the isoelectric point of psilocybin, and psilocin's polarity is such that it is partitioned onto the resin, thus allowing effective binding of the psychoactive alkaloids psilocybin and psilocin to the macroporous resin. Norbaeocystin and baeocystin are phosphorylated and behave in the same way as psilocybin. The supernatant obtained was loaded onto a column of Amberlite® XAD4, a non-ionic macroporous resin (50.34 g of dry resin) at a flow rate of 2 bed volumes per hour, to allow components in the supernatant to be adsorbed onto the macroporous resin. After all 2.5 L of the extract was loaded onto the column of macroporous resin, the column was washed in a single pass with 5 bed volumes of reverse osmosis water at room temperature. This was followed by elution with 5 bed volumes of 5% ethanol (by weight), again at room temperature. Finally, the column was washed in a single pass with 5 bed volumes of 100% ethanol. The elution was performed at room temperature. Each of these three fractions was collected separately. The particular order for the washing steps and the elution was selected to be in the order of the polarity of the solvents. If the order were different, an inferior result may have ensued, such as a lower yield. The first fraction using reverse osmosis water removed the most polar compounds from the resin. The hydro-ethanol fraction eluted compounds of lesser polarity, and the 100% ethanol solvent removed the least polar compounds. Less polar solvents could also be used to elute less polar compounds.

The 5% ethanol fraction (i.e. the purified psychoactive alkaloid solution) was then concentrated in a rotary evaporator to form 3.90 g of concentrated aqueous slurry at 30% solids, containing 195.1 mg of total alkaloids, i.e. psilocybin, psilocin, norbaeocystin, and baeocystin. The result was a purified psychoactive alkaloid slurry having a total psychoactive alkaloid concentration of 5.00% by weight.

As described below, it is possible to replace the solvent with an equivalent weight of excipients to provide a purified extract with a psychoactive alkaloid content of 5.00% dry wt/wt %.

Example 16: Purifying the Psychoactive Alkaloid Extract Using Cation Exchange and Non-Ionic Macroporous Resins The combination of filtrates of Example 11 was taken as the starting point. The pH of the combined filtrate obtained was adjusted to a pH of 3.0 (+/−0.5) by adding 1M HCl. It was then mixed with 200 g of Amberlite® MAC-3 H, a strong cationic ion-exchange resin in its hydrogen form, to result in a filtrate-resin mixture, in which components of the psychoactive alkaloid filtrate were adsorbed onto the cation exchange resin. The pH of 3 ensured that the psychoactive alkaloid (i.e. psilocybin) was in its protonated form, and thus adsorbed onto the cationic exchange resin efficiently. The filtrate-resin mixture was agitated for 4 hours at room temperature (21° C.-25° C.) and then filtered. The filtrate was discarded, and the resin was rinsed with 2.0 L of 100% EtOH and then 2.0 L of $H_2O$ to remove any impurities. Finally, the psilocybin/psilocin fraction was eluted with 2.0 L of 2% HCl/80% EtOH, for 4 hours at room temperature.

The eluted fraction was brought to a pH of 4.0 (i.e. the isoelectric point of psilocybin) by adding 2M NaOH. The filtrate was then centrifuged at 3000 g to remove any solid precipitate. The resultant filtrate, in form of an aqueous solution, was then placed into a rotary evaporator and the solvent was removed until the aqueous solution reached a volume of 400 mL. The aqueous solution was then again centrifuged for 15 minutes at 3000 g to remove any solid precipitate. The supernatant was loaded onto a column of Amberlite® XAD4 macroporous resin (45.53 g of dry resin) at a flow rate of 2 bed volumes per hour. After all the 400 mL of the supernatant was loaded onto the column, it was initially washed with 5 bed volumes of reverse osmosis water, followed by elution with 5 bed volumes of 5% ethanol (by weight) and then washed with 100% ethanol. Each of these fractions was collected separately. The 5% ethanol fraction (i.e. the purified psychoactive alkaloid solution) was concentrated in a rotary evaporator to form 258 mg of solution containing 175 mg of total alkaloids (i.e. psilocybin, psilocin, norbaeocystin, and baeocystin). Thus, a purified psychoactive alkaloid slurry with a total alkaloid concentration of 68% dry wt/wt % was obtained.

Example 17: Purifying the Psychoactive Alkaloid Extract Using Anion Exchange and Non-Ionic Macroporous Resins The combination of filtrates of Example 11 was taken as the starting point. The pH of the filtrate combination was adjusted to 9.5 (+/−0.5) by adding 1 M NaOH and then mixed with 150 g of Amberchrom® 50WX8 strong anionic ion-exchange resin in its hydrogen form to result in a filtrate-resin mixture, in which components of the psychoactive alkaloid filtrate were adsorbed onto the anion exchange resin. The pH of 9.5 (+/−0.5) ensured that the psilocybin, psilocin, norbaeocystin, and baeocystin were deprotonated and had a net negative charge for efficient adsorption onto the strong anion exchanger.

The filtrate-resin mixture was agitated for 4 hours and then filtered out, and the filtrate was discarded. The resin was rinsed with 2.0 L of 100% EtOH and then 2.0 L of $H_2O$ to remove impurities. Finally, the psilocybin/psilocin fraction was eluted with 2.0 L of 2% NaCl/80% EtOH for 4 hours.

The eluted fraction was brought to a pH of 4.0 with the addition 2 M HCl. The extract was then centrifuged at 3000 g to remove any solid precipitate. The resultant extract, in from of a solution, was then placed into a rotary evaporator and the solvent was removed to result in a volume of 400 mL.

The resultant 400 mL aqueous solution was centrifuged for 15 minutes at 3000 g to remove any solid precipitate. The supernatant was loaded onto a column of Amberlite® XAD4 macroporous resin (45.53 g of dry resin) at a flow rate of 2 bed volumes per hour, to allow components of the supernatant to be adsorbed onto the macroporous resin. After all 400 mL of supernatant was loaded onto the column, the column was initially washed with 5 bed volumes of reverse osmosis water, followed by elution with 5 bed volumes of 5% ethanol (by weight) and then a final wash with 100% ethanol was performed. Each of these fractions was collected separately. The 5% ethanol fraction (i.e. the purified psychoactive alkaloid solution) was concentrated in a rotary evaporator to form 325 mg of solution containing 175 mg of total alkaloids (i.e. psilocybin, psilocin, norbaeocystin, and baeocystin). A purified psychoactive alkaloid slurry with a concentration of 54% dry wt/wt % of total alkaloids was therefore obtained.

Example 18: Purifying the *Anadenanthera peregrina* Seed Extract

The aqueous extract with about 6.8% solids, from Example 17, was adjusted to pH 4.0 (+/−0.5) with 2 M phosphoric acid and centrifuged for 15 minutes at 3000 g to remove any solid precipitate. The supernatant was loaded onto a column of Seplite® LXA17 macroporous resin (54.21 g of dry resin) at a flow rate of 2 bed volumes per hour. After all 6.0 L of the extract was loaded onto the column, it was initially washed with 5 bed volumes of reverse osmosis water, followed by a second wash with 5 bed volumes of 10% ethanol (by weight) and then eluted with 3 bed volumes of 50% ethanol, and finally the resin was washed with 5 bed volumes of 100% ethanol. Fewer bed volumes of solvent were possible in the elution step than in the washing steps due to the sharper elution peak. This in turn led to a shorter evaporation time than if more bed volumes of the solvent had been used. Each of these fractions was collected separately. The 50% ethanol fraction was concentrated in a rotary evaporator to form 355 g of concentrated aqueous slurry at 30% solids, containing 3.03 g of total alkaloids.

Example 19: Process for Preparing Standardized Psychoactive Alkaloid Extract

The 3.90 g of purified psychoactive alkaloid slurry with a psychoactive alkaloid concentration of 5.00% by weight that was obtained in Example 15 was taken and standardized. To achieve this, the concentrated slurry, 0.03 g of $SiO_2$, 0.02 g of ascorbic acid and 2.55 g of maltodextrin were added and thoroughly mixed to result in a final standardized slurry having a specific concentration of alkaloids. The final standardized slurry was then subjected to spray-drying and a final powdered alkaloid extract with a 5.00% total psilocybin, psilocin, baeocystin and norbaeocystin concentration by dry weight was obtained.

Example 20: Process for Preparing Standardized Psychoactive Alkaloid Extract from *Anadenanthera peregrina* Seeds The aqueous slurry from Example 18 was used as the starting point. Next, 0.3 g of $SiO_2$, 0.15 g of citric acid and 4.10 g of maltodextrin were added to the slurry, which was thoroughly mixed. The final formulated slurry was then subjected to spray-drying to yield a final powdered alkaloid extract with a combined bufotenin/bufotenidine/5-MeO-DMT concentration of 20.00% by dry weight.

Example 21: Preparation of a Non-Purified Psychoactive Alkaloid Extract

Fresh *Psilocybe cubensis*, 2.5 kg, was dried in a forced air oven at 25° C. for 5-10 hours, to result in 140 g of dried biomass. The dried biomass was pulverized to a size of 200 mesh with a hammer mill. The dried powdered biomass was then placed into an agitated, heat-controlled vessel with 5 kg of solvent. The solvent was a hydro-ethanol mixture of 3 parts ethanol to 1 part water by weight. The extraction was controlled to a constant 70° C., and the time of extraction was 4 hours.

The extraction slurry was filtered while hot, and the filter residue was placed back into the extraction vessel, and extracted with an additional 5 kg of 3:1 ethanol:water mixture by weight. The temperature of extraction was again 70° C., and the time was 4 hours. The extraction slurry was filtered while hot and the filtrates from the first and second extractions were mixed together to obtain a bulk filtrate. The bulk filtrate was immediately placed into a rotary evaporator, and the solvent was concentrated in the rotary evaporator to obtain 186.6 g of the psychoactive alkaloid extract in form of a concentrated aqueous slurry at 30% solids, containing 700 mg of total alkaloids, which would be a concentration of 1.25% dry wt/wt %, if the slurry were to be dried.

Example 22: Preparation of a Purified Psychoactive Alkaloid Extract

Fresh *Psilocybe cubensis*, 2.5 kg, was dried in a forced air oven at 25° C. for 5-10 hours, resulting in 140 g of dried biomass. The dried biomass was then pulverized to a size of 200 mesh with a hammer mill. The dried powdered biomass was placed into an agitated, heat-controlled vessel with 5 kg of solvent. The solvent used was a hydro-ethanol mixture of 3 parts ethanol to 1 part water by weight. The extraction was controlled to a constant 70° C., and the time of extraction was 4 hours.

The extraction slurry was filtered while hot, and the filter residue was placed back into the extraction vessel, and extracted with an additional 5 kg of 3:1 ethanol:water mixture by weight. The temperature of extraction was again 70° C. and the time was 4 hours. The extraction slurry was filtered while hot and the filtrates from the first and second extractions were mixed together to obtain a bulk filtrate. The bulk filtrate was left to cool, in case any precipitate had formed, the insoluble material was filtered out and discarded.

The bulk filtrate's pH was then adjusted to 9.5 (+/−0.5) with 1 M NaOH to form a specific pH psychoactive alkaloid solution. This solution was then mixed with 150 g of Amberchrom® 50WX8 Strong Anion Exchange resin in its hydrogen form. The solution was agitated for 4 hours and then filtered. The filtrate was discarded. The resin was rinsed with 2.0 L of 100% EtOH and then 2.0 L of $H_2O$. Finally, the psilocybin fraction was eluted with 2.0 L of 2% NaCl/ 80% EtOH for 4 hours.

The eluted fraction was brought to a pH of 4.0 with 2 M HCl to result in another specific pH psychoactive alkaloid solution. This solution was then centrifuged at 3000 g to remove any solid precipitates. The solvent from the solution was then evaporated in a rotary evaporator to result in a volume of solvent evaporated was 400 mL.

This solution was again centrifuged for 15 minutes at 3000 g to remove any solid precipitate. The supernatant was loaded onto a column of Amberlite® XAD4 macroporous resin (45.53 g of dry resin) at a flow rate of 2 bed volumes per hour. All 400 mL of the extract was loaded onto the column and washed with 5 bed volumes of reverse osmosis water. The washing step was followed by elution with 5 bed volumes with 5% ethanol (by weight). A final washing was carried out with 100% ethanol. Each of these fractions was collected separately. The 5% ethanol fraction was collected and concentrated in a rotary evaporator to obtain 1.143 g of 30% liquid slurry containing 175 mg of total alkaloids, a concentration of 54% dry wt/wt %.

Example 23: Preparation of a Psychoactive Alkaloid Composition with a Non-Purified Psychoactive Alkaloid Extract The psychoactive alkaloid extract obtained in Example 12 was mixed with 2.8 g of silicon dioxide (flow agent), 0.140 g of ascorbic acid (preservative), and 81.06 g of tapioca maltodextrin (carrier). The final formulated slurry was then subjected to spray-drying and 140 g of the standardized powdered composition was produced with the desired specific amount of psychoactive alkaloid. The total psilocybin/psilocin concentration by dry weight was 0.5% in this composition. The exact weight percentages of the components in the composition are depicted Table 1.

Example 24: Preparation of a Psychoactive Alkaloid Composition with a Purified Psychoactive Alkaloid Extract The purified psychoactive alkaloid extract obtained in Example 22 was mixed with 5.85 mg of ascorbic acid (preservative) and 822 mg of rice maltodextrin (carrier). The final formulated slurry was then subjected to lyophilization and 1.171 g of the standardized powdered composition was produced. The total psilocybin/psilocin concentration by dry weight was 15.01% in the composition. The exact weight percentages of the components in the composition are depicted Table 1.

Example 25: Process for Preparing Standardized Psychoactive Alkaloid Extract

A purified psychoactive alkaloid solution resulting from resin treatment after extraction from 140 g of dried *Psilocybe cubensis* was concentrated in a rotary evaporator to form 3.90 g of concentrated aqueous slurry at 30% solids, containing 195.1 mg of total psychoactive alkaloids. The slurry, with a psychoactive alkaloid concentration of 5.00% by weight, was mixed with 0.03 g of $SiO_2$, 0.02 g of ascorbic acid and 2.55 g of maltodextrin. This standardized slurry was then subjected to spray-drying, and a final powdered alkaloid extract with a 5.00% total psilocybin, psilocin, baeocystin and norbaeocystin concentration by dry weight was obtained.

Example 26: Process for Preparing Standardized Psychoactive Alkaloid Extract

An extract from 140 g dried *Psilocybe cubensis* mushrooms using a 75% ethanol solvent resulted in a concentrated slurry, for which the alkaloid content was 2.16 g and the total solid content was 46.4 g. To the slurry, 4.7 g of ascorbic acid, 1.9 g of $SiO_2$ and 47 g of maltodextrin were added. After spray drying, this resulted in 100 g of powdered psychedelic mushroom extract with a total alkaloid concentration of 1.00% by weight.

Example 27: Process for Preparing Standardized Psychoactive Alkaloid Extract

Psychoactive compounds were extracted from 140 g of dried *Psilocybe cubensis* using 100% reverse osmosis water as the solvent. Water was evaporated to result in a concentrated slurry, for which the alkaloid content was 1.82 g and the total solid content was 68.18 g. In this example, 6.3 g of ascorbic acid, 2.5 g of $SiO_2$ and 63 g of maltodextrin are added to the concentrated slurry, which was then dried. This resulted in 140 g of powdered psilocybin mushroom extract with a total alkaloid concentration of 0.50% by weight.

Example 28: Process for Preparing Standardized Psychoactive Alkaloid Extract

An extraction of psychoactive compounds from 140 g dried *Psilocybe cyanescens* mushrooms was performed using 100% methanol as the solvent. The extraction slurry was filtered to remove residue with undissolved *Psilocybe cyanescens* from the filtrate. All the methanol was evaporated from the filtrate, then 1.25 liters of reverse osmosis water at room temperature was added to the remaining solid to form a slurry, for which the alkaloid content was 2.87 g and total solid content was 47.14 g. Next, 1.84 g of $SiO_2$ and 46 g of maltodextrin were added to the slurry, which was then dried. This resulted in 95 g of powdered psychedelic mushroom extract with a total alkaloid concentration of 1.50% by weight.

Example 29-3.7: Process for Preparing Standardized Psychoactive Alkaloid Extract An extract obtained according to Example 22 was used as the starting point. Compared to Example 24, greater amounts of preservative (351 mg), flow agent (351 mg) and carrier (16.515 g) were added to the composition. This resulted in a standardization of the amount psychoactive alkaloid in the composition to 1.00% instead of 15.01%.

Example 30: Process for Preparing Standardized Psychoactive Alkaloid Extract

A purified psychoactive alkaloid solution resulting from resin treatment after extraction from 140 g of dried *Psilocybe cubensis* was concentrated in a rotary evaporator to form 3.90 g of concentrated aqueous slurry at 30% solids, containing 195.1 mg of total psychoactive alkaloids. Compared to Example 25, greater amounts of preservative (0.49 g), flow agent (0.39 g), and carrier (18.43 g) were added to the composition. This resulted in a standardization of the amount psychoactive alkaloid in the composition to 1.00% instead of 5.00%.

Example 31: Process for Preparing Standardized Psychoactive Alkaloid Extract A purified psychoactive alkaloid solution was obtained after multiple cation exchange resin treatments following extraction from 140 g of dried *Psilocybe cubensis*. Silicon dioxide, maltodextrin and ascorbic acid were added to form a composition standardized to 60.00%.

Example 32: Process for Preparing Standardized Psychoactive Alkaloid Extract This is as Example 31, except that the only excipient that was added was preservative (ascorbic acid). This resulted in a standardization of the psychoactive alkaloid content of the composition to 75.00%.

The exemplary compositions obtained are depicted in Table 1. Compositions of Examples 23 and 26-28 are compositions with a psychoactive alkaloid extract that has not been purified. Compositions of Examples 24, 25, and 29-32 are compositions with a purified psychoactive alkaloid extract.

Example 33: 95% Methanol/5% Acetic Acid (Psilocybin-Rich Extract)

Figure 24:
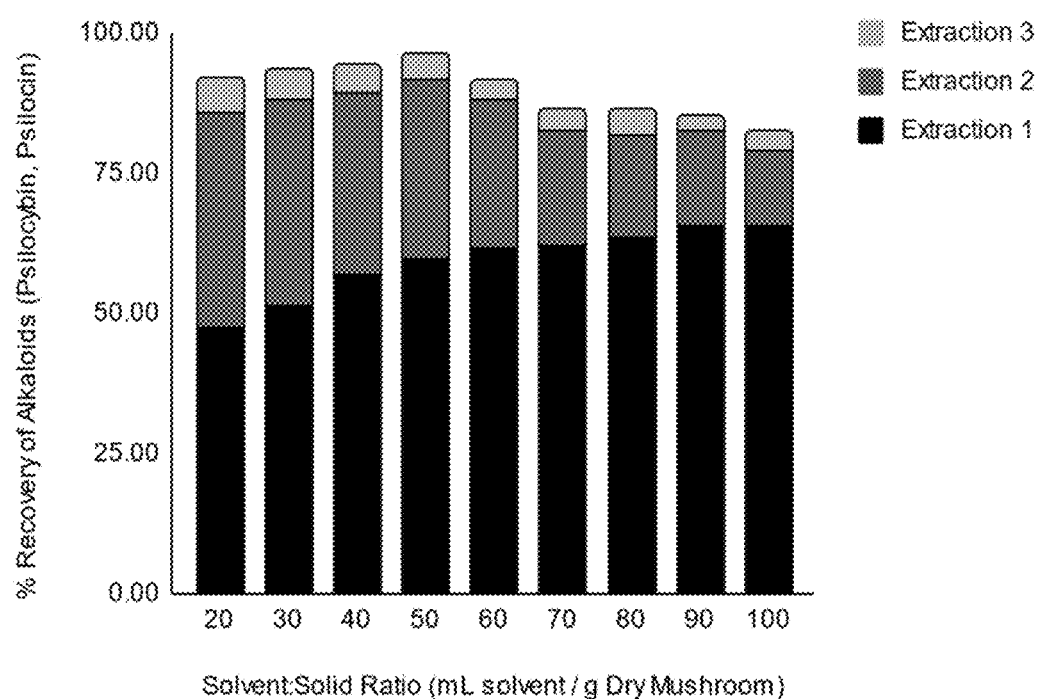
FIG. 24 is a chart demonstrating a relationship between solvent to solid ratio and % recovery of alkaloids.
Figure 25:
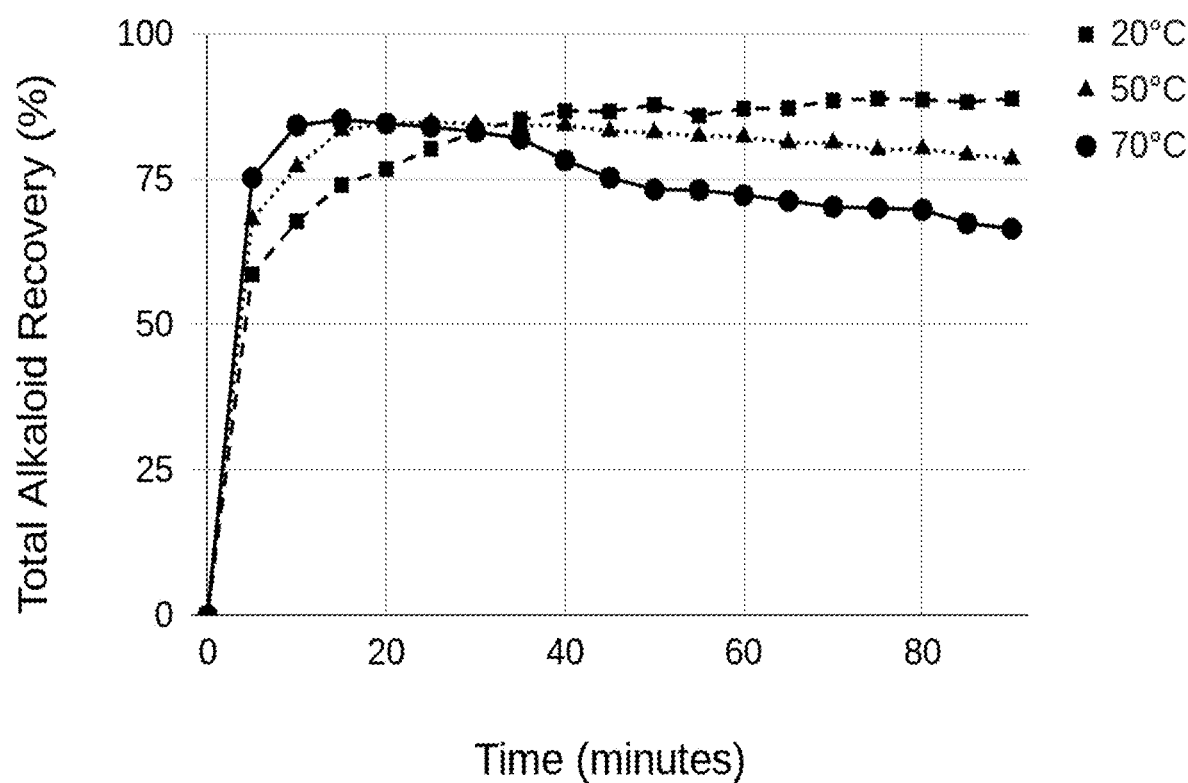
FIG. 25 is a chart demonstrating a relationship between time and total alkaloid recovery (%).

14.5 kg of fresh *Psilocybe cubensis* were dried in a forced air oven at 30° C. for 48 hours, resulting in 1.45 kg of dried biomass mushroom fruiting body. The content of psilocybin in the biomass was 0.523% by dry weight, resulting in 7.25 g of psilocybin available for extraction. The dried biomass was reduced to a size of 200 mesh with a cutting mill. The dried powdered biomass was placed into an agitated, heat-controlled vessel with 58 L of solvent (40 L/kg). FIG. 24 shows a chart for solvent to solid ratio optimization. A S:S (solvent:solid) ratio of 20-30 L/kg can achieve >90% alkaloid yield over 3 extractions while the optimal condition was chosen as 40-50 L/kg, achieving >90% alkaloid yield in only two extractions, reducing the amount of solvent waste, time, and energy during the evaporation step. In this embodiment, the solvent was acidified methanol (5% acetic acid/95% anhydrous methanol v/v %). It is noteworthy that methanol works very well, and acidified methanol works 10-15% better. Both are acceptable extraction methods for psilocybin. The extraction was controlled to a constant 25° C. temperature and was under atmospheric pressure. The extraction was carried out under these conditions for 30 minutes, after which the extraction slurry was filtered through a 5 μm stainless steel filter. The filtrate was placed into another vessel and put aside. FIG. 25 shows a graph of

TABLE 1

Compositions of Examples 23-32

| Ex. | Extract Mass (dry %) | Preservative Mass (dry %) | Flow Agent Mass (dry %) | Carrier Mass (dry %) | Total Mass (dry %) | Alkaloid Amount in Extract (wt/wt %) | Alkaloid Amount in Standardized Composition (wt/wt %) |
|---|---|---|---|---|---|---|---|
| 23 | 40.0 | 0.1 | 2.0 | 57.9 | 100.0 | 1.25 | 0.50 |
| 24 | 29.3 | 0.5 | 0.0 | 70.2 | 100.0 | 51.23 | 15.01 |
| 25 | 31.0 | 0.5 | 0.8 | 67.6 | 100.0 | 16.12 | 5.00 |
| 26 | 46.4 | 4.7 | 1.9 | 47.0 | 100.0 | 2.16 | 1.00 |
| 27 | 48.7 | 4.5 | 1.8 | 45.0 | 100.0 | 1.03 | 0.50 |
| 28 | 49.6 | 0.0 | 1.9 | 48.4 | 100.0 | 3.02 | 1.50 |
| 29 | 2.0 | 2.0 | 2.0 | 94.0 | 100.0 | 51.23 | 1.00 |
| 30 | 6.2 | 2.5 | 2.0 | 89.3 | 100.0 | 16.12 | 1.00 |
| 31 | 79.6 | 5.0 | 1.0 | 14.4 | 100.0 | 75.22 | 60.00 |
| 32 | 99.7 | 0.3 | 0.0 | 0.0 | 100.0 | 75.22 | 75.00 |

In the columns, the extract mass (dry %), preservative mass (dry %), flow agent mass (dry %), and carrier mass (dry %) are the dry weight percentages of the psychoactive alkaloid extract, preservative, flow agent and carrier in the standardized composition respectively. The total mass (dry %) is the total dry weight percentage of the standardized composition. The alkaloid amount in the extract (wt/wt %) is the dry weight percentage of the psychoactive alkaloid in the extract, as if the extract were in its dried state. Note that it is possible for the extract to remain in the slurry state as the excipients are added. The alkaloid amount in the standardized composition (wt/wt %) is the dry weight percentage of the psychoactive alkaloid in the final composition. It can be seen that a wide variability in extract concentration from different batches can be standardized to the same concentration in the composition, e.g., by looking at examples 26, 29, and 30.

time and temperature optimization, which indicates that the temperature increases the extraction efficiency, but also shows degradation when extended beyond 20-30 minutes. Given that, at scale, the increased complexity of elevating the temperature of the extraction vessel would introduce a significant warming and cooling time, it was decided to select the extraction temperature of 20° C., and keep the extended extraction time at 30-50 minutes to avoid degradation of the alkaloids. The now-dry filter cake was again placed into the extraction vessel and an additional 58 liters of extraction solvent was added to the vessel. The extraction was again carried out under the same conditions for 30 minutes. The slurry was then filtered and combined to create the pooled filtrate. The pooled filtrate was placed into a rotary-evaporator, and the methanol was evaporated until the volume was reduced to around 5.8 L, forming a concentrated solution. 5.8 L was roughly 5% of the pooled filtrate volume, which was entirely acetic acid at this point and around pH 2.4. Basically, it is required to remove all of the methanol for further purification. It may be also possible to take this solution and evaporate it fully to dryness, add excipient and have a shelf-stable low purity extract (0.5-2.0% alkaloid content by weight). It is possible to have this material continue onto purification. The content of psilocybin in this concentrated solution was 1.18 g/L, and the yield was 94.2%. The dry mass yield at this stage was 44.23%. Components that are still present in the extract at this point are: small chain carbohydrates/polysaccharides, free sugars, polyphenols, alkaloids, some glycoproteins, ergothioneine, tocopherols, ergosterols, fats. Many of these components are targeted for removal with purification. Components that are present in the mushroom that are left behind in the biomass: proteins, large carbohydrates/polysaccharides, B-glucans.

Figure 26:
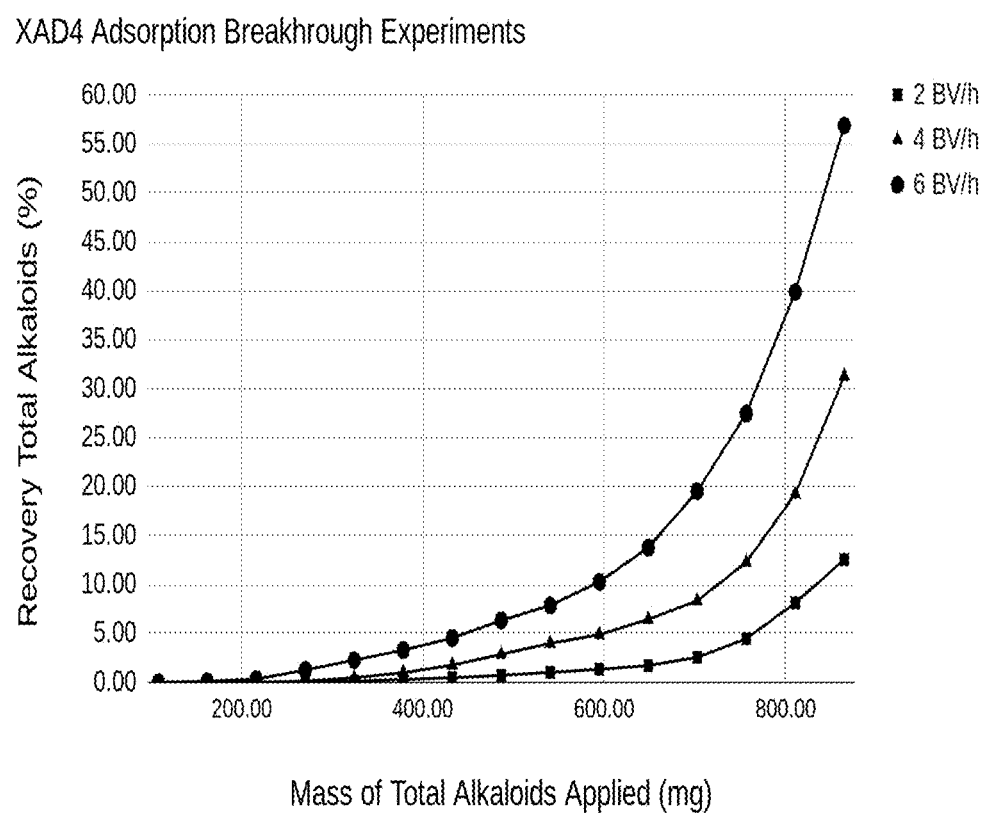
FIG. 26 is a chart demonstrating a relationship between mass of total alkaloids applied (mg) and recovery total alkaloids (%).
Figure 27:
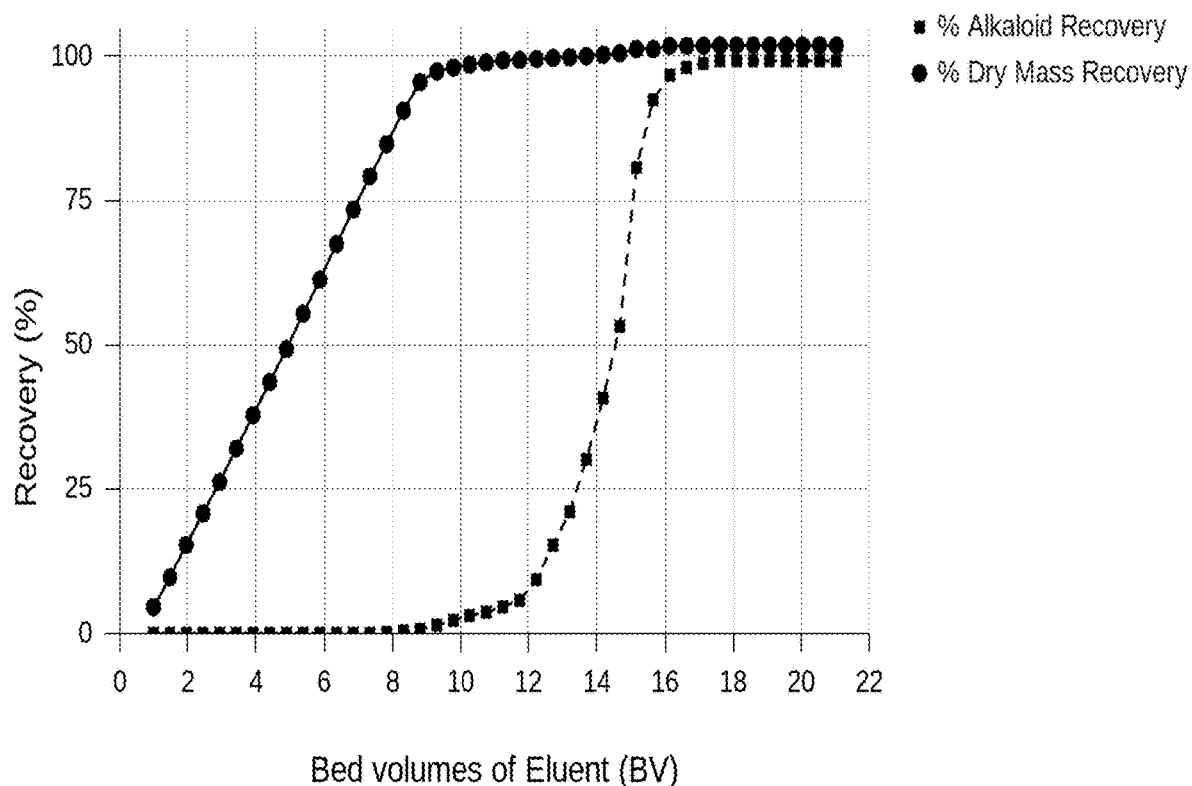
FIG. 27 is a chart demonstrating a relationship between bed volumes of eluent (BV) and recovery (%).
Figure 28:
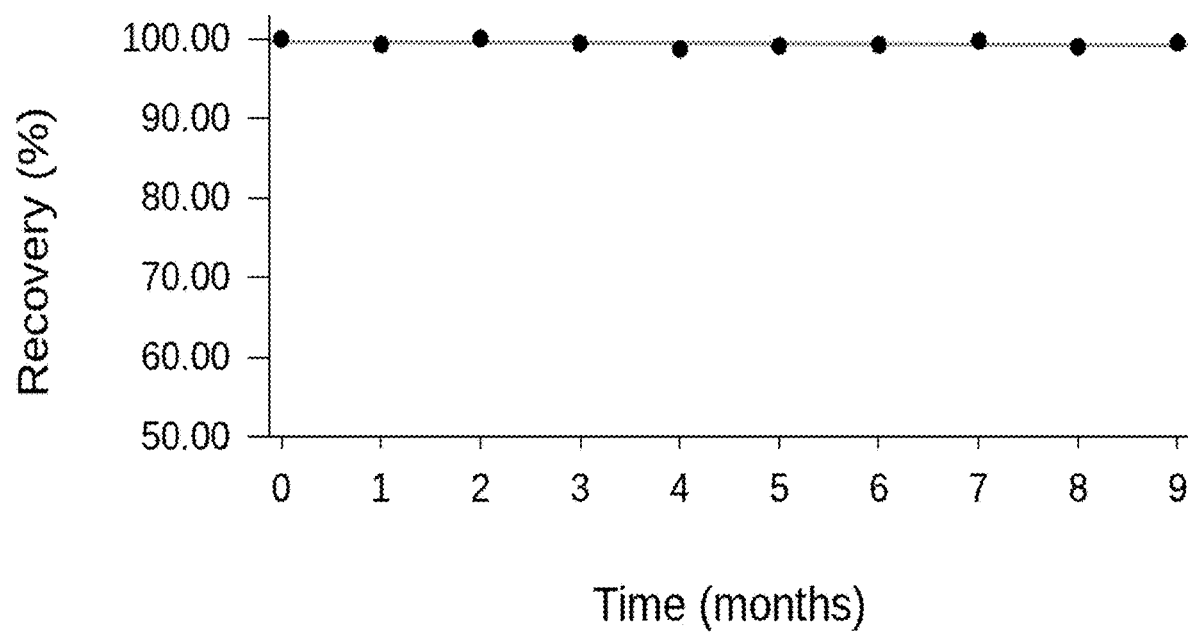
FIG. 28 is a chart demonstrating psilocybin content in sample PYEX-FP-200820 over 9 months at 25° C. and 65% RH

The concentrated solution was diluted with RO water to 50 L (1.28% dry mass concentration). The aqueous extract was then adjusted to pH 4.0 (+/−0.5) with 2 M sodium hydroxide and filtered through a 5 μm stainless steel filter to remove any solid precipitate. It is very important to have the extract be at pH 4.0 before application to the adsorbent resin, because pH 4 is the isoelectric point of psilocybin, and it is also the maximum stability pH for psilocin. The supernatant was loaded onto a column of Amberlite® XAD4 macroporous resin (5000 mL of hydrated resin, ~1.39 mg psilocybin/mL of hydrated resin) at a flow rate of 2 bed volumes per hour. Optimization of breakthrough and determination of capacity is shown in FIG. 26 (see also Table 2). After all 50 L of extract is loaded onto the column, it was washed with 3 bed volumes of reverse osmosis water at a flow rate of 2 BV/h, followed by elution with 5 bed volumes of 15% ethanol (by weight) and then finally washed with 100% ethanol. Each of these fractions was collected separately. FIG. 27 shows a graph of optimized recovery of psilocybin on XAD4 with 1 pass. Desorption with 15% ethanol resulted in 99.2% recovery of psilocybin while retaining only 2.5% of the dry mass in the same fraction. This resulted in a ~40× increase in concentration over the extract and a 45% dry wt/wt % content of psilocybin in the first pass purified extract. In one embodiment, it is preferred to stop here and bring in the excipients for stabilization and standardization to a dry powder. If it is intended to go higher and purer, it is preferred to expose the concentrated extract to another pass on the XAD4 or to an Isolute® SCX resin or antisolvent addition, or liquid/liquid extraction. The 15% ethanol fraction contained 6.79 g of psilocybin and 16.03 g of dry mass, resulting in an extract of 42.35% psilocybin by weight. The 15% ethanol fraction was then concentrated in a rotary evaporator to form 53.45 g of concentrated aqueous slurry at 30% solids.

1.09 g of $SiO_2$, 1.36 g of ascorbic acid, 1.36 g of citric acid, 17.24 g of maltodextrin, and 17.24 g of mannitol were added to the concentrated aqueous slurry, and it was thoroughly mixed. The final formulated slurry was then subjected to lyophilization, and the final powdered alkaloid extract concentration was 12.5% total psilocybin concentration and less than 0.4% psilocin by dry weight. $SiO_2$ and maltodextrin were added as flowability enhancers. Mannitol is a cryoprotectant (allowing for efficient freeze-drying) and bulking agent. Ascorbic acid is an antioxidant (allowing protection from oxidation by first oxidizing itself), and citric acid is a chelating agent that may impart increased bioavailability and pH buffering once inside the stomach. This composition has been developed and has shown 9 months of shelf stability (see Table 3).

TABLE 2

XAD4 Psilocybin Capacity at Three Different Flow Rates

|  | 2 BV/h | 4 BV/h | 6 BV/h |
| --- | --- | --- | --- |
| Capacity (mg Alkaloids) | 765 mg | 600 mg | 463 mg |
| mL Resin | 550 | 550 | 550 |
| mg Alkaloids/mL XAD4 | 1.39 | 1.09 | 0.84 |

TABLE 3

Individual Time-Point Data of Psilocybin, Psilocin and Moisture Content of PYEX-FP-200820

| Months | Psilocybin (wt/wt %) | Psilocin (wt/wt %) | Moisture Content (%) |
| --- | --- | --- | --- |
| 0 | 13.99 ± 0.12 | 0.91 ± 0.02 | 7.23 |
| 1 | 13.89 ± 0.11 | 0.90 ± 0.02 | 6.94 |
| 2 | 14.00 ± 0.19 | 0.91 ± 0.02 | 6.77 |
| 3 | 13.91 ± 0.28 | 0.92 ± 0.03 | 6.93 |
| 4 | 13.81 ± 0.22 | 0.92 ± 0.02 | 7.14 |
| 5 | 13.86 ± 0.10 | 0.92 ± 0.04 | 7.22 |
| 6 | 13.89 ± 0.07 | 0.92 ± 0.04 | 6.87 |
| 7 | 13.95 ± 0.09 | 0.93 ± 0.03 | 6.9 |
| 8 | 13.85 ± 0.16 | 0.96 ± 0.02 | 7.31 |
| 9 | 13.93 ± 0.17 | 0.93 ± 0.04 | 6.93 |

Example 34: 0.15 M Citric Acid/Water (Psilocin Extract)

Figure 29:
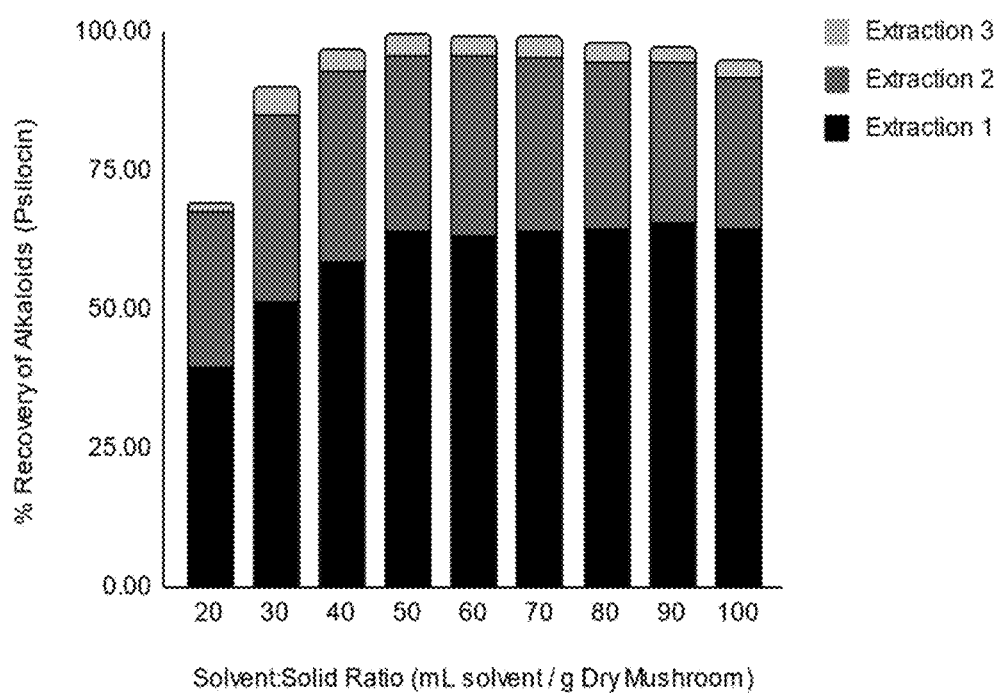
FIG. 29 is a chart demonstrating a relationship between solvent:solid ratio (mL of solvent/g of dry mushroom) and % recovery of alkaloids (psilocin).

15.7 kg of fresh *Psilocybe cubensis* mushrooms were dried in a forced air oven at 30° C. for 48 hours, resulting in 1.57 kg of dried biomass mushroom fruiting body. The content of psilocybin in the biomass was 0.523% by dry weight, resulting in 8.21 g of psilocybin available to convert to 5.90 g psilocin (stoichiometrically). The dried biomass was reduced to a size of 200 mesh with a cutting mill. The dried powdered biomass was placed into an agitated, heat-controlled vessel with 78.5 L of solvent (50 L/kg). FIG. 29 shows a chart of solvent to solid ratio optimization for water. The optimal is 50 L/kg which was the lowest S:S ratio that can obtain >90% psilocin yield in two extractions. In this embodiment, the solvent was acidified water (0.15 M citric acid, pH 2.0). The extraction was controlled to a constant 25° C. temperature and was under atmospheric pressure. The extraction was carried out under these conditions for 60 minutes, and the extraction slurry was filtered through a 5 μm stainless steel filter. The filtrate was placed into another vessel and put aside. The now-dry filter cake was again placed into the extraction vessel, and an additional 78.5 L of extraction solvent was added to the vessel. The extraction was again carried out under the same conditions for 60 minutes. The slurry was then filtered and combined to create the pooled filtrate. The pooled filtrate had a content of psilocin of 0.034 g/L, and the yield was 91.23%. The dry mass yield at this stage was 68.92%. The dry mass yield was so high because of the citric acid content.

Figure 30:
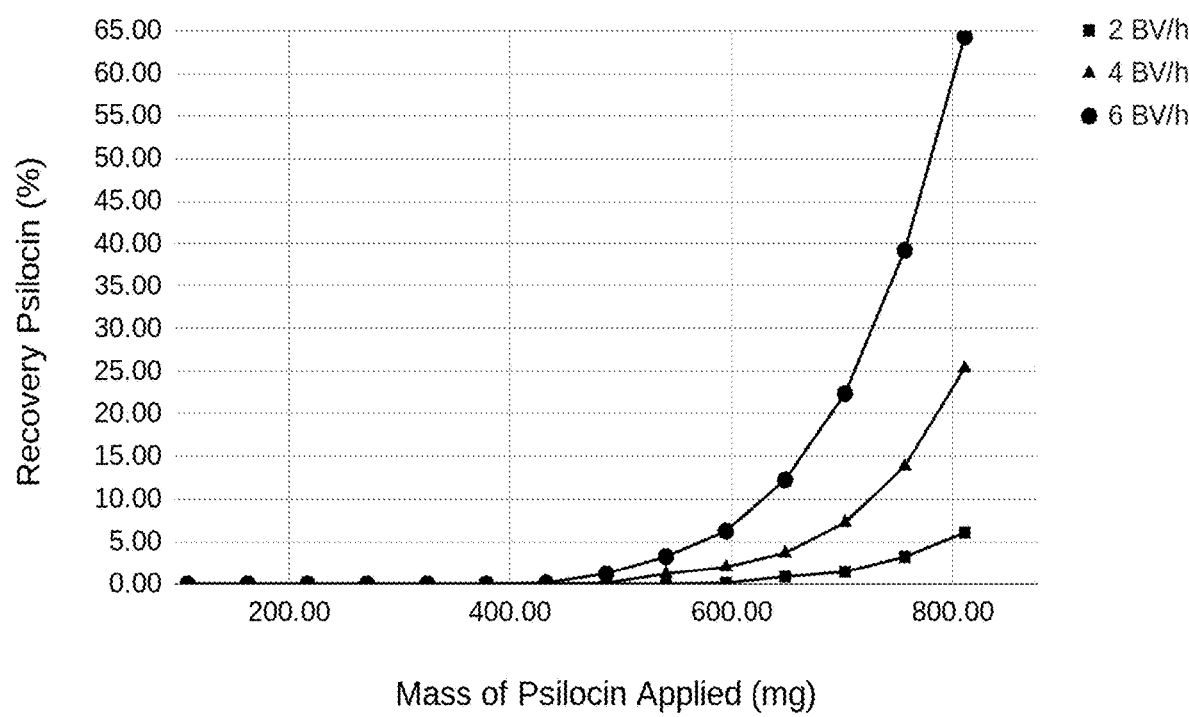
FIG. 30 is a chart demonstrating a relationship between mass of psilocin applied (mg) and recovery of psilocin (%) from XAD4 adsorption breakthrough experiments.
Figure 31:
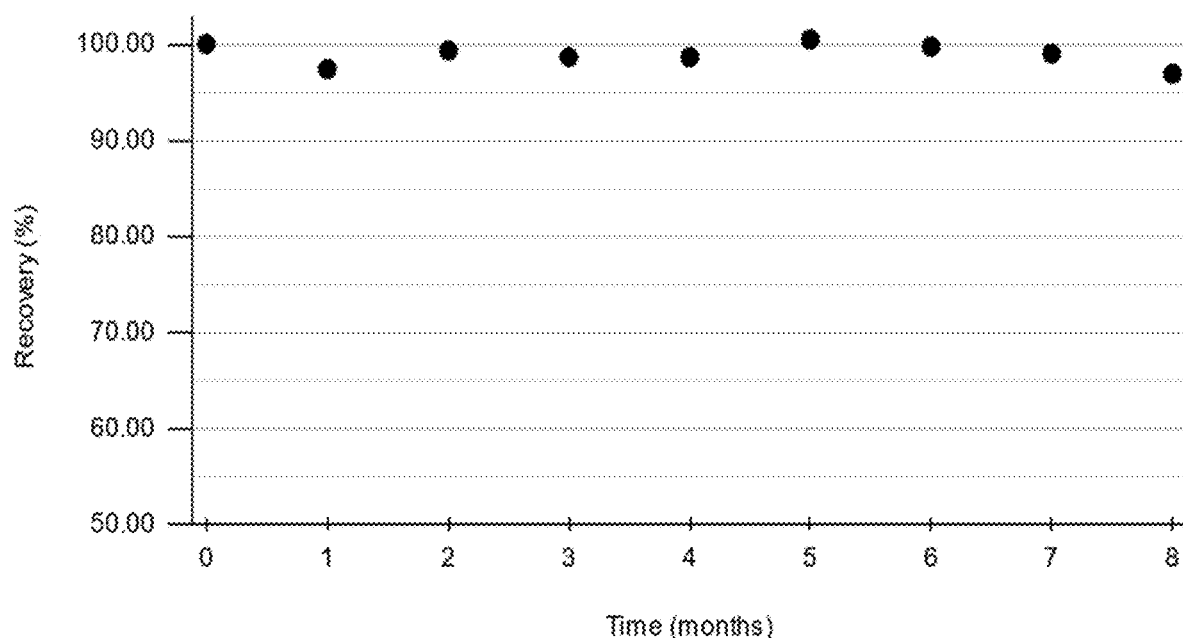
FIG. 31 is a chart demonstrating a relationship between time (months) and recovery (%) from PIEX long-term stability measurement.

The filtrate was directly loaded onto a column of Amberlite™ XAD4 macroporous resin (2700 mL of hydrated resin, ~1.98 mg psilocin/mL of hydrated resin) at a flow rate of 2 bed volumes per hour (FIG. 30).

After all 157 L of extract was loaded onto the column, it was washed with 3 bed volumes of reverse osmosis water at a flow rate of 2 BV/h, followed by elution with 5 bed volumes of 15% ethanol (by weight) and then finally washed with 100% ethanol. Each of these fractions was collected separately. The 15% ethanol fraction contained 5.11 g of psilocin and 14.94 g of dry mass, resulting in an extract of 34.20% psilocin by weight. The 15% ethanol fraction was then concentrated in a rotary evaporator to form 49.80 g of concentrated aqueous slurry at 30% solids.

0.82 g of $SiO_2$, 1.64 g of ascorbic acid, 0.41 g of citric acid, 11.54 g of potato starch, and 11.54 g of mannitol was added to the slurry and thoroughly mixed. The final formulated slurry was then subjected to lyophilization, and the final powdered alkaloid extract concentration was 12.5% total psilocin concentration and no psilocybin was present in the formulation.

TABLE 4

XAD4 psilocybin capacity at three different flow rates

|  | 2 BV/h | 4 BV/h | 6 BV/h |
|---|---|---|---|
| Capacity (mg Alkaloids) | 811 mg | 678 mg | 595 mg |
| mL Resin | 410 | 550 | 550 |
| mg Alkaloids/mL XAD4 | 1.98 | 1.65 | 1.45 |

Example 35. *Psilocybe Cubensis* Extraction, Purification, and Stabilization Rationale The indole alkaloids present in psilocybe mushrooms can be separated into two categories, the phosphorylated prodrugs (psilocybin, norbaeocystin, baeocystin and aeruginascin) and their dephosphorylated active constituents (psilocin, 4-hydroxytryptamine, norpsilocin and 4-hydroxy-N,N,N-trimethyltryptamine respectively). When these molecules are consumed (whether in the raw mushroom, purified extracts, or synthetic preparations of the compounds) the phosphorylated analogues are enzymatically metabolized by the human gut, liver, and kidneys to the active dephosphorylated forms. When considering a standardized extract composition, there are benefits to controlling whether the extraction conditions will favor producing the dephosphorylated or phosphorylated forms.

The dephosphorylated indole alkaloids are well known to be unstable. Internal experiments have also quantified and substantiated these findings under aqueous conditions across the pH spectrum (Tables 5 and 6).

TABLE 5 pH Stability of purified psilocybin over time.
Recovery (%)

| Psilocybin | T = 0 | T = 4 h | T = 16 h |
|---|---|---|---|
| pH 1 | 98.43 | 97.23 | 98.32 |
| pH 2 | 97.56 | 95.72 | 95.64 |
| pH 3 | 90.46 | 102.32 | 102.08 |
| pH 4 | 95.60 | 102.69 | 102.20 |
| pH 5 | 94.01 | 93.89 | 93.23 |
| pH 6 | 103.30 | 102.30 | 101.09 |
| pH 7 | 95.72 | 100.21 | 98.90 |
| pH 8 | 98.41 | 98.44 | 97.31 |
| pH 9 | 97.92 | 95.67 | 95.46 |
| pH 10 | 102.32 | 103.19 | 102.60 |
| pH 11 | 105.36 | 105.50 | 104.66 |
| pH 12 | 100.86 | 100.24 | 96.33 |

TABLE 6 pH Stability of purified psilocin over time.
Recovery (%)

| Psilocin | T = 0 | T = 4 h | T = 16 h |
|---|---|---|---|
| pH 2 | 102.75 | 77.06 | 57.80 |
| pH 3 | 90.83 | 90.83 | 72.02 |
| pH 4 | 93.58 | 99.08 | 81.47 |
| pH 5 | 84.40 | 69.27 | 59.45 |
| pH 6 | 95.41 | 74.22 | 62.66 |
| pH 7 | 96.33 | 74.40 | 48.72 |
| pH 8 | 90.83 | 74.40 | 46.62 |
| pH 9 | 78.07 | 43.49 | 0.00 |
| pH 10 | 88.99 | 42.39 | 20.46 |
| pH 11 | 86.24 | 39.17 | 0.00 |
| pH 12 | 88.07 | 22.29 | 10.37 |

Figure 32A:
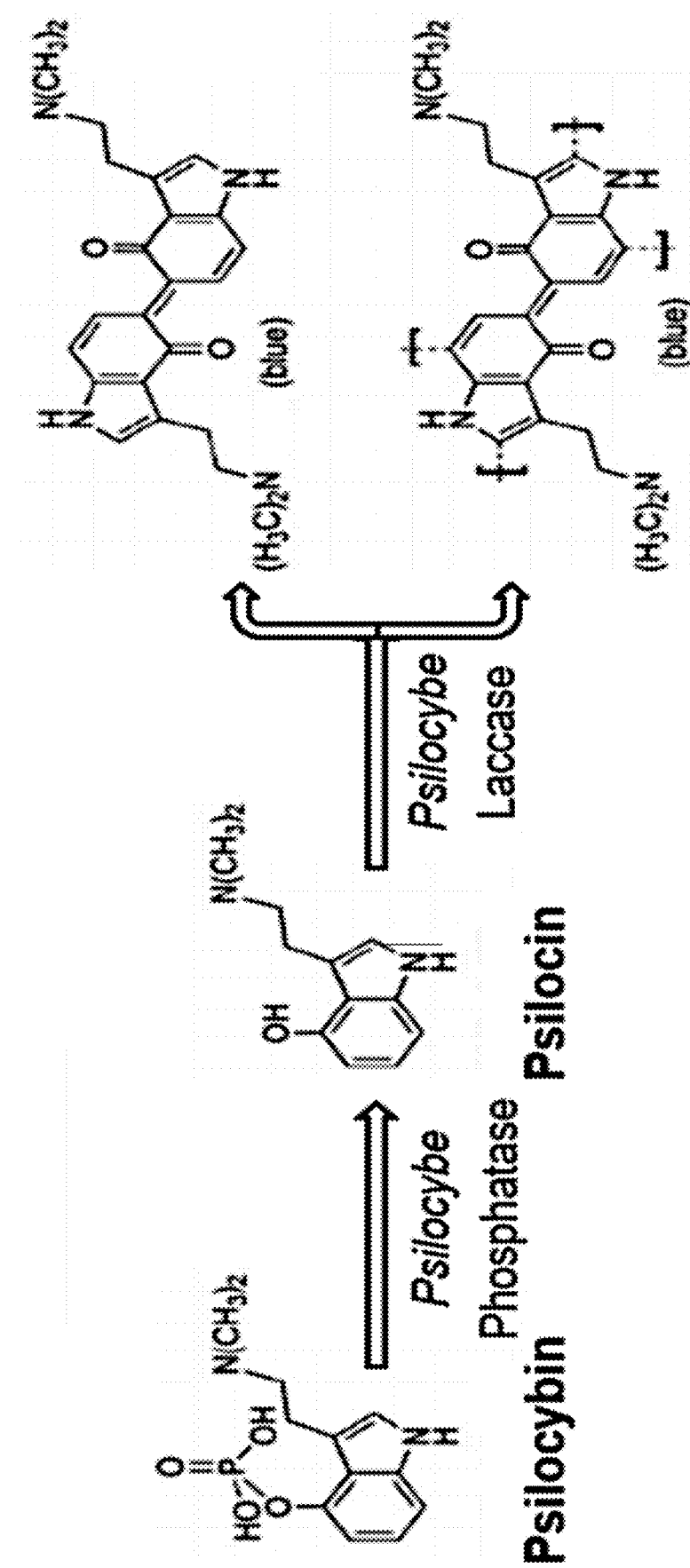
FIG. 32A is a reaction scheme of dephosphorylation of psilocybin by *Psilocybe phosphatase* followed by *Psilocybe laccase*.

While the dephosphorylation reaction is inevitable when consumed by humans, it also happens rapidly within the *Psilocybe* mushrooms themselves as a defense mechanism. The "bluing reaction" that occurs when the fresh mushrooms are bruised (while harvesting or handling) is a result of enzymatic dephosphorylation of psilocybin to psilocin, followed by enzymatic oxidation and dimerization of psilocin to semiquinoid dimers and polymers (FIG. 32A) (Lenz 2020). In the present disclosure, a method that either promotes or inhibits various steps of this degradation cascade and uses them has been developed to be advantageous during the extraction of indole alkaloids from psilocybe mushrooms.

Figure 32B:
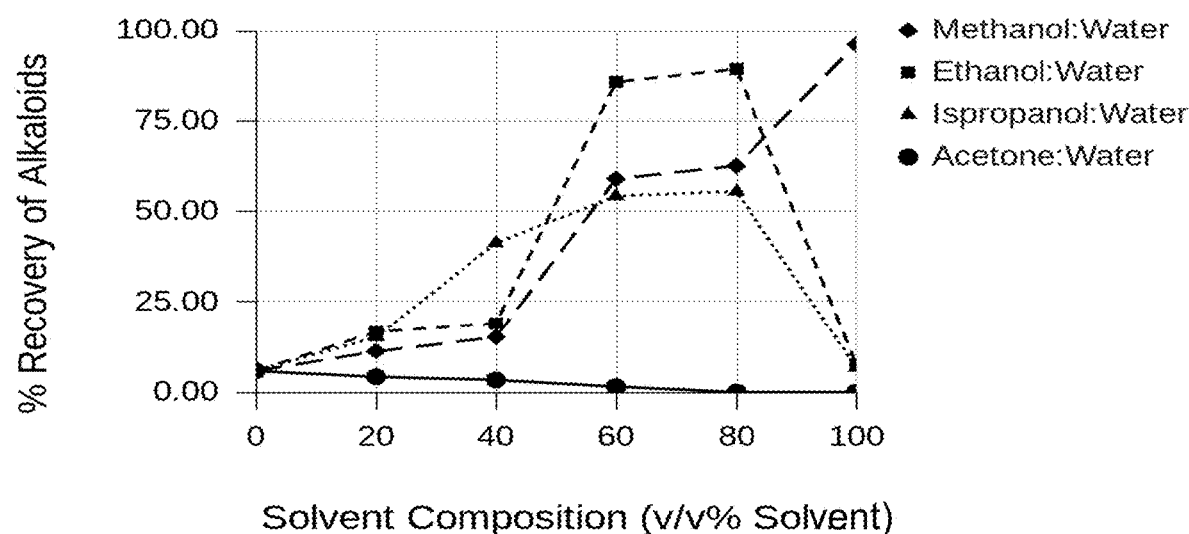
FIG. 32B is a chart demonstrating a relationship between solvent composition (v/v % solvent) and % recovery of alkaloids for the effect of aqueous extraction solvent composition.
Figure 32C:
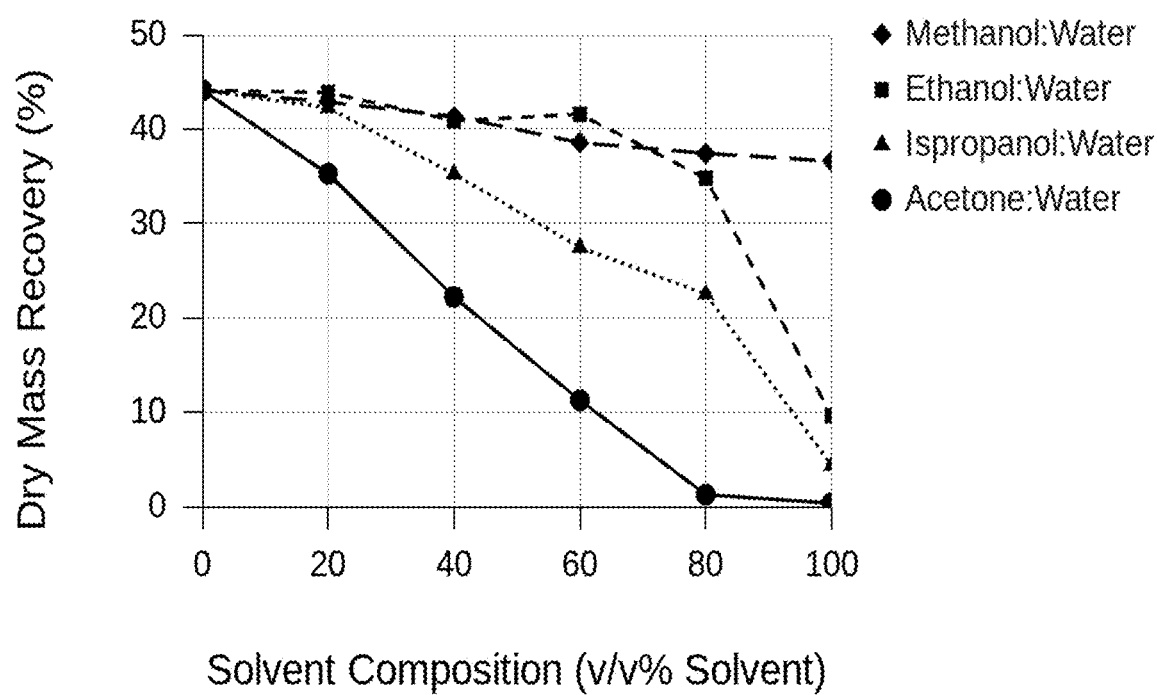
FIG. 32C is a chart demonstrating a relationship between solvent composition (v/v % solvent) and dry mass recovery (%) in aqueous solvent composition.

Psilocybin and psilocin are soluble in methanol and water and are not soluble in isopropanol, ethanol and acetone. Experiments were performed to determine the best solvent compositions for extraction (FIGS. 32B and 32C; Table 7)

TABLE 7

Dry weight concentration of each extract produced from each composition
(dried)

| | wt/wt % Alkaloid concentration in Dry Extract | | | |
|---|---|---|---|---|
| % Solvent | Methanol | Ethenol | Isopropanol | Acetone |
| 0 | 0.066 | 0.066 | 0.066 | 0.066 |
| 20 | 0.131 | 0.190 | 0.180 | 0.060 |
| 40 | 0.184 | 0.233 | 0.586 | 0.075 |
| 60 | 0.765 | 1.031 | 0.988 | 0.068 |
| 80 | 0.836 | 1.283 | 1.233 | 0.000 |
| 100 | 1.313 | 0.399 | 0.780 | 0.000 |

Methanol was shown to be the superior solvent of choice for extracting these alkaloids in general; the optimal composition was 100% anhydrous methanol which resulted in a near 100% extracted yield of psilocybin and psilocin. Any percentage of water in the extraction was shown to decrease yield of both analytes, indicating that the mushroom biomass should be as dry as possible so as to introduce a minimal amount of water. It is likely that any amount of water present in the extraction solvent allows phosphatase to act upon the phosphorylated alkaloids, converting them to their dephosphorylated counterparts. In the solvent compositions that have low total yield, laccase enzyme is also actively oxidizing psilocin to their semiquinoid breakdown products.

80% ethanol was also an effective solvent, however, it was observed that while the total alkaloid yield was high (>90%), some psilocybin was converted to psilocin during the extraction.

Figure 32D:
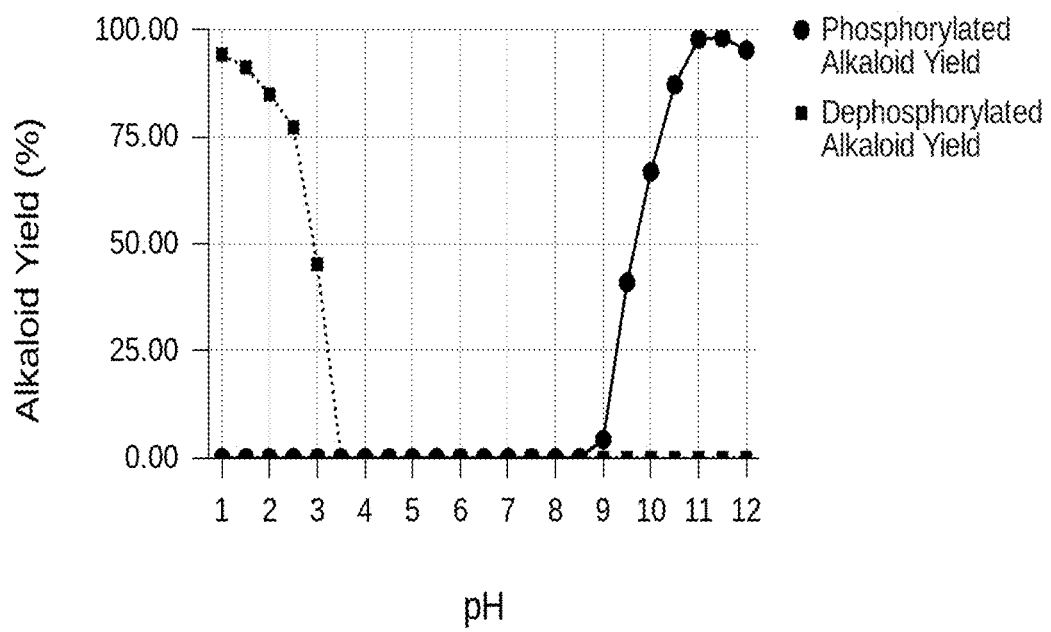
FIG. 32D is a chart demonstrating a relationship between pH and alkaloid yield (%) for the effect of pH on alkaloid extraction yield.

Since psilocybin and psilocin are soluble in water, experiments were conducted to determine if pH modulation could be beneficial in the extraction process (FIG. 32D).

High pH water was shown to extract and prevent degradation of phosphorylated alkaloids, while low pH was shown to extract and dephosphorylate psilocybin but prevent laccase oxidation activity. This process was validated and can be used reliably to control the dephosphorylation process. On first look, it would appear that a drawback is that the use of high and low pH appears to be an "all or none" process where there is no modulation of the dephosphorylation cascade.

Figure 32E:
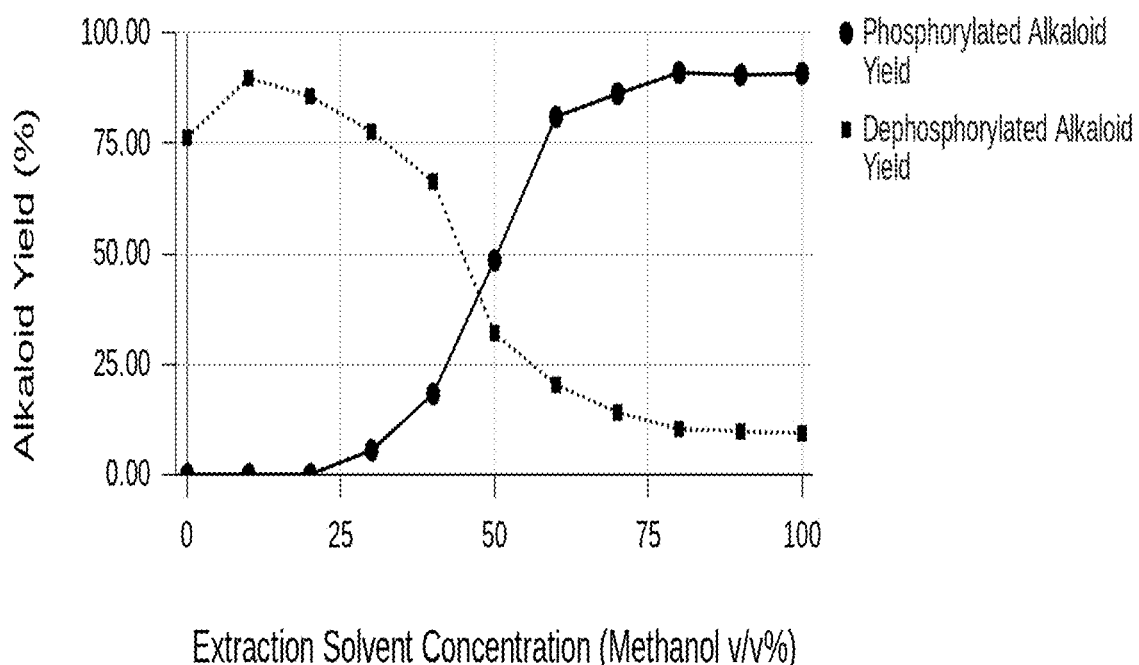
FIG. 32E is a chart demonstrating a relationship between extraction solvent concentration (methanol v/v %) and alkaloid yield (%) for the effect of solvent composition on alkaloid yield.

However, combining the information gained from the water extraction pH study with the superior ability of methanol to extract these alkaloids, experiments were performed to see how this could be used to improve the process. An interesting result was revealed by varying the methanol/water ratio while fixing the pH with 5% acetic acid (~pH 2.5, range 1-4) (FIG. 32E).

It was evident that the oxidation of psilocin during extraction was only weakly observed at the 0% methanol ratio, validating the previous experimental data with low pH water extraction. Either protonation of the 4-hydroxy position on the psilocin molecule was inhibiting laccase's ability to catalyze the oxidation and free radical formation, or the enzyme was denatured and not active at this pH. Gradually, as the methanol concentration in the extraction solvent is increased, a higher proportion of the total alkaloid content is retained as the phosphorylated form, indicating that methanol is inhibiting or drastically slowing phosphatase's ability to cleave the phosphate bond. Another possibility is that at a certain concentration, methanol is no longer able to extract or solvate the phosphatase enzyme, leaving it behind in the solid residue during extraction. This process can be used to modulate the phosphorylated/dephosphorylated content of the extract.

Macroporous resin adsorption/desorption was chosen as a simple and efficient purification platform to concentrate the total alkaloid content since the concentration factor from extraction alone was underwhelming. Once the proper composition of alkaloids is determined (Table 8), a number of purification permutations can be utilized (Table 9).

TABLE 8

Summary of extraction processes and conditions used
EXTRACTION

| Goal: | Most preferred | Less Preferred |
|---|---|---|
| Phosphorylated alkaloids left intact (Psilocybin, Baeocystin, Norbaeocystin, Aeruginascin) | Acidified Anhydrous Methanol Anhydrous Methanol | High pH adjusted Water 80% Ethanol/Water High pH Adjusted 80% Ethanol/Water |
| Dephosphorylated Alkaloids (Psilocin) | Acidified Water Acidified 0-20% methanol/water | 50-70% Ethanol/Water |
| Specific Ratio of Psilocybin to Psilocin | Combine extracts from different methods AFTER purification at specific ratio acidified 20-80% Methanol | |

TABLE 9

Summary of purification processes and condition
PURIFICATION

| Goal: | Most preferred | Less Preferred |
|---|---|---|
| Highest Purity Psilocybin | Repeated XAD4 column runs | SCX, SAX or other Resin Antisolvent addition with acetone Liquid/liquid extraction |
| Highest Purity Psilocin | XAD4 column run + LXA817 | XAD4 + SCX or antisolvent or liquid extraction |
| Partial Purification of psilocybin or psilocin | Single XAD4 run | |

Throughout the description, specific details have been set forth in order to provide a more thorough understanding of the invention. However, the invention may be practised without these particulars. In other instances, well known elements have not been shown or described in detail and repetitions of steps and features have been omitted to avoid unnecessarily obscuring the invention. Accordingly, the specification and drawings are to be regarded in an illustrative, rather than a restrictive, sense.

All parameters, dimensions, materials, quantities and configurations described herein are examples only and may be changed depending on the specific embodiment. Numbers and percentages are given to the nearest significant figure. For example, 10% includes the range between exactly 9.5% and exactly 10.5%. Accordingly, the scope of the invention is to be construed in accordance with the substance defined by the claims. The process may be scaled up using larger quantities and a modified apparatus.

The invention claimed is:

1. A method for generating a psychoactive alkaloid extract comprising 0.1% to 99% by weight of a psychoactive alkaloid from a psychoactive organism, the method comprising:
   a. providing a biomass of the psychoactive organism;
   b. contacting the biomass with 10 to 100 milliliters (mL) of solvent per gram (g) of the biomass; and
   c. evaporating the solvent from the biomass to yield the psychoactive alkaloid extract comprising 0.1% to 99% by weight of the psychoactive alkaloid,
   wherein the solvent has a pH of 10 or greater and the psychoactive alkaloid extract comprises greater than 50% of a phosphorylated psychoactive alkaloid.

2. The method of claim 1, wherein, following (b), the biomass is contacted with a second solvent.

3. The method of claim 1, wherein the solvent is a mixture of an alcohol and basified water, wherein the alcohol comprises 60% to 99% of the mixture.

4. The method of claim 3, wherein the alcohol is a C1-C4 primary aliphatic alcohol.

5. The method of claim 4, wherein the C1-C4 primary aliphatic alcohol is ethanol or methanol.

6. The method of claim 1, wherein the psychoactive organism is *Psilocybe cyanescens, Psilocybe cubensis, Amanita muscaria*, or any selection thereof.

7. The method of claim 1, wherein the phosphorylated psychoactive alkaloid is psilocybin, baeocystin, norbaeocystin, aeruginascin, or any combination thereof.

* * * * *